US011613525B2

(12) United States Patent
Morrow et al.

(10) Patent No.: US 11,613,525 B2
(45) Date of Patent: Mar. 28, 2023

(54) SUBSTITUTED CONDENSED THIOPHENES AS MODULATORS OF STING

(71) Applicant: CTXT PTY LIMITED, Parkville (AU)

(72) Inventors: Benjamin Joseph Morrow, Parkville (AU); Michelle Ang Camerino, Parkville (AU); Scott Raymond Walker, Parkville (AU); Graeme Irvine Stevenson, Melbourne (AU); Paul Anthony Stupple, Parkville (AU)

(73) Assignee: CTXT PTY LIMITED, Parkville (AU)

( * ) Notice: Subject to any disclaimer, the term of this patent is extended or adjusted under 35 U.S.C. 154(b) by 40 days.

(21) Appl. No.: 17/054,850

(22) PCT Filed: May 16, 2019

(86) PCT No.: PCT/EP2019/062636
§ 371 (c)(1),
(2) Date: Nov. 12, 2020

(87) PCT Pub. No.: WO2019/219820
PCT Pub. Date: Nov. 21, 2019

(65) Prior Publication Data
US 2021/0214333 A1 Jul. 15, 2021

(30) Foreign Application Priority Data

May 16, 2018 (GB) .................................. 1807924.4

(51) Int. Cl.
| C07D 333/70 | (2006.01) |
| C07D 409/12 | (2006.01) |
| C07D 495/04 | (2006.01) |
| A61K 31/381 | (2006.01) |
| A61P 35/00 | (2006.01) |
| A61P 37/00 | (2006.01) |
| C07D 413/12 | (2006.01) |

(52) U.S. Cl.
CPC ......... *C07D 333/70* (2013.01); *C07D 409/12* (2013.01); *C07D 413/12* (2013.01); *C07D 495/04* (2013.01)

(58) Field of Classification Search
CPC .. C07D 333/70; C07D 409/12; C07D 495/04; A61K 31/381; A61P 35/00; A61P 37/00
See application file for complete search history.

(56) References Cited

U.S. PATENT DOCUMENTS

| 5,681,835 A | 10/1997 | Willson |
| 5,877,219 A | 3/1999 | Willson |
| 6,113,918 A | 9/2000 | Johnson et al. |
| 6,207,716 B1 | 3/2001 | Willson |
| 6,268,391 B1 | 7/2001 | Dickerson et al. |
| 6,310,224 B1 | 10/2001 | Grey |
| 6,479,508 B1 | 11/2002 | Beaulieu et al. |
| 6,525,028 B1 | 2/2003 | Johnson et al. |
| 6,911,434 B2 | 6/2005 | Baldridge et al. |
| 6,984,720 B1 | 1/2006 | Korman et al. |
| 7,112,600 B1 | 9/2006 | Hashimoto et al. |
| 7,129,219 B2 | 10/2006 | Johnson et al. |
| 7,488,802 B2 | 2/2009 | Collins et al. |
| 7,504,101 B2 | 3/2009 | Weinberg |
| 7,521,051 B2 | 4/2009 | Collins et al. |
| 7,550,140 B2 | 6/2009 | Bakker et al. |
| 7,595,048 B2 | 9/2009 | Honjo et al. |
| 7,605,238 B2 | 10/2009 | Korman et al. |
| 7,758,852 B2 | 7/2010 | Soto-Jara et al. |
| 7,858,765 B2 | 12/2010 | Soto-Jara et al. |
| 7,943,743 B2 | 5/2011 | Korman et al. |
| 7,960,515 B2 | 6/2011 | Min et al. |
| 8,008,449 B2 | 8/2011 | Korman et al. |
| 8,034,953 B2 | 10/2011 | Combs et al. |
| 8,168,179 B2 | 5/2012 | Honjo et al. |
| 8,168,757 B2 | 5/2012 | Finnefrock et al. |
| 8,217,149 B2 | 7/2012 | Irvin et al. |
| 8,354,509 B2 | 1/2013 | Carven et al. |
| 8,383,796 B2 | 2/2013 | Korman et al. |
| 8,552,154 B2 | 10/2013 | Freeman et al. |
| 8,779,108 B2 | 7/2014 | Queva et al. |
| 9,212,224 B2 | 12/2015 | Cogswell et al. |

(Continued)

FOREIGN PATENT DOCUMENTS

| EP | 1065213 A2 | 1/2001 |
| EP | 1125585 A1 | 8/2001 |
| EP | 1374901 A1 | 1/2004 |
| EP | 1374902 A1 | 1/2004 |
| GB | 2563642 A | 12/2018 |

(Continued)

OTHER PUBLICATIONS

International Search Report issued by the European Patent Office for PCT/EP2019/062636, dated Jul. 19, 2019.

(Continued)

*Primary Examiner* — Bruck Kifle
(74) *Attorney, Agent, or Firm* — Thomas | Horstemeyer, LLP

(57) ABSTRACT

A compound of formula (I), wherein $R^1$ is selected from (i) H, (ii) $C_{3-6}$cycloalkyl, (iii) $C_{3-7}$heterocyclyl optionally substituted with a group selected from: methyl and ester, and (iv) linear or branched $C_{1-4}$alkyl optionally substituted with a group selected from: alkoxy, amino, amido, acylamido, acyloxy, alkyl carboxyl ester, alkyl carbamoyl, alkyl carbamoyl ester, phenyl, phosphonate ester, $C_{3-7}$heterocyclyl optionally substituted with a group selected from methyl and oxo, and a naturally occurring amino acid, optionally N-substituted with a group selected from methyl, acetyl and boc; $A^1$ is $CR^A$ or N; $A^2$ is $CR^B$ or N; $A^3$ is $CR^C$ or N; $A^4$ is $CR^D$ or N; where no more than two of $A^1$, $A^2$, $A^3$, and $A^4$ may be N; one or two of $R^A$, $R^B$, $R^C$, and $R^D$, (if present) are selected from H, F, Cl, Br, Me, $CF_3$, cyclopropyl, cyano, OMe, OEt, $CH_2OH$, $CH_2OMe$ and $CH_2NMe_2$; the remainder of $R^A$, $R^B$, $R^C$, and $R^D$, (if present) are H; Y is O, NH or $CH_2$; $R^Y$ is selected from: (RYA) and (RYB).

19 Claims, No Drawings

Specification includes a Sequence Listing.

(56) References Cited

U.S. PATENT DOCUMENTS

| | | |
|---|---|---|
| 2002/0077304 A1 | 6/2002 | Persing et al. |
| 2002/0147160 A1 | 10/2002 | Bhat et al. |
| 2003/0215917 A1 | 11/2003 | Huang et al. |
| 2003/0236251 A1 | 12/2003 | Beaulieu et al. |
| 2004/0023958 A1 | 2/2004 | Borchardt et al. |
| 2004/0082635 A1 | 4/2004 | Hashimoto et al. |
| 2004/0106619 A1 | 6/2004 | Mitsuya et al. |
| 2004/0131608 A1 | 7/2004 | Watanabe |
| 2004/0171626 A1 | 9/2004 | Beaulieu et al. |
| 2004/0186125 A1 | 9/2004 | Poupart et al. |
| 2004/0229790 A1 | 11/2004 | Tezuka et al. |
| 2004/0253229 A1 | 12/2004 | Suzuki et al. |
| 2005/0176701 A1 | 8/2005 | Borchardt et al. |
| 2005/0203051 A1 | 9/2005 | Karaolis et al. |
| 2005/0222236 A1 | 10/2005 | Tsantrizos et al. |
| 2005/0227943 A1 | 10/2005 | Johnson et al. |
| 2006/0046983 A1 | 3/2006 | Hudyma et al. |
| 2006/0052408 A1 | 3/2006 | Peckham et al. |
| 2006/0052595 A1 | 3/2006 | Aquino et al. |
| 2006/0058284 A1 | 3/2006 | Yang et al. |
| 2006/0110383 A1 | 5/2006 | Honjo et al. |
| 2006/0122166 A1 | 6/2006 | Duan et al. |
| 2006/0122399 A1 | 6/2006 | Gonzalez et al. |
| 2006/0210567 A1 | 9/2006 | Collins et al. |
| 2006/0229336 A1 | 10/2006 | Kazmierski et al. |
| 2006/0258720 A1 | 11/2006 | Haigh et al. |
| 2007/0004711 A1 | 1/2007 | Zhang et al. |
| 2007/0042353 A1 | 2/2007 | Ago et al. |
| 2007/0270475 A1 | 11/2007 | Guidetti et al. |
| 2008/0025979 A1 | 1/2008 | Honjo et al. |
| 2008/0279851 A1 | 11/2008 | Coyle et al. |
| 2008/0311076 A1 | 12/2008 | Spencer et al. |
| 2009/0055944 A1 | 2/2009 | Korman et al. |
| 2009/0169609 A1 | 7/2009 | Ebensen et al. |
| 2009/0187021 A1 | 7/2009 | Youngman et al. |
| 2010/0203056 A1 | 8/2010 | Irving et al. |
| 2010/0266617 A1 | 10/2010 | Carven et al. |
| 2011/0195068 A1 | 8/2011 | Langermann et al. |
| 2011/0271358 A1 | 11/2011 | Freeman et al. |
| 2011/0280877 A1 | 11/2011 | Tamada |
| 2011/0293605 A1 | 12/2011 | Sathish et al. |
| 2013/0017199 A1 | 1/2013 | Langermann |
| 2013/0034559 A1 | 2/2013 | Queva et al. |
| 2013/0045201 A1 | 2/2013 | Irving et al. |
| 2013/0280275 A1 | 10/2013 | Liu et al. |
| 2014/0086923 A1 | 3/2014 | Faget et al. |
| 2014/0205653 A1 | 7/2014 | Dubensky, Jr. et al. |
| 2014/0341902 A1 | 11/2014 | Maecker et al. |
| 2015/0010613 A1 | 1/2015 | Dubensky, Jr. et al. |
| 2015/0056224 A1 | 2/2015 | Dubensky, Jr. et al. |
| 2015/0239978 A1 | 8/2015 | Marodon et al. |
| 2015/0274835 A1 | 10/2015 | Marasco et al. |
| 2016/0009805 A1 | 1/2016 | Kowanetz et al. |
| 2016/0215059 A1 | 7/2016 | Liu et al. |
| 2016/0287623 A1 | 10/2016 | Gajewski et al. |
| 2016/0304610 A1 | 10/2016 | Sazinsky et al. |
| 2018/0093964 A1 | 4/2018 | Altman et al. |
| 2018/0105514 A1 | 4/2018 | Mehlmann et al. |
| 2018/0186828 A1 | 7/2018 | Biggadike et al. |
| 2019/0300513 A1 | 10/2019 | Altman et al. |
| 2020/0138827 A1 | 5/2020 | Banerjee et al. |
| 2020/0147083 A1 | 5/2020 | Banerjee et al. |
| 2020/0291001 A1 | 9/2020 | Fosbenner et al. |
| 2020/0330427 A1 | 10/2020 | Cemerski et al. |
| 2021/0009608 A1 | 1/2021 | Altman et al. |
| 2021/0205321 A1 | 7/2021 | Lairson et al. |
| 2021/0214333 A1 | 7/2021 | Morrow et al. |
| 2021/0238172 A1 | 8/2021 | Charnley et al. |

FOREIGN PATENT DOCUMENTS

| | | |
|---|---|---|
| WO | 2001047883 A1 | 7/2001 |
| WO | 2001090129 A2 | 11/2001 |
| WO | 2002004425 A2 | 1/2002 |
| WO | 2002057245 A1 | 7/2002 |
| WO | 2002057287 A2 | 7/2002 |
| WO | 2002074769 A1 | 9/2002 |
| WO | 2003000254 A1 | 1/2003 |
| WO | 2003007945 A1 | 1/2003 |
| WO | 2003085375 A2 | 10/2003 |
| WO | 2003095441 A1 | 11/2003 |
| WO | 2004004771 A1 | 1/2004 |
| WO | 2004037818 A1 | 5/2004 |
| WO | 2004054581 A2 | 7/2004 |
| WO | 2004054974 A2 | 7/2004 |
| WO | 2004055010 A2 | 7/2004 |
| WO | 2004055011 A1 | 7/2004 |
| WO | 2004055012 A1 | 7/2004 |
| WO | 2004055016 A1 | 7/2004 |
| WO | 2004056875 A1 | 7/2004 |
| WO | 2004064925 A1 | 8/2004 |
| WO | 2004065367 A1 | 8/2004 |
| WO | 2004072286 A1 | 8/2004 |
| WO | 2004074270 A2 | 9/2004 |
| WO | 2005014543 A1 | 2/2005 |
| WO | 2005080388 A1 | 9/2005 |
| WO | 2005087238 A2 | 9/2005 |
| WO | 2005105761 A1 | 11/2005 |
| WO | 2006010697 A2 | 2/2006 |
| WO | 2006018725 A1 | 2/2006 |
| WO | 2006020082 A1 | 2/2006 |
| WO | 2006045613 A1 | 5/2006 |
| WO | 2006069656 A1 | 7/2006 |
| WO | 2006122011 A2 | 11/2006 |
| WO | 2007005874 A2 | 1/2007 |
| WO | 2007054279 A2 | 5/2007 |
| WO | 2008137915 A2 | 11/2008 |
| WO | 2008156712 A1 | 12/2008 |
| WO | 2010027827 A2 | 3/2010 |
| WO | 2010056804 A1 | 5/2010 |
| WO | 2010077634 A1 | 7/2010 |
| WO | 2011066342 A2 | 6/2011 |
| WO | 2011066389 A1 | 6/2011 |
| WO | 2012027328 A2 | 3/2012 |
| WO | 2012131004 A2 | 10/2012 |
| WO | 2013019906 A1 | 2/2013 |
| WO | 2013028231 A1 | 2/2013 |
| WO | 2013166000 A1 | 11/2013 |
| WO | 2013185052 A1 | 12/2013 |
| WO | 2014033327 A1 | 3/2014 |
| WO | 2014055897 A2 | 4/2014 |
| WO | 2014093936 A1 | 6/2014 |
| WO | 2014189805 A1 | 11/2014 |
| WO | 2015077354 A1 | 5/2015 |
| WO | 2015185565 A1 | 12/2015 |
| WO | 2016007235 A1 | 1/2016 |
| WO | 2016120789 A1 | 8/2016 |
| WO | 2017175147 A1 | 10/2017 |
| WO | 2017175156 A1 | 10/2017 |
| WO | 2018234805 A1 | 12/2018 |
| WO | 2018234807 A1 | 12/2018 |
| WO | 2018234808 A1 | 12/2018 |
| WO | 2019027858 A1 | 2/2019 |
| WO | 2019069269 A1 | 4/2019 |
| WO | 2019069270 A1 | 4/2019 |
| WO | 2019165032 A1 | 8/2019 |
| WO | 2019195063 A1 | 10/2019 |
| WO | 2019195124 A1 | 10/2019 |
| WO | 2019219820 A1 | 11/2019 |

OTHER PUBLICATIONS

Database Registry [Online] Chemical Abstracts Service, Columbus, Ohio, US; Aug. 3, 2012 (Aug. 3, 2012), XP002792682, retrieved from STN Database accession No. 1385933-29-8 REGISTRY abstract.

(56) References Cited

OTHER PUBLICATIONS

Database Registry [Online] Chemical Abstracts Service, Columbus, Ohio, US; Apr. 28, 2011 (Apr. 28, 2011), XP002792683, retrieved from STN Database accession No. 1286975-19-6 abstract.

Database Registry [Online] Chemical Abstracts Service, Columbus, Ohio, US; Feb. 8, 2007 (Feb. 8, 2007), XP002792684, Database accession No. 919921-65-6 abstract.

Abraham, R. T., "Phosphatidylinositol 3-kinase related kinases," Current Opinion in Immunology, 1996, vol. 8, pp. 412-418.

Aguirre et al., "DENV Inhibits Type I IFN Production in Infected Cells by Cleaving Human STING," PLOS Pathogens, Oct. 2012, vol. 8, Issue 10, e1002934.

Ashby, M. N., "CaaX converting enzymes," Current Opinion in Lipidology, Apr. 1998, vol. 9, No. 2: 99-102, pp. 1-7.

Bolen et al., "Leukocyte Protein Tyrosine Kinases: Potential Targets for Drug Discovery," Annual Review of Immunology, 1997, vol. 15, pp. 371-404.

Brekken et al., "Selective Inhibition of Vascular Endothelial Growth Factor (VEGF) Receptor 2 (KDR/Flk-1) Activity by a Monoclonal Anti-VEGF Antibody Blocks Tumor Growth in Mice," Cancer Research, Sep. 2000, vol. 60, pp. 5117-5124.

Brodt et al., "Inhibition of the type I insulin-like growth factor receptor expression and signaling: Novel strategies for antimetastatic therapy," Biochemical Pharmacology, Oct. 2000, vol. 60, Issue 8, pp. 1101-1107.

Burdette et al., "STING and the innate immune response to nucleic acids in the cytosol," Nature Immunology, Jan. 2013, vol. 14, No. 1, pp. 19-26.

Cai et al., "The cGAS-cGAMP-STING Pathway of Cytosolic DNA Sensing and Signaling," Molecular Cell, Apr. 2014, vol. 54, Issue 2, pp. 289-296.

Canman et al., "The role of ATM in DNA damage responses and cancer," Oncogene, Dec. 1998, vol. 17, No. 25, pp. 3301-3308.

Chen et al., "SARS coronavirus papain-like protease inhibits the type I interferon signaling pathway through interaction with the STING-TRAF3-TBK1 complex," Protein & Cell, May 2014, vol. 5, Issue 5, pp. 369-381.

Dhhabra et al., "Structure of S. aureus HPPK and the Discovery of a New Substrate Site Inhibitor," PLOS One, Jan. 2012, vol. 7, Issue 1, e29444.

Cirulli et al., "Exome sequencing in amyotrophic lateral sclerosis identifies risk genes and pathways," Science, Mar. 2015, vol. 347, Issue 6229, pp. 1436-1441.

Collins et al., "Cyclic GMP-AMP Synthase is an Innate Immune DNA Sensor for Mycobacterium tuberculosis," Cell Host & Microbe, Jun. 10, 2015, vol. 17, pp. 820-828.

Conlon et al., "Mouse, but not Human STING, Binds and Signals in Response to the Vascular Disrupting Agent 5,6-Dimethylxanthenone-4-Acetic Acid," The Journal of Immunology, May 2013, vol. 190, Issue 10: 5216-5225, pp. 1-11.

Corrales et al., "Molecular Pathways: Targeting the Stimulator of Interferon Genes (STING) in the Immunotherapy of Cancer," Clinical Cancer Research, Nov. 2015, vol. 21, No. 21, pp. 4774-4779.

Crow et al., "Mutations in the gene encoding the 3'-5' DNA exonuclease TREX1 cause Aicardi-Goutières syndrome at the AGS1 locus," Nature Genetics, Aug. 2006, vol. 38, No. 8, pp. 917-920.

Diner et al., "The Innate Immune DNA Sensor cGAS Produces a Noncanonical Cyclic Dinucleotide that Activates Human STING," Cell Reports, May 2013, vol. 3, pp. 1355-1361.

Ding et al., "Hepatitis C virus NS4B blocks the interaction of STING and TBK1 to evade host innate immunity," Journal of Hepatology, Jul. 2013, vol. 59, pp. 52-58.

Dubensky et al., "Rationale, progress and development of vaccines utilizing STING-activating cyclic dinucleotide adjuvants," Therapeutic Advances in Vaccines and Immunotherapy, Sep. 2013, vol. 1, No. 4, pp. 131-143.

Freischmidt et al., "Haploinsufficiency of TBK1 causes familial ALS and fronto-temporal dementia," Nature Neuroscience, Mar. 2015, vol. 18, No. 5, pp. 631-638.

Gao et al., "Cyclic [G(2',5')pA(3',5')p] is the Metazoan Second Messenger Produced by DNA-Activated Cyclic GMP-AMP Synthase," Cell, May 2013, vol. 153, Issue 5, pp. 1094-1107.

Gao et al., "Cyclic GMP-AMP Synthase is an Innate Immune Sensor of HIV and Other Retroviruses," Science, Aug. 2013, vol. 341, No. 6148, pp. 903-906.

Gao et al., "Structure-Function Analysis of STING Activation by c[G(2',5')pA(3',5')p] and Targeting by Antiviral DMXAA," Cell, Aug. 2013, vol. 154, Issue 4, pp. 748-762.

Green et al., "Monoclonal antibody therapy for solid tumors," Cancer Treatment Reviews, Aug. 2000, vol. 26, Issue 4, pp. 269-286.

Herzner et al., "Sequence-specific activation of the DNA sensor cGAS by Y-form DNA structures as found in primary HIV-1 cDNA," Nature Immunology, Oct. 2015, vol. 16, No. 10, pp. 1025-1035.

Holm et al., "Influenza A virus targets a cGAS-independent STING pathway that controls enveloped RNA viruses," Nature Communications, Feb. 2016, vol. 7, Issue 10680, pp. 1-9.

Huber et al., "Cutting Edge: Type I IFN Reverses Human Th2 Commitment and Stability by Suppressing GATA3," The Journal of Immunology, Jun. 2010, vol. 185, Issue 2, pp. 813-817.

Hutloff et al., "ICOS is an inducible T-cell co-stimulator structurally and functionally related to CD28," Nature, Jan. 1999, vol. 397, pp. 263-266.

Isaacs et al., Virus interference. I. The interferon, Proceedings of the Royal Society B: Biological Sciences, Sep. 1957, vol. 147, Issue 927, pp. 258-267.

Shikawa et al., "STING is an endoplasmic reticulum adaptor that facilitates innate immune signalling," Nature, Oct. 2008, vol. 455, Issue 7219, pp. 674-678.

Shikawa et al., "STING regulates intracellular DNA-mediated, type I interferon-dependent innate immunity," Nature, Sep. 2009, vol. 461, Issue 7265, pp. 788-792.

Jackson, S. P., "DNA-dependent protein kinase," International Journal of Biochemistry and Cell Biology, Jul. 1997, vol. 29, No. 7, pp. 935-938.

Jin et al., "Identification and Characterization of a Loss-of-Function Human MPYS Variant," Genes and Immunity, Jan. 2011, vol. 12, pp. 263-269.

Jin et al., "MPYS is Required for IFN Response Factor 3 Activation and Type I IFN Production in the Response of Cultured Phagocytes to Bacterial Second Messengers Cyclic-di-AMP and Cyclic-di-GMP," The Journal Immunology, Sep. 2011, vol. 187, No. 5:2595-2601, pp. 1-8.

Karlsson et al., "Analyzing a kinetic titration series using affinity biosensors," Analytical Biochemistry, Feb. 2006, vol. 349, No. 1, pp. 136-147.

Kath, J. C., "Patent focus: inhibitors of tumour cell growth," Expert Opinion on Therapeutic Patents, 2000, vol. 10, Issue 6, pp. 803-818.

Lackey et al., "The discovery of potent cRafl kinase inhibitors," Bioorganic and Medicinal Chemistry Letters, Feb. 2000, vol. 10, Issue 3, pp. 223-226.

Lau et al., "DNA tumor virus oncogenes antagonize the cGAS-STING DNA-sensing pathway," Science, Sep. 2015, vol. 350, Issue 6260, pp. 568-571.

Lemos et al., "Activation of the STING Adaptor Attenuates Experimental Autoimmune Encephalitis," The Journal of Immunology, Jun. 2014, vol. 192, Issue 12, pp. 5571-5578.

Lemos et al., "STING Promotes the Growth of Tumors Characterized by Low Antigenicity via IDO Activation," Cancer Research, Apr. 2016, vol. 76, Issue 8, pp. 2076-2081.

Libanova et al., "Cyclic di-nucleotides: new era for small molecules as adjuvants," Microbial Biotechnology, Sep. 2012, vol. 5, No. 2, pp. 168-176.

Liu et al., "RIG-I-Mediated STING Upregulation Restricts Herpes Simplex Virus 1 Infection," Journal of Virology, Oct. 2016, vol. 90, No. 20, pp. 9406-9419.

Lofts et al., "Growth Factor Receptors as Targets," in: Kerr et al., New Molecular Targets for Cancer Chemotherapy, London, CRC Press, 1994, pp. 45-66.

(56) References Cited

OTHER PUBLICATIONS

Ma et al., "Modulation of the cGAS-STING DNA sensing pathway by gammaherpesviruses," PNAS, Jul. 2015, vol. 112, No. 31, pp. E4306-E4315.

Ma et al., "The cGAS-STING Defense Pathway and Its Counteraction by Viruses," Cell Host & Microbe, Feb. 2016, Mol. 19, Issue 2, pp. 150-158.

Martínez-Lacaci et al., "RAS transformation causes sustained activation of epidermal growth factor receptor and elevation of mitogen-activated protein kinase in human mammary epithelial cells," International Journal of Cancer, Oct. 2000, vol. 88, Issue 1, pp. 44-52.

Massagué et al., "Serine/threonine kinase receptors: mediators of transforming growth factor beta family signals," in: Parker et al., Cell Signalling, New York, Cold Spring Harbor Laboratory Press, 1996, pp. 41-64.

McNab et al., "Type I interferons in infectious disease," Nature Reviews Immunology, Feb. 2015, vol. 15, No. 2, pp. 37-103.

Moisan et al., "TLR7 ligand prevents allergen-induced airway hyperresponsiveness and eosinophilia in allergic asthma by a MYD88-dependent and MK2-independent pathway," American Journal of Physiology—Lung Cellular Molecular Physiology, May 2006, vol. 290, Issue 5, pp. L987-L995.

Munn et al., "IDO in the Tumor Microenvironment: Inflammation, Counter-Regulation, and Tolerance," Trends in Immunology, Mar. 2016, vol. 37, No. 3: 193-207, pp. 1-26.

Niesen et al., "The use of differential scanning fluorimetry to detect ligand interactions that promote protein stability," Nature Protocols, Sep. 2007, vol. 2, No. 9, pp. 2212-2221.

Nitta et al., "Hepatitis C virus NS4B protein targets STING and abrogates RIG-I-mediated type I interferon-dependent innate immunity," Hepatology, Jan. 2013, vol. 57, No. 1, pp. 46-58.

Oliff, A., "Farnesyltransferase inhibitors: targeting the molecular basis of cancer," Biochimica et Biophysica Acta (BBA)—Reviews on Cancer, May 1999, vol. 1423, No. 3, pp. C19-C30.

Papalia et al., "Comparative analysis of 10 small molecules binding to carbonic anhydrase II by different investigators using Biacore technology," Analytical Biochemistry, Dec. 2006, vol. 359, Issue 1, pp. 94-105.

Paulos et al.,"The Inducible Costimulator (ICOS) is Critical for the Development of Human TH17 Cells," Science Translational Medicine, Oct. 2010, vol. 2, Issue 55: 55ra78, pp. 1-15.

Persing et al., "Taking toll: lipid A mimetics as adjuvants and immunomodulators," Trends in Microbiology, Oct. 2002, vol. 10, Issue 10, pp S32-S37.

Philip et al., "Potential for protein kinase C inhibitors in cancer therapy," in: Muggia, F. M., Concepts, Mechanisms, and New Targets for Chemotherapy, New York, Springer Science+Business Media, 1995, pp. 3-27.

Powis et al., "Inhibitors of myo-Inositol Signaling," in: Kerr et al., New Molecular Targets for Cancer Chemotherapy, London, CRC Press, 1994, pp. 81-96.

Prantner et al., "Stimulator of IFN Gene is Critical for Induction of IFN-β during Chlamydia muridarum Infection," The Journal of Immunology, Mar. 2010, vol. 184, Issue 5, pp. 2551-2560.

Rakoff-Nahoum et al., "Recognition of Commensal Microflora by Toll-Like Receptors is Required for Intestinal Homeostasis," Cell, Jul. 2004, vol. 118, Issue 2, pp. 229-241.

Ramanjulu et al., "Design of amidobenzimidazole STING receptor agonists with systemic activity," Nature, Dec. 2018, vol. 564, pp. 439-443.

Rosa et al., "Meltdown: A Tool to Help in the Interpretation of Thermal Melt Curves Acquired by Differential Scanning Fluorimetry," Journal of Biomolecular Screening, Aug. 2015, vol. 20, Issue 7, pp. 898-905.

Rosania et al., "Targeting hyperproliferative disorders with cyclin dependent kinase inhibitors," Expert Opinion on Therapeutic Patents, 2000, vol. 10, Issue 2, pp. 215-230.

Scharovsky et al., "Inhibition of ras Oncogene: A Novel Approach to Antineoplastic Therapy," Journal of Biomedical Science, Jan. 2000, vol. 7, No. 4, pp. 292-298.

Seabrook et al., "High-Throughput Thermal Scanning for Protein Stability: Making a Good Technique More Robust," ACS Combinatorial Science, May 2013, vol. 15, Issue 8, pp. 387-392.

Sharma et al., "Innate Immune Recognition of an AT-Rich Stem-Loop DNA Motif in the Plasmodium falciparum Genome," Immunity, Aug. 2011, vol. 35, No. 2: 194-207, pp. 1-25.

Shawver et al., "Receptor tyrosine kinases as targets for inhibition of angiogenesis," Drug Discovery Today (DDT), Feb. 1997, vol. 2, No. 2, pp. 50-63.

Sinha et al., "Implications for Src Kinases in Hematopoiesis: Signal Transduction Therapeutics," Journal of Hematotherapy and Stem Cell Research, Oct. 1999, vol. 8, pp. 465-480.

Smithgall, T. E., "SH2 and SH3 domains: Potential targets for Anti-Cancer Drug Design," Journal of Pharmacological and Toxicological Methods, Nov. 1995, vol. 34, Issue 3, pp. 125-132.

Stern, D. F., "Tyrosine kinase signalling in breast cancer: ErbB family receptor tyrosine kinases," Breast Cancer Research, Mar. 2000, vol. 2, No. 3: 176-183, pp. 1-8.

Stetson et al., "Trex1 Prevents Cell-Intrinsic Initiation of Autoimmunity," Cell, Aug. 2008, vol. 134, Issue 4: 587-598, pp. 1-21.

Storek et al., "cGAS and Ifi204 Cooperate To Produce Type I IFNs in Response to Francisella Infection," The Journal of Immunology, Apr. 2015, vol. 194, Issue 7: 3236-3245, pp. 1-11.

Sun et al., "Coronavirus Papain-like Proteases Negatively Regulate Antiviral Innate Immune Response through Disruption of STING-Mediated Signaling," PLOS One, Feb. 2012, vol. 7, Issue 2, e30802.

Takeuchi et al., "Pattern Recognition Receptors and Inflammation," Cell, Mar. 2010, vol. 140, Issue 6, pp. 805-820.

Wakamatsu et al., "Convergent and divergent effects of costimulatory molecules in conventional and regulatory CD4+ T cells," PNAS, Jan. 2013, vol. 110, No. 3, pp. 1023-1028.

Wassermann et al., "*Mycobacterium tuberculosis* Differentially Activates cGAS- and Inflammasome-Dependent Intracellular Immune Responses through ESX-1," Cell Host & Microbe, Jun. 2015, vol. 17, Issue 6, pp. 799-810.

Watson et al., "The Cytosolic Sensor cGAS Detects *Mycobacterium tuberculosis* DNA to Induce Type I Interferons and Activate Autophagy," Cell Host & Microbe, Jun. 2015, vol. 17, Issue 6, pp. 811-819.

World Health Organization, INN Proposed List 109, WHO Drug Information, 2013, vol. 27, No. 2: 135-209, pp. 161-162.

World Health Organization, INN Recommended List 69, WHO Drug Information, 2013, vol. 27, No. 1: 41-93, pp. 68-69.

Wu et al., "Inhibition of cGAS DNA Sensing by a Herpesvirus Virion Protein," Cell Host & Microbe, Sep. 2015, vol. 18, Issue 3: 333-344, pp. 1-26.

Yamamoto et al., "Ras-Induced Transformation and Signaling Pathway," The Journal of Biochemistry, Nov. 1999, vol. 126, Issue 5, pp. 799-803.

Yao et al., "B7-H2 is a Costimulatory Ligand for CD28 in Human," Immunity, May 2011, vol. 34, Issue 5: 729-740, pp. 1-23.

Yi et al., "Single Nucleotide Polymorphisms of Human STING Can Affect Innate Immune Response to Cyclic Dinucleotides," PLOS One, Oct. 2013, vol. 8, Issue 10, e77846.

Zender et al., "Discovery and Biophysical Characterization of 2-Amino-oxadiazoles as Novel Antagonists of PqsR, an Important Regulator of Pseudomonas aeruginosa Virulence," Journal of Medicinal Chemistry, Aug. 2013, vol. 56, Issue 17, pp. 6761-6774.

Zhong et al., "Modulation of Hypoxia-inducible Factor 1a Expression by the Epidermal Growth Factor/Phosphatidylinositol 3-Kinase/PTEN/AKT/FRAP Pathway in Human Prostate Cancer Cells: Implications for Tumor Angiogenesis and Therapeutics," Cancer Research, Mar. 2000, vol. 60, Issue 6, pp. 1541-1545.

Zitvogel et al., "Type I interferons in anticancer immunity," Nature Reviews Immunology, Jul. 2015, vol. 15, pp. 105-414.

SUBSTITUTED CONDENSED THIOPHENES AS MODULATORS OF STING

SEQUENCE LISTING

This application contains a sequence listinq filed in ST.25 format entitled "320604-1010 Sequence Listinq" created on Jan. 24, 2023. The content of the sequence listinq is incorporated herein in its entirety.

The present invention relates to substituted benzothiophenes, thienopyridines and thienopyrimidines and their use as pharmaceuticals, and in particular, in treating diseases ameliorated by the modulation of STING.

BACKGROUND TO THE INVENTION

Vertebrates are constantly threatened by the invasion of microorganisms and have evolved mechanisms of immune defense to eliminate infective pathogens. In mammals, this immune system comprises two branches; innate immunity and adaptive immunity. The innate immune system is the first line of defense which is initiated by Pattern Recognition Receptors (PRRs) which detect ligands from the pathogens as well as damage associated molecular patterns (Takeuchi 2010). A growing number of these receptors have been identified including Toll-like receptors (TLRs), C-type lectin receptors, retinoic acid inducible gene I (RIG-I)-like receptors and NOD-like receptors (NLRs) and also double stranded DNA sensors. Activation of PRRs leads to up-regulation of genes involved in the inflammatory response including type 1 interferons, pro-inflammatory cytokines and chemokines which suppress pathogen replication and facilitate adaptive immunity.

The adaptor protein STING (Stimulator of Interferon Genes), also known as TMEM 173, MPYS, MITA and ERIS, has been identified as a central signalling molecule in the innate immune response to cytosolic nucleic acids (Ishikawa 2008; WO2013/166000). Activation of STING results in up-regulation of IRF3 and NF$_K$B pathways leading to induction of type 1 interferons including Interferon-δ and other cytokines. STING is critical for responses to cytosolic DNA of pathogen or host origin, and of unusual nucleic acids called Cyclic Dinucleotides (CDNs).

CDNs were first identified as bacterial secondary messengers responsible for controlling numerous responses in the prokaryotic cell. Bacterial CDNs, such as c-di-GMP, are symmetrical molecules characterized by two 3',5' phosphodiester linkages.

Direct activation of STING by bacterial CDNs has recently been confirmed through X-ray crystallography (Burdette 2013). Bacterial CDNs and their analogues have consequently attracted interest as potential vaccine adjuvants (Libanova 2012; WO2007/054279; WO2005/087238).

More recently, the response to cytosolic DNA has been elucidated and shown to involve generation, by an enzyme called cyclic GMP-AMP synthase (cGAS, previously known as C6orf150 or MB21D1), of a novel mammalian CDN signalling molecule identified as cGAMP, which then activates STING. Unlike bacterial CDNs, cGAMP is an asymmetrical molecule characterized by its mixed 2',5' and 3',5' phosphodiester linkages (Gao 2013A). Interaction of cGAMP (II) with STING has also been demonstrated by X-ray crystallography (Cai 2014).

Interferon was first described as a substance which could protect cells from viral infection (Isaacs 1957). In man, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent modulators of the immune response, acting on cells of the immune system.

Administration of a small molecule compound which could modulate the innate immune response, including the activation or inhibition of type I interferon production and other cytokines, could become an important strategy for the treatment or prevention of human diseases including viral infections and autoimmune disease. This type of immunomodulatory strategy has the potential to identify compounds which may be useful not only in infectious diseases but also in cancer (Zitvogel 2015), allergic diseases (Moisan 2006), neurodegenerative diseases such as amyotrophic lateral sclerosis and multiple sclerosis (Lemos 2014; Cirulli 2015; Freischmidt 2015), other inflammatory conditions such as irritable bowel disease (Rakoff-Nahoum 2004), and as vaccine adjuvants (Persing 2002; Dubensky 2013).

STING is essential for antimicrobial host defense, including protection against a range of DNA and RNA viruses and bacteria (reviewed in McNab 2015; Ma 2016). Herpesviridae, Flaviviridae, Coronaviridae, Papillomaviridae, Adenoviridae, Hepadnaviridae, ortho- and paramyxoviridae and rhabdoviridae have evolved mechanisms to inhibit STING mediated Type I interferon production and evade host immune control (Holm 2016; Ma 2015; Wu 2015; Liu 2016; Chen 2014; Lau 2013; Ding 2013; Nitta 2013; Sun 2012; Aguirre 2012; Ishikawa 2009). Thus, small molecule activation of STING could be beneficial for treatment of these infectious diseases.

In contrast, increased and prolonged type I IFN production is associated with a variety of chronic infections, including Mycobacteria (Collins 2015; Wassermann 2015; Watson 2015), Franciscella (Storek 2015; Jin 2011A), Chlamydia (Prantner 2010), Plasmodium (Sharma 2011), and HIV (Herzner 2015; Gao 2013B). Similarly, excess type I interferon production is found among patients with complex forms of autoimmune disease. Genetic evidence in humans and support from studies in animal models support the hypothesis that inhibition of STING results in reduced type I interferon that drives autoimmune disease (Crow 2006; Stetson 2008). Therefore, inhibitors of STING provide a treatment to patients with chronic type I interferon and proinflammatory cytokine production associated with infec-

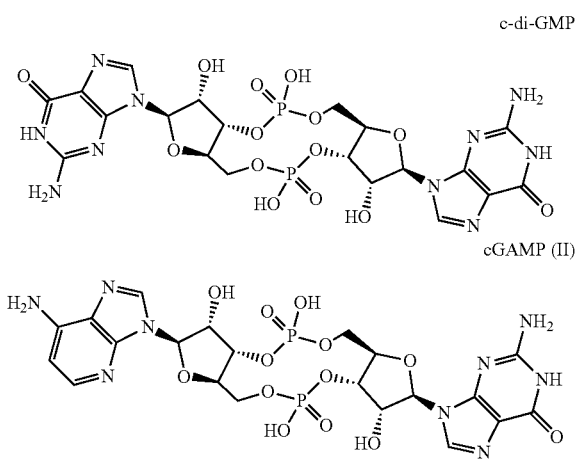

c-di-GMP cGAMP (II)

tions or complex autoimmune diseases. Allergic diseases are associated with a Th2-biased immune-response to allergens. Th2 responses are associated with raised levels of IgE, which, via its effects on mast cells, promotes a hypersensitivity to allergens, resulting in the symptoms seen, for example, in allergic rhinitis and asthma. In healthy individuals the immune-response to allergens is more balanced with a mixed Th2/Th1 and regulatory T cell response. Induction of Type 1 interferons have been shown to result in reduction of Th2-type cytokines in the local environment and promote Th1/Treg responses. In this context, induction of type 1 interferons by, for example, activation of STING, may offer benefit in treatment of allergic diseases such as asthma and allergic rhinitis (Huber 2010).

Compounds that bind to STING and act as agonists have been shown to induce type 1 interferons and other cytokines on incubation with human PBMCs. Compounds which induce human interferons may be useful in the treatment of various disorders, for example the treatment of allergic diseases and other inflammatory conditions for example allergic rhinitis and asthma, the treatment of infectious diseases, neurodegenerative disease, pre-cancerous syndromes and cancer, and may also be useful as immugenic composition or vaccine adjuvants. Compounds that bind to STING may act as antagonists and could be useful in the treatment, for example of autoimmune diseases. It is envisaged that targeting STING with activation or inhibiting agents may be a promising approach for preventing and treating diseases and conditions in which modulation for the type 1 IFN pathway is beneficial, including inflammatory, allergic and autoimmune diseases, infectious diseases, cancer, pre-cancerous syndromes and as immugenic compositions or vaccine adjuvants.

Skin cancers and various skin viral infections involve immune privileged environment and activation of local immune response to the lesions may be a topical therapeutic approach.

STING agonists may be used for treating viral warts, superficial skin cancers and premalignant actinic keratoses. By a dual mechanism of action, STING activation (e.g., via microneedle patch delivery or topical formulation) may be used to control HPV directly via antiviral type I interferon production and indirectly by enhancing the adaptive immune response downstream of innate immune activation. STING agonist can activate the innate immune response in the lesion and drive the anti-HPV T-cell response.

Recent evidence has indicated that spontaneous activation of the STING pathway within tumor-resident dendritic cells leads to type I IFN production and adaptive immune responses against tumors. Furthermore, activation of this pathway in antigen presenting cells (APCs) within the tumor microenvironment drives the subsequent T-cell priming against tumor-associated antigens (Corrales 2015). International Patent Applications WO2014/093936, WO2014/189805, WO2013/185052, WO2015/077354 and WO2015/185565 disclose certain cyclic di-nucleotides and their use in inducing an immune response via activation of STING.

Additionally non-CDN compounds have been described as active based agonists of STING.

Applications WO2019/069269, WO2019/069270, WO2017/175156, and WO2017/175147 and Ramanjulu 2018 describe certain amidobenzimidazole-based and diamidobenzimidazole-based compounds and their use in modulation of STING.

Applications WO2019/027858 and US2018/0093964 describe certain benzo[b]thiophene compounds and their use as aagonists of STING.

Applications WO2018/234808, WO2018/234807, GB2563642A, WO2018/234805 describe certain arylamido compounds and their use as modulators of STING.

STING has known polymorphisms, including alleles encoding histidine at position 232, which are refractory to bis-3',5' (canonical) CDNs, but not 2',5'-3',5' (non-canonical, mixed linkage) CDNs (Diner 2013; Jin 2011B). Single nucleotide polymorphisms in the STING gene have been reported to affect the responsiveness to bacterial-derived canonical CDNs (Diner 2013; Gao 2013C; Conlon 2013). Five major haplotypes of STING have been reported (WT, R232H, HAQ, AQ and Q alleles), which vary at amino acid positions 71, 230, 232 and 293 (Jin 2011B; Yi 2013).

The compounds of this invention modulate the activity of STING, and accordingly, may provide a beneficial therapeutic impact in the prevention and treatment of diseases, disorders and/or conditions in which modulation of STING (Stimulator of Interferon Genes) is beneficial, for example for inflammation, allergic and autoimmune diseases, infectious diseases, cancer, pre-cancerous syndromes and as vaccine adjuvants.

SUMMARY OF THE INVENTION

A first aspect of the present invention provides a compound of formula I:

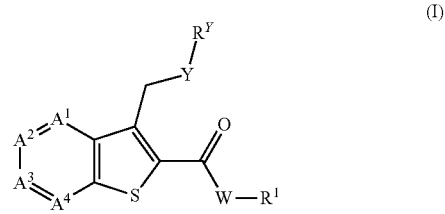

(I)

wherein:
W is O or NH;
$R^1$ is selected from:
  (i) H;
  (ii) $C_{3-6}$ cycloalkyl;
  (iii) $C_{3-7}$heterocyclyl optionally substituted with a group selected from:
    methyl; and
    ester; and
  (iv) linear or branched $C_{1-4}$alkyl optionally substituted with a group selected from:
    alkoxy;
    amino;
    amido;
    acylamido;
    acyloxy;
    alkyl carboxyl ester;
    alkyl carbamoyl;
    alkyl carbamoyl ester;
    phenyl;
    phosphonate ester;
    $C_{3-7}$heterocyclyl optionally substituted with a group selected from methyl and oxo; and
    a naturally occurring amino acid, optionally N-substituted with a group selected from methyl, acetyl and boc;
$A^1$ is $CR^A$ or N;
$A^2$ is $CR^B$ or N;
$A^3$ is $CR^C$ or N;
$A^4$ is $CR^D$ or N;

where no more than two of $A^1$, $A^2$, $A^3$, and $A^4$ may be N;
one or two of $R^A$, $R^B$, $R^C$ and $R^D$, (if present) are selected from H, F, Cl, Br, Me, $CF_3$, cyclopropyl, cyano, OMe, OEt, $CH_2OH$, $CH_2OMe$ and OH;
the remainder of $R^A$, $R^B$, $R^C$ and $R^D$, (if present) are H;
Y is O, NH or $CH_2$;
$R^Y$ is selected from:

(a)

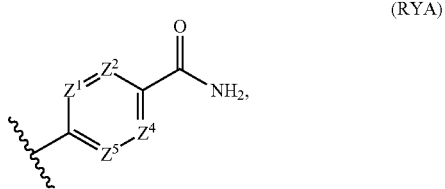

(RYA)

wherein: $Z^1$ is $CR^{Z1}$ or N;
$Z^2$ is $CR^{Z2}$ or N;
$Z^4$ is $CR^{Z4}$ or N;
$Z^5$ is $CR^{Z5}$ or N;
where no more than two of $Z^1$, $Z^2$, $Z^4$ and $Z^5$ may be N;
one or two of $R^{Z1}$, $R^{Z2}$, $R^{Z4}$ and $R^{Z5}$, (if present) are selected from H, F, Cl, Br, Me, OMe, cyano, $CF_3$, $CH_2OH$, $CH_2OMe$, $C_{2-4}$ alkenyl, and C5heterocyclyl;
the remainder of $R^{Z1}$, $R^{Z2}$, $R^{Z4}$ and $R^{Z5}$, present) are H;

(b)

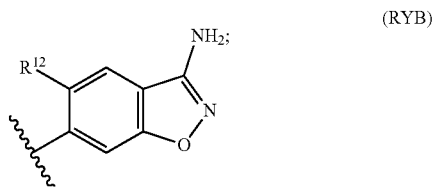

(RYB)

where $R^{12}$ is selected from H, F, Cl, Br, OMe, cyano and $CF_3$;
with the proviso that when $A^1$ is CF; $A^2$, $A^3$ and $A^4$ are CH; Y is O or NH; $R^Y$ is RYA, where $Z^1$, $Z^2$, $Z^4$ and $Z^5$ are CH; $R^1$ is not Et; and
when $A^1$ is CF; $A^2$, $A^3$ and $A^4$ are CH; Y is NH; $R^Y$ is RYA, where $Z^1$ and $Z^5$ are CH, one of $Z^2$ and $Z^4$ is CF, and the other of $Z^2$ and $Z^4$ is CH; $R^1$ is not Et.

A second aspect of the present invention provides a compound of the first aspect (including the compound of the proviso) for use in a method of therapy. The second aspect also provides a pharmaceutical composition comprising a compound of the first aspect (including the compound of the proviso) and a pharmaceutically acceptable excipient.

A third aspect of the present invention provides a method of treatment or prevention of a disease ameliorated by the modulation of STING, comprising administering to a patient in need of treatment, a compound of the first aspect of the invention (including the compound of the proviso) or a pharmaceutical composition of the second aspect of the invention. The third aspect of the present invention also provides the use of a compound of the first aspect of the invention (including the compound of the proviso) in the manufacture of a medicament for treating or preventing disease ameliorated by the modulation of STING, and a compound of the first aspect of the invention (including the compound of the proviso) or pharmaceutical composition thereof for use in the treatment or preventing of disease ameliorated by the modulation of STING.

Definitions $C_{3-6}$ Cycloalkyl: The term "Cm cycloalkyl" as used herein, pertains to a monovalent moiety obtained by removing a hydrogen atom from a carbon atom of a saturated cyclic hydrocarbon compound having from 3 to 6 carbon atoms. Examples of Cm cycloalkyl groups include, but are not limited to, cyclopropyl ($C_3$), cyclobutyl ($C_4$), cyclopentyl ($C_5$) and cyclohexyl ($C_6$).

$C_{3-7}$ Heterocyclyl: The term "$C_{3-7}$heterocyclyl" as used herein, pertains to a monovalent moiety obtained by removing a hydrogen atom from a ring atom of a monocyclic heterocyclic compound, which moiety has from 3 to 7 ring atoms; of which from 1 to 2 atoms are heteroatoms, chosen from oxygen or nitrogen.

In this context, the prefixes (e.g. $C_{3-7}$) denote the number of ring atoms, or range of number of ring atoms, whether carbon atoms or heteroatoms.

Examples of $C_{3-7}$heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), pyrrole ($C_5$), piperidine ($C_6$), dihydropyridine ($C_6$), tetrahydropyridine ($C_6$), pyridine ($C_6$), azepine ($C_7$), azepane ($C_7$);
$N_2$: diazirine ($C_3$) diazetidine ($C_4$), imidazolidine ($C_5$), pyrazolidine (diazolidine) ($C_5$), imidazoline ($C_5$), pyrazoline (dihydropyrazole) ($C_5$), imidazole ($C_5$), pyrazole ($C_5$), piperazine ($C_6$), pyrazine ($C_6$), pyrimidine ($C_6$), pyridazine ($C_6$), diazepine ($C_7$), diazepane ($C_7$);
$O_1$: oxetane ($C_4$), tetrahydrofuran ($C_5$); oxane ($C_6$);
$O_2$: dioxetane ($C_4$), dioxolane ($C_5$); dioxane ($C_6$), dioxole ($C_6$);
$N_1O_1$: tetrahydrooxazole ($C_5$), dihydrooxazole ($C_5$), tetrahydroisoxazole ($C_5$), dihydroisoxazole ($C_5$), isoxazole ($C_5$), oxazole ($C_5$), morpholine ($C_6$), tetrahydrooxazine ($C_6$), dihydrooxazine ($C_6$), oxazine ($C_6$).

$C_{1-4}$ Alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms.

Examples of saturated alkyl groups include, but are not limited to, Me: methyl ($C_1$), Et: ethyl ($C_2$), Pr: propyl ($C_3$), and Bu: butyl ($C_4$).

Examples of saturated linear alkyl groups include, but are not limited to, methyl ($C_1$), ethyl ($C_2$), nPr: n-propyl ($C_3$), and nBu: n-butyl ($C_4$).

Examples of saturated branched alkyl groups include, but are not limited to, iPr: iso-propyl ($C_3$, —$C(CH_3)_2$), iBu: iso-butyl ($C_4$), sBu: sec-butyl ($C_4$) and tBu: tert-butyl ($C_4$).

$C_{2-4}$ Alkenyl: The term "$C_{2-4}$ alkenyl" as used herein, pertains to an alkyl group having from 2 to 4 carbon atoms and having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$) and butenyl ($C_4$).

$C_{1-4}$ fluoroalkyl: The term "$C_{1-4}$ fluoroalkyl" as used herein, pertains to a $C_{1-4}$alkyl group, substituted with one or more fluorine atoms.

Alkoxy: —OR wherein R is a $C_{1-4}$ alkyl group as defined above. It can be represented as —O—$C_{1-4}$ alkyl. Examples of alkoxy groups include, but are not limited to, methoxy ($C_1$), ethoxy ($C_2$), propyloxy ($C_3$), and butyloxy ($C_4$).

Alkyl carbamoyl: —NHC(=O)OR wherein R is a $C_{1-4}$ alkyl group as defined above. Examples of alkyl carbamoyl groups include, but are not limited to, —N(H)O(=O)OCH$_3$, —N(H)O(=O)OCH$_2$CH$_3$, and —N(H)O(=O)OC(CH$_3$)$_3$.

Alkyl carbamoyl ester: —OC(=O)NRR' wherein R and R' are independently selected from H and $C_{1-4}$ alkyl as defined above. Examples of alkyl carbamoyl ester groups include, but are not limited to, —OC(=O)N(CH$_3$)$_2$, and —OC(=O)N(H)CH$_3$.

Alkyl carboxyl ester: —OC(=O)OR wherein R is a $C_{1-4}$ alkyl group as defined above. Examples of alkyl carboxyl ester groups include, but are not limited to, —OC(=O)OCH$_3$, —OC(=O)OCH$_2$CH$_3$, —OC(=O)OC(CH$_3$)$_3$, and —OC(=O)OCH(CH$_3$)$_2$.

Amino: —N(R)R' wherein R and R' are independently selected from H and $C_{1-4}$ alkyl as defined above. Examples of an amino group include, but are not limited to, —NH$_2$, —N(H)CH$_3$, —N(H)C(CH$_3$)$_2$, —N(CH$_3$)$_2$, —N(CH$_2$CH$_3$)$_2$.

Amido (carbamoyl, carbamyl, aminocarbonyl, carboxamide, aminoacyl):
—C(=O)N(R)R' wherein R and R' are independently selected from H and $C_{1-4}$ alkyl as defined above. Examples of an amido group include, but are not limited to, C(=O)NH$_2$, —C(=O)N(H)CH$_3$, —C(=O)N(CH$_3$)$_2$, —C(=O)N(H)CH$_2$CH$_3$, and —C(=O)N(CH$_2$CH$_3$)$_2$.

Acylamido: —N(R)C(=O)R' wherein R and R' are independently selected from H and $C_{1-4}$ alkyl as defined above. Examples of an acylamido group include, but are not limited to, —N(H)C(=O)CH$_2$CH$_3$, —N(H)C(=O)CH$_3$ and —N(CH$_3$)C(=O)CH$_3$.

Phenyl: —C$_6$H$_5$, wherein the phenyl may itself be optionally substituted by one or more $C_{1-4}$alkyl groups, one or more $C_{1-4}$ fluoroalkyl groups, one or more $C_{1-4}$ alkoxy groups, one or more halo substituents and one or more cyano substituents.

Benzyl: —CH$_2$-Phenyl, wherein phenyl is as defined above.

Ester (carboxylate, carboxylic acid ester, oxycarbonyl): —C(=O)OR, wherein R is an ester substituent, for example, a $C_{1-4}$ alkyl group, a $C_{3-7}$heterocyclyl group, or a phenyl group, as defined above, preferably a $C_{1-4}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-4}$alkyl group, a $C_{3-7}$heterocyclyl group, or a phenyl group, as defined above, preferably a $C_{1-4}$alkyl group. Examples of acyloxy groups include, but are not limited to, —OC(=O)CH$_3$ (acetoxy), —OC(=O)CH$_2$CH$_3$, —OC(=O)C(CH$_3$)$_3$ and —OC(=O)Ph. Further examples of acyloxy groups include, but are not limited to, methylester ($C_1$), ethylester ($C_2$), propylester ($C_3$) and butylester ($C_4$).

Naturally occurring amino acid: The term "a naturally occurring amino acid", as used herein, pertains to a monovalent moiety obtained by removing a hydrogen atom from a carboxyl group or an amino group on one of the amino acid compounds found commonly in nature (for example, alanine, arginine, asparagine, aspartate, cysteine, glycine, glutamine, glutamate, histidine, isoleucine, leucine, lysine, methionine, phenylalanine, proline, serine, threonine, tryptophan, tyrosine and valine). The amino acid is particularly selected from isoleucine, leucine and valine, most particularly valine.

In each of these groups the carbon atom which is bonded to both a carboxyl and an amino group is known as the α carbon and the carboxyl and amino groups to which it is attached are the α-carboxyl and α-amino groups. Naturally occurring amino acids are optionally substituted with a protecting group on the a-amino group or any other amino group on the moiety, protecting groups include but are not limited to acetyl, methyl and tertbutyl carbamate (boc) groups.

Phosphonate ester: —P(O)(OR)OR', wherein R and R' are independently selected from $C_{1-4}$alkyl as defined above. Examples of a phosphonate ester include, but are not limited to —P(O)(OEt)$_2$.

Cyano: —C≡N.

Pivaloyloxymethyl: A group of formula

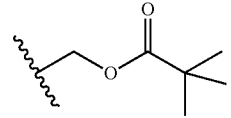

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

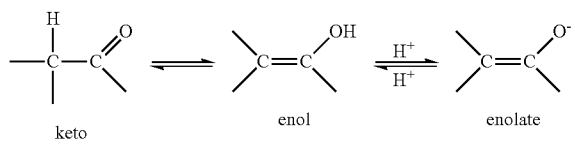

keto enol enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to, $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as $^3$H, $^{13}$C, and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Therapeutic Indications

Compounds disclosed herein may provide a therapeutic benefit in a number of disorders, in particular, in the treatment or prevention of diseases ameliorated by the modulation of STING.

One aspect of the invention provides methods of treatment or prevention of STING mediated diseases and disorders, in which agonizing STING is beneficial. Exemplary diseases/disorders includes, but are not limited to, cancer and infectious disease (such as those caused by viruses, e.g., HIV, HBV, HCV, HPV, and influenza, and bacteria). Another aspect of the invention provides the use of a STING agonist as a vaccine adjuvant.

In one embodiment, this invention provides a compound of the invention for use in therapy. This invention also provides a compound of Formula I, or a pharmaceutically acceptable salt thereof, for use in therapy. This invention particularly provides a compound of Formula I, or a pharmaceutically acceptable salt thereof, for use in the treatment of a STING-mediated disease or disorder.

This invention also provides a compound of Formula I, or a pharmaceutically acceptable salt thereof, for use as a vaccine adjuvant. There is also therefore provided an immugenic composition or vaccine adjuvant comprising a compound of Formula I, or a pharmaceutically acceptable salt thereof. In a further embodiment of the invention, there is provided a composition comprising a compound of Formula I, or a pharmaceutically acceptable salt thereof, and one or more immunostimulatory agents.

In another embodiment, this invention provides a compound of the invention for use in the treatment of a STING-mediated disease or disorder and/or for use as an immugenic composition or a vaccine adjuvant. In another embodiment, this invention provides a compound of Formula I, or a pharmaceutically acceptable salt thereof, for use in the amelioration of organ injury or damage sustained as a result of a STING-mediated disease or disorder.

The invention further provides for the use of a compound of the invention in the manufacture of a medicament for treatment of a STING-mediated disease or disorder. The invention further provides for the use of a compound of Formula I, or a salt thereof, particularly a pharmaceutically acceptable salt thereof, in the manufacture of a medicament for treatment of a STING-mediated disease or disorder, for example the diseases and disorders recited herein.

The invention further provides for the use of a compound of Formula I, or a salt thereof, particularly a pharmaceutically acceptable salt thereof, in the manufacture of a vaccine. There is further provided the use of a compound of Formula I, or a pharmaceutically acceptable salt thereof, for the manufacture of an immugenic composition comprising an antigen or antigenic composition, for the treatment or prevention of disease. There is further provided the use of a compound of Formula I, or a pharmaceutically acceptable salt thereof, for the manufacture of a vaccine composition comprising an antigen or antigenic composition, for the treatment or prevention of disease.

In another embodiment, the invention is directed to a method of treating a STING-mediated disease or disorder comprising administering a therapeutically effective amount of a compound of this invention to a human in need thereof. In another embodiment, the invention is directed to a method of treating a STING-mediated disease or disorder comprising administering a therapeutically effective amount of a compound of Formula I or a salt, particularly a pharmaceutically acceptable salt thereof, to a human in need thereof.

Infectious Diseases

The compounds of this invention may be used to treat an infectious disease, which is any disease instigated by or coincident with an infection from a pathogen. Pathogens are broadly defined as any species of organism that is foreign to a human tissue environment. Common disease causing pathogens include bacteria (many like TB), viruses (many like HBV, HIV, flu) and parasitic protozoans (like P falciparum that causes malaria). The compounds of this invention may be used to treat infectious diseases derived from bacteria, such as TB infection *Mycobacterium tuberculosis*), Chlamydia, Tularemia infection *Francisella tularensis*), Plasmodium infection or infections from DNA or RNA virus. The compounds of this invention may be used to treat infectious diseases derived from the DNA virus families: Herpesviridae (herpes simplex virus-1, Kaposi's sarcoma-associated virus and Epstein-Barr virus), Papillomaviridae (human papilloma virus), Adenovirus and Hepadnaviridae (Hepatitis B virus). Examples of RNA virus families include Retroviridae (human immunodeficiency virus) Flaviviridae (Dengue virus, Hepatitis C virus), Orthomyxoviridae (influenza), and Coronaviridae (human coronavirus and SARS coronavirus).

Cancer

As used herein, the terms "cancer", "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias, such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblasts) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polycythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent B cell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphomas (T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extra medullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

Examples of cancer diseases and conditions in which a compounds of this invention may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemangioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hamartoma; mesothelioma; Hodgkin's Disease or a combination of one or more of the foregoing cancers.

Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, Hodgkin's lymphoma, non-Hodgkin's lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In some embodiments, the compounds of the present invention may be used to treat solid or liquid tumors. In some embodiments, the compounds of the present invention may be used to treat sarcoma, breast cancer, colorectal cancer, gastroesophageal cancer, melanoma, non-small cell lung cancer (NSCLC), clear cell renal cell carcinoma (RCC), lymphomas, squamous cell carcinoma of the head and neck (SCCHN), hepatocellular carcinoma (HCC), and/or Non Hodgkin lymphoma (NHL). Suitably the present invention relates to a method for treating or lessening the severity of pre-cancerous syndromes in a mammal, including a human, wherein the pre-cancerous syndrome is selected from: cervical intraepithelial neoplasia, monoclonal gammopathy of unknown significance (MGUS), myelodysplastic syndrome, aplastic anemia, cervical lesions, skin nevi (pre-melanoma), prostatic intraepithelial (intraductal) neoplasia (PIN), Ductal Carcinoma in situ (DCIS), colon polyps and severe hepatitis or cirrhosis.

In one aspect the human has a solid tumor. In one aspect the tumor is selected from head and neck cancer, gastric cancer, melanoma, renal cell carcinoma (RCC), esophageal cancer, non-small cell lung carcinoma, prostate cancer, colorectal cancer, ovarian cancer and pancreatic cancer. In one aspect the human has one or more of the following: colorectal cancer (CRC), esophageal, cervical, bladder, breast, head and neck, ovarian, melanoma, renal cell carcinoma (RCC), EC squamous cell, non-small cell lung carcinoma, mesothelioma, and prostate cancer. In another aspect the human has a liquid tumor such as diffuse large B cell lymphoma (DLBCL), multiple myeloma, chronic lymphoblastic leukemia (CLL), follicular lymphoma, acute myeloid leukemia and chronic myelogenous leukemia.

In one embodiment, the compounds of the present invention may be useful for treatment of skin cancers (e.g., non-melanoma skin cancer, squamous cell carcinoma, basal cell carcinoma) or actinic keratosis. In addition to a field effect for clearing superficial skin cancers, the compounds of the present invention may prevent the development of subsequent skin cancers and pre-malignant actinic keratosis in treated patients.

Autoimmune Diseases

Autoimmune diseases associated include, but are not limited to STING associated vasculitis with onset at infancy (SAVI), Aicardi Goutieres syndrome (AGS), chilblain lupus, ataxia telanogiectasia (also referred to as Louis-Bar Syndrome), retinal vasculopathy with cerebral leukodystrophy (RCVL), systemic lupus erythematosus (SLE), cutaneous lupus, lupus nephritis, psoriasis, diabetes mellitus including insulin-dependent diabetes mellitus (IDDM), dermatomyositis, human immunodeficiency virus (HIV), AIDS, polymyositis, systemic sclerosis (scleroderma), and Sjogren's syndrome (SS), rheumatoid arthritis, psoriatic arthritis, polyarthritis, myasthenia gravis, polyarteritis nodosa, vasculitis, cutaneous vasculitis, anti-neutrophil cytoplasmic antibody (ANCA)-associated vasculitis, Henoch-Schonlein purpura, autoimmune hepatitis, primary sclerosing cholangitis, Wegener's granulomatosis, microscopi polyangiitis, Behcet's disease, spondylitis, giant cell arteritis, polymyalgia rheumatic, Raynaud's phenomenon, primary biliary cirrhosis, primary angiitis of the central nervous system microscopic polyangiitis, neuromyelitis optica and mixed connective tissue disease.

Inflammation

Inflammation represents a group of vascular, cellular and neurological responses to trauma. Inflammation can be characterized as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self-tissues.

The aim of anti-inflammatory therapy is therefore to reduce this inflammation, to inhibit autoimmunity when present, and to allow for the physiological process or healing and tissue repair to progress.

The compounds of this invention may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knee, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of the invention include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated with the compounds of the invention include encephalitis, Guillain-Barre syndrome, meningitis, neuromyotonia, narcolepsy, multiple sclerosis, myelitis, CNS vasculitis, and schizophrenia.

Examples of inflammation of the vasculature or lymphatic system which may be treated with the compounds of the invention include arthrosclerosis, arthritis, phlebitis, vasculitis, and lymphangitis.

Examples of inflammatory conditions of the digestive system which may be treated with the compounds of the invention include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of the invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The compounds of this invention may be used to treat autoimmune conditions having an inflammatory component. Such conditions include acute disseminated alopecia universalise, Behcet's disease, Chagas' disease, STING associated vasculitis with onset at infancy (SAVI), Aicardi Goutieres syndrome (AGS), chilblain lupus, ataxia telangiectasia (also referred to as Louis-Bar Syndrome), retinal vasculopathy with cerebral leukodystrophy (RCVL), ANCA)-associated vasculitis, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune hemolytic anemia, interstitial cystitis, lyme disease, morphea, psoriasis, sarcoidosis, scleroderma, ulcerative colitis, and vitiligo.

The compounds of this invention may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celiac disease).

Other inflammatory conditions which may be treated with the compounds of this invention include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonitis, pharyngitis, pleuritis, pneumonitis, prostatitis, pyelonephritis, and stomatitis, transplant rejection (involving organs such as kidney, liver, heart, lung, pancreas (e.g., islet cells), bone marrow, cornea, small bowel, skin allografts, skin homografts, and heart valve xenografts, serum sickness, and graft vs host disease), acute pancreatitis, chronic pancreatitis, acute respiratory distress syndrome, Sezary syndrome, congenital adrenal hyperplasia, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemia and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosus, psoriasis, chronic pulmonary disease, and inflammation accompanying infectious conditions (e.g., sepsis). In one embodiment, the compounds of this invention may be used to treat asthma.

Cellular Proliferation

The compounds of the present invention may also be useful in the treatment of one or more diseases afflicting mammals which are characterized by cellular proliferation in the area of disorders associated with neo-vascularization and/or vascular permeability including blood vessel proliferative disorders including arthritis (rheumatoid arthritis) and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and metabolic disorders include psoriasis, diabetes mellitus, chronic wound healing, inflammation and neurodegenerative diseases.

Neurodegenerative Diseases

The compounds of this invention may be used to treat neurodegenerative diseases. Exemplary neurodegenerative diseases includes, but are not limited to, multiple sclerosis, Huntington's disease, Alzheimer's disease, Parkinson's disease, amyotrophic lateral sclerosis (ALS).

Combinations

The compounds of this invention may be employed alone or in combination with other therapeutic agents. As modulators of the immune response, the compounds of this invention may also be used in monotherapy or used in combination with another therapeutic agent in the treatment of diseases and conditions in which modulation of STING is beneficial. Combination therapies according to the present invention thus comprise the administration of a compound of Formula I or a pharmaceutically acceptable salt thereof, and at least one other therapeutically active agent. In one embodiment, combination therapies according to the present invention comprise the administration of at least one compound of Formula I or a pharmaceutically acceptable salt thereof, and at least one other therapeutic agent. The compound(s) of Formula I and pharmaceutically acceptable salts thereof, and the other therapeutic agent(s) may be administered together in a single pharmaceutical composition or separately and, when administered separately this may occur simultaneously or sequentially in any order. The amounts of the compound(s) of Formula I and pharmaceutically acceptable salts thereof, and the other therapeutic agent(s) and the relative timings of administration will be selected in order to achieve the desired combined therapeutic effect. Thus in a further aspect, there is provided a combination comprising a compound of Formula I, or a pharmaceutically acceptable salt thereof, together with one or more other therapeutic agents.

The compounds of Formula I and pharmaceutically acceptable salts thereof may be used in combination with one or more other therapeutic agents which may be useful in the prevention or treatment of allergic disease, inflammatory disease, or autoimmune disease, for example; antigen immunotherapy, anti-histamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF, anti-IL-5, anti-IL-6, anti-IL-12, anti-IL-1 and similar agents; receptor therapies e.g. etanercept and similar agents; antigen non-specific immunotherapies (e.g. interferon or other cytokines/chemokines, cytokine/chemokine receptor modulators, cytokine agonists or antagonists, TLR agonists and similar agents).

The compounds of Formula I and pharmaceutically acceptable salts thereof may be used in combination with radiotherapy and/or surgery and/or at least one other therapeutic agent which may be useful in the treatment of cancer and pre-cancerous syndromes. Any anti-neoplastic agent that has activity versus a susceptible tumor being treated may be utilized in the combination. Typical anti-neoplastic agents useful include, but are not limited to, (a) anti-microtubule agents such as diterpenoids (e.g. paclitaxel, docetaxel) and vinca alkaloids (e.g. vinblastine, vincristine, and vinorelbine); (b) platinum coordination complexes (e.g. oxaliplatin, cisplatin and carboplatin); (c) alkylating agents such as nitrogen mustards (e.g. cyclophosphamide, melphalan, and chlorambucil), oxazaphosphorines, alkylsulfonates (e.g. busulfan), nitrosoureas (e.g. carmustine), and triazenes (e.g. dacarbazine); (d) antibiotic agents such as anthracyclins (e.g. daunorubicin and doxorubicin), actinomycins (e.g. dactinomycin) and bleomycins; (e) topoisomerase II inhibitors such as epipodophyllotoxins (e.g. etoposide and teniposide); (f) antimetabolites such as purine and pyrimidine analogues and anti-folate compounds (e.g. fluorouracil, methotrexate, cytarabine, mercaptopurine, thioguanine, and gemcitabine); (g) topoisomerase I inhibitors such as camptothecins (e.g. irinotecan, topotecan, and various optical forms of 7-(4-methylpiperazino-methylene)-10,11-ethylenedioxy-20-camptothecin); (h) hormones and hormonal analogues (e.g. adrenocorticosteroids such as prednisone and prednisolone which are useful in the treatment of malignant lymphoma and acute leukemia in children; aminoglutethimide and other aromatase inhibitors such as anastrozole, letrozole, vorozole, and exemestane useful in the treatment of adrenocortical carcinoma and hormone dependent breast carcinoma containing estrogen receptors; progestins such as megestrol acetate useful in the treatment of hormone dependent breast cancer and endometrial carcinoma; estrogens, and anti-estrogens such as fulvestrant, flutamide, nilutamide, bicalutamide, cyproterone acetate and 5-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and leuprolide); (i) signal transduction pathway inhibitors; (j) non-receptor tyrosine angiogenesis inhibitors; (k) immunotherapeutic agents (e.g. ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies); (l) proapoptotic agents (e.g. bcl-2 antisense oligonucleotides); (m) cell cycle signalling inhibitors; (n) immuno-oncology agents and (o) immunostimulatory agents.

Signal Transduction Pathway Inhibitors

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signalling, and Ras oncogenes.

Several protein tyrosine kinases catalyze the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath 2000; Shawver 1997; and Lofts 1994.

Tyrosine kinases, which are not growth factor receptor kinases, are termed nonreceptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh 1999; and Bolen 1997.

SH2/SH3 domain blockers are agents that disrupt SH2 or SH3 domain binding in a variety of enzymes or adaptor proteins including, PI3-K p85 subunit, Src family kinases, adaptor molecules (She, Crk, Nek, Grb2) and Ras-GAP. SH2/SH3 domains as targets for anticancer drugs are discussed in Smithgall 1995.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto 1999; Brodt 2000; Massague 1996; Philip 1995; Lackey 2000; U.S. Pat. No. 6,268,391; and Martinez-Lacaci 2000.

Inhibitors of Phosphotidyl inositol-3 Kinase family members including blockers of Pekinese, ATM, DNA-PK, and Ku are also useful in the present invention. Such kinases are discussed in Abraham 1996; Canman 1998; Jackson 1997; and Zhong 2000.

Also useful in the present invention are Myo-inositol signalling inhibitors such as phospholipase C blockers and Myoinositol analogues. Such signal inhibitors are described in Powis 1994.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky 2000; Ashby 1998; and Oliff 1999.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example lmclone C225 EGFR specific antibody (see Green 2000); Herceptin® erbB2 antibody (see Stern 2000); and 2CB VEGFR2 specific antibody (see Brekken 2000).

Non-Receptor Tyrosine Angiogenesis Inhibitors

Anti-angiogenic therapeutic agents including non-receptor MEK angiogenesis inhibitors may also be useful. Anti-angiogenic agents such as those which inhibit the effects of vascular endothelial growth factor, (for example the anti-vascular endothelial cell growth factor antibody bevacizumab [Avastin™], and compounds that work by other mechanisms (for example linomide, inhibitors of integrin αvβ3 function, endostatin and angiostatin).

Cell Cycle Signalling Inhibitors

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania 2000.

Immuno-Modulators

Additional examples of other therapeutic agents (e.g., anti-neoplastic agent) for use in combination or co-administered with a compound of Formula I are immuno-modulators. As used herein "immuno-modulators" refer to any substance including monoclonal antibodies that affects the immune system. Immuno-modulators can be used as anti-neoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/pembrolizumab). Other immuno-modulators include, but are not limited to, ICOS antibodies, OX-40 antibodies, PD-L1 antibodies, LAG3 antibodies, TIM-3 antibodies, 41BB antibodies and GITR antibodies.

Anti-PD-L1 Agents

Additional examples of other therapeutic agents (anti-neoplastic agent) for use in combination or co-administered with a compound of this invention are anti-PD-L1 agents. Anti-PD-L1 antibodies and methods of making the same are known in the art. Such antibodies to PD-L1 may be polyclonal or monoclonal, and/or recombinant, and/or humanized. Exemplary PD-L1 antibodies are disclosed in U.S. Pat. Nos. 8,217,149, 8,383,796, 8,552,154, 9,212,224, and 8,779,108, and US Patent Appln. Pub. Nos. 2011/0280877, 2014/0341902 and 2013/0045201. Additional exemplary antibodies to PD-L1 (also referred to as CD274 or B7-H1) and methods for use are disclosed in U.S. Pat. Nos. 7,943, 743, 8,168,179, and 7,595,048; WO2014/055897, WO2016/007235; and US Patent Appln. Pub. Nos. 2013/0034559 and 2015/0274835. PD-L1 antibodies are in development as immuno-modulatory agents for the treatment of cancer.

In one embodiment, the antibody to PD-L1 is an antibody disclosed in U.S. Pat. No. 8,217,149. In another embodiment, the anti-PD-L1 antibody comprises the CDRs of an antibody disclosed in U.S. Pat. No. 8,217,149. In another embodiment, the antibody to PD-L1 is an antibody disclosed in U.S. Pat. No. 8,779,108. In another embodiment, the anti-PD-L1 antibody comprises the CDRs of an antibody disclosed in US Application No. 8779108. In another embodiment, the antibody to PD-L1 is an antibody disclosed in US Patent Appln. Pub. No. 2013/0045201. In another embodiment, the anti-PD-L1 antibody comprises the CDRs of an antibody disclosed in US Patent Appln. Pub. No. 2013/0045201. In one embodiment, the anti-PD-L1 antibody is BMS-936559 (MDX-1105), which was described in WO 2007/005874. In another embodiment, the anti-PD-L1 antibody is MPDL3280A (RG7446). In another embodiment, the anti-PD-L1 antibody is MED14736, which is an anti-PD-L1 monoclonal antibody described in WO 2011/066389 and US 2013/034559. In another embodiment, the anti-PD-L1 antibody is TECENTRIQ™ (atezolizumab), which is an anti-PD-L1 cancer immunotherapy which was approved in the US in May 2016 for specific types of bladder cancer. In another embodiment, anti-PD-L1 antibody is YW243.55.570 which is an anti-PD-L1 described in WO 2010/077634 and U.S. Pat. No. 8,217,149. Examples of anti-PD-L1 antibodies useful for the methods of this invention, and methods for making thereof are described in PCT patent application WO 2010/077634, WO 2007/005874, WO 2011/066389, U.S. Pat. No. 8,217,149, and US 2013/034559.

PD-1 Antagonist

Additional examples of other therapeutic agents (antineoplastic agent) for use in combination or co-administered with a compound of this invention are PD-1 antagonists. "PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCDI, PDI, CD279 and SLEB2 for PD-1; PDCDILI, PDLI, B7H1, B7-4, CD274 and B7-H for PD-LI; and PDCD1L2, PDL2, B7-DC, Btdc and CD273 for PD-L2. In any embodiments of the aspects or embodiments of the present invention in which a human individual is to be treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgGI, IgG2, IgG3 and IgG4 constant regions, and in preferred embodiments, the human constant region is an IgGI or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. Nos. 7,488,802, 7,521,051, 8,008,449, 8,354,509, 8,168,757, WO2004/004771, WO2004/072286, WO2004/056875, and US2011/0271358. Specific anti-human PD-1 mAbs useful as the PD-1 antagonist in any of the aspects and embodiments of the present invention include: MK-3475, a humanized IgG4 mAb with the structure described in WHO Drug Information, Vol. 27, No. 2, pages 161-162 (2013) and which comprises the heavy and light chain amino acid sequences shown in Figure 6; nivolumab, a human IgG4 mAb with the structure described in WHO Drug Information, Vol. 27, No. 1, pages 68-69 (2013) and which comprises the heavy and light chain amino acid sequences shown in Figure 7; the humanized antibodies h409AII, h409A16 and h409A17, which are described in WO2008/156712, and AMP-514, which is being developed by Medimmune.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Other examples of mAbs that bind to human PD-L1, and useful in the treatment method, medicaments and uses of the present invention, are described in WO2013/019906, WO2010/077634 and U.S. Pat. No. 8,383,796. Specific anti-human PD-L1 mAbs useful as the PD-1 antagonist in the treatment method, medicaments and uses of the present invention include MPDL3280A, BMS-936559, MED14736, MSB0010718C.

KEYTRUDA/pembrolizumab is an anti-PD-1 antibody marketed for the treatment of lung cancer by Merck. The amino acid sequence of pembrolizumab and methods of using are disclosed in U.S. Pat. No. 8,168,757.

Opdivo/nivolumab is a fully human monoclonal antibody marketed by Bristol Myers Squibb directed against the negative immunoregulatory human cell surface receptor PD-1 (programmed death-1 or programmed cell death-I/POD-1) with immunopotentiation activity. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of PI3K/Akt pathway activation. Other names for nivolumab include: BMS-936558, MDX-1106, and ONO-4538. The amino acid sequence for nivolumab and methods of using and making are disclosed in U.S. Pat. No. 8,008,449.

Antibodies to ICOS

Additional examples of other therapeutic agents (antineoplastic agent) for use in combination or co-administered with a compound of Formula I are antibodies to ICOS. ICOS is a co-stimulatory T cell receptor with structural and functional relation to the CD28/CTLA-4-Ig superfamily (Hutloff 1999). Activation of ICOS occurs through binding by ICOS-L (B7RP-1/B7-H2). Neither B7-1 nor B7-2 (ligands for CD28 and CTLA4) bind or activate ICOS. However, ICOS-L has been shown to bind weakly to both CD28 and CTLA-4 (Yao 2011). Expression of ICOS appears to be restricted to T cells. ICOS expression levels vary between different T cell subsets and on T cell activation status. ICOS expression has been shown on resting TH17, T follicular helper (TFH) and regulatory T (Treg) cells; however, unlike CD28; it is not highly expressed on naive THI and TH2 effector T cell populations (Paulos 2010). ICOS expression is highly induced on CD4+ and CD8+ effector T cells following activation through TCR engagement (Wakamatsu 2013).

CDRs for murine antibodies to human ICOS having agonist activity are shown in PCT/EP2012/055735 (WO 2012/131004). Antibodies to ICOS are also disclosed in WO 2008/137915, WO 2010/056804, EP1374902, EP1374901, and EP1125585.

Agonist antibodies to ICOS or ICOS binding proteins are disclosed in WO2012/131004, WO 2014/033327, WO2016/120789, US20160215059, and US20160304610. In one embodiment, agonist antibodies to ICOS include ICOS binding proteins or antigen binding portions thereof comprising one or more of: CDRHI as set forth in SEQ ID NO:1; CDRH2 as set forth in SEQ ID NO:2; CDRH3 as set forth in SEQ ID NO:3; CDRLI as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR as disclosed in WO2016/120789, which is incorporated by reference in its entirety herein. In one embodiment, the ICOS binding protein or antigen binding portion thereof is an agonist antibody to ICOS comprising a VH domain comprising an amino acid sequence at least 90% identical to the amino acid sequence set forth in SEQ ID NO:7 and/or a VL domain comprising an amino acid sequence at least 90% identical to the amino acid sequence as set forth in SEQ ID NO:8 as set forth in WO2016/120789 wherein said ICOS binding protein specifically binds to human ICOS. In one embodiment, the ICOS binding protein is an agonist antibody to ICOS comprising a VH domain comprising the amino acid sequence set forth in SEQ ID NO:7 and a VL domain comprising the amino acid sequence set forth in SEQ ID NO:8 as set forth in WO2016/120789.

Yervoy (ipilimumab) is a fully human CTLA-4 antibody marketed by Bristol Myers Squibb. The protein structure of ipilimumab and methods are using are described in U.S. Pat. Nos. 6,984,720 and 7,605,238.

CD134, also known as OX40, is a member of the TNFR-superfamily of receptors which is not constitutively expressed on resting naive T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels. OX-40 antibodies, OX-40 fusion proteins and methods of using them are disclosed in US Patent Nos: U.S. Pat. Nos. 7,504,101; 7,758,852; 7,858,765; 7,550,140; 7,960,515; WO2012/027328; WO2013/028231. In one embodiment, the OX40 antigen binding protein is one disclosed in WO2012/027328 (PCT/US2011/048752), international filing date 23 Aug. 2011. In another embodiment, the antigen binding protein comprises the CDRs of an antibody disclosed in WO2012/027328 (PCT/US2011/048752), international filing date 23 Aug. 2011, or CDRs with 90% identity to the disclosed CDR sequences. In a further embodiment the antigen binding protein comprises a VH, a VL, or both of an antibody disclosed in WO2012/027328 (PCT/US2011/048752), international filing date 23 Aug. 2011, or a VH or a VL with 90% identity to the disclosed VH or VL sequences.

In another embodiment, the OX40 antigen binding protein is disclosed in WO2013/028231 (PCT/US2012/024570), international filing date 9 Feb. 2012, which is incorporated by reference in its entirety herein. In another embodiment, the antigen binding protein comprises the CDRs of an antibody disclosed in WO2013/028231 (PCT/US2012/024570), international filing date 9 Feb. 2012, or CDRs with 90% identity to the disclosed CDR sequences. In a further embodiment, the antigen binding protein comprises a VH, a VL, or both of an antibody disclosed in WO2013/028231 (PCT/US2012/024570), international filing date 9 Feb. 2012, or a VH or a VL with 90% identity to the disclosed VH or VL sequences. In one embodiment, the OX40 antigen binding protein is an isolated agonist antibody to OX40 comprising a light chain variable region having a sequence at least 90% identical to the amino acid sequence of SEQ ID NO: 10 as set forth in WO2013/028231 and a heavy chain variable region having a sequence at least 90% identical to the amino acid sequence of SEQ ID NO:4 as set forth in WO2013/028231. In one embodiment, the OX40 antigen binding protein is an isolated antibody comprising a light chain variable comprising the amino acid sequence of SEQ ID NO:10 as set forth in WO2013/028231 and a heavy chain variable region comprising the amino acid sequence of SEQ ID NO:4 as set forth in WO2013/028231.

Immunostimulatory Agent

Additional examples of other therapeutic agents for use in combination or coadministered with a compound of Formula I, or a salt thereof are immunostimulatory agents.

As used herein "immunostimulatory agent" refers to any agent that can stimulate the immune system. As used herein immunostimulatory agents include, but are not limited to, vaccine adjuvants, such as Toll-like receptor agonists, T-cell checkpoint blockers, such as mAbs to PD-1 and CTL4 and T-cell checkpoint agonist, such as agonist mAbs to OX-40 and ICOS. As used herein "immunostimulatory agent" refers to any agent that can stimulate the immune system. As used herein immunostimulatory agents include, but are not limited to, vaccine adjuvants.

The term "Toll-like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll-like receptors (TLRs) are a family of pattern recognition receptors that were initially identified as sensors of the innate immune system that recognize microbial pathogens. TLRs recognize distinct structures in microbes, often referred to as "PAMPs" (pathogen associated molecular patterns). Ligand binding to TLRs invokes a cascade of intra-cellular signalling pathways that induce the production of factors involved in inflammation and immunity. In humans, ten TLRs have been identified. TLRs that are expressed on the surface of cells include TLR-1, -2, -4, -5, and -6, while TLR-3, -7/8, and -9 are expressed with the ER compartment. Human DC subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following: Pam3Cys, a TLRI/2 agonist; CFA, a TLR2 agonist; MALP2, a TLR2 agonist; Pam2Cys, a TLR2 agonist; FSL-I, a TLR-2 agonist; Hib-OMPC, a TLR-2 agonist; polyinosinic:polycytidylic acid (Poly I:C), a TLR3 agonist; polyadenosine-polyuridylic acid (poly AU), a TLR3 agonist; Polyinosinic-Polycytidylic acid stabilized with poly-L-lysine and carboxymethylcellulose (Hiltonol), a TLR3 agonist; bacterial flagellin a TLR5 agonist; imiquimod, a TLR7 agonist; resiquimod, a TLR7/8 agonist; loxoribine, a TLR7/8 agonist; and unmethylated CpG dinucleotide (CpG-ODN), a TLR9 agonist.

Additional TLR agonists known in the art and finding use in the present invention further include, but are not limited to aminoalkyl glucosaminide phosphates (AGPs) which bind to the TLR4 receptor are known to be useful as vaccine adjuvants and immunostimulatory agents for stimulating cytokine production, activating macrophages, promoting innate immune response, and augmenting antibody production in immunized animals. An example of a naturally occurring TLR4 agonist is bacterial LPS. An example of a semisynthetic TLR4 agonist is monophosphoryl lipid A (MPL). AGPs and their immunomodulating effects via TLR4 are disclosed in patent publications such as WO 2006/016997, WO 2001/090129, and/or U.S. Pat. No. 6,113,918 and have been reported in the literature. Additional AGP derivatives are disclosed in U.S. Pat. Nos. 7,129,219, 6,525,028 and 6,911,434. Certain AGPs act as agonists of TLR4, while others are recognized as TLR4 antagonist In addition to the immunostimulatory agents described above, the compositions of the present invention may further comprise other therapeutic agents which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated Listeriamonocytogenes), compositions which mediate innate immune activation via, (NOD)-like receptors (NLRs), Retinoic acid inducible gene-based (RIG)-I-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive bacteria. Lipopolysaccharides are expressed by most bacteria, with MPL being one example. Flagellin refers to the structural component of bacterial flagella that is secreted by pathogenic and commensal bacteria, rt-Galactosylceramide (rt.-GalCer) is an activator of natural killer T (NKT) cells. Muramyl dipeptide is a bioactive peptidoglycan motif common to all bacteria.

Because of their adjuvant qualities, TLR agonists are preferably used in combinations with other vaccines, adjuvants and/or immune modulators, and may be combined in various combinations. Thus, in certain embodiments, the herein described compounds of Formula I that bind to STING and induce STING-dependent TBKI activation and an inactivated tumor cell which expresses and secretes one or more cytokines which stimulate DC induction, recruitment and/or maturation, as described herein can be administered together with one or more TLR agonists for therapeutic purposes.

Indoleamine 2,3-dioxygenase 1 (IDO1) is a key immunosuppressive enzyme that modulates the anti-tumor immune response by promoting regulatory T cell generation and blocking effector T cell activation, thereby facilitating tumor growth by allowing cancer cells to avoid immune surveillance (Lemos 2016; Munn 2016). Further active ingredients (antineoplastic agents) for use in combination or co-administered with the presently invented compounds of Formula I are IDO inhibitors. Epacadostat, ((Z)—N-(3-bromo-4-fluorophenyl)-N'-hydroxy-4-[2-(sulfamoylamino) ethylamino]-I,2,5-oxadiazole-3-carboxamidine) is a highly potent and selective oral inhibitor of the IDO1 enzyme that reverses tumor-associated immune suppression and restores effective anti-tumor immune responses. Epacadostat is disclosed in U.S. Pat. No. 8,034,953.

Additional examples of other therapeutic agents (antineoplastic agent) for use in combination or co-administered with a compound of Formula I are CD73 inhibitors and A2a and A2b adenosine antagonists.

The compounds of Formula I and pharmaceutically acceptable salts thereof may be used in combination with at least one other therapeutic agent useful in the prevention or treatment of bacterial and viral infections. Examples of such agents include, without limitation: polymerase inhibitors such as those disclosed in WO 2004/037818, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents;

replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, tenofovir disproxil fumarate, tenofovir alafenamide fumarate/hemifumarate, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, rilpivirine and similar agents; entry inhibitors such as enfuvirtide (T-20), T-1249, PRO-542, PRO-140, TNX-355, BMS-806, 5-Helix and similar agents; integrase inhibitors such as dolutegravir, elvitegravir, raltegravir L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; pharmacokinetic enhancers such as cobicistat; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents.

The compounds of Formula I and pharmaceutically acceptable salts thereof may also be used in combination with other therapeutic agents which may be useful in the treatment of Kaposi's sarcoma-associated herpesvirus infections (KSHV and KSHV-related) include, without limitation chemotherapeutic agents such as bleomycin, vinblastine, vincristine, cyclophosphamide, prednisone, alitretinoin and liposomal anthracyclines such as doxorubicin, daunorubicin, immunotherapeutics such as Rituximab, Tocilizumab, Siltuximab and others such as Paclitaxel and Rapamycin.

In one embodiment of this invention, the at least one other therapeutic agent is an antimycobacterial agent or a bactericidal antibiotic. The compounds of Formula I and pharmaceutically acceptable salts thereof may also be used in combination with at least one other therapeutic agent which may be useful in the treatment of TB infection *Mycobacterium tuberculosis*) and Tularemia (*Francisella tularensis*) include without limitation to first line oral agents isoniazid, Rifampicin, pyrazinamide, ethambutol, streptomycin, rifabutin; injectable agents including kanamycin, amikacin, capreomycin, streptomycin; fluoroquinolones including levofloxacin moxifloxacin ofloxacin; oral bacteriostatic agents para-aminosalicylic acid cycloserine terizidone thionamide protionamide; SQ-109 PNU-100480, Rifapentine Linezolid, PA-824 AZD5847, Gatifloxacin Moxifloxacin, Sirturo (bedaquiline) Delamanid (OPC-67683) and agents with undetermined mechanism of action in the treatment of drug-resistant TB, including clofazimine, linezolid, amoxicillin/clavulanate thioacetazone imipenem/cilastatin high dose isoniazid clarithromycin, ciprofloxacin. The compounds of Formula I and pharmaceutically acceptable salts thereof may also be used in combination with an antimycobacterial agent (such as isoniazid (INH), ehambutol (Myambutol®), rifampin (Rifadin®), and pyrazinamide (PZA)) a bactericidal antibiotic (such as rifabutin (Mycobutin®) or rifapentine (Priftin®)), an aminoglycoside (Capreomycin®), a fluorquinolone (levofloxacin, moxifloxicin, ofloxacin), thioamide (ehionamide), cyclosporine (Sandimmune®), para-aminosalicyclic acid (Paser®), cycloserine (Seromycin®), kanamycin (Kantrex®), streptomycin, viomycin, capreomycin (Capastat®)), bedaquiline fumarate (Sirturo®), oxazolidinone (Sutezolid®), PNU-100480, or delamanid (OPC-67683).

The compounds of Formula I and pharmaceutically acceptable salts thereof may also be used in combination with at least one other therapeutic agent which may be useful in the treatment of Chlamydia include, without limitations Azithromycin, Doxycycline, Erythromycin, Levofloxacin, Ofloxacin.

The compounds of this invention may also be used in combination with at least one other therapeutic agent which may be useful in the treatment of Plasmodium infection include, without limitations to chloroquine, atovaquone-proguanil, artemether-lumefantrine, mefloquine, quinine, quinidine, doxycycline, cindamycin, artesunate, primaquine.

In the treatment of amyotrophic lateral sclerosis (ALS), a compound of Formula I or a pharmaceutically acceptable salts thereof may be used in combination with a glutamate blocker (Riluzole (Rilutek®)), quinidine (Nuedexta®), anticholinergics (Amitriptyline®, Artane®, scopolamine patch (Transderm Scop®)), sympathomimetics (pseudoephedrine), mucolytics (guaifenesin), or analgesics (tramadol (Ultram®); ketorolac (Toradol®); morphine; fentanyl patch (Duragesic®)).

In the treatment of multiple scelrosis, a compound of Formula I or pharmaceutically acceptable salts thereof may be used in combination with corticosteroids (prednisone, methylprednisolone), Interferon Beta 1-A (Avonex®, Extavia®, Rebif®, Betaseron®), peginterferon beta-IA (Plegridy®), Glatiramer acetate (Copaxone®); glatiramer acetate (Glatopa®-generic equivalent of Copaxone); Dimethyl fumarate (Tecfidera®); Fingolimod (Gilenya®)); teriflunomide (Aubagio®); dalfampridine (Ampyra®); daclizumab (Zinbryta); alemtuzumab (Lemtrada®); natalizumab (Tysabri®); or mitoxantrone hydrochloride (Novantrone®).

The compounds of this invention may also be used as adjuvants to improve the immune response raised to any given antigen and/or reduce reactogenicity/toxicity in a patient, particularly a human, in need thereof. As such, a compound of this invention may be used in combination with vaccine compositions to modify, especially to enhance, the immune response for example by increasing the level or duration of protection and/or allowing a reduction in the antigenic dose.

The compounds of Formula I and pharmaceutically acceptable salts thereof may be used in combination with one or more vaccines or immugenic antigens useful in the prevention or treatment of viral infections. Such vaccines or immugenic antigens include, without limitation to pathogen derived proteins or particles such as attenuated viruses, virus particles, and viral proteins typically used as immugenic substances. Examples of viruses and viral antigens include, without limitations to Polioviruses, Coronaviridae and Coronaviruses, Rhinovirus (all subtypes), Adenoviruses (all subtypes), Hepatitis A, Hepatitis B, Hepatitis C, Hepatitis D, Human papillomavirus (including all subtypes), Rabies viruses, Human T-cell lympotropic virus (all subtypes), Rubella virus, Mumps virus, Coxsackie virus A (all subtypes), Cosackie virus B (all subtypes), human enteroviruses, herpesviruses including cytomegalovirus, Epstein-Barr virus, human herepesvi ruses (all subtypes), herpes simplex virus, varicella zoster virus, human immunodeficiency virus (HIV) (all subtypes), Epstein-Barr virus, Reoviruses (all subtypes), Filoviruses including Marburg virus and Ebola virus (all stains), Arenaviruses including Lymphocytic choriomeningitis virus, Lassa virus, Junin virus, and Machupo virus, Arboviruses including West Nile virus, Dengue viruses (all serotypes), Zika virus, Colorado tick fever virus, Sindbis virus, Togaviraidae, Flaviviridae, Bunyaviridae, Reoviridae, Rhabdoviridae, Orthomyxoviridae, Poxviruses including orthopoxvirus (variola virus, monkypox virus, vaccinia virus, cowpox virus), yatapoxviruses (tanapox virus, Yaba monkey tumor virus), parapoxvirus, molluscipoxvirus, Yellow fever, Hantaviruses including Hantaan, Seoul, Dobrava, Sin Nombre, Puumala, and Dobrava-like Saaremaa, human para influenza viruses and influenza viruses (all types), HINI influenza and swine influenza viruses, respiratory syncytial virus (all subgroups), rotaviruses including human rotaviruses A-E, bovine rotavirus, rhesus monkey rotavirus, Polyomaviruses including simian virus 40, JC virus, BK virus, Coltiviruses, eyach virus, calciviruses, and Parvoviridae including dependovirus, parvovirus and erythrovirus.

Accordingly, this invention provides an immugenic composition comprising an antigen or antigenic composition and a compound of Formula I, or a pharmaceutically acceptable salt thereof. There is further provided a vaccine composition comprising an antigen or antigenic composition and a compound of Formula I, or a pharmaceutically acceptable salt thereof. The compounds of Formula I and pharmaceutically acceptable salts thereof may also be used in combination with at least one other therapeutic agent which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, anti-fibrotic agents, antiinflammatory agents such as corticosteroids or NSAIDs (non-steroidal anti-inflammatory agents) and similar agents.

A compound that modulates STING, particularly a compound of Formula I or a pharmaceutically acceptable salt thereof, may be administered in combination with other antiinflammatory agents, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-IL6 biologics, anti-ILI agents, anti-IL17 biologies, anti-CD22, anti-integrin agents, anti-IFNa, anti-CD20 or CD4 biologies and other cytokine inhibitors or biologies to T-cell or B-cell receptors or interleukins.

For example, in the treatment of systemic lupus erythematosus and related lupus disorders, a compound that modulates STING, particularly a compound of Formula I, or a pharmaceutically acceptable salt thereof, may be administered in combination with at least one other therapeutic agent, including, a corticosteroid (such as prednisolone (Delatsone®, Orapred, Millipred, Omnipred, Econopred, Flo-Pred), an immunosuppressive agent (such as methotrexate (Rhuematrex®, Trexall®), dexamethasone (Decadron®, Solurex®), Mycophenolate mofetil (Cellcept®), Tacrolimus®, Sirolimus®), B-cell therapy (belimumab (Benlysta®), B-cell inhibitor (Atacicept®, Apratuzumab® (anti-CD22), SBI-087 (anti-CD20), an anti-BAFF antibody (LY2127399, A623), Velcade®), azathioprine (Azasan®, Imuran®), triamcinolone (Clinacort®, Kenalog-10®), hydroxychloroquine (Plaquenil®), thalidomide (Immunoprin®, Contergan®), immunoglobulin therapy (HyQiva®, Flebogamma®, Gamunex®, Privigen®, Gammagard®), anti-interferon-alpha therapy (Rontalizumab®, Sifalimumab®, AGS-009®, IFN Kinoid), TLR7 and TLR9 blockers (IMO-3100), anti-cytokine therapies (anti-IL6 (ONTO-136), anti-interferon-gamma (AMG811), immunomodulatory therapy (Lupuzor™, Abatacept, Orencia®, AMG557, Laquinimod, Paquinimod, Leflunomide, anti-ICOS (Medi-570), anti-CD40 ligand antibody (CDP7657)), and/or a platelet aggregation inhibitor (aspirin).

In treatment of vasculitis and disease with inflammation of small or medium size blood vessels, a compound that modulates STING, particularly a compound of Formula I, or a pharmaceutically acceptable salt thereof, may be administered in combination with alkylating agents (cyclophosphamide, Cytoxan®), anti-rheumatic anti-CD20 antibody (Rituxan®, Rituximab®), and anti-TNF inhibitors (Etanrcept®).

In the treatment of psoriasis, a compound that modulates STING, particularly a compound of Formula I, or a pharmaceutically acceptable salt thereof, may be administered in combination with ixekizumab, tildrakizumab (MK-3222), or secukinumab (AIN457).

In one embodiment of this invention, the at least one other therapeutic agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. For example, in the treatment of asthma, a compound that inhibits STING, particularly a compound of Formula I or a pharmaceutically acceptable salt thereof, may be administered in combination with an inhaled corticosteroid ((ICS) such as fluticasone proprionate (Flovent®), beclomethasone dipropionate (QVAR®), budesonide (Pulmicort), trimcinolone acetonide (Azmacort®), flunisolide (Aerobid®), mometasone fuorate (Asmanex® Twisthaler®), or Ciclesonide (Alvesco®)), a long acting beta agonist ((LABA) such as formoterol fumarate (Foradil®), salmeterol xinafoate (Serevent®)), a combination of an ICS and LABA (such as fluticasone furoate and vilanterol (Breo Ellipta®), formoterol/budesonide inhalation (Symbicort®), beclomethasone dipropionate/formoterol (Inuvair®), and fluticasone propionate/salmeterol (Advair®), a short acting beta agonist ((SABA) such as albuterol sulfate (ProAir®, Proventil HFA®, Ventolin HFA®, AccuNeb® Inhalation Solution), levalbuterol tartrate (Xopenex® HFA), ipratropium bromide/albuterol (Combivent® Respimat®), ipratropium bromide (Atrovent® HFA), a leukotriene modifier (such as montelukast sodium (Singulair®), zafirlukast (Accolate®), or zileuton (Zyflo®), and anti-IgE (such as omalizumab (Xolair®)), a methylxanthine bronchodilator (such as theophylline (Accurbron®, Aerolate®, Aquaphyllin®, Asbron®, Bronkodyl®, Duraphyl®, Elixicon®, Elixomin®, Elixophyllin®, Labid®, Lanophyllin®, Quibron-T®, Slo-Bid®, Slo-Phyllin®, Somophyllin®, Sustaire®, Synophylate®, T-Phyll®, Theo-24®, Theo-Dur®, Theobid®, Theochron®, Theoclear®, Theolair®, Theolixir®, Theophyl®, Theovent®, Uni-dur®, Uniphyl®), a mast cell inhibitor (such as cromulyn sodium (Nasalcrom®) and nedocromil sodium (Tilade®)), a long-acting muscarinic antagonist ((LAMA) such as mometasone furoate/formoterol fumarate dihydrate (Dulera®)).

Other agents that may be suitable for use in combination therapy in the treatment of asthma include a protein tyrosine kinase inhibitor (masitinib), CRTH2/D-prostanoid receptor antagonist (AMG 853), indacaterol (Arcapta® Neohaler®), an epinephrine inhalation aerosol (E004), fluticasone furoate/fluticasone proprionate, vinanterol inhalation/ fluticasone furoate powder (Relovair™), fluticasone propionate/eformoterol fumarate dehydrate (Flutiform®), reslizumab, salbutamol dry-powder inhalation, tiotropium bromide (Spiriva® HandiHaler®), formoterol/budesonide (SymbicortOSMART®), fluticasone furoate (Veramyst®), Vectura's VR506, lebrikizumab (RG3637), a combination phosphodiesterase (PDE)-3 and (PDE)-4 inhibitor (RPL554).

In one embodiment of this invention, the at least one other therapeutic agent is selected from a long acting beta agonist, a long-acting inhaled anticholinergic or muscarinic antagonist, a phosphodiesterase inhibitor, a combination of an inhaled corticosteroid long acting beta agonist, a short acting beta agonist, and an inhaled corticosteroid. For example, in the treatment of COPD, a compound that modulates STING, particularly a compound of Formula I or a pharmaceutically acceptable salt thereof, may be administered in combination with a LABA (such as salmeterol xinafoate (Serevent), umeclidinium/vilanterol (Anoro Ellipta®), umeclidinium (Incruse Ellipta®), aformoterol tartrate (Brovana®), formoterol fumarate inhalation powder (Foradil®), indacterol maleate (Arcapta® Neohaler®), or fluticasone propionate/ eformoterol fumarate dehydrate (Flutiform®)), a long-acting inhaled anticholinergic (or muscarinic antagonist, such as tiotropium bromide (Spiriva®), and aclidinium bromide (Tudorza® Pressair®), a phosphodiesterase (PDE-r) inhibitor (such as roflumilast, Daliresp®), a combination ICS/ LABA (such as fluticasone furoate and vilanterol (Breo Ellipta®), fluticasone propionate/salmeterol (Advair®), budesonide/formoterol (Symbicort®), mometasone/formoterol (Dulera®), ipratropium bromide/albuterol sulfate (Duoneb®, Atrovent®), albuterol/ipratropium (Combivent Respimat®)), a SABA (such as ipratropium bromide (Atrovent®), and albuterol sulfate (ProAir®, Proventil®)), and an ICS (such as budesonide (Pulmicort®) and fluticasone propionate (Flovent®), beclometasone dipropionate (QVAR®).

Other agents that may be suitable for use in combination therapy in the treatment of COPD include SCH527123 (a CXCR2 antagonist), glycoprronium bromide ((NVA237)

Seebri® Breezhaler®), glycopyrronium bromide and indacaterol maleate ((QVA149) Ultibro® Breezhaler®), glycopyrrolate and formoterol fumarate (PT003), indacaterol maleate (QVA149), olodaterol (Striverdi® Respimat®), tiotropium (Spiriva®)/olodaterol (Striverdi® Respimat®), and aclidinium/formoterol inhalation.

In one embodiment of this invention, the at least one other therapeutic agent is selected from an oral corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor or imatinib, ARG201, and tocilizumab. For example, in the treatment of systemic scleroderma, a compound that modulates STING, particularly a compound of Formula I or a pharmaceutically acceptable salt thereof, may be administered in combination with an oral corticosteroid (such as prednisolone (Delatsone®, Orapred, Millipred, Omnipred, Econopred, Flo-Pred), an immunosuppressive agent (such as methotrexate (Rhuematrex®, Trexall®), cyclosporine (Sandimmune®), anti-thymocyte globulin (Atgam®), mycophenolate mofetil (CellCept®), cyclophosphamide (Cytoxan®), FK506 (tacrolimus), thalidomide (Thalomid®), chlorambucil (Leukeran®), azathioprine (Imuran®, Azasan®)), a calcium channel blocker (such as nifedipine (Procardia®, Adalat®) or nicardipine (Cardene®), a topical emollient (nitroglycerin ointment), an ACE inhibitor (such as lisinopril (Zestril®, Prinivil®), diltaizem (Cardizem®, Cardizem SR®, Cardizem CD®, Cardia®, Dilacor®, Tiazac®)), a serotonin reuptake inhibitor (such as fluoxetine (Prozac®)), an endothelin-1 receptor inhibitor (such as bosentan (Tracleer®) or epoprostenol (Flolan®, Veletri®, Prostacyclin®)) an anti-fibrotic agent (such as colchicines (Colcrys®), para-aminobenzoic acid (PABA), dimethyl sulfoxide (DMSO), and D-penicillamine (Cuprimine®, Depen®), interferon alpha and interferon gamma (INF-g)), a proton-pump Inhibitor (such as omeprazole (Prilosec®), metoclopramide (Reglan®), lansoprazole (Prevacid®), esomeprazole (Nexium®), pantoprazole (Protonix®), rabeprazole (Aciphex®)) or imatinib (Gleevec®) ARG201 (arGentis Pharmaceutical), belimumab (Benlysta®), tocilizumab (Actema®).

In the treatment of Sjogren's syndrome, a compound that modulates STING, particularly a compound of Formula I or a pharmaceutically acceptable salt thereof, may be administered in combination with anti-rheumatic agents (hydroxychloroquine and Plaquenil®, Ridaura®, Kineret®), cholinergic agonists (Salagen®, Evoxac®), a JAK inhibitor (Xelijanz®, and anti-TNF treatments (Remicade®, Humira®, Enbrel®, Cimzia®, Simponi®).

In one embodiment of this invention, the at least one other therapeutic agent is a ciliary neurotrophic growth factor or a gene transfer agent. For example, in the treatment of retinitis pigmentosa, a compound that modulates STING, particularly a compound of Formula I or a pharmaceutically acceptable salt thereof, may be administered in combination with a ciliary neurotrophic growth factor (NT-501-CNTF) or gene transfer agent, UshStat®.

In one embodiment of this invention, the at least one other therapeutic agent is selected from a trivalent (11V3) inactivated influenza vaccine, a quadrivalent (I1V4) inactivated influenza vaccine, a trivalent recombinant influenza vaccine, a quadrivalent live attenuated influenza vaccine, an antiviral agent, or inactivated influenza vaccine. For example, in the treatment of influenza, a compound that modulates STING, particularly a compound of Formula I or a pharmaceutically acceptable salt thereof, may be administered in combination with a trivalent (I1V3) inactivated influenza vaccine (such as Afluria®, Fluarix®, Flucelvax®, FluLaval®, Fluvirin®, Fluzone®), a quadrivalent (I1V4) inactivated influenza vaccine (such as Fluarix® Quadrivalent, Flulaval® Quadrivalent, Fluzone® Quadrivalent), a trivalent recombinant influenza vaccine (such as FluBlok®), a quadrivalent live attenuated influenza vaccine (such as Flu Mist® Quadrivalent), an antiviral agent (such as oseltamivir (Tamiflu®), zanamivir (Relenza®), rimantadine (Flumadine®), or amantadine (Symmetrel®)), or Fluad®, Fludase, FluNhance®, Preflucel, or VaxiGrip®

In the treatment of a staphylococcus infection, a compound that modulates STING, particularly a compound of Formula I or a pharmaceutically acceptable salt thereof, may be administered in combination with an antibiotic (such as a β-Lactam cephalosporin (Duricef®, Kefzol®, Ancef®, Biocef®, etc), nafcillin (Unipen®), a sulfonamide (sulfamethoxazole and trimethoprim (Bacrim®, Septra®) sulfasalazine (Azulfidine®), acetyl sulfisoxazole (Gantrisin®), etc), or vancomycin (Vancocin®)).

In one embodiment of this invention, the at least one other therapeutic agent is selected from a topical immunomodulator or calcineurin inhibitor, a topical corticosteroid, an oral corticosteroid, an interferon gamma, an antihistamine, or an antibiotic. For example, in the treatment of atopic dermatitis, a compound that modulates STING, particularly a compound of Formula I, or a pharmaceutically acceptable salt thereof, may be administered in combination with a topical immunomodulator or calcineurin inhibitor (such as pimecrolimus (Elidel®) or tacrolimus ointment (Protopic®)), a topical corticosteroid (such as hydrocortisone (Synacort®, Westcort®), betamethasone (Diprolene®), flurandrenolide (Cordan®), fluticasone (Cutivate®), triamcinolone (Kenalog®), fluocinonide (Lidex®), and clobetasol (Temovate®)), an oral corticosteroid (such as hydrocortisone (Cortef®), methyl prednisolone (Medrol®), or prednisolone (Pediapred®, Prelone®)), an immunosuppressant (such as cyclosporine (Neoral®) or interferon gamma (Alferon N®, Infergen®, Intron A, Roferon-A®)), an antihistamine (for itching such as Atarax®, Vistaril®, Benadryl®), an antibiotic (such as penicillin derivatives flucloxacillin (Floxapen®) or dicloxacillin (Dynapen®), erythromycin (ErycO, T-Stat®, Erythra-Derm®, etc.)), a non-steroidal immunosuppressive agent (such as azathioprine (Imuran®, Azasan®), methotrexate (Rhuematrex®, Trexall®), cyclosporin (Sandimmune®), or mycophenolate mofetil (CellCept®)).

The compounds of the invention may also be formulated with vaccines as adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminum salts, oil and water emulsions, heat shock proteins, lipid A preparations and derivatives, glycolipids, other TLR agonists such as CpG DNA or similar agents, cytokines such as GM-CSF or IL-12 or similar agents.

In a further aspect of the invention, there is provided a vaccine adjuvant comprising a compound of Formula I, or a pharmaceutically acceptable salt thereof. There is further provided a vaccine composition comprising a compound of Formula I, or a pharmaceutically acceptable salt thereof, and an antigen or antigen composition.

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In one embodiment where treating tumours, intratumoural injection may used.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or exosomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or exosomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition.

Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

General Synthesis Methods

The compounds of the invention can be prepared employing the following general methods and using procedures described in detail in the examples. The reaction conditions referred to are illustrative and non-limiting, for example one skilled in the art may use a diverse range of synthetic methods to synthesise the desired compounds such as but not limited to methods described in literature (for example but not limited to March's Advanced Organic Chemistry: Reactions, Mechanisms, and Structure, 7th Edition or Larock's Comprehensive Organic Transformations: Comprehensive Organic Transformations: A Guide to Functional Group Preparations).

Compounds of formula I as described above, can be prepared by synthetic strategies outlined below, wherein the definitions above apply.

General synthesis 1

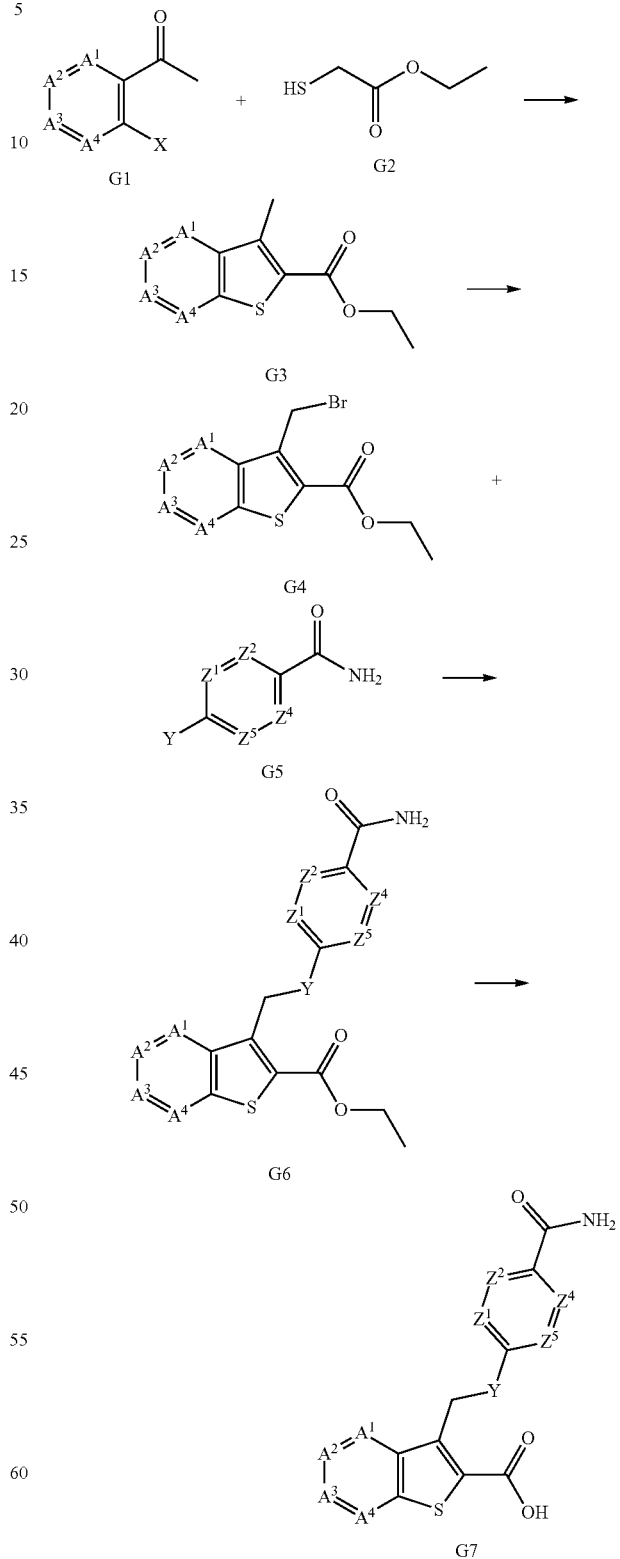

Scheme 1 illustrates the synthesis of compounds with the structure G7. The first step involves reaction of a suitably substituted ketone G1 with ethyl 2-mercaptoacetate G2 in the presence of a suitable base such as, but not limited to, $K_2CO_3$. Bromination of product G3 to form alkyl bromide G4 may be performed using a suitable bromine source such as, but not limited to, N-bromosuccinimide, in the presence of an initiator such as, but not limited to, benzoyl peroxide. A substitution reaction of G4 with a suitable nucleophile G5 may be carried out in the presence of a suitable base such as, but not limited to, cesium carbonate to give compounds of the type G6. Carboxylic acid G7 can be formed by hydrolysis of ester G6 with a base such as an alkali metal hydroxide or an acid such as aqueous hydrochloric acid.

It will be appreciated by those skilled in the art that substituents $R^A$ (when $A^1=CR^A$), $R^B$ (when $A^2=CR^B$), $R^C$ (when $A^3=CR^C$), and $R^D$ (when $A^4=CR^D$) on compound G3, and $R^{Z1}$ (when $Z^1=CR^{Z1}$), $R^{Z2}$ (when $Z^2=CR^{Z2}$), $R^{Z4}$ (when $Z^4=CR^{Z4}$) and $R^{Z5}$ (when $Z^5=CR^{Z5}$) on compound G5, and $R^A$ (when $A^1=CR^A$), $R^B$ (when $A^2=CR^B$), $R^C$ (when $A^3=CR^C$), and $R^D$ (when $A^4=CR^D$) on compound G6 and G7, and $R^{Z1}$ (when $Z^1=CR^{Z1}$), $R^{Z2}$ (when $Z^2=CR^{Z2}$), $R^{Z4}$ (when $Z^4=CR^{Z4}$) and $R^{Z5}$ (when $Z^5=CR^{Z5}$) on compounds G6 and G7 may be a halogen atom to allow for transition-metal catalysed transformations such as Ulmann, Negishi, Stille, Suzuki-Miyaura, Sonogashira and Buchwald-Hartwig couplings, or for SnAr displacements to produce further examples of the type of compound I.

General Synthesis 2

Scheme 2

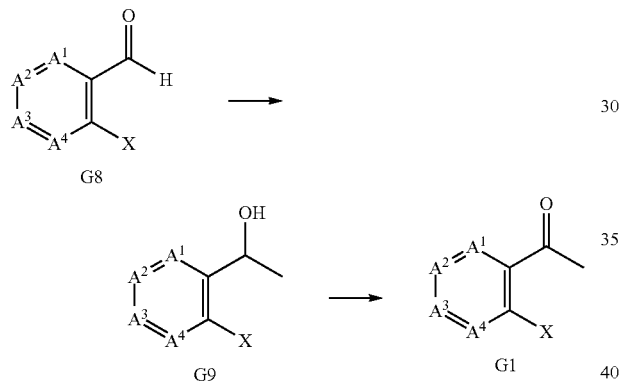

Compounds of the structure G1 can be obtained by reaction of a suitably substituted aldehyde G8 with a Grignard reagent such as methyl magnesium bromide to give alcohol G9. Methods for oxidation of alcohol G9 to give ketone G1 will be apparent to those skilled in the art, but include for example the use of reagents such as chromium trioxide and sulphuric acid.

General Synthesis 3

Scheme 3

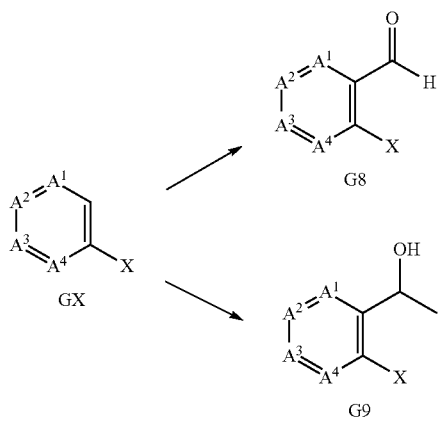

Compounds of the structure G8 can be made by treatment of a suitably substituted arene or heteroarene GX with either an alkyl lithium such as, but not limited to, n-butyllithium, or a lithium amide base such as, but not limited, to lithium diisopropylamide, and subsequent quenching of the resultant lithiated species with N,N-dimethylformamide. Alternatively, the lithiated species formed from treatment of GX with alkyl lithium or lithium amide may be quenched with acetaldehyde to give compound G9 directly.

General Synthesis 4

Scheme 4a

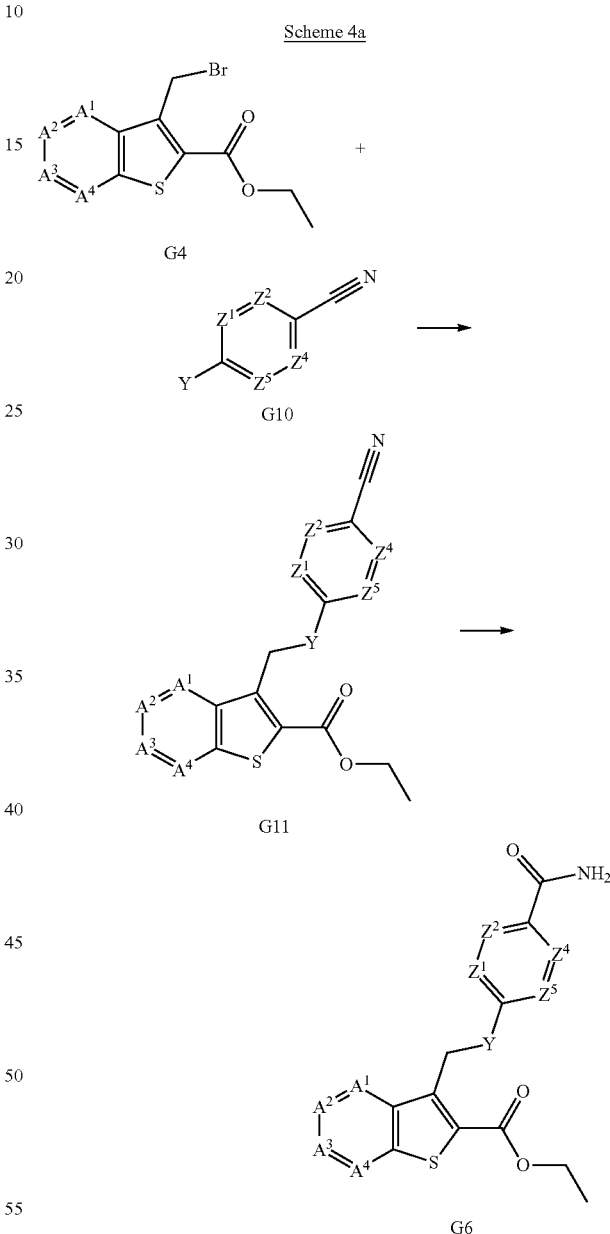

Scheme 4a illustrates an alternative method to access compound G6. A substitution reaction of G4 with a suitable nucleophile G10 may be carried out in the presence of a suitable base such as, but not limited to, cesium carbonate to give compounds of the type G11. Methods for selective hydrolysis of nitrile G11 to give compound G6 will be apparent to those skilled in the art, but include for example the use of $H_2O_2$ and $K_2CO_3$ in DMSO or aqueous sodium hydroxide solution or sulphuric acid.

Alternatively, compound G6 can be accessed by reversing the order of nucleophilic substitution and hydrolysis as shown in Scheme 4b. Methods for hydrolysis of nitrile G10 to primary amide G5 will be apparent to those skilled in the art and include for example the use of aqueous sodium hydroxide solution or sulphuric acid. Compound G5 can be employed to access compound G6 and G7 as described in Scheme 1.

Scheme 4b

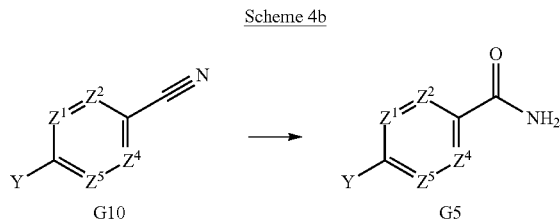

G10     G5

General Synthesis 5

Scheme 5a

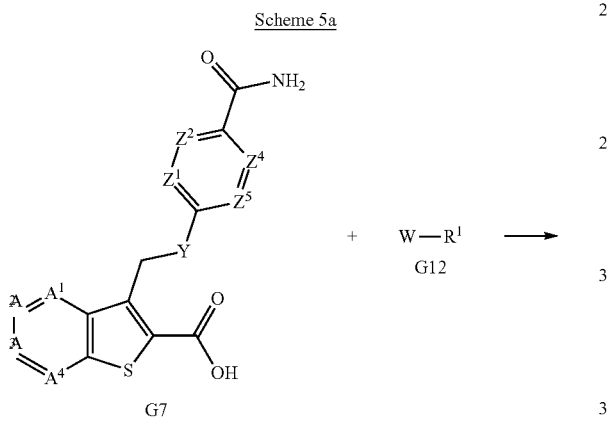

G7    G12    G13

Conditions for conversion of acid G7 to ester or amide G13 will be apparent to those skilled in the art, but include an excess of a suitable nucleophile G12 and a catalyst such as concentrated sulphuric acid (for formation of an ester). Alternatively G7 may be first activated by a coupling agent such as, but not limited to, 1-[bis(dimethylamino)methylene]-1H-1,2,3-triazolo[4,5-b]pyridinium 3-oxide hexafluorophosphate, 1-ethyl-3-(3-dimethylaminopropyl)carbodiimide or N,N'-dicyclohexylcarbodiimide before reaction with nucleophile G12 in the presence of a catalyst such as, but not limited to, 4-dimethylaminopyridine (for formation of an ester or amide) or in the presence of a base such as, but not limited to, N,N-diisopropylethylamine (for formation of an amide).

Ester G15 can be accessed by reaction of acid G7 with a suitable alkyl halide G14 in the presence of a suitable base such as, but not limited to, cesium carbonate as shown in Scheme 5b.

Scheme 5b

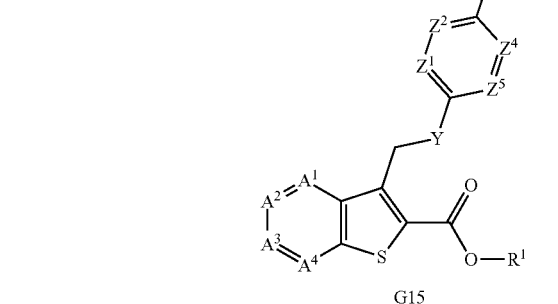

G7    G14

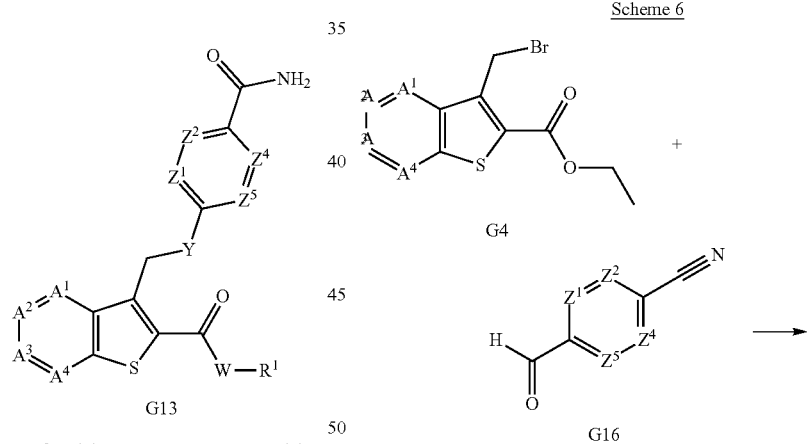

G15

General Synthesis 6

Scheme 6

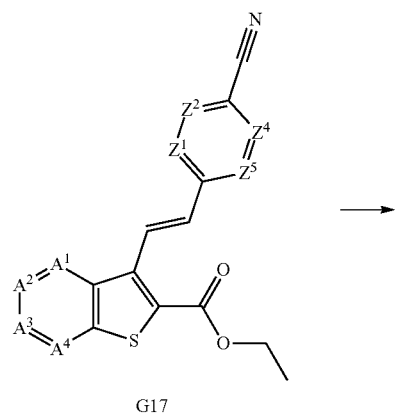

G4

G16

G17

-continued

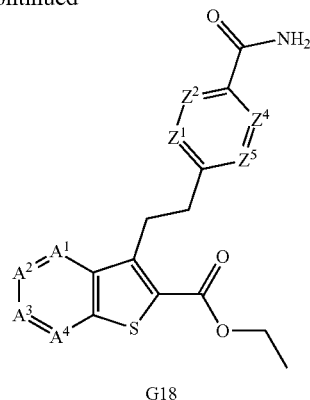

G18

Synthesis of compound G18 can be carried out as illustrated in Scheme 6. Alkyl bromide G4 can be converted to an ylide with triphenylphosphine and a suitable base such as potassium t-butoxide, which may then react with a suitable aldehyde G16 in a Wittig transformation to give G17. Conditions for reduction of alkene G17 to give G18 will be apparent to those skilled in the art, but include stirring under a hydrogen atmosphere in the presence of a suitable catalyst such as, but no limited to, palladium.

FURTHER EMBODIMENTS $R^1$

In some embodiments, W is O and $R^1$ is H. In these embodiments, the compounds are of formula Ia:

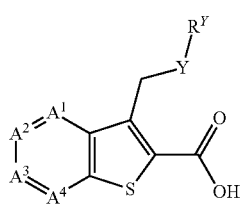

(Ia)

where $A^1$-$A^4$, Y, and $R^Y$ are as defined above.

In other embodiments, W is NH and $R^1$ is H. In these embodiments, the compounds are of formula Ic:

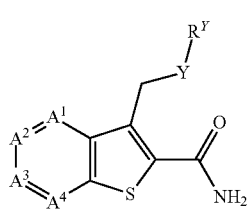

(Ic)

where $A^1$-$A^4$, Y, and $R^Y$ are as defined above.

In other embodiments, W is O or NH and $R^1$ is $R^{1B}$. $R^{1B}$ is selected from $C_{3-6}$cycloalkyl, optionally substituted $C_{3-7}$heterocyclyl and optionally substituted linear or branched $C_{1-4}$alkyl. In these embodiments, the compounds are of formula Ib:

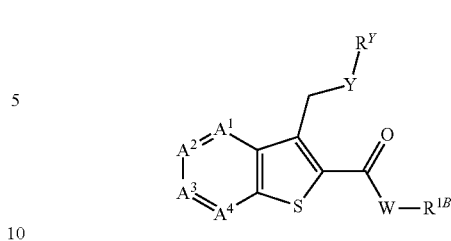

(Ib)

where $A^1$-$A^4$, Y, and $R^Y$ are as defined above and $R^{1B}$ is selected from $C_{3-6}$ cycloalkyl, optionally substituted $C_{3-7}$heterocyclyl and optionally substituted linear or branched $C_{1-4}$alkyl.

In some embodiments $R^1/R^{1B}$ is optionally substituted linear or branched $C_{1-4}$alkyl. In some embodiments $R^1/R^{1B}$ is unsubstituted $C_{1-4}$alkyl. In some embodiments $R^1/R^{1B}$ is substituted $C_{1-4}$alkyl.

When $R^1/R^{1B}$ is $C_{1-4}$ alkyl, in some of these embodiments $R^1/R^{1B}$ is methyl. In other of these embodiments, $R^1/R^{1B}$ is ethyl. In other of these embodiments, $R^1/R^{1B}$ is propyl (e.g. iso-propyl, n-propyl). In other of these embodiments, $R^1/R^{1B}$ is butyl (e.g. iso-butyl, sec-butyl, tert-butyl).

In some embodiments, $R^1/R^{1B}$ is $C_{3-6}$ cycloalkyl. In some of these embodiments, $R^1/R^{1B}$ is cyclopropyl. In other of these embodiments, $R^1/R^{1B}$ is cyclobutyl. In other of these embodiments, $R^1/R^{1B}$ is cyclopentyl. In other of these embodiments, $R^1/R^{1B}$ is cyclohexyl.

In some embodiments, $R^1/R^{1B}$ is $C_{3-7}$heterocyclyl. In some of these embodiments, the $C_{3-7}$heterocyclyl has a single nitrogen ring atom. In some of these embodiments, $R^1/R^{1B}$ is azetidinyl, pyrrolidinyl or piperidinyl. In some of these embodiments, $R^1/R^{1B}$ is azetidinyl. In some of these embodiments, $R^1/R^{1B}$ is piperidinyl.

Substituents on $R^1$

In some embodiments, when $R^1/R^{1B}$ is $C_{3-7}$heterocyclyl, it is substituted with a group selected from methyl and ester. In some embodiments, when $R^1/R^{1B}$ is $C_{3-7}$heterocyclyl, it is substituted with methyl. In some embodiments, when $R^1/R^{1B}$ is $C_{3-7}$heterocyclyl, it is substituted with ester.

In some embodiments, when $R^1/R^{1B}$ is linear or branched $C_{1-4}$alkyl, it is substituted with a group selected from alkoxy, amino, amido, acylamido, acyloxy, alkyl carboxyl ester, alkyl carbamoyl, alkyl carbamoyl ester, phenyl, phosphonate ester $C_{3-7}$heterocyclyl optionally substituted with group selected from methyl and oxo, and a naturally occurring amino acid, optionally N-substituted with a group selected from methyl, acetyl and boc.

In some embodiments, when $R^1/R^{1B}$ is linear or branched $C_{1-4}$alkyl, it is substituted with a group selected from acyloxy and phenyl. In some embodiments, when $R^1/R^{1B}$ is linear or branched $C_{1-4}$alkyl substituted with acyloxy, it is pivaloyloxymethyl; a group of formula:

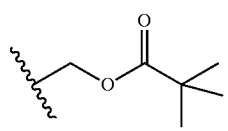

In some embodiments, when $R^1/R^{1B}$ is linear or branched $C_{1-4}$alkyl substituted with acyloxy, it is propanoyloxy-isobutyl; a group of formula:

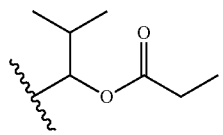

In some embodiments, when $R^1/R^{1B}$ is linear or branched $C_{1-4}$alkyl substituted with phenyl, it is benzyl.

In some embodiments, when $R^1/R^{1B}$ is linear or branched $C_{1-4}$alkyl, it is substituted with a naturally occurring amino acid, optionally N-substituted with a group selected from methyl, acetyl and boc. In some embodiments when $R^1/R^{1B}$ is linear or branched $C_{1-4}$alkyl substituted with a naturally occurring amino acid, the naturally occurring amino acid is valine. In some embodiments when $R^1/R^{1B}$ is linear or branched $C_{1-4}$alkyl substituted with a naturally occurring amino acid, the naturally occurring amino acid is N-methyl valine. In some embodiments when $R^1/R^{1B}$ is linear or branched $C_{1-4}$alkyl substituted with a naturally occurring amino acid, the naturally occurring amino acid is N-acetyl valine. In some embodiments when $R^1/R^{1B}$ is linear or branched $C_{1-4}$alkyl substituted with a naturally occurring amino acid, the naturally occurring amino acid is N-boc valine.

In some embodiments, when $R^1/R^{1B}$ is linear or branched $C_{1-4}$alkyl, it is substituted with amino. In some embodiments, when $R^1/R^{1B}$ is linear or branched $C_{1-4}$alkyl, it is substituted with amido. In some embodiments, when $R^1/R^{1B}$ is linear or branched $C_{1-4}$alkyl, it is substituted with acylamido. In some embodiments, when $R^1/R^{1B}$ is linear or branched $C_{1-4}$alkyl, it is substituted with acyloxy. In some embodiments, when $R^1/R^{1B}$ is linear or branched $C_{1-4}$alkyl, it is substituted with alkyl carboxyl ester. In some embodiments, when $R^1/R^{1B}$ is linear or branched $C_{1-4}$alkyl, it is substituted with alkyl carbamoyl. In some embodiments, when $R^1/R^{1B}$ is linear or branched $C_{1-4}$alkyl, it is substituted with alkyl carbamoyl ester. In some embodiments, when $R^1/R^{1B}$ is linear or branched $C_{1-4}$alkyl, it is substituted with phenyl. In some embodiments, when $R^1/R^{1B}$ is linear or branched $C_{1-4}$alkyl, it is substituted with phosphonate ester.

In some embodiments, when $R^1/R^{1B}$ is linear or branched $C_{1-4}$alkyl, it is substituted with $C_{3-7}$heterocyclyl, optionally substituted with a group selected from methyl and oxo. In some embodiments when $R^1/R^{1B}$ is linear or branched $C_{1-4}$alkyl substituted with $C_{3-7}$heterocyclyl, the $C_{3-7}$heterocyclyl is dioxole, optionally substituted with a group selected from methyl and oxo.

The compounds of formula (Ib) and (Ic) are prodrugs of the acids of formula (Ia).

In some embodiments, the compounds of formula I are compounds of formula II:

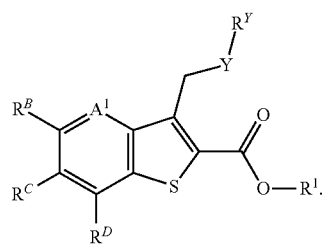

(II)

In some embodiments of compounds of formula II, $R^1$ is H. In these embodiments, the compounds are of formula IIa:

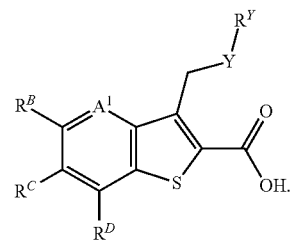

(IIa)

In other embodiments of compounds of formula II, $R^1$ is selected from Me, Et, iPr, benzyl and pivaloyloxymethyl. In these embodiments, the compounds are of formula IIb:

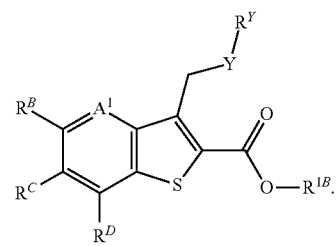

(IIb)

where $R^{1B}$ is selected from Me, Et, iPr, benzyl and pivaloyloxymethyl. In some of these embodiments, $R^1/R^{1B}$ may be Me. In other of these of these embodiments, $R^1/R^{1B}$ may be Et. In other of these of these embodiments, $R^1/R^{1B}$ may be iPr. In other of these embodiments, $R^1/R^{1B}$ may be benzyl. In other of these embodiments, $R^1/R^{1B}$ may be pivaloyloxymethyl.

The esters of formula (IIb) are prodrugs of the acids of formula (IIa).

$A^1$-$A^4$

In some embodiments, $A^1$ is $CR^A$.
In other embodiments, $A^1$ is N.
In some embodiments, $A^2$ is $CR^B$.
In other embodiments, $A^2$ is N.
In some embodiments, $A^3$ is $CR^C$.
In other embodiments, $A^3$ is N.
In some embodiments, $A^4$ is $CR^D$.
In other embodiments, $A^4$ is N.
In some embodiments, two of $A^1$, $A^2$, $A^3$ and $A^4$ are N.
In other embodiments, one of $A^1$, $A^2$, $A^3$ and $A^4$ are N.
In other embodiments, none of $A^1$, $A^2$, $A^3$ and $A^4$ are N, i.e. $A^1$, $A^2$, $A^3$ and $A^4$ are $CR^A$, $CR^B$, $CR^C$, and $CR^D$ respectively.

In some embodiments, the compound of formula I is selected from compounds of formulae (IIIa)-(IIIe):

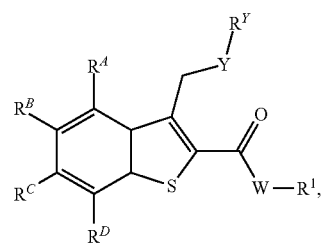

(IIIa)

-continued

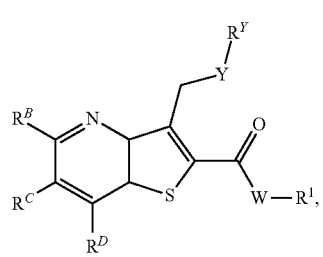
(IIIb)

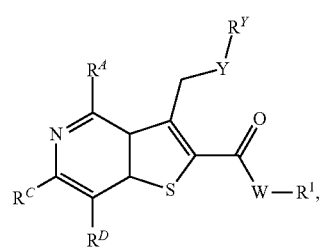
(IIIc)

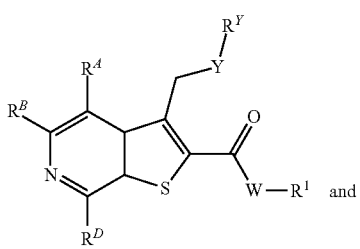
(IIId)

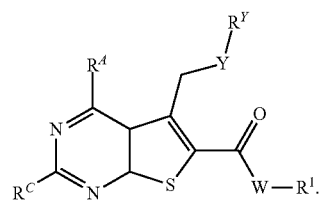
(IIIe)

$R^A$, $R^B$, $R^C$ and $R^D$, (if Present)

In some embodiments, $R^A$, $R^B$, $R^C$ and $R^D$, (if present) are selected from H, F, Cl, Br, Me, $CF_3$, cyclopropyl, cyano, OMe, OEt, $CH_2OH$, $CH_2OMe$ and OH.

In some embodiments one of $R^A$, $R^B$, $R^C$ and $R^D$, (if present) is selected from H, F, Cl, Br, Me, $CF_3$, cyclopropyl, cyano, OMe, OEt, $CH_2OH$, $CH_2OMe$ and OH. The remainder (if present) are H.

In other embodiments two of $R^A$, $R^B$, $R^C$ and $R^D$, (if present) are selected from H, F, Cl, Br, Me, $CF_3$, cyclopropyl, cyano, OMe, OEt, $CH_2OH$, $CH_2OMe$ and OH. The remainder (if present) are H.

In some embodiments, one or two of $R^A$, $R^B$, $R^C$ and $R^D$, (if present) are selected from H, F, Cl, Br, Me, $CF_3$, cyclopropyl, cyano and OMe. The remainder (if present) are H. In some of these embodiments, one or two of $R^A$, $R^B$, $R^C$ and $R^D$, (if present) are selected from H, F, Cl, Br, Me, $CF_3$ and cyclopropyl. The remainder (if present) are H. In some of these embodiments, one or two of $R^A$, $R^B$, $R^C$ and $R^D$, (if present) are selected from H, F, Cl, Br, Me and $CF_3$.

In some embodiments $R^A$ and $R^D$ are selected from H, F, Cl, Br, Me, $CF_3$, cyclopropyl, cyano and OMe; and $R^B$ and $R^C$ are H.

In some embodiments $R^A$ is selected from H, F, Cl, Br, Me, $CF_3$, cyclopropyl, cyano, OMe, OEt and $CH_2OMe$. In some embodiments $R^A$ is selected from F, Cl, Br, Me, $CF_3$, cyclopropyl, cyano and OMe. In some embodiments $R^A$ is selected from Cl and Br. In some embodiments $R^A$ is Cl. In some embodiments $R^A$ is Br.

In some embodiments $R^D$ is selected from H, F, Cl, Br, Me, $CF_3$, cyclopropyl, cyano, OMe, $CH_2OH$, $CH_2OMe$ and $CH_2NMe_2$. In some embodiments $R^D$ is selected from H, F, Cl, Br, Me, $CF_3$, cyclopropyl, cyano and OMe. In some embodiments $R^D$ is selected from H, F, Br, Me and OMe. In some embodiments $R^D$ is H. In some embodiments $R^D$ is F. In some embodiments $R^D$ is Br. In some embodiments $R^D$ is Me. In some embodiments $R^D$ is OMe.

In some embodiments, $A^1$, $A^2$, $A^3$ and $A^4$ are selected from combinations 1-7 in the following table:

| Combination | $A^1$ | $A^2$ | $A^3$ | $A^4$ |
|---|---|---|---|---|
| 1 | CCl | CH | CH | CH |
| 2 | CCl | CH | CH | $CCH_3$ |
| 3 | CCl | CH | CH | CBr |
| 4 | CBr | CH | CH | CH |
| 5 | CCl | CH | CH | CF |
| 6 | CCl | CH | CH | $COCH_3$ |
| 7 | CBr | CH | CH | CF |

Y

In some embodiments, Y is O.
In other embodiments, Y is NH.
In other embodiments, Y is $CH_2$.
In some preferred embodiments, Y is O or $CH_2$.
In some further preferred embodiments, Y is O.

$R^Y$

In some embodiments, $R^Y$ is RYA:

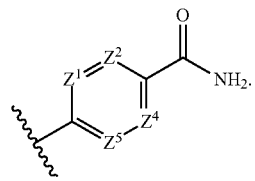
(RYA)

In some embodiments $R^Y$ is RYA(I):

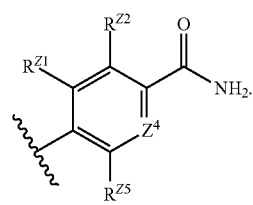
(RYA(I))

In other embodiments, $R^Y$ is RYB:

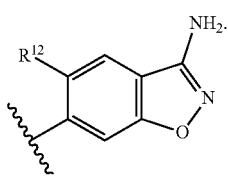
(RYB)

In some preferred embodiments $R^Y$ is RYA.
In some further preferred embodiments $R^Y$ is RYA(I).
In some yet further preferred embodiments $R^Y$ is selected from:

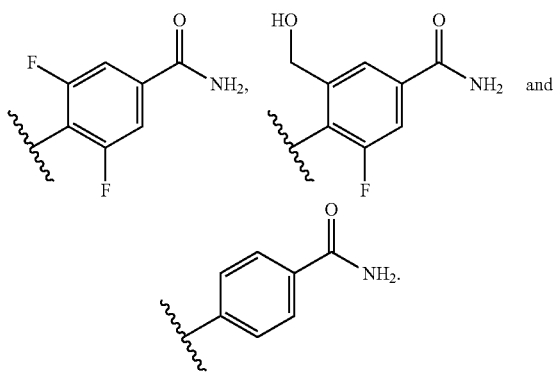

In some embodiments, $R^Y$ is:

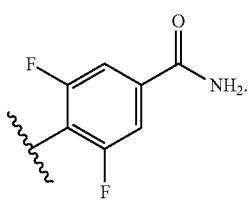 [SMILES: *c1c(F)cc(C(N)=O)cc1F]

In some embodiments, $R^Y$ is:

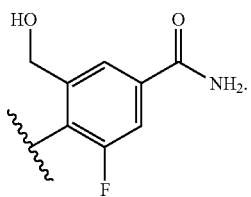 [SMILES: *c1c(F)cc(C(N)=O)cc1CO]

In some embodiments, $R^Y$ is:

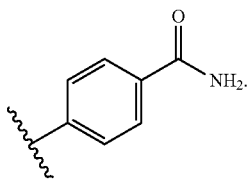 [SMILES: *c1ccc(C(N)=O)cc1]

$Z^1$-$Z^5$

When $R^Y$ is RYA:
In some embodiments, $Z^1$ is $CR^{Z1}$.
In other embodiments, $Z^1$ is N.
In some embodiments, $Z^2$ is $CR^{Z2}$.
In other embodiments, $Z^2$ is N.
In some embodiments, $Z^4$ is $CR^{Z4}$.
In other embodiments, $Z^4$ is N.
In some embodiments, $Z^5$ is $CR^{Z5}$.
In other embodiments, $Z^5$ is N.
In some embodiments, two of $Z^1$, $Z^2$, $Z^4$ and $Z^5$ are N.
In other embodiments, one of $Z^1$, $Z^2$, $Z^4$ and $Z^5$ are N.
In other embodiments, none of $Z^1$, $Z^2$, $Z^4$ and $Z^5$ are N, i.e. $Z^1$, $Z^2$, $Z^4$ and $Z^5$ are $CR^{Z1}$, $CR^{Z2}$, $CR^{Z4}$ and $CR^{Z5}$ respectively.

In some embodiments, $R^{Z1}$, $R^{Z2}$, $R^{Z4}$ and $R^{Z5}$, (if present) are selected from H, F, Cl, Br, Me, OMe, cyano, $CF_3$, $CH_2OMe$, $CH_2OH$, $C_{2-4}$ alkenyl and $C_{3-7}$heterocyclyl.

In some embodiments $R^{Z1}$ and $R^{Z5}$, (if present) are selected from H, F, Cl, Br, Me, OMe, cyano, $CF_3$, $CH_2OMe$, $CH_2OH$, $C_{2-4}$ alkenyl and $C_{3-7}$heterocyclyl. In some embodiments $R^{Z1}$ and $R^{Z5}$, (if present) are selected from H, F, Cl, Br, Me, OMe, cyano, $CF_3$, $CH_2OH$. In some embodiments $R^{Z1}$ and $R^{Z5}$, (if present) are selected from H, F, $CH_2OH$. In some embodiments $R^{Z1}$ and $R^{Z5}$, (if present) are both F. In some embodiments $R^{Z1}$ and $R^{Z5}$, (if present) are both H. In some embodiments one of $R^{Z1}$ and $R^{Z5}$, (if present) is F and the other is $CH_2OH$.

In some embodiments $R^{Z1}$ and $R^{Z5}$, (if present) are selected from H, F, Cl, Br, Me, OMe, cyano, $CF_3$, $CH_2OMe$, $CH_2OH$, $C_{2-4}$ alkenyl and $C_{3-7}$heterocyclyl, $R^{Z2}$ and $R^{Z4}$, (if present) are both H. In some embodiments $R^{Z1}$ and $R^{Z5}$, (if present) are selected from H, F, Cl, Br, Me, OMe, cyano, $CF_3$, $CH_2OH$, $R^{Z2}$ and $R^{Z4}$, (if present) are both H. In some embodiments $R^{Z1}$ and $R^{Z5}$, (if present) are selected from H, F, $CH_2OH$, $R^{Z2}$ and $R^{Z4}$, (if present) are both H. In some embodiments $R^{Z1}$ and $R^{Z5}$, (if present) are both F, $R^{Z2}$ and $R^{Z4}$, (if present) are both H. In some embodiments $R^{Z1}$ and $R^{Z5}$, (if present) are both H, $R^{Z2}$ and $R^{Z4}$, (if present) are both H. In some embodiments one of $R^{Z1}$ and $R^{Z5}$, (if present) is F and the other is $CH_2OH$, $R^{Z2}$ and $R^{Z4}$, (if present) are both H.

In some embodiments $R^{Z2}$ and $R^{Z4}$, (if present) are selected from H, F, Cl, Br, Me, OMe, cyano, $CF_3$, $CH_2OMe$, $CH_2OH$, $C_{2-4}$ alkenyl and $C_{3-7}$heterocyclyl. In some embodiments $R^{Z2}$ and $R^{Z4}$, (if present) are selected from H, F, Cl, Br, Me, OMe, $CF_3$, $CH_2OMe$, $C_{2-4}$ alkenyl and $C_{3-7}$heterocyclyl. In some embodiments $R^{Z2}$ and $R^{Z4}$, (if present) are both H.

In some embodiments one of $R^{Z2}$ and $R^{Z4}$, (if present) is selected from H, F, Cl, Br, Me, OMe, cyano, $CF_3$, $CH_2OMe$, $CH_2OH$, $C_{2-4}$ alkenyl and $C_{3-7}$heterocyclyl; and the other is H. In some embodiments one of $R^{Z2}$ and $R^{Z4}$, (if present) is selected from H, F, Cl, Br, Me, OMe, $CF_3$, $CH_2OMe$, $C_{2-4}$ alkenyl and $C_{3-7}$heterocyclyl; and the other is H. In some embodiments one of $R^{Z2}$ and $R^{Z4}$, (if present) is selected from H, F, Br, OMe, $CH_2OMe$, $C_{2-4}$ alkenyl and $C_{3-7}$heterocyclyl; and the other is H. In some embodiments one of $R^{Z2}$ and $R^{Z4}$, (if present) is selected from H and F; and the other is H.

When $R^Y$ is RYA(I), in some embodiments $Z^4$ is $CR^{Z4}$. In other embodiments, $Z^4$ is N.

In some embodiments, one of $R^{Z1}$, $R^{Z2}$, $R^{Z5}$ and $R^{Z4}$, (if present) is selected from H, F, Cl, Br, Me, OMe, cyano and $CF_3$.

In other embodiments, two of $R^{Z1}$, $R^{Z2}$, $R^{Z5}$ and $R^{Z4}$, (if present) are selected from H, F, Cl, Br, Me, OMe, cyano and $CF_3$.

In some embodiments, one or two of $R^{Z1}$, $R^{Z2}$, $R^{Z5}$ and $R^{Z4}$, (if present) are selected from H, F, Cl, Br and Me. In some of these embodiments, one or two of $R^{Z1}$, $R^{Z2}$, $R^{Z5}$ and $R^{Z4}$ (if present) are selected from H, F and Cl.

When $R^Y$ is RYB, $R^{12}$ is selected from H, F, Cl, Br, OMe, cyano and $CF_3$. In some embodiments, $R^{12}$ is selected from H and F. In some of these embodiments, $R^{12}$ is H. In other of these embodiments, $R^{12}$ is F.

In some embodiments, the compounds are of formula (II):

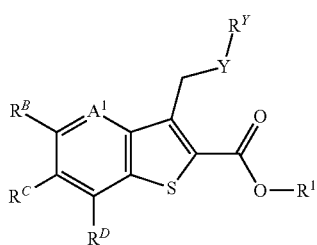

(II)

wherein:
$R^1$ is H, Me, Et, iPr, benzyl or pivaloyloxymethyl;
$A^1$ is $CR^A$ or N;
one or two of $R^A$ (if present), $R^B$, $R^C$ and $R^D$ are selected from H, F, Cl, Br, Me, $CF_3$, cyclopropyl, cyano and OMe;
the remainder of $R^A$ (if present), $R^B$, $R^C$ and $R^D$ are H;
Y is O, NH or $CH_2$;
$R^Y$ is selected from:

(a)

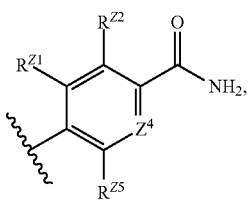

(RYA(I))

where $Z^4$ is $CR^{Z4}$ or N;
one or two of $R^{Z1}$, $R^{Z2}$, $R^{Z5}$ and $R^{Z4}$ (if present) are selected from H, F, Cl, Br, Me, OMe, cyano and $CF_3$;
the remainder of $R^{Z1}$, $R^{Z2}$, $R^{Z5}$ and $R^{Z4}$ (if present) are H;

(b)

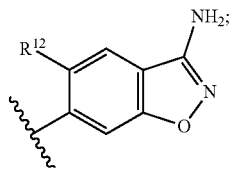

(RYB)

where $R^{12}$ is selected from H, F, Cl, Br, OMe, cyano and $CF_3$;
with the proviso that when $A^1$ is CF; $R^B$, $R^C$ and $R^D$ are H; Y is O; $R^Y$ is RYA, where $Z^4$ is CH, $R^2$, $R^3$ and $R^5$ are H; $R^1$ is not Et.
  In some embodiments $R^1$ is H.
  In some embodiments $R^1$ is selected from Me, Et, iPr, benzyl and pivaloyloxymethyl.
  In some embodiments $R^1$ is Me.
  In some embodiments $R^1$ is Et.
  In some embodiments $R^1$ is iPr.
  In some embodiments $R^1$ is benzyl.
  In some embodiments $R^1$ is pivaloyloxymethyl.
  In some embodiments $A^1$ is $CR^A$.
  In some embodiments $A^1$ is N.

In some embodiments one of $R^A$ (if present), $R^B$, $R^C$ and $R^D$ is selected from H, F, Cl, Br, Me, $CF_3$, cyclopropyl, cyano and OMe.
  In some embodiments two of $R^A$ (if present), $R^B$, $R^C$ and $R^D$ is selected from H, F, Cl, Br, Me, $CF_3$, cyclopropyl, cyano and OMe.
  In some embodiments one or two of $R^A$ (if present), $R^B$, $R^C$ and $R^D$ are selected from H, F, Cl, Br, Me, $CF_3$ and cyclopropyl.
  In some embodiments one or two of $R^A$ (if present), $R^B$, $R^C$ and $R^D$ are selected from H, F, Cl and $CF_3$.
  In some embodiments Y is O.
  In some embodiments Y is NH.
  In some embodiments Y is $CH_2$.
  In some embodiments $R^Y$ is RYA(I).
  In some embodiments $Z^4$ is $CR^{Z4}$.
  In some embodiments $Z^4$ is N.
  In some embodiments one of $R^{Z1}$, $R^{Z2}$, $R^{Z5}$ and $R^{Z4}$ (if present) is selected from H, F, Cl, Br, OMe, cyano and $CF_3$.
  In some embodiments two of $R^{Z1}$, $R^{Z2}$, $R^{Z5}$ and $R^{Z4}$ (if present) are selected from H, F, Cl, Br, OMe, cyano and $CF_3$.
  In some embodiments one or two of $R^{Z1}$, $R^{Z2}$, $R^{Z5}$ and $R^{Z4}$ (if present) are selected from H, F, Cl, Br and Me.
  In some embodiments one or two of $R^{Z1}$, $R^{Z2}$, $R^{Z5}$ and $R^{Z4}$ (if present) are selected from H, F and Cl.
  In some embodiments $R^Y$ is RYB.
  In some embodiments $R^{12}$ is selected from H and F.
  In some embodiments $R^{12}$ is H.
  In some embodiments $R^{12}$ is F.

EXAMPLES

The following examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), isopropyl (iPr), n-butyl (nBu), tert-butyl (tBu), phenyl (Ph), benzyl (Bn), methoxy (MeO), ethoxy (EtO), trimethylsilyl (TMS), and acetyl (Ac).

For convenience, many chemical compounds are represented using well known abbreviations, including but not limited to, methanol (MeOH), deuterated methanol (MeOD-$d_4$ or $CD_3OD$) ethanol (EtOH), isopropanol (i-PrOH), ether or diethyl ether ($Et_2O$), ethyl acetate (EtOAc), acetic acid (AcOH), acetonitrile (MeCN), dichloromethane (methylene chloride, DCM), trifluoroacetic acid (TFA), dimethylformamide (DMF), tetrahydrofuran (THF), dimethylsulfoxide (DMSO), deuterated chloroform ($CDCl_3$), diethylamine (DEA), deuterated dimethylsulfoxide (DMSO-$d_6$), N-ethyl-N'-(3-dimethylaminopropyl)carbodiimide hydrochloride (EDCl.HCl), meta-chloroperoxybenzoic acid (mCPBA), 1,1'-bis(diphenylphosphino)ferrocene (dppf), tert-butyloxycarbonyl (Boc, BOC), 2-(trimethylsilyl)ethoxymethyl (SEM), triethylamine ($Et_3N$ or TEA), 2-(1H-7-azabenzotriazol-1-yl)-1,1,3,3-tetramethyluronium hexafluorophosphate (HATU), 4-dimethylaminopyridine (DMAP), N,N-diisopropylethylamine (DIPEA or DIEA), 1,1'-bis(diphenylphosphino)ferrocene dichloropalladium (II) ($PdCl_2$(dppf)), trans-dichlorobis(triphenylphosphine)palladium(II) ($PdCl_2(PPh_3)_2$), tris(dibenzylideneacetone) dipalladium(0) ($Pd_2(dba)_3$), tetrakis(triphenylphosphine)palladium(0) (Pd($PPh_3)_4$), propylphosphonic anhydride (T3P), hexamethylphosphoramide (HMPA), 1,2-dichloroethane (DCE), chromium (VI) oxide ($CrO_3$), n-bromosuccinimide (NBS), potassium hydroxide (KOH), benzoyl peroxide (BPO), carbon tetrachloride ($CCl_4$), petroleum ether (Pet. Ether), potassium carbonate ($K_2CO_3$), sodium sulfate ($Na_2SO_4$), lithium diisopropylamine (LDA), azobisisobutyronitrile (AIBN), N-methylmorpholine N-oxide (NMO), benzoyl peroxide (BPO) and 1-hydroxybenzotriazole (HOBt).

In addition, TLC refers to thin layer chromatography.

General Experimental Details

Unless otherwise stated the following generalisations apply. $^1$H NMR spectra were recorded on a Bruker Ultrashield Plus (400 MHz) or a Bruker AVANCE III (400 MHz). The multiplicity of a signal is designated by the following abbreviations: s, singlet; d, doublet; t, triplet; q, quartet; dd, doublet of doublets; dt, doublet of triplets; tt, triplet of triplets; td, triplet of doublets; ddd, doublet of doublet of doublets br, broad; m, multiplet. All observed coupling constants, J, are reported in Hertz.

LCMS data was generated using the conditions described below. Chlorine isotopes are reported as $^{35}Cl$, Bromine isotopes are reported as either $^{79}Br$ or $^{81}Br$ or both $^{79}Br/^{81}Br$.

LCMS Method A (LCMS-A):
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector
LC conditions:
Reverse Phase HPLC analysis
Column: Luna C8 (2) 5 µm 50×4.6 mm 100 Å
Column temperature: 30° C.
Injection Volume: 5 µL
Solvent A: Water 0.1% Formic Acid
Solvent B: MeCN 0.1% Formic Acid
Gradient: 5-100% solvent B over 10 min
Detection: 254 nm or 214 nm
MS conditions:
Ion Source: Quadrupole
Ion Mode: Multimode-ES
Drying gas temp: 300° C.
Vaporizer temperature: 200° C.
Capillary voltage (V): 2000 (positive)
Capillary voltage (V): 4000 (negative)
Scan Range: 100-1000
Step size: 0.1 sec
Acquisition time: 10 min LCMS Method B (LCMS-B):
Instrument: Agilent 1260 Infinity Series UPLC/MS
Pump: 1260 Infinity G1312B Binary pump
Autosampler: 1260 Infinity G1367E 1260 HiP ALS
Detector: 1290 Infinity G4212A 1290 DAD
LC conditions:
Reverse Phase HPLC analysis
Column: Poroshell 120 EC-C18 2.7 µm 50×3.0 mm
Column temperature: 35° C.
Injection Volume: 1 µL
Solvent A: Water 0.1% Formic Acid
Solvent B: MeCN 0.1% Formic Acid
Gradient: 5-100% solvent B over 3.8 min
Detection: monitored at 254 nm and 214 nm
MS conditions:
Ion Source: Quadrupole
Ion Mode: API-ES
Drying gas temp: 350° C.
Capillary voltage (V): 3000 (positive)
Capillary voltage (V): 3000 (negative)
Scan Range: 100-1000
Step size: 0.1 sec
Acquisition time: 5 min LCMS Method C (LCMS-C):
Instrument: Agilent 1200 (Pump type: Binary Pump, Detector type: DAD)
MS model: Agilent G6110A Quadrupole
LC Conditions
LC: Column: Xbridge-C18, 2.5 µm, 2.1×30 mm
Column temperature: 30° C.
Acquisition of wavelength: 214 nm, 254 nm
Mobile phase: A: 0.07% HCOOH aqueous solution, B: MeOH

| MS: Ion source: ES+ (or ES−) | MS range: 50-900 m/z |
|---|---|
| Fragmentor: 60 | Drying gas flow: 10 L/min |
| Nebulizer pressure: 35 psi | Drying gas temperature: 350° C. |
| Vcap: 3.5 kV | |

Gradient Table:

| Flow (mL/min) | T (min) | A (%) | B (%) |
|---|---|---|---|
| 0.5 | 0.0 | 70 | 30 |
| 0.5 | 0.2 | 70 | 30 |
| 0.5 | 1.8 | 5 | 95 |
| 0.5 | 2.4 | 5 | 95 |
| 0.5 | 2.6 | 70 | 30 |
| 0.5 | 3.5 | 70 | 30 |

Sample Preparation

The sample was dissolved in methanol, the concentration about 0.11~1 mg/mL, then filtered through syringe filter with 0.22 µm (Injection volume: 1~10 µL).

LCMS Method D (LCMS-D):
Instrument: Agilent 1200 (Pump type: Binary Pump, Detector type: DAD)
MS model: Agilent G6110A Quadrupole
LC Conditions:
LC: Column: Xbridge-C18, 2.5 µm, 2.1×30 mm
Column temperature: 30° C.
Acquisition of wavelength: 214 nm, 254 nm
Mobile phase: A: 0.07% HCOOH aqueous solution, B: MeOH

| MS: Ion source: ES+ (or ES−) | MS range: 50-900 m/z |
|---|---|
| Fragmentor: 60 | Drying gas flow: 10 L/min |
| Nebulizer pressure: 35 psi | Drying gas temperature: 350° C. |
| Vcap: 3.5 kV | |

Gradient Table:

| Flow (mL/min) | T (min) | A (%) | B (%) |
|---|---|---|---|
| 0.5 | 0.0 | 70 | 30 |
| 0.5 | 0.3 | 70 | 30 |
| 0.5 | 0.6 | 50 | 50 |
| 0.5 | 0.9 | 40 | 60 |
| 0.5 | 1.2 | 30 | 70 |
| 0.5 | 3.2 | 5 | 95 |
| 0.5 | 3.5 | 5 | 95 |
| 0.5 | 4.0 | 70 | 30 |
| 0.5 | 5.0 | 70 | 30 |

Sample Preparation

The sample was dissolved in methanol, the concentration about 0.11~1 mg/mL, then filtered through the syringe filter with 0.22 µm (Injection volume: 1~10 µL).

LC-MS method E (LCMS-E):
Instrument: Waters 2695 alliance (Pump type: Quaternary Pump, Detector type: 2996
Photodiode Array Detector)
MS model: Micromass ZQ
LC Conditions:
LC Column: Xbridge-C18, 3.5 μm, 2.1×50 mm
Column temperature: 30° C.
Acquisition of wavelength: 214 nm, 254 nm
Mobile phase: A: 0.07% HCOOH aqueous solution, B: MeOH

| MS: Ion source: ES+ (or ES−) | MS range: 50-900 m/z |
|---|---|
| Capillary: 3 kV | Cone: 3 V |
| Extractor: 3 V | Drying gas flow: 600 L/hr |
| Cone: 50 L/hr | Desolvation temperature: 300° C. |

Source temperature: 100° C.
Gradient Table:

| Flow (mL/min) | T (min) | A (%) | B (%) |
|---|---|---|---|
| 0.3 | 0.0 | 80 | 20 |
| 0.3 | 0.5 | 80 | 20 |
| 0.3 | 0.8 | 50 | 50 |
| 0.3 | 1.2 | 35 | 65 |
| 0.3 | 2.0 | 20 | 80 |
| 0.3 | 4.0 | 5 | 95 |
| 0.3 | 5.0 | 5 | 95 |
| 0.3 | 5.8 | 15 | 85 |
| 0.3 | 6.2 | 80 | 20 |
| 0.3 | 8.0 | 80 | 20 |

Sample Preparation
The sample was dissolved in methanol at a concentration of ~0.11~1 mg/mL, then filtered through a 0.22 μm syringe filter (injection volume: 1~10 μL).
LC-MS method F (LCMS-F):
Instrument: Waters 2695 alliance (Pump type: Quaternary Pump, Detector type: 2996
Photodiode Array Detector)
MS model: Micromass ZQ
LC conditions
LC Column: Xbridge-C18, 2.5 μm, 2.1×30 mm
Column temperature: 30° C.
Acquisition of wavelength: 214 nm, 254 nm
Mobile phase: A: 0.05% HCOOH aqueous solution, B: MeOH
Run time: 5 min

| MS: Ion source: ES+ (or ES−) | MS range: 50-900 m/z |
|---|---|
| Capillary: 3.5kV | Cone: 35 V |
| Extractor: 3 V | Drying gas flow: 350 L/hr |
| cone: 50 L/hr | Desolvation temperature: 300° C. |

Source temperature: 120° C.
Run time: 5 min
Gradient Table:

| Flow (mL/min) | T (min) | A (%) | B (%) |
|---|---|---|---|
| 0.5 | 0.0 | 70 | 30 |
| 0.5 | 0.3 | 70 | 30 |
| 0.5 | 0.6 | 50 | 50 |
| 0.5 | 0.9 | 40 | 60 |
| 0.5 | 1.2 | 30 | 70 |
| 0.5 | 3.2 | 5 | 95 |
| 0.5 | 3.5 | 5 | 95 |
| 0.5 | 4.0 | 70 | 30 |
| 0.5 | 5.0 | 70 | 30 |

Sample Preparation
The sample was dissolved in methanol at a concentration of ~0.11~1 mg/mL, then filtered through a 0.22 μm syringe filter (injection volume: 1~10 μL).
Preparative RP-HPLC:
Instrument type: Varian 940-LC series;
Pump type: Quaternary Pump;
Detector type: Diode Array Detector
HPLC conditions: Waters Sunfire prep C18 OBD, 5 μm 19×100 mm column, eluting with a gradient of MeOH in water with 0.07% TFA at a flow rate of 15 mL/min. Acquisition wavelength 214 nm, 254 nm.
Analytical thin-layer chromatography was performed on Merck silica gel 60 F254 aluminium-backed plates which were visualised using fluorescence quenching under UV light or a basic KMnO$_4$ dip or Ninhydrin dip.
Preparative thin-layer chromatography (prep TLC) was performed using Tklst (China), grand grade: (HPTLC): 8±2 μm>80%; (TLC): 10-40 μm. Type: GF254. Compounds were visualised by UV (254 nm).
Flash chromatography was performed using a Biotage Isolera purification system using either Grace or RediSep® silica cartridges.
Column chromatography was performed using Tklst (China), grand grade, 100-200 meshes silica gel.
Microwave irradiation was achieved using a CEM Explorer SP Microwave Reactor.
Where necessary, anhydrous solvents were purchased from Sigma-Aldrich or dried using conventional methods. Solutions of inorganic acids or bases where made up as aqueous solutions unless stated otherwise.
Additional Cartridges used are as follows:
Phase Separator:
Manufacturer: Biotage
Product: ISOLUTE® Phase Separator (3 mL unless otherwise stated)
SCX and SCX-2 cartridges:
Manufacturer: Biotage
Product: ISOLUTE® SCX 1 g, (6 mL SPE Column unless otherwise stated)
Manufacturer: Biotage
Product: ISOLUTE® SCX-2 1 g (6 mL Column)
Manufacturer: Silicycle
Product: SCX-2 500 mg or 5 g
Manufacturer: Agilent
Product: Bond Elut® SCX 10 g
Sample Extraction Cartridge:
Manufacturer: Waters
Product: Oasis® HLB 35 cc (6 g) LP extraction cartridge
Solutions of hydrogen chloride, sodium hydroxide, potassium carbonate and sodium bicarbonate are aqueous, unless otherwise stated.

Intermediate Preparations (i) Ethyl 3-methylbenzo[b]thiophene-2-carboxylate (I1)

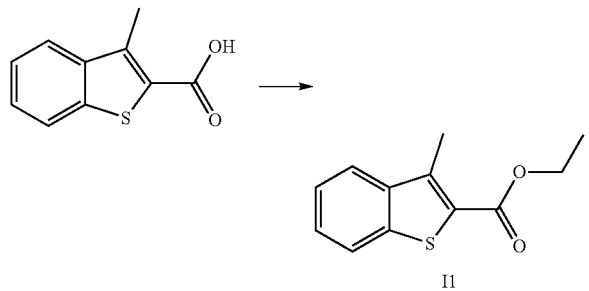

To a solution of 3-methylbenzo[b]thiophene-2-carboxylic acid (800 mg, 4.16 mmol) in EtOH (40 mL) at 0° C. was added $SOCl_2$ (30 mL) and the mixture was heated at 85° C. overnight then concentrated under reduced pressure. The residue was purified by silica gel chromatography (Pet. Ether/EtOAc=1:0 to 30:1) to give the title product (754 mg, 82%) as a white solid. LCMS-C: rt 2.62 min; m/z 221.0 $[M+H]^+$.

(ii) Ethyl 3-(bromomethyl)-4-fluorobenzo[b]thiophene-2-carboxylate (I3)

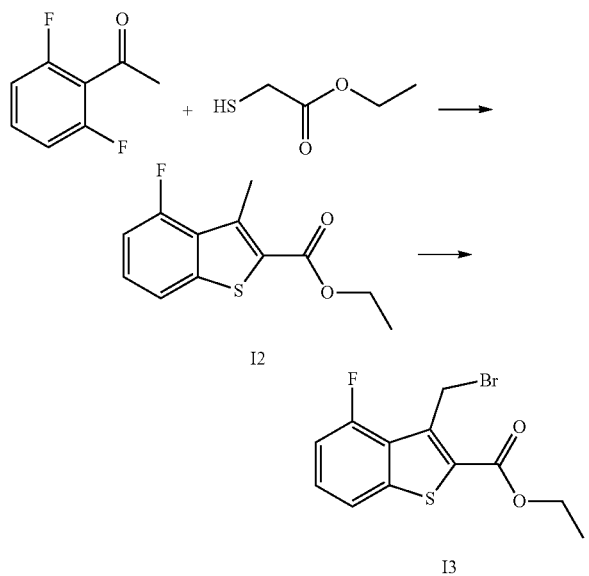

(a) Ethyl 4-fluoro-3-methylbenzo[b]thiophene-2-carboxylate (I2) A solution of 1-(2,6-difluorophenyl)ethanone (5.0 g, 32.0 mmol), ethyl 2-mercaptoacetate (3.85 g, 32.0 mmol) and $K_2CO_3$ (6.63 g, 48.0 mmol) in DMF (150 mL) was heated at 100° C. overnight. The mixture was cooled to room temperature then poured into water and extracted twice with EtOAc. The combined organic extracts were washed with water, brine, dried over anhydrous $Na_2SO_4$, filtered and concentrated under reduced pressure. The residue was purified by re-crystallization from EtOAc/Pet. Ether to give the title product (5.85 g, 76%) as a white solid. LCMS-C: rt 3.36 min; m/z 239.0 $[M+H]^+$, 260.9 $[M+Na]^+$. $^1H$ NMR (400 MHz, DMSO-$d_6$) δ 7.81 (d, J=8.1 Hz, 1H), 7.52 (td, J=8.0, 5.0 Hz, 1H), 7.22 (dd, J=12.3, 8.0 Hz, 1H), 4.33 (q, J=7.1 Hz, 2H), 2.84 (d, J=2.2 Hz, 3H), 1.33 (t, J=7.1 Hz, 3H).

(b) Ethyl 3-(bromomethyl)-4-fluorobenzo[b]thiophene-2-carboxylate (I3)

A solution of ethyl 4-fluoro-3-methylbenzo[b]thiophene-2-carboxylate 12 (5.10 g, 21.4 mmol), NBS (3.81 g, 21.4 mmol) and BPO (519 mg, 2.14 mmol) in $CCl_4$ (250 mL) was heated at reflux for 1 h. The mixture was allowed to cool to room temperature, concentrated under reduced pressure and the residue was purified by silica gel chromatography (Pet. Ether/EtOAc=1:0 to 50:1) to give the title product (6.24 g, 92%) as a white solid. LCMS-D: rt 3.26 min; m/z 338.8, 340.8 $[M+Na]^+$. $^1H$ NMR (400 MHz, $CDCl_3$) δ 7.63 (dd, J=8.1, 0.6 Hz, 1H), 7.46 (td, J=8.0, 4.8 Hz, 1H), 7.18-7.10 (m, 1H), 5.36 (s, 2H), 4.47 (q, J=7.1 Hz, 2H), 1.46 (t, J=7.1 Hz, 3H).

(iii) Ethyl 3-(bromomethyl)-4-chlorobenzo[b]thiophene-2-carboxylate (I5)

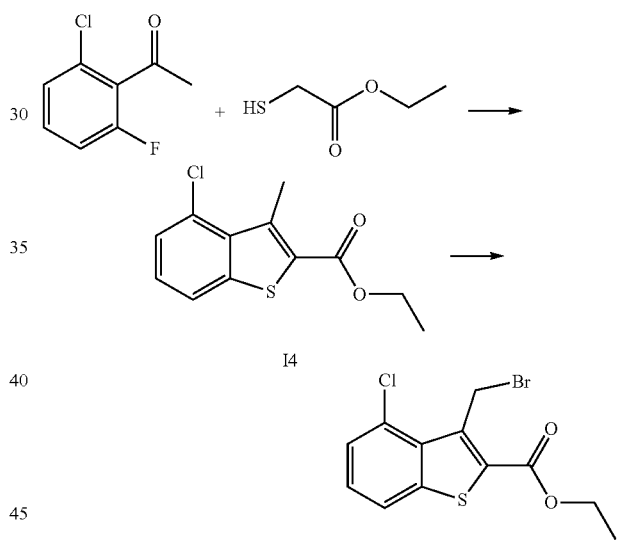

(a) Ethyl 4-chloro-3-methylbenzo[b]thiophene-2-carboxylate (I4) A solution of 1-(2-chloro-6-fluorophenyl)ethanone (25.0 g, 145 mmol), ethyl 2-mercaptoacetate (17.4 g, 145 mmol) and $K_2CO_3$ (30.0 g, 217 mmol) in DMF (200 mL) was heated at 100° C. overnight. The mixture was allowed to cool to room temperature then poured into water (1.0 L) and EtOAc (500 mL). The organic layer was separated and the aqueous layer was extracted with EtOAc (500 mL×3). The combined organic extracts were dried over anhydrous $Na_2SO_4$, filtered and concentrated under reduced pressure. The residue was purified by re-crystallization from Pet. Ether/EtOAc to give the title product (28.0 g, 76%) as a yellow solid. LCMS-C: rt 2.82 min; m/z 255.0 $[M+H]^+$.

(b) Ethyl 3-(bromomethyl)-4-chlorobenzo[b]thiophene-2-carboxylate (I5)

A suspension of ethyl 4-chloro-3-methylbenzo[b]thiophene-2-carboxylate 14 (28.0 g, 0.11 mol), NBS (19.6 g, 0.11 mol) and BPO (2.67 g, 0.011 mol) in CCl₄ (200 mL) was heated at 115° C. for 1.5 h. The mixture was allowed to cool to room temperature then concentrated under reduced pressure and the residue was purified by re-crystallization from DCM/Pet. Ether to give the title product (26.0 g, 71%) as a purple solid. ¹H NMR (400 MHz, CDCl₃) δ 7.74 (dd, J=8.0, 1.2 Hz, 1H), 7.46 (dd, J=7.6, 0.8 Hz, 1H), 7.40 (t, J=8.0 Hz, 1H), 5.61 (s, 2H), 4.44 (q, J=7.1 Hz 2H), 1.44 (t, J=7.1 Hz, 3H).

(iv) 3-Aminobenzo[d]isoxazol-6-ol (I8)

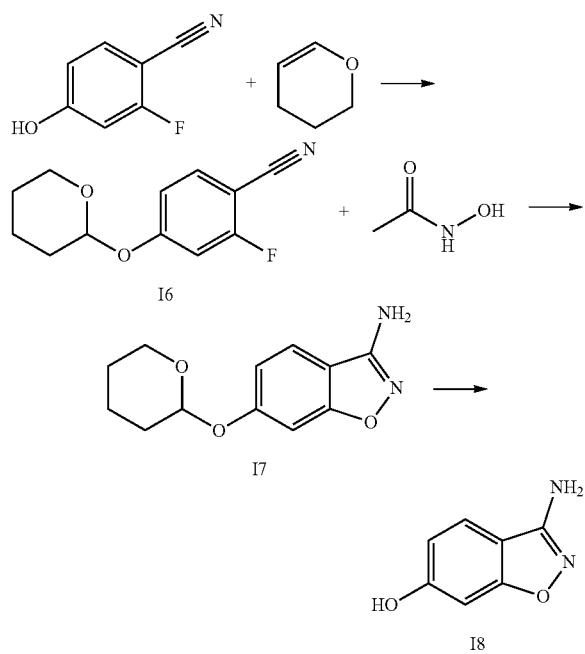

(a) 2-Fluoro-4-((tetrahydro-2H-pyran-2-yl)oxy)ben-zonitrile (I6)

A mixture of 2-fluoro-4-hydroxybenzonitrile (5.42 g, 39.6 mmol), 3,4-dihydro-2H-pyran (7.20 mL, 79.1 mmol) and pyridinium p-toluenesulfonate (170 mg, 0.68 mmol) in DCM (100 mL) was stirred at room temperature overnight. The solvent was removed under reduced pressure and the residue was purified by silica gel chromatography (Pet. Ether/EtOAc=100/1 to 1/1) to give title product (7.8 g, 89%) as a white solid. LCMS-C: rt 1.874 min; m/z 221.9 [M+H]⁺.

(b) 6-((Tetrahydro-2H-pyran-2-yl)oxy)benzo[d]isoxazol-3-amine (I7)

To a solution of N-hydroxyacetamide (7.75 g, 103 mmol) in DMF (180 mL) was added t-BuOK (11.6 g, 103 mmol) portion-wise and the mixture was stirred at room temperature for 1 h. A solution of 2-fluoro-4-((tetrahydro-2H-pyran-2-yl)oxy)benzonitrile 16 (7.6 g, 34 mmol) in DMF (30 mL) was then added and the resulting mixture was stirred at room temperature overnight. Water (200 mL) was added and the mixture was extracted with EtOAc (300 mL×3). The combined organic extracts were washed with water (500 mL×3), brine, dried over anhydrous Na₂SO₄, filtered and concentrated under reduced pressure. The residue was purified by silica gel chromatography (Pet. Ether/EtOAc=100/1 to 0/1) to give the title product (4.0 g, 49%) as a grey solid. LCMS-C: rt 1.291 min; m/z 235.0 [M+H]⁺.

(c) 3-Aminobenzo[d]isoxazol-6-ol (I8)

To a solution of 6-((tetrahydro-2H-pyran-2-yl)oxy)benzo[d]isoxazol-3-amine 17 (1.37 g, 5.85 mmol) in MeOH (30 mL) was added aqueous 1 M HCl (10 mL) and the mixture was stirred at room temperature for 1 h. The mixture was concentrated under reduced pressure and the residue was purified by silica gel chromatography (DCM/MeOH=100/1 to 30/1) to give the title product (600 mg, 68%) as a light yellow solid. LCMS-C: rt 0.78 min; m/z 151.0 [M+H]⁺.

(v) 3-Chloro-4-hydroxybenzamide (I9)

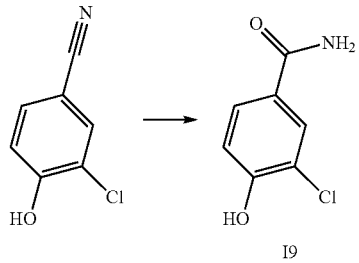

A mixture of 3-chloro-4-hydroxybenzonitrile (300 mg, 1.96 mmol) and concentrated sulfuric acid (15 mL) was stirred at room temperature overnight. The mixture was poured slowly into water (200 mL) and extracted with EtOAc (100 mL×3). The combined organic extracts were washed with brine (200 mL), dried over anhydrous Na₂SO₄, filtered and concentrated under reduced pressure to give the title product (300 mg, 89%) as a pale yellow solid. LCMS-C: rt 0.99 min, m/z 172.0 [M+H]⁺.

(vi) 4-Hydroxy-3,5-dimethoxybenzamide (I10)

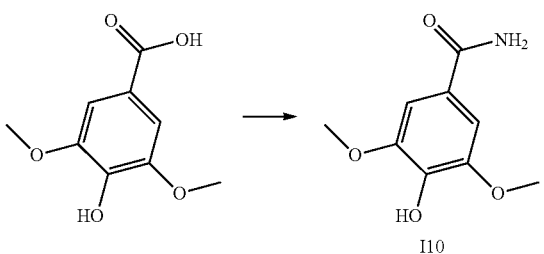

To a solution of 4-hydroxy-3,5-dimethoxybenzoic acid (200 mg, 1.01 mmol) in DCM (2 mL) and THF (5 mL) at 0° C. was added oxalyl chloride (641 mg, 5.05 mmol) drop-wise followed by DMF (two drops) and the mixture was stirred at room temperature for 3 h. The solvent was removed under reduced pressure and the residue was dissolved in THF (5 mL) and added drop-wise to a concentrated aqueous ammonia solution (20 mL). The mixture was stirred at room temperature for 20 min. The resulting precipitate was collected by filtration, washed with water (20 mL) and dried to give the title product (250 mg, 91%) as a light yellow solid. LCMS-C: rt 0.38 min, m/z 198.0 [M+H]⁺.

(vii) 5-Hydroxypicolinamide (I11)

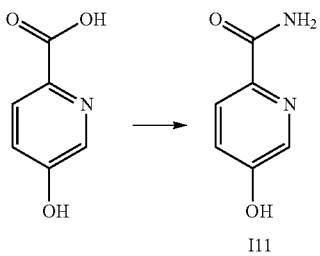 [SMILES: O=C(O)c1ccc(O)cn1 ; "I11" ; NC(=O)c1ccc(O)cn1]

A suspension of 5-hydroxypicolinic acid (1 g, 7.2 mmol), NH$_4$Cl (3.8 g, 72 mmol), HATU (3.3 g, 8.64 mmol) and DIPEA (2.8 g, 21.6 mmol) in DMF (20 mL) was stirred at room temperature overnight. Water (100 mL) was added and the mixture was extracted with EtOAc (50 mL×3). The combined organic extracts were washed with brine (100 mL), dried over anhydrous Na$_2$SO$_4$, filtered and concentrated under reduced pressure to give the title product (65 mg, 7%) as a white solid. LCMS-C: rt 0.98 min, m/z 139.1 [M+H]$^+$.

(viii) 3,5-Dichloro-4-hydroxybenzamide (I12)

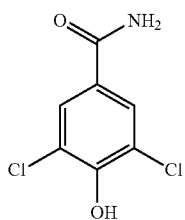

Prepared from 3,5-dichloro-4-hydroxybenzonitrile according to the procedure described for 3-chloro-4-hydroxybenzamide 19. LCMS-C: rt 1.13 min, m/z 205.9 [M+H]$^+$.

(ix) 4-Hydroxy-3-methoxybenzamide (I13)

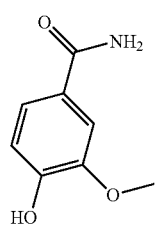

Prepared from 4-hydroxy-3-methoxybenzonitrile according to the procedure described for 3-chloro-4-hydroxybenzamide 19. LCMS-C: rt 0.33 min, m/z 168.0 [M+H]$^+$.

(x) 3-Cyano-4-hydroxybenzamide (I14)

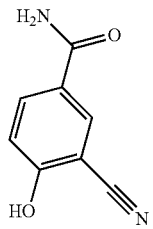

Prepared from 3-cyano-4-hydroxybenzoic acid according to the procedure described for 4-hydroxy-3,5-dimethoxybenzamide 110. LCMS-C: rt 0.34 min, m/z 162.9 [M+H]$^+$.

(xi) 2-Bromo-4-hydroxybenzonitrile (I15)

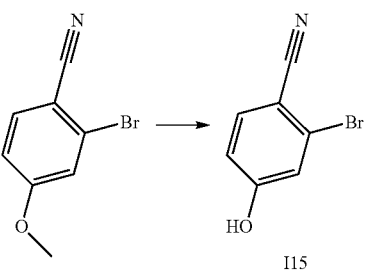

To a solution of 2-bromo-4-methoxybenzonitrile (1.0 g, 4.7 mmol) in DCM (15 mL) was added BBr$_3$ (1 M solution in DCM, 14.2 mL, 14.2 mmol) and the mixture was heated at 50° C. overnight. The mixture was quenched with methanol and then poured into water and extracted with EtOAc (200 mL). The organic extract was washed with water (200 mL), brine (200 mL), dried over anhydrous Na$_2$SO$_4$, filtered and concentrated under reduced pressure. The residue was purified by silica gel chromatography (Pet. Ether/EtOAc=5:1) to give the title product (700 mg, 75%) as a white solid. LCMS-C: rt 0.93 min; m/z 197.9 [M+H]$^+$.

(xii) 3-Bromo-5-fluoro-4-hydroxybenzamide (I16)

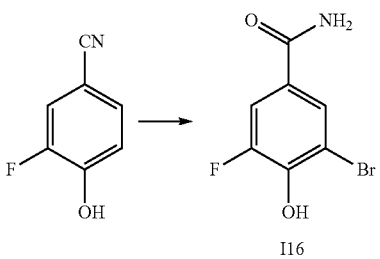

3-Fluoro-4-hydroxybenzonitrile (2.00 g, 14.6 mmol) was dissolved in acetic acid (20 mL) and bromine (0.785 mL, 15.3 mmol) was added dropwise. The mixture was stirred at room temperature for two hours then diluted with water (100 mL). The resulting precipitate was collected by filtration, washed with water (4×50 mL) and air dried. The precipitate was dissolved in DMSO (100 mL) and potassium carbonate (3.02 g, 21.9 mmol) was added. The mixture was stirred for five minutes then cooled with a room temperature water bath while 30% w/w aq. hydrogen peroxide (4.51 mL, 43.8 mmol) was added. The mixture was stirred at room temperature for two hours. Additional 30% w/w aq. hydrogen peroxide (4.51 mL, 43.8 mmol) was added and the mixture was stirred overnight. Another addition of 30% w/w aq hydrogen peroxide (4.51 mL, 43.8 mmol) was made and the mixture again stirred overnight. The mixture was added to water (500 mL) and the pH adjusted to ~1 with aq. HCl (1 M). Brine (100 mL) was added and the mixture extracted with ethyl acetate (3×200 mL). The pooled ethyl acetate phases were washed with aq. HCl (0.5 M, 2×300 mL), brine (300 mL), dried over sodium sulfate and concentrated in vacuo. The residue was recrystallised from methanol to give the title compound as a white solid (0.716 g, 21% yield). LCMS-B rt 2.48 min; m/z 231.8 [M−H]⁻.

(xiii) Ethyl 4-chloro-5-fluoro-3-methylbenzo[b]thiophene-2-carboxylate (I23) and Ethyl 4,7-difluoro-3-methylbenzo[b]thiophene-2-carboxylate (I24)

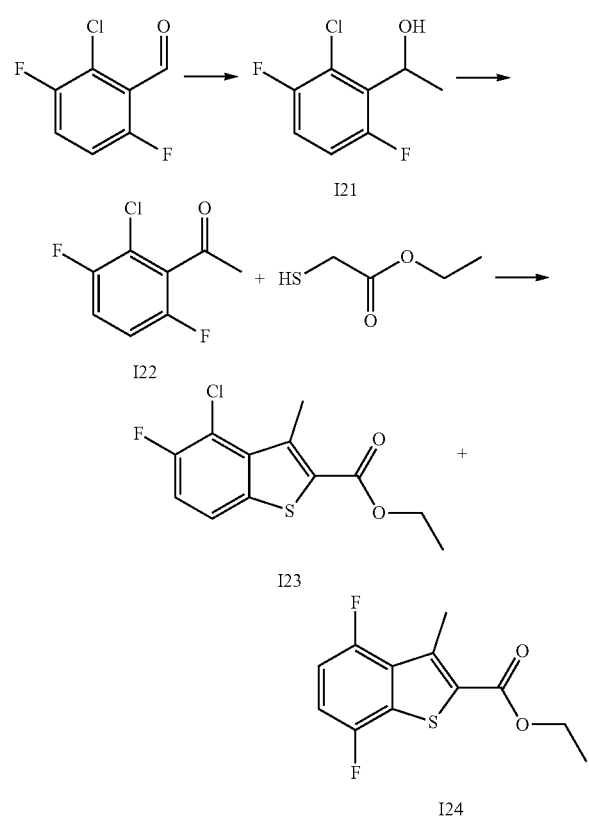

(a) 1-(2-Chloro-3,6-difluorophenyl)ethan-1-ol (I21)

To a solution of 2-chloro-3,6-difluorobenzaldehyde (5 g, 28 mmol) in dry THF (60 mL) at 0° C. under nitrogen was added methyl magnesium bromide (3 M solution in THF, 40 mL, 113 mmol) dropwise and the mixture was stirred at room temperature overnight. A saturated aqueous ammonium chloride solution (200 mL) was added and the mixture was extracted with EtOAc (150 mL×2). The combined organic extracts were washed with brine, dried over anhydrous Na₂SO₄, filtered and concentrated under reduced pressure to give the title compound (5.35 g, 98%) as a white solid. LCMS-C: rt 1.98 min; m/z 192.9 [M+H]⁺.

(b) 1-(2-Chloro-3,6-difluorophenyl)ethan-1-one (I22)

To a solution of 1-(2-chloro-3,6-difluorophenyl)ethan-1-ol I21 (5.35 g, 27.9 mmol) in acetone (150 mL) at 0° C. was added a solution of CrO₃ (3.8 g, 38 mmol) and concentrated sulfuric acid (4 mL) in water (15 mL) dropwise over 1 h. Water (150 mL) was then added and the mixture was extracted with EtOAc (100 mL×3). The combined organic extracts were washed with brine, dried over anhydrous Na₂SO₄, filtered and concentrated under reduced pressure. The residue was purified by column chromatography (DCM/MeOH=1:0 to 100:1) to afford the title compound (4 g, 75%) as a pale yellow oil. LCMS-C: rt 0.98 min; m/z 191.0 [M+H]⁺.

(c) Ethyl 4-chloro-5-fluoro-3-methylbenzo[b]thiophene-2-carboxylate (I23) and Ethyl 4,7-difluoro-3-methylbenzo[b]thiophene-2-carboxylate (I24)

A suspension of 1-(2-chloro-3,6-difluorophenyl)ethan-1-one 122 (1.15 g, 6.05 mmol), ethyl 2-mercaptoacetate (727 mg, 6.05 mmol) and K₂CO₃ (1.26 g, 9.08 mmol) in DMF (20 mL) was heated at 50° C. overnight. The mixture was cooled to room temperature then poured into water and extracted with EtOAc (150 mL×2). The combined organic extracts were washed with water (150 mL×2), brine (150 mL), dried over anhydrous Na₂SO₄, filtered and concentrated under reduced pressure. The residue was purified by column chromatography (Pet. Ether/EtOAc=1:0 to 100:1) followed by C18 reverse-phase chromatography (95% MeOH, 4% H₂O, 1% TFA) to afford ethyl 4-chloro-5-fluoro-3-methylbenzo[b]thiophene-2-carboxylate (I23) (247 mg, 15%) as a white solid, LCMS-C: rt 2.89 min; m/z 272.9 [M+H]⁺ and ethyl 4,7-difluoro-3-methylbenzo[b]thiophene-2-carboxylate (I24) (520 mg, 32%) as a white solid, LCMS-C: rt 2.89 min; m/z 256.9, [M+H]⁺.

(xiv) 3,5-Difluoro-4-hydroxybenzamide (I25)

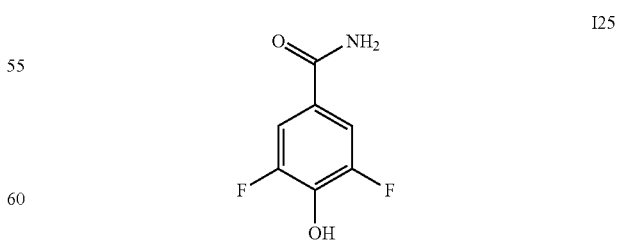

Prepared from 3,5-difluoro-4-hydroxybenzonitrile according to the procedure described for 3-chloro-4-hydroxybenzamide 19. LCMS-C: R10.34 min; m/z 174.0 [M+H]⁺.

(xv) Ethyl 3-(bromomethyl)-4-methoxythieno[3,2-c]
pyridine-2-carboxylate (I29)

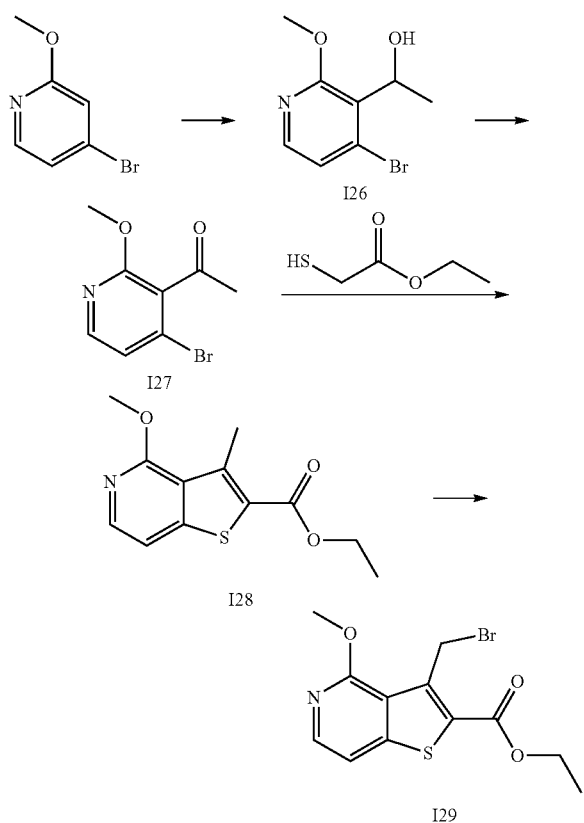

(a) 1-(4-Bromo-2-methoxypyridin-3-yl)ethan-1-ol
(I26)

To a solution of diisopropylamine (2.9 g, 28.7 mmol) in dry THF (30 mL) at −78° C. under nitrogen was added n-BuLi (2.5 M solution in hexanes, 12.5 mL, 31.1 mmol) dropwise and the mixture was stirred at −78° C. for 45 min. The resulting LDA solution was then added slowly to a solution of 4-bromo-2-methoxypyridine (4.5 g, 23.9 mmol) in THF (30 mL) at −78° C. and the mixture was stirred at −78° C. for 1 h. A solution of acetaldehyde (3.2 g, 71.8 mmol) in THF (20 mL) was then added dropwise and the mixture was allowed to warm to room temperature and stirred overnight. A saturated aqueous NH$_4$Cl solution (150 mL) was added and the mixture was extracted with EtOAc (200 mL×3). The combined organic extracts were washed with brine (200 mL), dried over Na$_2$SO$_4$, filtered and concentrated under reduced pressure to give the title compound (3.70 g, 67%) as a yellow oil. LCMS-C: rt 1.32 min; m/z 233.9 [M+H]$^+$.

(b) 1-(4-Bromo-2-methoxypyridin-3-yl)ethan-1-one
(I27)

To a solution of 1-(4-bromo-2-methoxypyridin-3-yl)ethan-1-ol (I26) (3.70 g, 15.9 mmol) in dichloromethane (200 mL) was added MnO$_2$ (13.9 g, 159 mmol) and the mixture was heated at reflux overnight. The mixture was filtered and the filtrate was concentrated under reduced pressure. The residue was purified by silica gel chromatography (Pet. Ether/EtOAc=100:1 to 80:1) to give the title compound (2.21 g, 60%) as a yellow oil. LCMS-C: rt 1.72 min; m/z 229.9 [M+H]$^+$. $^1$H NMR (400 MHz, DMSO-d$_6$) δ 8.11 (d, J=5.5 Hz, 1H), 7.34 (d, J=5.5 Hz, 1H), 3.91 (s, 3H), 2.47 (s, 3H).

(c) Ethyl 4-methoxy-3-methylthieno[3,2-c]pyridine-
2-carboxylate (I28)

A suspension of 1-(4-bromo-2-methoxypyridin-3-yl)ethan-1-one (I27) (2.21 g, 9.6 mmol), ethyl 2-mercaptoacetate (1.39 g, 11.5 mmol) and K$_2$CO$_3$ (3.98 g, 28.8 mmol) in DMF (50 mL) was stirred at room temperature under nitrogen overnight. The mixture was poured into water and extracted with EtOAc (350 mL×3). The combined organic extracts were washed with brine (500 mL), dried over Na$_2$SO$_4$, filtered and concentrated under reduced pressure. The residue was purified by silica gel chromatography (Pet. Ether/EtOAc=100:1 to 80:1) to give the title compound (835 mg, 35%) as a white solid. LCMS-F: rt 3.46 min; m/z 252.1 [M+H]$^+$.

(d) Ethyl 3-(bromomethyl)-4-methoxythieno[3,2-c]
pyridine-2-carboxylate (I29)

To a solution of ethyl 4-methoxy-3-methylthieno[3,2-c]pyridine-2-carboxylate (I28) (735 mg, 2.92 mmol) in 0014 (25 mL) was added NBS (531 mg, 2.98 mmol) and BPO (95 mg, 0.29 mmol) and the mixture was heated at reflux under nitrogen overnight. The mixture was concentrated under reduced pressure and the residue was purified by silica gel chromatography (Pet. Ether/EtOAc=1:0 to 40:1) to give the title compound (742 mg, 77%) as a white solid. LCMS-F: rt 3.47 min; m/z 330.0/332.0 [M+H]$^+$.

(xvi) Ethyl 7-bromo-3-(bromomethyl)-4-chlorobenzo[b]thiophene-2-carboxylate (I34)

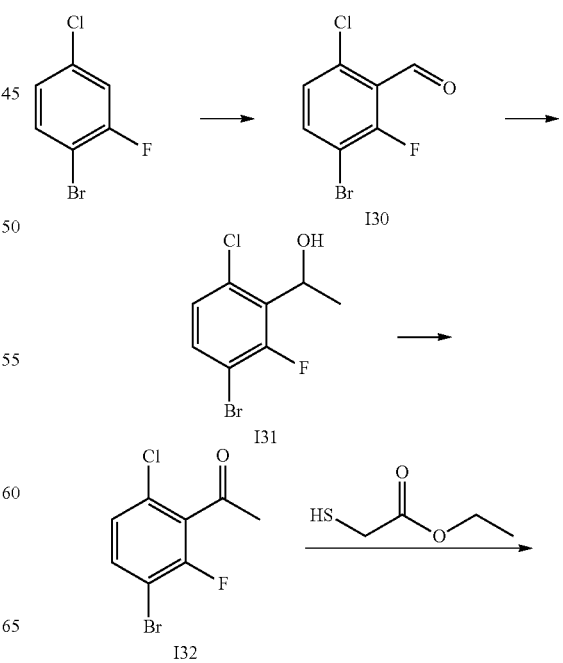

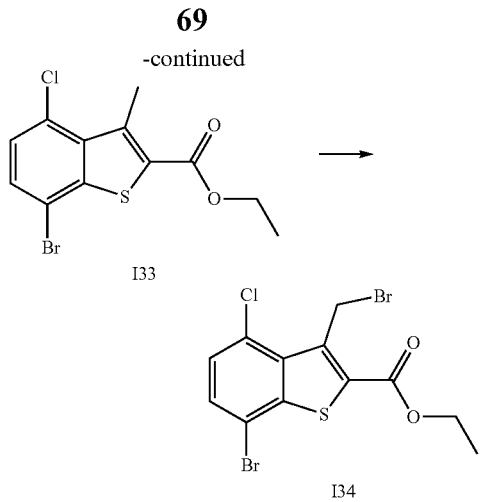

(a) 3-Bromo-6-chloro-2-fluorobenzaldehyde (I30)

To a solution of 1-bromo-4-chloro-2-fluorobenzene (10.0 g, 47.8 mmol) in dry THF (300 mL) at −78° C. under nitrogen was added LDA (2.0 M solution in THF, 31 mL, 62.1 mmol) dropwise and the mixture was stirred at −78° C. for 15 min. DMF (7.00 g, 95.8 mmol) was added and the mixture was allowed to warm to room temperature. The reaction mixture was quenched with a saturated aqueous NH$_4$Cl solution and the mixture was extracted with EtOAc (400 mL×3). The combined organic extracts were washed with brine (300 mL), dried over Na$_2$SO$_4$, filtered and concentrated under reduced pressure. The residue was purified by silica gel chromatography (100% Pet. Ether) to give the title compound (4.0 g, 35%) as a white solid, which was used directly in the next step.

(b) 1-(3-Bromo-6-chloro-2-fluorophenyl)ethan-1-ol (I31)

To a solution of 3-bromo-6-chloro-2-fluorobenzaldehyde (I30) (4.00 g, 16.8 mmol) in dry THF (48 mL) at 0° C. under nitrogen was added methyl magnesium bromide (3 M solution in THF, 7 mL, 20.5 mmol) dropwise and the mixture was allowed to warm to room temperature and stirred overnight. A saturated aqueous NH$_4$Cl solution (40 mL) was added and the mixture was extracted with EtOAc (200 mL×3). The combined organic extracts were washed with brine, dried over Na$_2$SO$_4$, filtered and concentrated under reduced pressure. The residue was purified by silica gel chromatography (Pet. Ether/EtOAc=200:1 to 5:1) to give the title compound (3.58 g, 84%) as a yellow oil. LCMS-C: rt 2.10 min; m/z 275.9/277.9 [M+H]$^+$.

(c) 1-(3-Bromo-6-chloro-2-fluorophenyl)ethan-1-one (I32)

To a solution of 1-(3-bromo-6-chloro-2-fluorophenyl)ethan-1-ol (I31) (3.58 g, 14.1 mmol) in dichloromethane (200 mL) was added MnO$_2$ (12.3 g, 141.2 mmol) and the mixture was stirred at room temperature overnight. The mixture was filtered and the filtrate was concentrated under reduced pressure. The residue was purified by silica gel chromatography (Pet. Ether/EtOAc=1:0 to 100:1) to give the title compound (2.0 g, 56%) as a yellow oil. LCMS-F: rt 2.59 min; m/z 250.9 [M+H]$^+$.

(d) Ethyl 7-bromo-4-chloro-3-methylbenzo[b]thiophene-2-carboxylate (I33)

A suspension of 1-(3-bromo-6-chloro-2-fluorophenyl)ethan-1-one (I32) (2.0 g, 7.95 mmol), ethyl 2-mercaptoacetate (1.15 g, 9.57 mmol) and K$_2$CO$_3$ (3.3 g, 23.9 mmol) in DMF (160 mL) was stirred at room temperature under nitrogen overnight. The mixture was poured into water and extracted with EtOAc (200 mL×3). The combined organic extracts were washed with brine (200 mL), dried over Na$_2$SO$_4$, filtered and concentrated under reduced pressure. The residue was purified by silica gel chromatography (Pet. Ether/EtOAc=1:0 to 100:1) to give the title compound (2.0 g, 76%) as a white solid, which was used directly in the next step.

(e) Ethyl 7-bromo-3-(bromomethyl)-4-chlorobenzo[b]thiophene-2-carboxylate (I34)

A mixture of ethyl 7-bromo-4-chloro-3-methylbenzo[b]thiophene-2-carboxylate (I33) (2.0 g, 6.0 mmol), NBS (1.09 g, 6.12 mmol) and BPO (194 mg, 0.60 mmol) in 0014 (50 mL) was heated at reflux under nitrogen overnight. The mixture was concentrated under reduced pressure and the residue was purified by silica gel chromatography (Pet. Ether/EtOAc=1:0 to 100:1) to give the title compound (2.20 g, 89%) as a white solid. $^1$H NMR (400 MHz, DMSO-d$_6$) δ 7.86 (d, J=8.2 Hz, 1H), 7.60 (d, J=8.3 Hz, 1H), 5.51 (s, 2H), 4.43 (q, J=7.1 Hz, 2H), 1.37 (t, J=7.1 Hz, 3H).

(xvii) Ethyl 5-(bromomethyl)-4-methoxythieno[2,3-d]pyrimidine-6-carboxylate (I37)

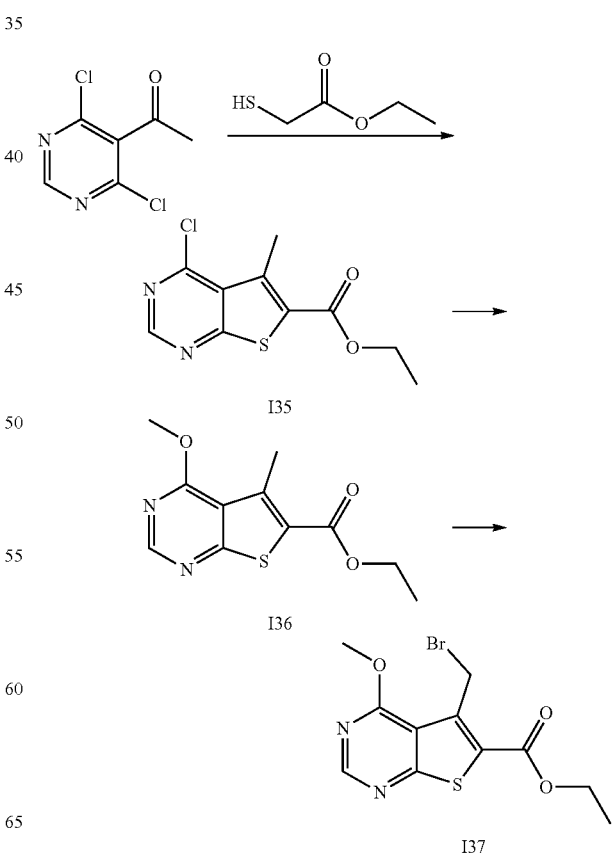

(a) Ethyl 4-chloro-5-methylthieno[2,3-d]pyrimidine-6-carboxylate (I35)

To a solution of 1-(4,6-dichloropyrimidin-5-yl)ethan-1-one (1.00 g, 5.24 mmol) in DMF (30 mL) was added ethyl 2-mercaptoacetate (755 mg, 6.29 mmol) and $K_2CO_3$ (2.17 g, 15.7 mmol) and the mixture was stirred at room temperature under nitrogen overnight. The mixture was poured into water and extracted with EtOAc (100 mL×3). The combined organic extracts were washed with brine (100 mL), dried over $Na_2SO_4$, filtered and concentrated under reduced pressure. The residue was purified by silica gel chromatography (Pet. Ether/EtOAc=200:1 to 40:1) to give the title compound (276 mg, 41%) as a white solid.

LCMS-F: rt 3.12 min; m/z 257.0 [M+H]$^+$.

(b) Ethyl 4-methoxy-5-methylthieno[2,3-d]pyrimidine-6-carboxylate (I36)

A mixture of ethyl 4-chloro-5-methylthieno[2,3-d]pyrimidine-6-carboxylate (I35) (576 mg, 2.24 mmol) and sodium methoxide (303 mg, 5.60 mmol) in THF (30 mL) was stirred at room temperature under nitrogen overnight. The mixture was concentrated under reduced pressure and the residue was purified by silica gel chromatography (Pet. Ether/EtOAc=100:1 to 50:1) to give the title compound (116 mg, 21%) as a white solid. LCMS-F: rt 3.15 min; m/z 253.1 [M+H]$^+$.

(c) Ethyl 5-(bromomethyl)-4-methoxythieno[2,3-d]pyrimidine-6-carboxylate (I37)

To a solution of ethyl 4-methoxy-5-methylthieno[2,3-d]pyrimidine-6-carboxylate (I36) (183 mg, 0.73 mmol) in 0014 (10 mL) was added NBS (132 mg, 0.75 mmol) and BPO (24 mg, 0.07 mmol) and the mixture was heated at reflux under nitrogen overnight. The mixture was concentrated under reduced pressure and the residue was purified by silica gel chromatography (Pet. Ether/EtOAc=100:1 to 50:1) to give the title compound (160 mg, 67%) as a white solid. LCMS-F: rt 3.15 min; m/z 330.9/332.9 [M+H]$^+$.

(xviii) Ethyl 3-(bromomethyl)-4-ethoxybenzo[b]thiophene-2-carboxylate (I40)

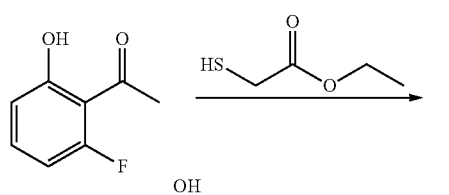

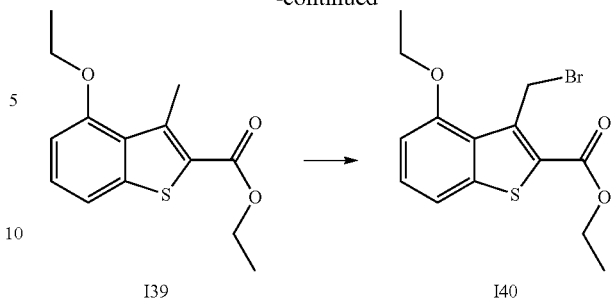

(a) Ethyl 4-hydroxy-3-methylbenzo[b]thiophene-2-carboxylate (I38)

To a solution of 1-(2-fluoro-6-hydroxyphenyl)ethan-1-one (2.0 g, 3.24 mmol) in DMF (20 mL) was added ethyl 2-mercaptoacetate (2.4 g, 4.86 mmol) and $K_2CO_3$ (3.6 g, 26.1 mmol) and the mixture was heated at 100° C. under nitrogen overnight. Water (100 mL) was added and the mixture was extracted with EtOAc (100 mL×3). The combined organic extracts were washed with water (100 mL×3), brine (100 mL), dried over $Na_2SO_4$, filtered and concentrated under reduced pressure. The residue was purified by silica gel chromatography (Pet. Ether/EtOAc=1:0 to 10:1) to give the title compound (1.8 g, 60%) as a grey solid. LCMS-C: rt 2.64 min; m/z 259.0 [M+Na]$^+$.

(b) Ethyl 4-ethoxy-3-methylbenzo[b]thiophene-2-carboxylate (I39)

A mixture of ethyl 4-hydroxy-3-methylbenzo[b]thiophene-2-carboxylate (I38) (300 mg, 1.27 mmol), $K_2CO_3$ (877 mg, 6.34 mmol) and ethyl iodide (6 mL) in DMF (10 mL) was stirred at room temperature in a sealed tube overnight. The mixture was poured into water and extracted with EtOAc. The combined organic extracts were washed with brine, dried over $Na_2SO_4$, filtered and concentrated under reduced pressure. The residue was purified by silica gel chromatography (Pet. Ether/EtOAc=1:0 to 50:1) to give the title compound (230 mg, 68%) as a white solid. $^1$H NMR (400 MHz, DMSO-$d_6$) δ 7.50 (d, J=7.6 Hz, 1H), 7.42 (t, J=8.0 Hz, 1H), 6.91 (d, J=8.0 Hz, 1H), 4.31 (q, J=7.1 Hz, 2H), 4.16 (q, J=6.9 Hz, 2H), 2.94 (s, 3H), 1.43 (t, J=6.9 Hz, 3H), 1.32 (t, J=7.1 Hz, 3H).

(c) Ethyl 3-(bromomethyl)-4-ethoxybenzo[b]thiophene-2-carboxylate (I40)

A suspension of ethyl 4-ethoxy-3-methylbenzo[b]thiophene-2-carboxylate (I39) (200 mg, 0.76 mmol), NBS (136 mg, 0.76 mmol) and AIBN (63 mg, 0.38 mmol) in 0014 (10 mL) was heated at reflux overnight. The mixture was allowed to cool to room temperature, concentrated under reduced pressure and the residue was purified by silica gel chromatography (Pet. Ether/EtOAc=1:0 to 100:1) to give the title compound (200 mg, 77%) as a white solid. LCMS-D: rt 3.38 min; m/z 364.9/366.9 [M+Na]$^+$.

(xix) Ethyl 3-(bromomethyl)-4-(methoxymethyl)benzo[b]thiophene-2-carboxylate (I46)

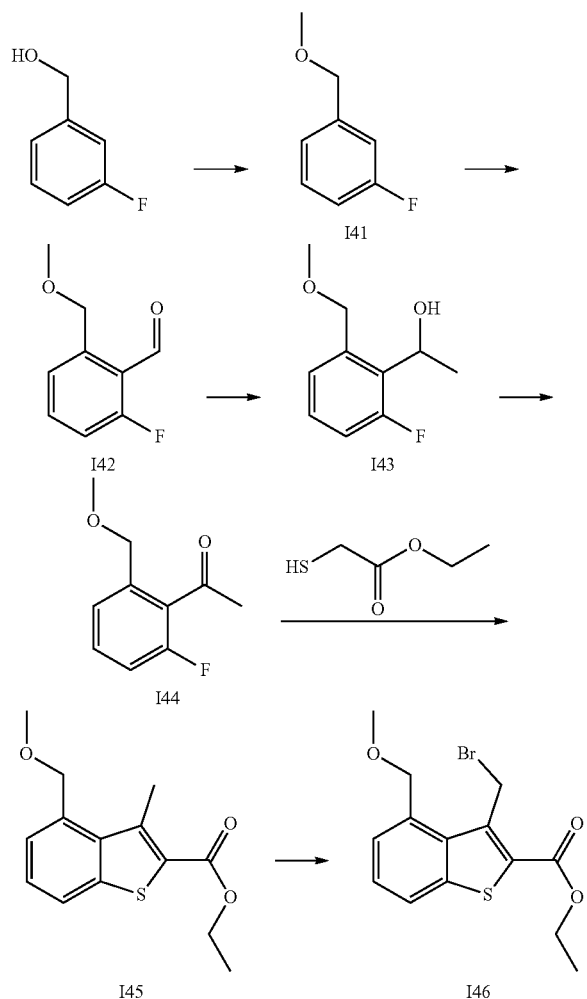

(a) 1-Fluoro-3-(methoxymethyl)benzene (I41)

To a solution of (3-fluorophenyl)methanol (15 g, 0.12 mol) in DMF (30 mL) at 0° C. was added NaH (60% dispersion in oil, 9.6 g, 0.24 mol) and the mixture was stirred for 30 min. MeI (15 mL, 0.24 mol) was then added and the mixture was allowed to warm to room temperature and stirred for 2 h. Water (300 mL) was added and the mixture was extracted with EtOAc (100 mL×3). The combined organic extracts were washed with water (150 mL×3), brine, dried over $Na_2SO_4$, filtered and concentrated under reduced pressure. The residue was purified by silica gel chromatography (Pet. Ether/EtOAc=1:0 to 100:1) to give the title compound (7.3 g, 43%) as a colorless oil. LCMS-C: rt 1.98 min; m/z 163.0 $[M+Na]^+$.

(b) 2-Fluoro-6-(methoxymethyl)benzaldehyde (I42)

To a solution of diisopropylamine (2.61 g, 25.8 mmol) in THF (20 mL) at −78° C. was added n-BuLi (2.5 M solution in hexanes, 11.2 mL, 28 mmol) and the mixture was stirred for 40 min. The resulting LDA solution was then added to a solution of 1-fluoro-3-(methoxymethyl)benzene (I41) (3.0 g, 21.5 mmol) in THF (20 mL) dropwise at −78° C. and the mixture was stirred for 1 h. A solution of DMF (2.1 mL, 25.8 mmol) in THF (10 mL) was then added dropwise and the mixture was stirred at −78° C. for a further 30 min. The reaction mixture was quenched with a saturated aqueous $NH_4Cl$ solution (30 mL) and the mixture was diluted with water (300 mL) and extracted with EtOAc (100 mL×3). The combined organic extracts were washed with water (150 mL×3), brine, dried over $Na_2SO_4$, filtered and concentrated under reduced pressure. The residue was purified by silica gel chromatography (Pet. Ether/EtOAc=1:0 to 100:1) to give the title compound (400 mg, 11%) as a yellow oil. LCMS-C: rt 1.19 min; m/z 169.0 $[M+H]^+$.

(c) 1-(2-Fluoro-6-(methoxymethyl)phenyl)ethan-1-ol (I43)

To a solution of 2-fluoro-6-(methoxymethyl)benzaldehyde (I42) (636 mg, 3.8 mmol) in dry THF (20 mL) at 0° C. was added methyl magnesium bromide (3.0 M solution in THF, 5.0 mL, 15.2 mmol) dropwise and the mixture was allowed to warm to room temperature and stirred overnight. The reaction mixture was quenched with a saturated aqueous $NH_4Cl$ solution (10 mL) and then extracted with EtOAc (100 mL×3). The combined organic extracts were washed with brine, dried over $Na_2SO_4$, filtered and concentrated under reduced pressure. The residue was purified by silica gel chromatography (Pet. Ether/EtOAc=1:0 to 50:1) to give the title compound (550 mg, 79%) as a yellow oil. LCMS-C: rt 0.86 min; m/z 207.0 $[M+Na]^+$.

(d) 1-(2-Fluoro-6-(methoxymethyl)phenyl)ethan-1-one (I44)

To a solution of 1-(2-fluoro-6-(methoxymethyl)phenyl)ethan-1-ol (I43) (550 mg, 3.0 mmol) in acetone (8 mL) at 0° C. was added a solution of $CrO_3$ (420 mg, 4.2 mmol) and concentrated $H_2SO_4$ (1 mL) in water (3 mL) dropwise. The mixture was stirred at 0° C. for 1 h then diluted with water (5 mL) and extracted with EtOAc (100 mL×3). The combined organic extracts were washed with brine, dried over $Na_2SO_4$, filtered and concentrated under reduced pressure. The residue was purified by silica gel chromatography (Pet. Ether/EtOAc=1:0 to 50:1) to give the title compound (516 mg, 94%) as a yellow oil. LCMS-C: rt 1.43 min; m/z 205.0 $[M+Na]^+$.

(e) Ethyl 4-(methoxymethyl)-3-methylbenzo[b]thiophene-2-carboxylate (I45)

A mixture of 1-(2-fluoro-6-(methoxymethyl)phenyl)ethan-1-one (I44) (516 mg, 2.84 mmol), ethyl 2-mercaptoacetate (517 mg, 4.2 mmol) and $K_2CO_3$ (785 mg, 5.68 mmol) in DMF (30 mL) was heated at 120° C. overnight. The mixture was allowed to cool to room temperature before being partitioned between water (300 mL) and EtOAc (100 mL). The layers were separated and the aqueous layer was extracted with EtOAc (100 mL×3). The combined organic layers were dried over $Na_2SO_4$, filtered and concentrated under reduced pressure. The residue was purified by silica gel chromatography (Pet. Ether/EtOAc=1:0 to 100:1) to give the title compound (365 mg, 49%) as a yellow oil. LCMS-C: rt 2.55 min; m/z 265.0 $[M+H]^+$.

(f) Ethyl 3-(bromomethyl)-4-(methoxymethyl)benzo[b]thiophene-2-carboxylate (I46)

A suspension of ethyl 4-(methoxymethyl)-3-methylbenzo[b]thiophene-2-carboxylate (I45) (350 mg, 1.3 mmol), NBS (285 mg, 1.6 mmol) and BPO (32 mg, 0.13 mmol) in CCl₄ (10 mL) was heated at reflux for 1.5 h. The mixture was allowed to cool to room temperature, concentrated under reduced pressure and the residue was purified by silica gel chromatography (Pet. Ether/EtOAc=1:0 to 100:1) to give the title compound (230 mg, 52%) as a white solid. LCMS-C: rt 2.78 min; m/z 342.9 [M+H]⁺.

(xx) Ethyl 4-bromo-3-(bromomethyl)-7-fluorobenzo[b]thiophene-2-carboxylate (I52)

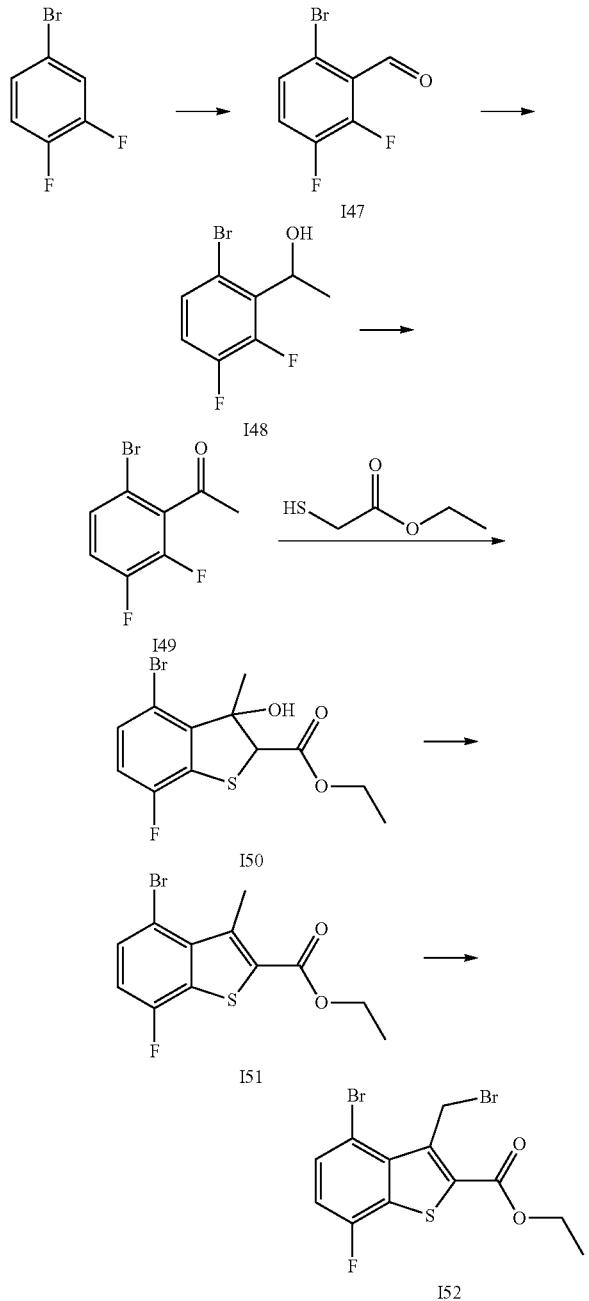

(a) 6-Bromo-2,3-difluorobenzaldehyde (I47)

To a solution of 4-bromo-1,2-difluorobenzene (5.0 g, 25.9 mmol) in dry THF (200 mL) at −78° C. under nitrogen was added LDA (2.0 M solution in THF, 17 mL, 33.7 mmol) dropwise and the mixture was stirred at −78° C. for 15 min. DMF (3.8 g, 51.8 mmol) was then added slowly and the mixture was allowed to warm to room temperature. The reaction mixture was quenched with a saturated aqueous NH₄Cl solution and then extracted with EtOAc (200 mL×3). The combined organic extracts were washed with brine, dried over Na₂SO₄, filtered and concentrated under reduced pressure. The residue was purified by silica gel chromatography (100% Pet. Ether) to give the title compound (1.3 g, 23%) as a yellow solid. ¹H NMR (400 MHz, DMSO-d₆) δ 10.3 (t, J=1.2 Hz, 1H), 7.77-7.66 (m, 2H).

(b) 1-(6-Bromo-2,3-difluorophenyl)ethan-1-ol (I48)

To a solution of 6-bromo-2,3-difluorobenzaldehyde (I47) (1.86 g, 8.46 mmol) in dry THF (25 mL) at 0° C. under nitrogen was added methyl magnesium bromide (3 M solution in THF, 3.5 mL, 10.3 mmol) dropwise before the mixture was allowed to warm to room temperature and stirred overnight. The reaction mixture was quenched with 2 M aqueous HCl and then extracted with EtOAc (200 mL×3). The combined organic extracts were washed with brine, dried over Na₂SO₄, filtered and concentrated under reduced pressure. The residue was purified by silica gel chromatography (Pet. Ether/EtOAc=100:1 to 5:1) to give the title compound (1.73 g, 93%) as a yellow solid. ¹H NMR (400 MHz, DMSO-d₆) δ 7.48-7.43 (m, 1H), 7.37-7.28 (m, 1H), 5.57 (d, J=4.4 Hz, 1H), 5.20-5.11 (m, 1H), 1.44 (d, J=6.7, 1.0 Hz, 3H).

(c) 1-(6-Bromo-2,3-difluorophenyl)ethan-1-one (I49)

A mixture of 1-(6-bromo-2,3-difluorophenyl)ethan-1-ol (I48) (1.73 g, 7.30 mmol) and MnO₂ (6.34 g, 73.0 mmol) in dichloromethane (100 mL) was stirred at room temperature overnight. The mixture was filtered and the filtrate was concentrated under reduced pressure. The residue was purified by silica gel chromatography (Pet. ether/EtOAc=100:1 to 5:1) to give the title compound (850 mg, 49%) as a yellow oil, which was used directly in the next step. ¹H NMR (400 MHz, DMSO-d₆) δ 7.63-7.51 (m, 2H), 2.59 (d, J=1.1 Hz, 3H).

(d) Ethyl 4-bromo-7-fluoro-3-hydroxy-3-methyl-2,3-dihydrobenzo[b]thiophene-2-carboxylate (I50)

To a solution of 1-(6-bromo-2,3-difluorophenyl)ethan-1-one (I49) (855 mg, 3.64 mmol) in DMF (100 mL) was added ethyl 2-mercaptoacetate (525 mg, 4.37 mmol) and K₂CO₃ (1.50 g, 10.9 mmol) and the mixture was stirred at room temperature overnight. The mixture was poured into water (400 mL), extracted with EtOAc (400 mL×3) and the combined organic extracts were washed with brine (400 mL), dried over Na₂SO₄, filtered and concentrated under reduced pressure. The residue was purified by silica gel chromatography (Pet. Ether/EtOAc=100:1 to 20:1) to give the title compound (726 mg, 63%) as a yellow oil. ¹H NMR (400 MHz, DMSO-d₆) δ 7.36 (dd, J=8.7, 4.8 Hz, 1H), 7.12 (t, J=8.7 Hz, 1H), 6.27 (s, 1H), 4.75 (s, 1H), 4.26-4.16 (m, 2H), 1.44 (s, 3H), 1.24 (t, J=7.1 Hz, 3H).

(e) Ethyl 4-bromo-7-fluoro-3-methylbenzo[b]thiophene-2-carboxylate (I51)

To a solution of ethyl 4-bromo-7-fluoro-3-hydroxy-3-methyl-2,3-dihydrobenzo[b]thiophene-2-carboxylate (I50)

(950 mg, 2.84 mmol) in DMF (70 mL) was added K$_2$CO$_3$ (1.65 g, 11.9 mmol) and the mixture was heated at 75° C. for 2 h. The mixture was poured into water (300 mL) and extracted with EtOAc (200 mL×3). The combined organic extracts were washed with brine (200 mL), dried over Na$_2$SO$_4$, filtered and concentrated under reduced pressure to give the title compound (902 mg, 100%) as a white solid, which was used directly in the next step.

(f) Ethyl 4-bromo-3-(bromomethyl)-7-fluorobenzo[b]thiophene-2-carboxylate (I52)

A mixture of ethyl 4-bromo-7-fluoro-3-methylbenzo[b]thiophene-2-carboxylate (I51) (1.0 g, 3.15 mmol), NBS (572 mg, 3.21 mmol) and BPO (102 mg, 0.32 mmol) in 0014 (50 mL) was heated at reflux under nitrogen for 16 h. The mixture was concentrated under reduced pressure and the residue was purified by silica gel chromatography (Pet. Ether/EtOAc=1:0 to 40:1) to give the title compound (660 mg, 53%) as a white solid. $^1$H NMR (400 MHz, DMSO-d$_6$) δ 7.85 (dd, J=8.5, 4.9 Hz, 1H), 7.46 (t, J=8.8 Hz, 1H), 5.55 (s, 2H), 4.42 (q, J=7.1 Hz, 2H), 1.37 (t, J=7.1 Hz, 3H).

(xxi) Ethyl 3-(bromomethyl)-4-chloro-7-fluorobenzo[b]thiophene-2-carboxylate (I56)

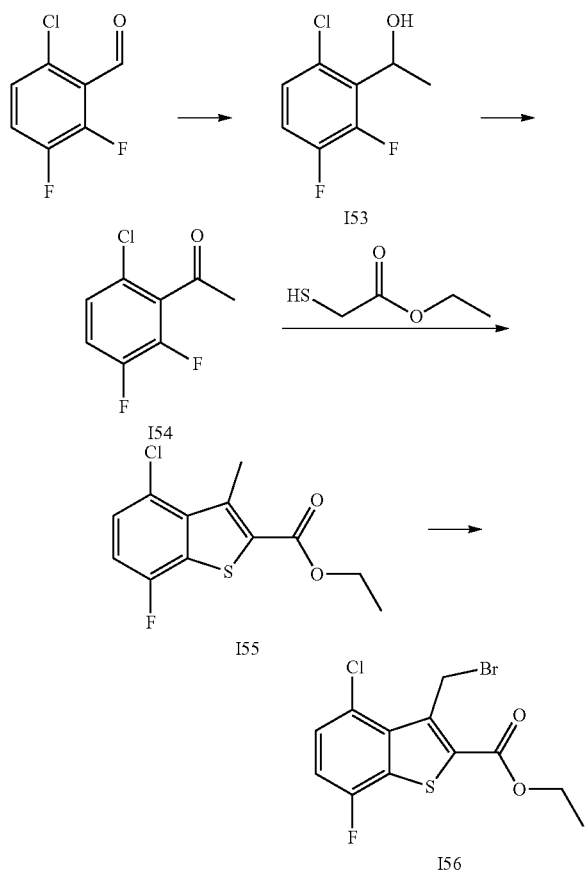

(a) 1-(6-Chloro-2,3-difluorophenyl)ethan-1-ol (I53)

To a solution of 6-chloro-2,3-difluorobenzaldehyde (1.0 g, 5.67 mmol) in dry THF (30 mL) under nitrogen was added methyl magnesium bromide (3 M solution in THF, 7.6 mL, 22.7 mmol) dropwise and the mixture was allowed to warm to room temperature and stirred overnight. A saturated aqueous NH$_4$Cl solution (100 mL) was added and the mixture was extracted with EtOAc (100 mL×2). The combined organic extracts were washed with brine, dried over Na$_2$SO$_4$, filtered and concentrated under reduced pressure to give the title compound (1.44 g, >100%), which was used in the next step without further purification. LCMS-C: rt 1.22 min; m/z 192.9 [M+H]$^+$.

(b) 1-(6-Chloro-2,3-difluorophenyl)ethan-1-one (I54)

To a solution of 1-(6-chloro-2,3-difluorophenyl)ethan-1-ol (I53) (1.44 g) in acetone (15 mL) at 0° C. was added a solution of CrO$_3$ (1.01 g, 10.1 mmol) and concentrated sulfuric acid (2 mL) in water (7 mL) dropwise. The mixture was stirred at 0° C. for 1 h then diluted with water (100 mL) and extracted with EtOAc (100 mL×2). The combined organic extracts were concentrated under reduced pressure and the residue was purified by silica gel chromatography (Pet. Ether/EtOAc=1:0 to 10:1) to give the title compound (960 mg, 89% over two steps) as a pale yellow oil. LCMS-C: rt 1.34 min; m/z 191.0 [M+H]$^+$.

(c) Ethyl 4-chloro-7-fluoro-3-methylbenzo[b]thiophene-2-carboxylate (I55)

A suspension of 1-(6-chloro-2,3-difluorophenyl)ethan-1-one (I54) (480 mg, 2.53 mmol), ethyl 2-mercaptoacetate (305 mg, 2.53 mmol) and K$_2$CO$_3$ (524 mg, 3.79 mmol) in DMF (20 mL) was heated at 50° C. under nitrogen overnight. Water (100 mL) was added and the mixture was extracted with EtOAc (50 mL×3). The combined organic extracts were washed with water (100 mL×3), brine (100 mL) and concentrated under reduced pressure. The residue was purified by silica gel chromatography (Pet. Ether/EtOAc=1:0 to 100:1) to give the title compound (740 mg, >100%) as a pale yellow solid. The material was used in the next step without further purification. $^1$H NMR (400 MHz, DMSO-d$_6$) δ 7.53 (dd, J=8.5, 4.7 Hz, 1H), 7.41 (t, J=8.7 Hz, 1H), 4.35 (q, J=7.1 Hz, 2H), 2.98 (s, 3H), 1.33 (t, J=7.1 Hz, 3H).

(d) Ethyl 3-(bromomethyl)-4-chloro-7-fluorobenzo[b]thiophene-2-carboxylate (I56)

A suspension of ethyl 4-chloro-7-fluoro-3-methylbenzo[b]thiophene-2-carboxylate (I55) (740 mg), NBS (581 mg, 3.27 mmol) and BPO (66 mg, 0.27 mmol) in 0014 (25 mL) was heated at reflux under nitrogen overnight. The mixture was concentrated under reduced pressure and the residue was purified by silica gel chromatography (Pet. Ether/EtOAc=1:0 to 100:1) to give the title compound (840 mg, 95% over two steps) as a yellow solid. $^1$H NMR (400 MHz, DMSO-d$_6$) δ 7.67-7.60 (m, 1H), 7.50 (t, J=8.7 Hz, 1H), 5.47 (s, 2H), 4.41 (q, J=7.1 Hz, 2H), 1.36 (t, J=7.0 Hz, 3H).

(xxii) Ethyl 3-(bromomethyl)-4-chlorothieno[3,2-c]pyridine-2-carboxylate (I60)

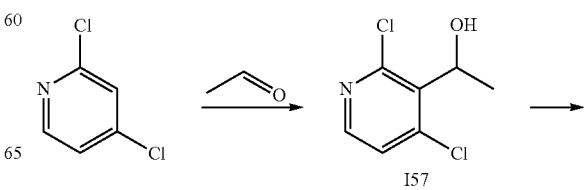

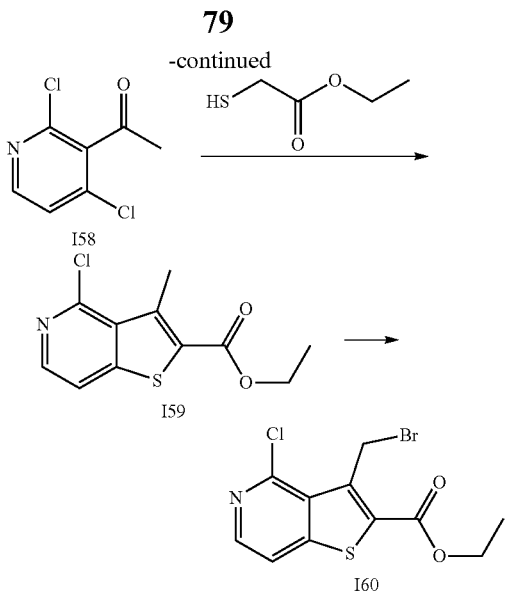

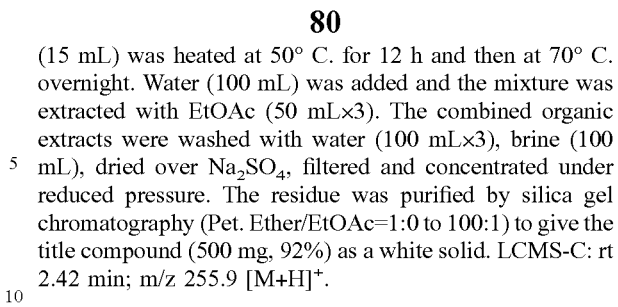

(a) 1-(2,4-Dichloropyridin-3-yl)ethan-1-ol (I57)

To a solution of diisopropylamine (4.1 g, 40.6 mmol) in dry THF (30 mL) at −78° C. under nitrogen was added n-BuLi (2.5 M solution in hexane, 17.6 mL, 43.9 mmol) dropwise and the mixture was stirred at −78° C. for 45 min. The resulting LDA solution was added slowly to a solution of 2,4-dichloropyridine (5.0 g, 33.8 mmol) in THF (30 mL) and the mixture was stirred at −78° C. for 1 h. A solution of acetaldehyde (4.5 g, 101 mmol) in THF (20 mL) was added dropwise and the mixture was allowed to warm to room temperature and stirred overnight. A saturated aqueous $NH_4Cl$ solution (200 mL) was added and the mixture was extracted with EtOAc (200 mL×3). The combined organic extracts were washed with a saturated aqueous $NH_4Cl$ solution, brine, dried over $Na_2SO_4$, filtered and concentrated under reduced pressure. The residue was purified by silica gel chromatography (Pet. Ether/EtOAc=100:1 to 10:1) to give the title compound (2.7 g, 42%) as a yellow oil. LCMS-C: rt 0.64 min; m/z 191.9/193.9 [M+H]+.

(b) 1-(2,4-Dichloropyridin-3-yl)ethan-1-one (I58)

Freshly activated 4 Å molecular sieves (3.5 g) and NMO (2.5 g, 21.2 mmol) were added to a solution of 1-(2,4-dichloropyridin-3-yl)ethan-1-ol (I57) (2.7 g, 14.1 mmol) in DCM (30 mL) and the mixture was stirred for 15 min. TPAP (248 mg, 0.71 mmol) was added and the mixture was stirred at room temperature for 2 h. The solids were removed by filtration and the filtrate was diluted with water (100 mL) and extracted with EtOAc (100 mL×3). The combined organic layers were washed with brine, dried over $Na_2SO_4$, filtered and concentrated under reduced pressure. The residue was purified by silica gel chromatography (Pet. Ether/EtOAc=1:0 to 30:1) to give the title compound (2.4 g, 90%) as a pale yellow oil. LCMS-C: rt 1.17 min; m/z 189.9 [M+H]+.

(c) Ethyl 4-chloro-3-methylthieno[3,2-c]pyridine-2-carboxylate (I59)

A suspension of 1-(2,4-dichloropyridin-3-yl)ethan-1-one (I58) (400 mg, 2.12 mmol), ethyl 2-mercaptoacetate (255 mg, 2.12 mmol) and $K_2CO_3$ (440 mg, 3.18 mmol) in DMF (15 mL) was heated at 50° C. for 12 h and then at 70° C. overnight. Water (100 mL) was added and the mixture was extracted with EtOAc (50 mL×3). The combined organic extracts were washed with water (100 mL×3), brine (100 mL), dried over $Na_2SO_4$, filtered and concentrated under reduced pressure. The residue was purified by silica gel chromatography (Pet. Ether/EtOAc=1:0 to 100:1) to give the title compound (500 mg, 92%) as a white solid. LCMS-C: rt 2.42 min; m/z 255.9 [M+H]+.

(d) Ethyl 3-(bromomethyl)-4-chlorothieno[3,2-c]pyridine-2-carboxylate (I60)

A mixture of ethyl 4-chloro-3-methylthieno[3,2-c]pyridine-2-carboxylate (I59) (489 mg, 1.92 mmol), NBS (684 mg, 3.84 mmol) and BPO (47 mg, 0.2 mmol) in $CCl_4$ (20 mL) was heated at reflux for 3 h. The mixture was concentrated under reduced pressure and the residue was purified by silica gel chromatography (Pet. Ether/EtOAc=1:0 to 100:1) to give the title compound (500 mg, 78%) as a white solid. LCMS-C: rt 2.53 min; m/z 333.8 [M+H]+.

(xxiii) Ethyl 4-bromo-3-(bromomethyl)benzo[b]thiophene-2-carboxylate (I62)

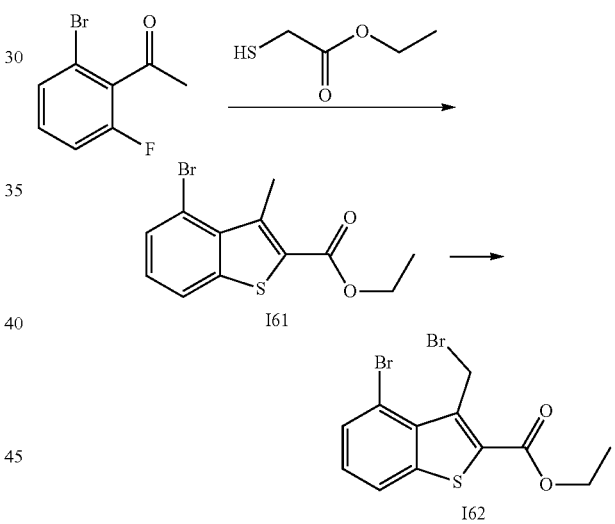

(a) Ethyl 4-bromo-3-methylbenzo[b]thiophene-2-carboxylate (I61)

A solution of 1-(2-bromo-6-fluorophenyl)ethanone (2.85 g, 13.1 mmol), ethyl 2-mercaptoacetate (2.37 g, 19.7 mmol) and $K_2CO_3$ (3.63 g, 26.3 mmol) in DMF (30 mL) was heated at 100° C. overnight. Water (100 mL) was added and the mixture was extracted with EtOAc (200 mL×3). The combined organic extracts were washed with water (200 mL×3), brine, dried over $Na_2SO_4$, filtered and concentrated under reduced pressure. The residue was purified by silica gel chromatography (Pet. Ether/EtOAc=1:0 to 100:1) to give the title compound (1.85 g, 47%) as a white solid. LCMS-C: rt 2.23 min; m/z 299.1 [M+H]+. 1H NMR (400 MHz, DMSO-$d_6$) δ 8.06 (dd, J=8.1, 1.0 Hz, 1H), 7.87-7.76 (m, 1H), 7.73 (dd, J=7.7, 1.0 Hz, 1H), 4.34 (q, J=8.0 Hz, 2H), 3.05 (s, 3H), 1.32 (t, J=8.0 Hz, 3H).

(b) Ethyl 4-bromo-3-(bromomethyl)benzo[b]thiophene-2-carboxylate (I62)

A suspension of ethyl 4-bromo-3-methylbenzo[b]thiophene-2-carboxylate (I61) (1.82 g, 6.15 mmol), NBS (1.2 g, 6.77 mmol) and BPO (149 mg, 0.615 mmol) in 0014 (40 mL) was heated at reflux for 1.5 h. The mixture was allowed to cool to room temperature, concentrated under reduced pressure and the residue was diluted with water and extracted with EtOAc (200 mL×3). The combined organic extracts were washed with brine, dried over $Na_2SO_4$, filtered and concentrated under reduced pressure. The residue was purified by silica gel chromatography (Pet. Ether/EtOAc=1:0 to 100:1) to give the title compound (1.88 g, 82%) as a white solid. LCMS-C: rt 2.27 min; m/z 376.8 [M+H]$^+$. $^1$H NMR (400 MHz, DMSO-$d_6$) δ 8.16 (d, J=8.1 Hz, 1H), 7.82 (d, J=7.6 Hz, 1H), 7.48 (t, J=7.9 Hz, 1H), 5.59 (s, 2H), 4.40 (q, J=7.1 Hz, 2H), 1.36 (t, J=7.8 Hz, 3H).

(xxiv) 3-Fluoro-4-hydroxy-5-(hydroxymethyl)benzamide (I69)

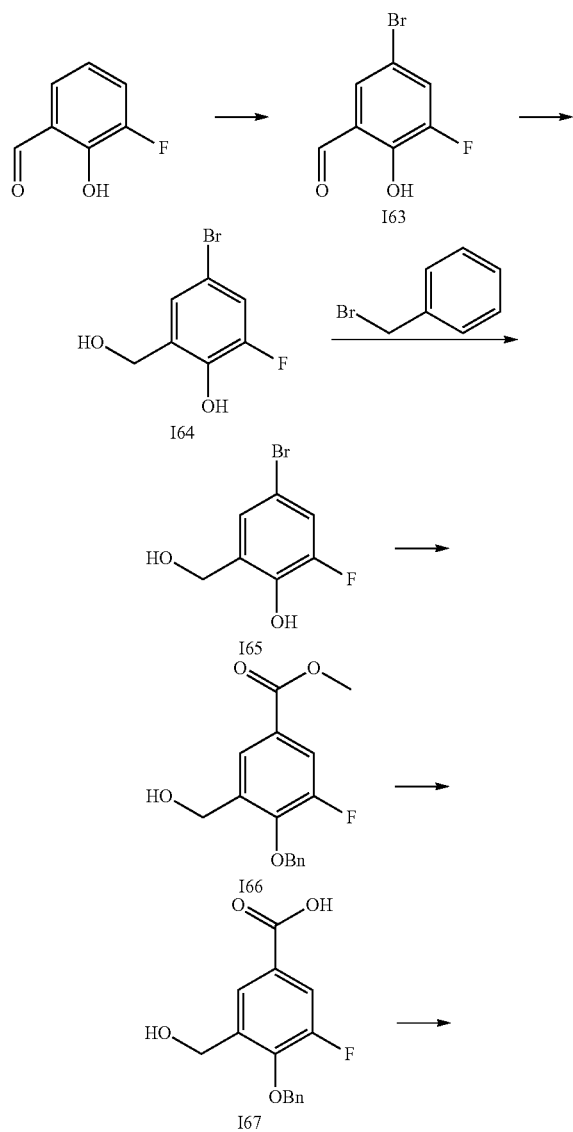

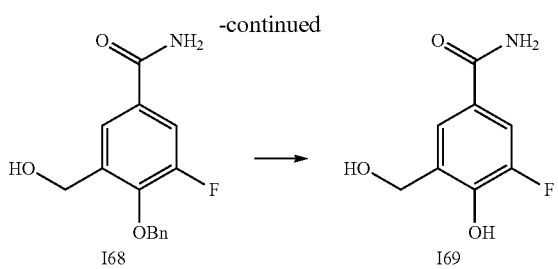

(a) 5-Bromo-3-fluoro-2-hydroxybenzaldehyde (I63)

To a solution of 3-fluoro-2-hydroxybenzaldehyde (3.43 g, 24.5 mmol) in acetonitrile (30 mL) under nitrogen was added NBS (4.36 g, 24.5 mmol) and ammonium acetate (189 mg, 2.45 mmol) and the mixture was stirred at room temperature overnight. The mixture was concentrated under reduced pressure and the residue was diluted with EtOAc and washed with brine, dried over $Na_2SO_4$, filtered and concentrated under reduced pressure to give the title compound (5.0 g, 94%) as a white solid. LCMS-F: rt 3.70 min; m/z 217.0/219.0 [M−H]$^-$.

(b) 4-Bromo-2-fluoro-6-(hydroxymethyl)phenol (I64)

To a solution of 5-bromo-3-fluoro-2-hydroxybenzaldehyde (I63) (5.0 g, 23.0 mmol) in MeOH (50 mL) at 0° C. was added $NaBH_4$ (1.8 g, 45.9 mmol) portion-wise over 30 min. The mixture was then allowed to warm to room temperature and stirred overnight. The mixture was acidified with a 2 M aqueous HCl solution and extracted with EtOAc. The combined organic extracts were washed with water, brine, dried over $Na_2SO_4$, filtered and concentrated under reduced pressure to give the title compound (6.5 g, >100%) as a brown solid, which was used in the next step without further purification. LCMS-F: rt 3.01 min; m/z 219.0/221.0 [M−H]$^-$.

(c) (2-(Benzyloxy)-5-bromo-3-fluorophenyl)methanol (I65)

To a solution of 4-bromo-2-fluoro-6-(hydroxymethyl)phenol (I64) (5.35 g, 27.9 mmol) in DMF (300 mL) was added benzyl bromide (7.6 g, 44.3 mmol) and $K_2CO_3$ (12.3 g, 88.6 mmol) and the mixture was stirred at room temperature overnight. The mixture was poured into water and extracted with EtOAc. The combined organic extracts were washed with water, brine, dried over $Na_2SO_4$, filtered and concentrated under reduced pressure. The residue was purified by silica gel chromatography (Pet. Ether/EtOAc=20:1) to give the title compound (6.8 g, 74%) as a white solid. $^1$H NMR (400 MHz, DMSO-$d_6$) δ 7.49 (dd, J=10.8, 2.5 Hz, 1H), 7.45-7.32 (m, 6H), 5.45-5.40 (m, 1H), 5.04 (s, 2H), 4.45 (d, J=5.7 Hz, 2H).

(d) Methyl 4-(benzyloxy)-3-fluoro-5-(hydroxymethyl)benzoate (I66)

A mixture of (2-(benzyloxy)-5-bromo-3-fluorophenyl)methanol (I65) (6.8 g, 21.9 mmol), Pd(dppf)Cl$_2$ (800 mg, 1.1 mmol) and triethylamine (6.6 g, 65.6 mmol) in methanol (20 mL) was heated at 110° C. in a sealed tube under a carbon monoxide atmosphere overnight. The mixture was diluted with water, extracted with EtOAc and the combined organic extracts were washed with water, brine, dried over $Na_2SO_4$, filtered and concentrated under reduced pressure. The residue was purified by silica gel chromatography (Pet. Ether/EtOAc=10:1) to give the title compound (2.0 g, 32%) as a yellow oil. LCMS-F: rt 3.92 min; m/z 313.1 [M+Na]+ $^1$H NMR (400 MHz, DMSO-$d_6$) δ 7.89 (s, 1H), 7.66 (dd, J=12.0, 2.1 Hz, 1H), 7.47-7.30 (m, 5H), 5.37 (t, J=5.5 Hz, 1H), 5.18 (s, 2H), 4.51 (d, J=4.4 Hz, 2H), 3.85 (s, 3H).

(e) 4-(Benzyloxy)-3-fluoro-5-(hydroxymethyl)benzoic acid (I67)

To a solution of methyl 4-(benzyloxy)-3-fluoro-5-(hydroxymethyl)benzoate (I66) ZXW-785-093 (2.0 g, 6.9 mmol) in THF/$H_2O$ (50 mL/25 mL) was added LiOH.$H_2O$ (867 mg, 20.7 mmol) and the mixture was stirred at room temperature overnight. The solvent was removed under reduced pressure and the residue was diluted with water (30 mL), acidified to pH 4-5 with a 2 M aqueous HCl solution and the resulting precipitate was collected by filtration and dried under reduced pressure to give the title compound (1.8 g, 95%) as a white solid. LCMS-F: rt 2.25 min; m/z 299.0 [M+Na]+.

(f) 4-(Benzyloxy)-3-fluoro-5-(hydroxymethyl)benzamide (I68)

To a solution of 4-(benzyloxy)-3-fluoro-5-(hydroxymethyl)benzoic acid (I67) (1.8 g, 6.0 mmol) in DMF (20 mL) was added $NH_4Cl$ (691 mg, 13.0 mmol) and the mixture was stirred at room temperature for 30 min. HATU (3.0 g, 7.8 mmol) and DIPEA (2.5 g, 19.5 mmol) were added and the mixture was stirred at room temperature overnight. The mixture was diluted with water, extracted with EtOAc and the combined organic extracts were washed with brine, dried over $Na_2SO_4$, filtered and concentrated under reduced pressure. The residue was purified by silica gel chromatography (DCM/MeOH=20:1 to 10:1) to give the title compound (1.5 g, 83%) as a yellow oil. LCMS-F: rt 1.14 min; m/z 275.9 [M+H]+.

(g) 3-Fluoro-4-hydroxy-5-(hydroxymethyl)benzamide (I69)

A mixture of 4-(benzyloxy)-3-fluoro-5-(hydroxymethyl)benzamide (I68) (1.5 g, 5.5 mmol) and 10% Pd/C (wetted with ca. 55% water, 150 mg) in methanol (30 mL) was heated at 80° C. in a sealed tube under a hydrogen atmosphere overnight. The mixture was filtered and the filtrate was concentrated under reduced pressure. The residue was purified by silica gel chromatography (DCM/MeOH=20:1 to 10:1) to give the title compound (900 mg, 90%) as a white solid. LCMS-F: rt 0.64 min; m/z 207.8 [M+Na]+.

(xxvi) 4-Hydroxy-2-methoxybenzamide (I75)

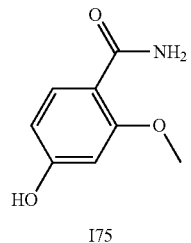

(a) Methyl 4-hydroxy-2-methoxybenzoate (I74)

To a solution of 4-bromo-3-methoxyphenol (500 mg, 2.46 mmol) in MeOH (5 mL) was added $Et_3N$ (1.47 g, 9.85 mmol) and Pd(dppf)$Cl_2$ (180 mg, 0.246 mmol) and the mixture was heated at 90° C. in a sealed tube under a CO atmosphere overnight. Water was added and the mixture was extracted with EtOAc. The combined organic extracts were concentrated under reduced pressure and the residue was purified by silica gel chromatography (DCM/MeOH=50:1) to give the title compound (100 mg, 22%) as a red solid. LCMS-F: rt 0.87 min; m/z 204.9 [M+Na]+.

(b) 4-Hydroxy-2-methoxybenzamide (I75)

To a solution of methyl 4-hydroxy-2-methoxybenzoate (I74) (100 mg, 0.55 mmol) in MeOH (6 mL) was added a 7% aqueous $NH_3$ solution (4 mL), the flask was sealed and the mixture was heated at 90° C. overnight. After cooling to room temperature, water was added and the mixture was extracted with EtOAc. The combined organic extracts were concentrated under reduced pressure and the residue was purified by silica gel chromatography (Pet. Ether/EtOAc=5:1) to give the title compound (32 mg, 35%) as a white solid. LCMS-F: rt 0.67 min; m/z 167.9 [M+H]+.

(xxvii) tert-Butyl (1-chloroethyl) carbonate (I76)

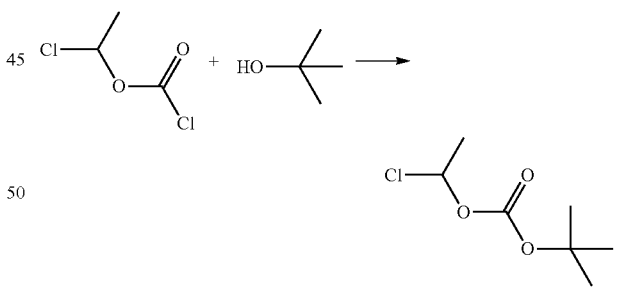

To a solution of 1-chloroethyl carbonochloridate (5.0 g, 35 mmol) in hexane (30 mL) at 0° C. was added a solution of pyridine (6.92 g, 87.4 mmol) in hexane (10 mL) dropwise. A white precipitate formed after complete addition. A solution of t-butanol (3.9 g, 52.4 mmol) in hexane (10 mL) was added and the mixture was stirred at 0° C. for 2 h then allowed to warm to room temperature and stirred for a further 1 h. The mixture was diluted with hexane and washed with a saturated aqueous $NaHCO_3$ solution followed by water. The organic layer was dried over $Na_2SO_4$, filtered and concentrated under reduced pressure to give the title compound (900 mg, 14%) as a colorless oil. $^1$H NMR (400 MHz, DMSO-d$_6$) δ 6.50-6.41 (m, 1H), 1.73 (dd, J=5.7, 2.0 Hz, 3H), 1.45 (d, J=2.0 Hz, 9H).

(xxviii) tert-Butyl (chloromethyl) carbonate (I77)

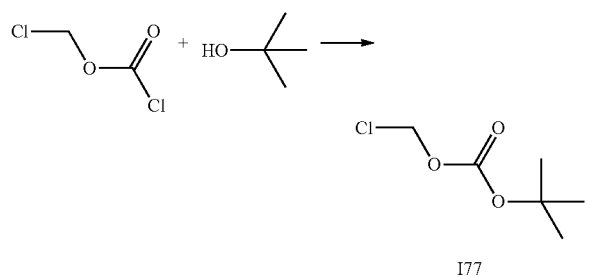

To a solution of chloromethyl carbonochloridate (5 g, 39 mmol) in hexane (30 mL) at 0° C. was added a solution of pyridine (7.7 g, 97.0 mmol) in hexane (10 mL) dropwise. A white precipitate formed after complete addition. A solution of t-butanol (4.31 g, 58.2 mmol) in hexane (10 mL) was added and the mixture was stirred at 0° C. for 2 h then allowed to warm to room temperature and stirred for a further 1 h. The mixture was diluted with hexane and washed with a saturated aqueous NaHCO$_3$ solution followed by water. The organic layer was dried over Na$_2$SO$_4$, filtered and concentrated under reduced pressure to give the title compound (2.5 g, 39%) as a colorless oil. $^1$H NMR (400 MHz, DMSO-d$_6$) δ 5.83 (s, 2H), 1.45 (s, 9H).

(xxiv) 1-Chloroethyl isopropyl carbonate (I78)

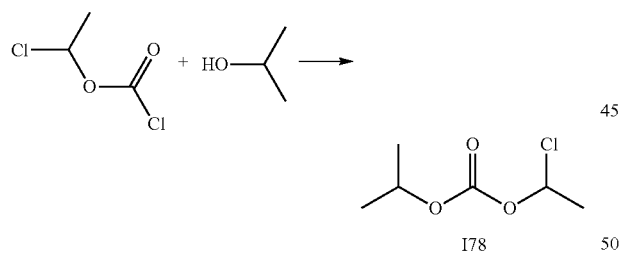

To a solution of 1-chloroethyl carbonochloridate (5 g, 35.0 mmol) in hexane (30 mL) at 0° C. was added a solution of pyridine (6.9 g, 87.4 mmol) in hexane (10 mL) dropwise. A white precipitate formed after complete addition. A solution of propan-2-ol (3.15 g, 52.5 mmol) in hexane (10 mL) was added and the mixture was stirred at 0° C. for 2 h then allowed to warm to room temperature and stirred for a further 1 h. The mixture was diluted with hexane and washed with a saturated aqueous NaHCO$_3$ solution followed by water. The organic layer was dried over Na$_2$SO$_4$, filtered and concentrated under reduced pressure to give the title compound (3.0 g, 52%) as a pale yellow oil. $^1$H NMR (400 MHz, DMSO-d$_6$) δ 6.49 (q, J=5.7 Hz, 1H), 4.89-4.79 (m, 1H), 1.75 (d, J=5.7 Hz, 3H), 1.27-1.23 (m, 6H).

(xxvv) Chloromethyl (tert-butoxycarbonyl)-L-valinate (I79)

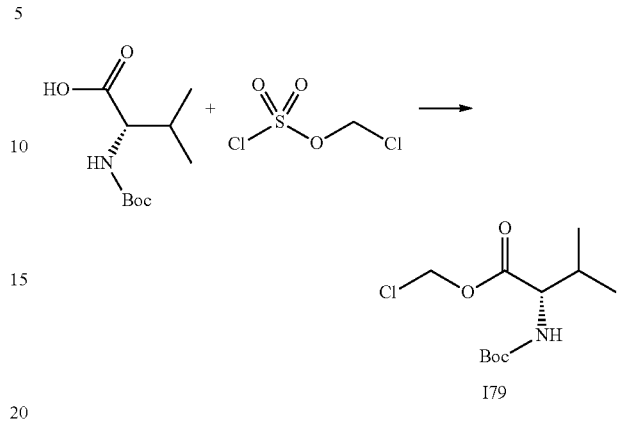

To a solution of (tert-butoxycarbonyl)-L-valine (7.9 g, 36 mmol) in DCM (20 mL) and water (20 mL) was added NaHCO$_3$ (10.18 g, 121.2 mmol) and tetrabutylammonium hydrogen sulfate (1.03 g, 3.03 mmol) and the mixture was stirred at room temperature for 5 min, then cooled to 0° C. Chloromethyl sulfurochloridate (5 g, 30 mmol) was added dropwise and the mixture was allowed to warm to room temperature and stirred for 2 h. Water (300 mL) was added, the layers were separated and the aqueous layer was extracted with DCM (200 mL×2). The combined organic layers were washed with brine, dried over Na$_2$SO$_4$, filtered and concentrated to give the title compound (4.8 g, 60%) as a colorless oil. $^1$H NMR (400 MHz, DMSO-d$_6$) δ 7.35 (d, J=8.0 Hz, 1H), 5.94 (d, J=6.2 Hz, 1H), 5.84 (d, J=6.2 Hz, 1H), 3.90 (dd, J=7.9, 6.5 Hz, 1H), 2.08-1.99 (m, 1H), 1.38 (s, 9H), 0.90-0.88 (m, 6H).

(xxvvi) 1-Chloroethyl acetate (I80)

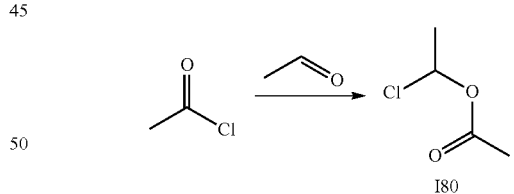

To a solution of AlCl$_3$ (2.04 g, 15.3 mmol) in DCM (40 mL) at 0° C. under a N$_2$ atmosphere was added acetyl chloride (2.0 g, 25.5 mmol) and the mixture was stirred at 0° C. for 20 min. Acetaldehyde (5.0 M in THF, 5.1 mL, 25.5 mmol) was added dropwise and the mixture was stirred at 0° C. for 1 h. The mixture was partitioned between water (300 mL) and DCM (300 mL), the layers were separated and the organic layer was washed with water, brine, dried over Na$_2$SO$_4$, filtered and concentrated under reduced pressure at 35° C. to give the title compound as a pale red oil (final volume of 6 mL), which was used directly in the next step without further purification.

(xxvvii) 1-Chloroethyl isobutyrate (I81)

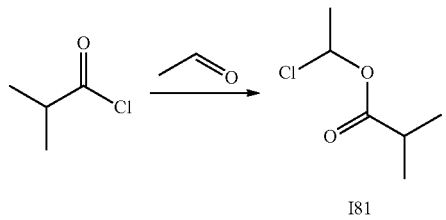

I81

To a solution of AlCl₃ (1.5 g, 11.3 mmol) in DCM (40 mL) at 0° C. under N₂ atmosphere was added isobutyryl chloride (2.0 g, 18.8 mmol) and the mixture was stirred at 0° C. for 20 min. Acetaldehyde (5 M in THF, 3.75 mL, 18.8 mmol) was added dropwise and the mixture was stirred at 0° C. for 1 h. The mixture was partitioned between water (300 mL) and DCM (300 mL), the layers were separated and the organic layer was washed with water, brine, dried over Na₂SO₄, filtered and concentrated under reduced pressure at 30° C. to give the title compound as a pale yellow oil (final volume of 6 mL), which was used directly in the next step without further purification.

(xxvviii) Chloromethyl dimethylcarbamate (I82)

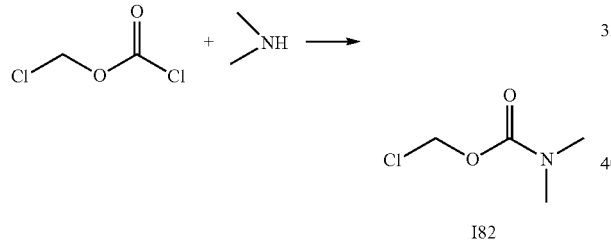

I82

To a solution of chloromethyl carbonochloridate (1.0 g, 7.76 mmol) in DCM (10 mL) was added dimethylamine (2 M in THF, 3.9 mL, 7.76 mmol) and K₂CO₃ (3.2 g, 23.3 mmol) and the mixture was stirred at room temperature overnight. The mixture was filtered and the filtrate was concentrated under reduced pressure to give the title compound (510 mg, 48%) as a yellow oil. LCMS-C: rt 0.64 min; m/z 138.0 [M+H]⁺.

(xxvviv) Chloromethyl acetyl-L-valinate (I83)

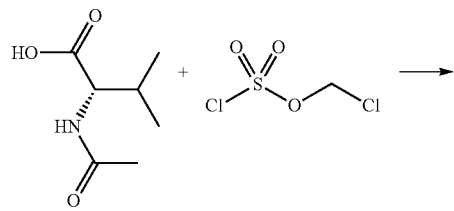

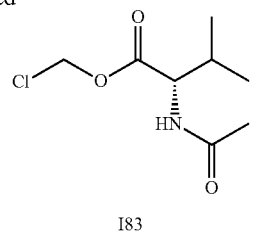

I83

To a solution of acetyl-L-valine (5.8 g, 36 mmol) in DCM (50 mL) and water (50 mL) was added NaHCO₃ (10.2 g, 121.2 mmol) and tetrabutylammonium hydrogen sulfate (1.03 g, 3.03 mmol) and the mixture was stirred at room temperature for 5 min, then cooled to 0° C. Chloromethyl sulfurochloridate (5 g, 30 mmol) was added dropwise and the mixture was allowed to warm to room temperature and stirred for 2 h. The layers were separated and the aqueous layer was extracted with DCM (3×200 mL). The combined organic layers were washed with water (2×150 mL), dried over MgSO₄, filtered and concentrated under reduced pressure to give the title compound (2.5 g, 40%) as a colorless oil. ¹H NMR (400 MHz, DMSO-d₆) δ 8.27 (d, J=7.6 Hz, 1H), 5.91 (d, J=6.2 Hz, 1H), 5.85 (d, J=6.2 Hz, 1H), 4.18 (dd, J=7.7, 6.2 Hz, 1H), 2.11-1.98 (m, 1H), 1.89 (s, 3H), 0.92-0.89 (m, 6H).

(xxvvv) Methyl 4-hydroxypiperidine-1-carboxylate (I84)

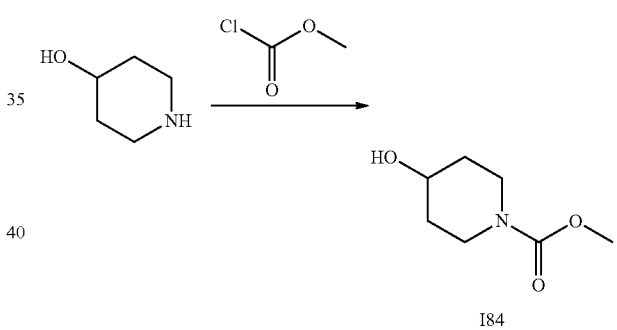

I84

To a mixture of piperidin-4-ol (1.00 g, 9.88 mmol) and K₂CO₃ (2.73 g, 19.8 mmol) in DCM (40 mL) was slowly added methyl chloroformate (1.12 g, 11.9 mmol) and the mixture was stirred at room temperature overnight. The mixture was filtered and filtrate was concentrated under reduced pressure to give the title compound (1.40 g, 89%) as a colorless oil, which was used in the next step without further purification. LCMS-C: rt 0.33 min; m/z 160.0 [M+H]⁺.

(xxvvvi) Ethyl 3-(bromomethyl)-4-chlorothieno[2,3-c]pyridine-2-carboxylate (I88)

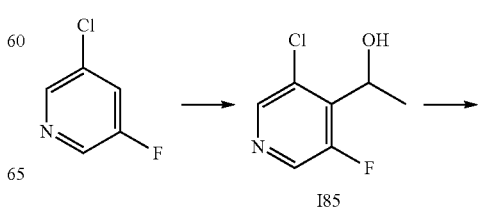

I85

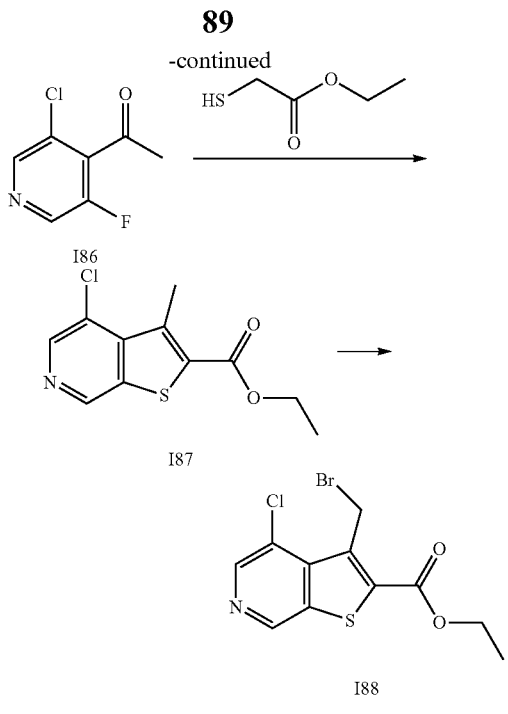

a) 1-(3-Chloro-5-fluoropyridin-4-yl)ethan-1-ol (I85)

A solution of lithium diisopropylamide (titrated 2.0 M) in THF/heptane/ethylbenzene (13.1 mL, 18.2 mmol) was slowly added to a cooled (−78° C.) solution of 3-chloro-5-fluoro-pyridine (2.00 g, 15.2 mmol) in THF (30 mL). The mixture was stirred at −78° C. for 1 h before a solution of acetaldehyde (2.5 mL, 3 eq) in THF (2.5 mL) added dropwise. The mixture was allowed to warm to room temperature and stirred overnight. The reaction mixture was quenched under nitrogen by the addition of a saturated aqueous solution of NH$_4$Cl. The mixture was extracted with EtOAc (×3), washed with saturated NH$_4$Cl$_{(aq)}$, brine and dried over MgSO$_4$. The organics were filtered and the filtrate evaporated in vacuo. The residue was purified by column chromatography (24 g SiO$_2$ cartridge, 0-30% EtOAc in petroleum benzine) to give the title compound (1.2 g, 44%) as a yellow oil. $^1$H NMR (400 MHz, Chloroform-d) δ 8.36 (s, 1H), 8.32 (d, J=1.7 Hz, 1H), 5.44-5.24 (m, 1H), 2.56 (s, 1H), 1.61 (dd, J=6.8, 0.9 Hz, 3H). LCMS-B: rt 3.085 min, m/z 176.0 [M+H]$^+$.

b) 1-(3-Chloro-5-fluoropyridin-4-yl)ethan-1-one (I86)

1-(3-Chloro-5-fluoro-4-pyridyl)ethanol (I85) (0.56 g, 3.2 mmol) in anhydrous DCM (10 mL) was added to a stirred suspension of pyridinium chlorochromate (1.0 g, 4.7 mmol) and freshly activated 4 Å sieves in anhydrous DCM (10 mL) and the mixture was stirred overnight. The reaction mixture was taken-up in EtOAc/petroleum benzine (3:1) and filtered through a plug of silica. The silica was washed with EtOAc/petroleum benzine and the filtrate dried in vacuo. The residue was purified by column chromatography (12 g SiO$_2$ cartridge, 0-30% EtOAc in petroleum benzine) to give the title compound (0.42 g, 77%) as a colourless liquid. $^1$H-NMR (400 MHz, Chloroform-d) δ 8.50 (s, 1H), 8.47 (s, 1H), 2.61 (d, J=1.0 Hz, 3H).

c) Ethyl 4-chloro-3-methylthieno[2,3-c]pyridine-2-carboxylate (I87)

A high pressure tube was charged with 1-(3-chloro-5-fluoro-4-pyridyl)ethanone (0.711 g, 4.10 mmol) (I86) (& (I86b), not described), ethyl 2-mercaptoacetate (0.449 mL, 4.10 mmol), potassium carbonate (0.85 g, 6.1 mmol) and N,N-dimethylformamide (10 mL). The reaction mixture was stirred at 70° C. overnight. Further portions of ethyl 2-mercaptoacetate (0.450 mL, 4.10 mmol) and DMF (5 mL) were added and the mixture stirred at 80° C. for 1 day. Water was added and the mixture extracted with EtOAc (3×35 mL). The combined organic layers were washed with water, brine, dried (MgSO$_4$) and filtered. The filtrate was evaporated in vacuo and the residue purified by column chromatography (12 g SiO$_2$ cartridge, 0-20% EtOAc in petroleum benzine) to give the title compound (0.28 g, 27% yield) as a white solid. LCMS-B: rt 3.727 min, m/z 255.9 [M+H]$^+$. $^1$H NMR (400 MHz, Chloroform-d) δ 8.97 (s, 1H), 8.47 (s, 1H), 4.43 (q, J=7.1 Hz, 2H), 3.09 (s, 3H), 1.43 (t, J=7.1 Hz, 3H).

d) Ethyl 3-(bromomethyl)-4-chlorothieno[2,3-c]pyridine-2-carboxylate (I88)

A solution of ethyl 4-chloro-3-methyl-thieno[2,3-c]pyridine-2-carboxylate (0.28 g, 1.1 mmol) (I87), N-bromosuccinimide (0.387 g, 2.17 mmol), benzoyl peroxide (75%, remainder water, 0.11 g, 0.34 mmol) in 1,2-dichloroethane (30 mL) was stirred at reflux for 3 h. The mixture was concentrated and purified by column chromatography to give the title compound (0.34 g, 94%) as a pale yellow solid. $^1$H NMR (400 MHz, Chloroform-d) δ 9.05 (s, 1H), 8.57 (s, 1H), 5.51 (s, 2H), 4.48 (q, J=7.1 Hz, 2H), 1.45 (t, J=7.1 Hz, 3H). LCMS-A: rt 6.876 min, m/z=334.0 [M+H]$^+$ for $^{79}$Br.

EXAMPLES 3-((4-Carbamoylphenoxy)methyl)-4-fluorobenzo[b]thiophene-2-carboxylic acid (1)

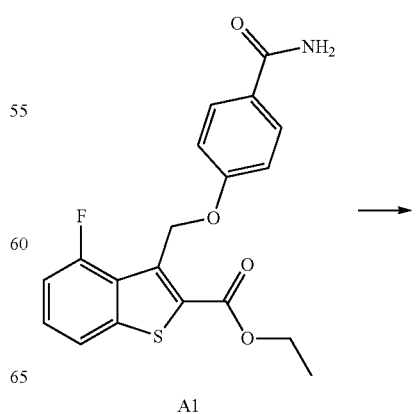

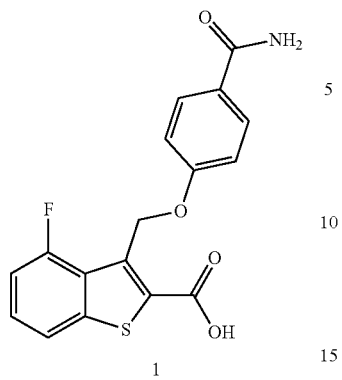

1

To a solution of ethyl 3-((4-carbamoylphenoxy)methyl)-4-fluorobenzo[b]thiophene-2-carboxylate A1 (200 mg, 0.53 mmol) in THF/H$_2$O (5 mL/1 mL) was added LiOH.H$_2$O (68 mg, 1.60 mmol) and the mixture was stirred at room temperature overnight. The solvent was removed under reduced pressure and the residue was diluted with water (150 mL) and acidified to pH 4-5 with aq. 1 M HCl. The resulting precipitate was collected by filtration, washed with water and dried at 60° C. overnight to give the title product (150 mg, 81%) as a white solid. LCMS-D: rt 2.54 min; m/z 345.9 [M+H]$^+$, 367.9 [M+Na]$^+$. $^1$H NMR (400 MHz, DMSO-d$_6$) δ 7.93 (d, J=8.1 Hz, 1H), 7.87 (d, J=8.7 Hz, 3H), 7.58 (td, J=8.0, 5.0 Hz, 1H), 7.28 (dd, J=11.9, 8.0 Hz, 1H), 7.20 (s, 1H), 7.08 (d, J=8.7 Hz, 2H), 5.72 (s, 2H), CO$_2$H not observed.

Ethyl 3-((4-carbamoyl-2,6-difluorophenoxy)methyl)-4-fluorobenzo[b]thiophene-2-carboxylate (2)

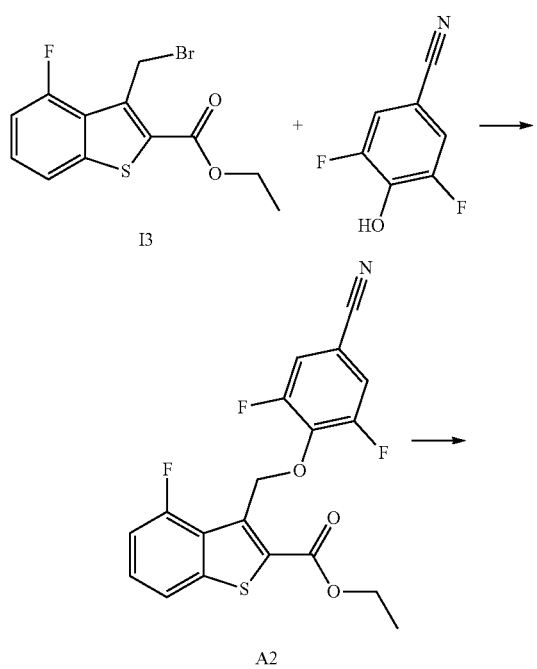

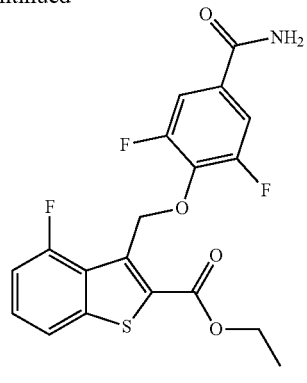

2

(a) Ethyl 3-((4-cyano-2,6-difluorophenoxy)methyl)-4-fluorobenzo[b]thiophene-2-carboxylate (A2)

A mixture of ethyl 3-(bromomethyl)-4-fluorobenzo[b]thiophene-2-carboxylate 13 (25 mg, 0.079 mmol), 3,5-difluoro-4-hydroxybenzonitrile (0.013 g, 0.087 mmol) and cesium carbonate, 60-80 mesh (0.0385 g, 0.118 mmol) was stirred in DMF (0.5 mL) at room temperature. After 1.5 hours the mixture was added to ice water (10 mL) and the mixture filtered, the collected solids washed with water (2×1 mL) and air dried to give the title compound as an off-white solid (25.0 mg, 81% yield). LCMS-A rt 6.61 min; no product ions detected. $^1$H NMR (400 MHz, CDCl$_3$) δ 7.64 (dd, J=8.2, 0.8 Hz, 1H), 7.46 (td, J=8.1, 4.8 Hz, 1H), 7.25-7.17 (m, 2H), 7.11 (ddd, J=11.7, 7.9, 0.8 Hz, 1H), 6.04 (s, 2H), 4.37 (q, J=7.1 Hz, 2H), 1.38 (t, J=7.1 Hz, 3H). $^{19}$F NMR (376 MHz, CDCl$_3$) δ −117.68 (t, J=4.1 Hz), −123.57 (d, J=4.1 Hz).

(b) Ethyl 3-((4-carbamoyl-2,6-difluorophenoxy)methyl)-4-fluorobenzo[b]thiophene-2-carboxylate (2)

A mixture of ethyl 3-((4-cyano-2,6-difluorophenoxy)methyl)-4-fluorobenzo[b]thiophene-2-carboxylate A2 (20 mg, 0.051 mmol), DMSO (0.5 mL), potassium carbonate (0.0035 g, 0.026 mmol) and 30% aq. hydrogen peroxide (0.0047 mL, 0.15 mmol) was stirred at room temperature. After three hours additional 30% aq. hydrogen peroxide (0.0047 mL, 0.15 mmol) was added. After five hours the mixture was diluted with water (10 mL), filtered and the collected solid was washed with water (2×1 mL) and air dried to give the title compound as a white solid (16.8 mg, 80% yield). LCMS-B rt 3.41 min; m/z 409.8 [M+H]$^+$. $^1$H NMR (400 MHz, MeOD-d$_4$) δ 7.76 (dd, J=8.2, 0.8 Hz, 1H), 7.56-7.49 (m, 1H), 7.51-7.44 (m, 2H), 7.19 (ddd, J=12.0, 7.9, 0.8 Hz, 1H), 5.98 (s, 2H), 4.30 (q, J=7.1 Hz, 2H), 1.31 (t, J=7.1 Hz, 3H). $^{19}$F NMR (376 MHz, MeOD-d$_4$) δ −119.08 (t, J=3.3 Hz), −127.78 (d, J=3.1 Hz).

Benzyl 3-((4-carbamoylphenoxy)methyl)-4-fluorobenzo[b]thiophene-2-carboxylate (3)

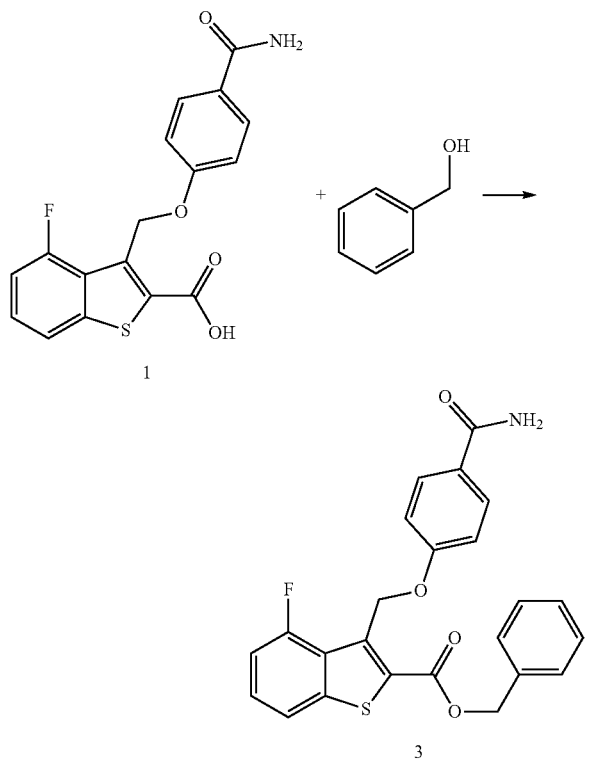

To a solution of 3-((4-carbamoylphenoxy)methyl)-4-fluorobenzo[b]thiophene-2-carboxylic acid 1 (100 mg, 0.29 mmol) in benzyl alcohol (6 mL) was added conc. $H_2SO_4$ (4 drops) and the mixture was heated at 70° C. overnight. The mixture was cooled to room temperature and purified directly by silica gel chromatography (Pet. Ether/EtOAc=100:0 then 10:1 to 0:100) followed by re-crystallization from DCM/Pet. Ether to give the title product (20 mg, 15%) as a white solid. LCMS-C: rt 2.41 min; m/z 436.0 [M+H]$^+$, 458.0 [M+Na]$^+$. $^1$H NMR (400 MHz, DMSO-d$_6$) δ 7.96 (d, J=8.1 Hz, 1H), 7.87-7.85 (m, 3H), 7.63-7.58 (m, 1H), 7.43 (dd, J=6.4, 2.8 Hz, 2H), 7.36-7.30 (m, 4H), 7.21 (s, 1H), 7.05 (d, J=8.7 Hz, 2H), 5.71 (s, 2H), 5.40 (s, 2H).

Isopropyl 3-((4-carbamoylphenoxy)methyl)-4-fluorobenzo[b]thiophene-2-carboxylate (4)

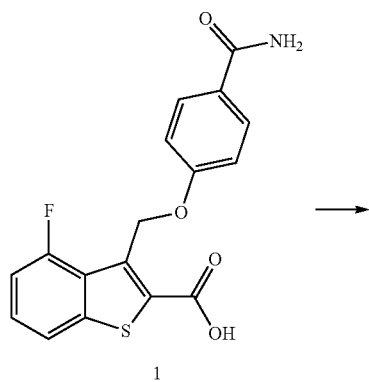

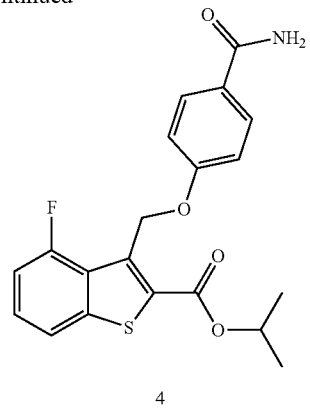

A mixture of 3-((4-carbamoylphenoxy)methyl)-4-fluorobenzo[b]thiophene-2-carboxylic acid 1 (60 mg, 0.17 mmol), i-PrOH (104 mg, 1.74 mmol), EDCl.HCl (67 mg, 0.34 mmol) and DMAP (5 mg) in DMF (5 mL) was stirred at room temperature overnight. The mixture was poured into water (50 mL) and extracted with EtOAc (50 mL×2). The combined organic extracts were washed with water, brine, dried over anhydrous $Na_2SO_4$, filtered and concentrated under reduced pressure. The residue was re-crystallized from DCM/Pet. Ether to give the title product (10 mg, 15%) as a white solid. LCMS-C: rt 2.34 min; m/z 388.0 [M+H]$^+$, 410.0 [M+Na]$^+$. $^1$H NMR (400 MHz, DMSO-d$_6$) δ 7.95 (d, J=8.0 Hz, 1H), 7.88-7.86 (m, 3H), 7.60-7.59 (m, 1H), 7.32-7.27 (m, 1H), 7.26 (s, 1H), 7.14 (d, J=8.5 Hz, 2H), 5.75 (s, 2H), 5.16-5.13 (m, 1H), 1.33 (d, J=6.2 Hz, 6H).

General Method A (Table 1)

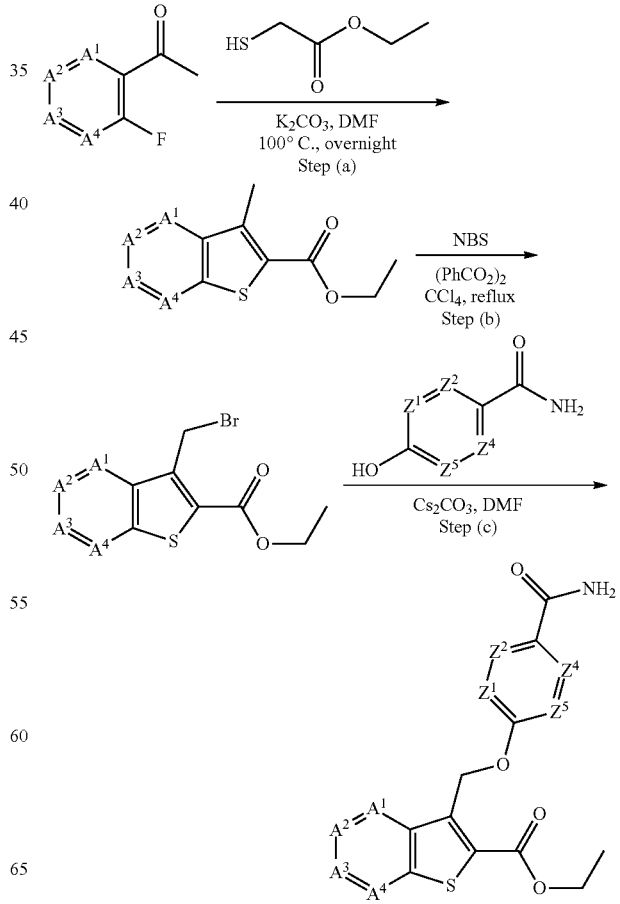

Step (a)

A solution of the appropriate ketone (1 equiv.), ethyl 2-mercaptoacetate (1 equiv.) and K₂CO₃ (1.5 equiv.) in DMF (0.1-0.3 M) was heated at 100° C. overnight. The mixture was cooled to room temperature then poured into water and extracted twice with EtOAc. The combined organic extracts were washed with water, brine, dried over anhydrous Na₂SO₄, filtered and concentrated under reduced pressure. The residue was purified by re-crystallization from EtOAc/Pet. Ether to give the desired product.

Step (b)

A solution of the ethyl ester (1 equiv.), NBS (1 equiv.) and BPO (0.1 equiv.) in 0014 (0.08-0.1 M) was heated at reflux for 1 h. The mixture was allowed to cool to room temperature, concentrated under reduced pressure and the residue was purified by silica gel chromatography (Pet. Ether/EtOAc=1:0 to 50:1) to give the desired product.

Step (c)

A solution of the alkyl bromide (1 equiv.), the appropriate phenol (1.05 equiv.) and Cs₂CO₃ (1.5 equiv.) in DMF (0.1-0.3 M) was stirred at room temperature overnight. The mixture was poured into water and extracted with EtOAc. The combined organic extracts were washed with water, brine, dried over anhydrous Na₂SO₄, filtered and concentrated under reduced pressure. The residue was purified by re-crystallization from DCM/Pet. Ether to give the desired product.

General Method B (Table 1)

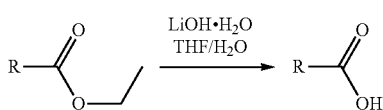

To a solution of the ester (1 equiv.) in THF/H₂O (5:1, 0.08-0.10 M) was added LiOH.H₂O (3 equiv.) and the mixture was stirred at room temperature overnight. The solvent was removed under reduced pressure and the residue was diluted with water and acidified to pH 4-5 with aqueous 1 M HCl. The resulting precipitate was collected by filtration, washed with water and dried at 60° C. overnight to give the desired product.

General Method C (Table 1)

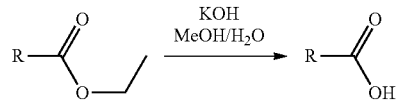

To a solution of the ester (1 equiv.) in MeOH/H₂O (3:1, 0.01-0.05 M) was added KOH (4.9 equiv.) and the mixture was heated at 60° C. for 1 h. Most of the methanol was removed under reduced pressure and the aqueous residue was adjusted to pH 5 with aqueous 1 M HCl. The resulting precipitate was collected by filtration, washed with water and dried under reduced pressure to give the desired product.

General Method D (Table 1)—Alternative Method to Step (c) of Method A

The appropriate alkyl bromide (1 eq), the appropriate phenol (1.1 eq), finely ground cesium carbonate (60-80 mesh, 1.5 eq) and DMF (to 0.1-0.3M) were stirred at room temperature for two hours. The mixture was diluted with ice cold water, the resulting precipitate collected by filtration or centrifugation, washed with the minimum water and air dried to give the ether product.

General Method E (Table 1)

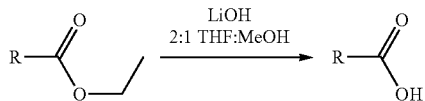

The ester (1 eq), 2:1 THF:MeOH (to 0.05-0.1 M) and 2 M aq. lithium hydroxide (7 eq) were stirred at room temperature for three hours. The volatile solvents were removed with a current of air and the residue diluted with cold 3 M aq. HCl. The precipitate was collected by filtration or centrifugation, washed with the minimum water and air dried to give the acid product.

The following examples were made according to the methods described in the general procedures:

| Ex | Starting materials | Name and structure | LCMS data | ¹H NMR data | Method |
|----|----|----|----|----|----|
| 5 | I1 | Ethyl 3-((4-carbamoylphenoxy)methyl)benzo[b]thiophene-2-carboxylate | LCMS-C: rt 2.24 min; m/z 356.0 [M + H]⁺ | ¹H NMR (400 MHz, DMSO-d₆) δ 8.11-8.08 (m, 2H), 7.87-7.84 (m, 3H), 7.59-7.49 (m, 2H), 7.19 (s, 1H), 7.11 (d, J = 8.7 Hz, 2H), 5.79 (s, 2H), 4.36 (q, J = 7.1 Hz, 2H), 1.29 (t, J= 7.1 Hz, 3H). | A Steps (b) and (c) |

-continued

| Ex | Starting materials | Name and structure | LCMS data | ¹H NMR data | Method |
|---|---|---|---|---|---|
| 6 | 5 | 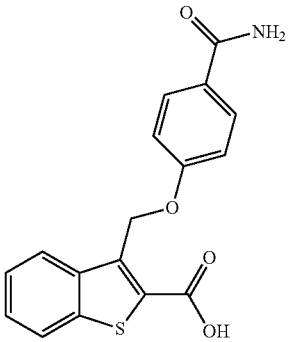 [SMILES: NC(=O)c1ccc(OCc2c(C(=O)O)sc3ccccc23)cc1]<br>3-((4-Carbamoylphenoxy)methyl)benzo[b]thiophene-2-carboxylic acid | LCMS-C: rt 1.59 min; m/z 328.0 [M + H]⁺ | ¹H NMR (400 MHz, DMSO-$d_6$) δ 8.07 (d, J = 8.5 Hz, 2H), 7.85-7.78 (m, 3H), 7.56-7.47 (m, 2H), 7.19 (s, 1H), 7.11 (d, J = 8.8 Hz, 2H), 5.82 (s, 2H), $CO_2H$ not observed. | B Reacted at 30° C. overnight |
| 7 | I5 | 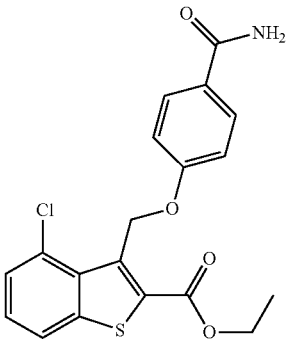 [SMILES: CCOC(=O)c1sc2cccc(Cl)c2c1COc1ccc(C(N)=O)cc1]<br>Ethyl 3-((4-carbamoylphenoxy)methyl)-4-chlorobenzo[b]thiophene-2-carboxylate | LCMS-C: rt 2.33 min; m/z 390.0 [M + H]⁺ | ¹H NMR(400 MHz, DMSO-$d_6$) δ 8.14 (d, J = 8.8 Hz, 1H), 7.88-7.84 (m, 3H), 7.20-7.18 (m, 2H), 7.19 (s, 1H), 7.09 (d, J = 8.4 Hz, 2H), 5.86 (s, 2H), 4.37 (q, J = 7.1 Hz, 2H), 1.29 (t, J = 7.1 Hz, 3H). | A Step (c), purified by silica gel chromatography (Pet. Ether/ EtOAc = 1:0 to 30:1) |
| 8 | 7 | 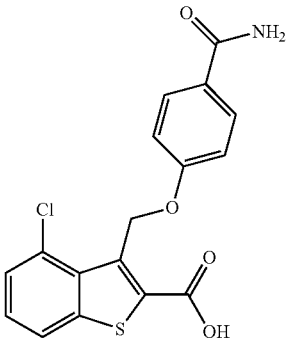 [SMILES: NC(=O)c1ccc(OCc2c(C(=O)O)sc3cccc(Cl)c23)cc1]<br>3-((4-Carbamoylphenoxy)methyl)-4-chlorobenzo[b]thiophene-2-carboxylic acid | LCMS-C: rt 1.86 min; m/z 362.0 [M + H]⁺, 383.9 [M + Na]⁺. | ¹H NMR(400 MHz, DMSO-$d_6$) δ 8.11 (d, J = 7.0 Hz, 1H), 7.87-7.85 (m, 3H), 7.56-7.50 (m, 2H), 7.18 (s, 1H), 7.09 (d, J = 8.4 Hz, 2H), 5.89 (s, 2H), $CO_2H$ not observed. | C |

-continued

| Ex | Starting materials | Name and structure | LCMS data | ¹H NMR data | Method |
|---|---|---|---|---|---|
| 9 | 1-(4-Chloro-2-fluoro-phenyl)eth-anone | Ethyl 3-((4-carbamoylphenoxy)methyl)-6-chlorobenzo[b]thiophene-2-carboxylate | LCMS-C: rt 2.41 min; m/z 390.0 [M + H]⁺. | ¹H NMR(400 MHz, DMSO-$d_6$) δ 8.29 (d, J = 1.3 Hz, 1H), 8.12 (d, J = 8.8 Hz, 1H), 7.86-7.84 (m, 3H), 7.57 (dd, J = 8.7, 1.5 Hz, 1H), 7.22 (s, 1H), 7.10 (d, J = 8.6Hz, 2H), 5.77 (s, 2H), 4.36 (q, J = 7.0 Hz, 2H), 1.29 (t, J = 7.1 Hz, 3H). | A Step b: Purified by re-crystal-lization from DCM/Pet. Ether |
| 10 | 9 | 3-((4-carbamoylphenoxy)methyl)-6-chlorobenzo[b]thiophene-2-carboxylic acid | LCMS-C: rt 2.06 min; m/z 361.9 [M + H]⁺. | ¹H NMR(400 MHz, DMSO-$d_6$) δ 14.0 (s, 1H), 8.26 (d, J = 1.7 Hz, 1H), 8.07 (d, J = 8.8 Hz, 1H), 7.85-7.65 (m, 3H), 7.54 (dd, J = 8.8, 1.8 Hz, 1H), 7.20 (s, 1H), 7.10 (d, J = 8.8 Hz, 2H), 5.80 (s, 2H). | B |
| 11 | 1-(3-Chloro-2-fluoro-phenyl)eth-anone | Ethyl 3-((4-carbamoylphenoxy)methyl)-7-chlorobenzo[b]thiophene-2-carboxylate | LCMS-C: rt 2.43 min; m/z 390.0 [M + H]⁺. | ¹H NMR(400 MHz, DMSO-$d_6$) δ 8.13 (d, J = 8.2 Hz, 1H), 7.87-7.84 (m, 3H), 7.74 (d, J = 7.7 Hz, 1H), 7.59-7.54 (m, 1H), 7.22 (s, 1H), 7.10 (d, J = 8.8 Hz, 2H), 5.78 (s, 2H), 4.38 (q, J = 7.1 Hz, 2H), 1.30 (t, J = 7.1 Hz, 3H). | A Step b: Purified by recrystal-lization from DCM/Pet. Ether |

-continued

| Ex | Starting materials | Name and structure | LCMS data | ¹H NMR data | Method |
|---|---|---|---|---|---|
| 12 | 11 | 3-((4-Carbamoylphenoxy)methyl)-7-chlorobenzo[b]thiophene-2-carboxylic acid | LCMS-C: rt 2.04 min; m/z 361.9 [M + H]⁺. | ¹H NMR(400 MHz, DMSO-d6) δ 14.2 (brs, 1H), 8.08 (d, J = 8.1 Hz, 1H), 7.86 (d, J = 8.8 Hz, 3H), 7.71 (d, J = 7.5 Hz, 1H), 7.56 (t, J = 7.9 Hz, 1H), 7.20 (s, 1H), 7.11 (d, J = 8.8 Hz, 2H), 5.81 (s, 2H). | B |
| 13 | 1-(5-Chloro-2-fluoro-phenyl)eth-anone | Ethyl 3-((4-carbamoylphenoxy)methyl)-5-chlorobenzo[b]thiophene-2-carboxylate | LCMS-C: rt 2.36 min; m/z 390.0 [M + H]⁺. | ¹H NMR(400 MHz, DMSO-d₆) δ 8.18-8.14 (m, 2H), 7.87-7.85 (m, 3H), 7.63 (d, J = 8.4 Hz, 1H), 7.22 (s, 1H), 7.10 (d, J = 8.3 Hz, 2H), 5.77 (s, 2H), 4.36 (q, J = 6.9 Hz, 2H), 1.28 (t, J = 6.9 Hz, 3H). | A Step b: Purified by recrystallization from DCM/Pet. Ether |
| 14 | 13 | 3-((4-Carbamoylphenoxy)methyl)-5-chlorobenzo[b]thiophene-2-carboxylic acid | LCMS-C: rt 2.00 min; m/z 361.9 [M + H]⁺. | ¹H NMR(400 MHz, DMSO-d₆) δ 8.13-8.11 (m, 2H), 7.86-7.84 (m, 3H), 7.60 (dd, J = 8.7, 1.7 Hz, 1H), 7.20 (s, 1H), 7.10 (d, J = 8.7 Hz, 2H), 5.80 (s, 2H), CO₂H not observed. | B |

-continued

| Ex | Starting materials | Name and structure | LCMS data | ¹H NMR data | Method |
|---|---|---|---|---|---|
| 15 | 1-(2,3,6-Trifluoro-phenyl)eth-anone | Ethyl 3-((4-carbamoylphenoxy)methyl)-4,5-difluorobenzo[b]thiophene-2-carboxylate | LCMS-C: rt 2.32 min; m/z 391.9 [M + H]⁺, 413.9 [M + Na]⁺. | ¹H NMR(400 MHz, DMSO-$d_6$) δ 7.88-7.85 (m, 3H), 7.55-7.50 (m, 1H), 7.40-7.34 (m, 1H), 7.21 (s, 1H), 7.09 (d, J = 8.9 Hz, 2H), 5.70 (s, 2H), 4.38 (q, J = 7.1 Hz, 2H), 1.29 (t, J = 7.1 Hz, 3H). | A |
| 16 | 15 | 3-((4-Carbamoylphenoxy)methyl)-4,5-difluorobenzo[b]thiophene-2-carboxylic acid | LCMS-C: rt 1.84 min; m/z 363.9 [M + H]⁺. | ¹H NMR(400 MHz, DMSO-$d_6$) δ 7.87-7.85 (m, 3H), 7.51-7.46 (m, 1H), 7.36-7.40 (m, 1H), 7.20 (s, 1H), 7.09 (d, J = 8.8 Hz, 2H), 5.71 (s, 2H), $CO_2H$ not observed. | B |
| 17 | 1-(2-Chloro-6-fluoro-3-methyl-phenyl)eth-anone | Ethyl 3-((4-carbamoylphenoxy)methyl)-4-chloro-5-methyl-benzo[b]thiophene-2-carboxylate | LCMS-C: rt 2.43 min; m/z 403.9 [M + H]⁺, 425.9 [M + Na]⁺. | ¹H NMR(400 MHz, DMSO-$d_6$) δ 8.03 (d, J = 8.3 Hz, 1H), 7.92-7.80 (m, 3H), 7.58 (d, J = 8.4 Hz, 1H), 7.19 (s, 1H), 7.08 (d, J = 8.8 Hz, 2H), 5.89 (s, 2H), 4.34 (q, J = 7.1 Hz, 2H), 2.45 (s, 3H), 1.28 (t, J = 7.1 Hz, 3H). | A Step a: 1) reacted at 85° C. 2) Purified by chroma-tography (Pet. Ether) Step b: Stirred overnight Step c: Purified by prep-HPLC |

-continued

| Ex | Starting materials | Name and structure | LCMS data | ¹H NMR data | Method |
|---|---|---|---|---|---|
| 18 | 17 | 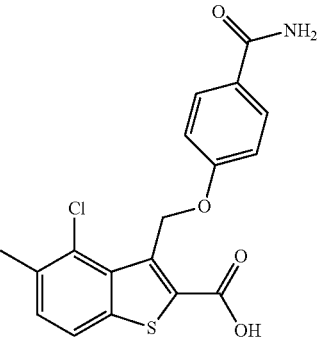 [SMILES: Cc1ccc2sc(C(=O)O)c(COc3ccc(C(N)=O)cc3)c2c1Cl]<br>3-((4-Carbamoylphenoxy)methyl)-4-chloro-5-methylbenzo[b]thiophene-2-carboxylic acid | LCMS-C: rt 2.07 min; m/z 375.9 [M + H]⁺, 397.9 [M + Na]⁺. | ¹H NMR(400 MHz, DMSO-d₆) δ 14.0 (s, 1H), 8.00 (d, J = 8.2 Hz, 1H), 7.86 (t, J = 7.7 Hz, 3H), 7.55 (d, J = 8.3 Hz, 1H), 7.19 (s, 1H), 7.08 (d, J = 8.7 Hz, 2H), 5.91 (s, 2H), 2.45 (s, 3H). | B Purified by prep-HPLC |
| 19 | 1-(4-Chloro-2,6-di-fluoro-phenyl)eth-anone | 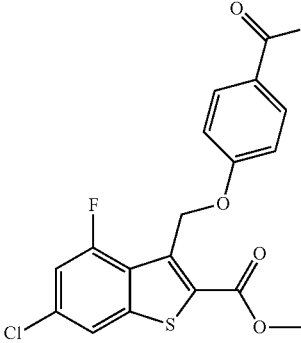<br>Ethyl 3-((4-carbamoylphenoxy)methyl)-6-chloro-4-fluorobenzo[b]thiophene-2-carboxylate | LCMS-C: rt 2.41 min; m/z 407.9 [M + H]⁺, 429.9 [M + Na]⁺. | ¹H NMR(400 MHz, DMSO-d₆) δ 8.20 (d, J = 1.6 Hz, 1H), 7.87-7.85 (m, 3H), 7.55 (dd, J = 11.4, 1.6 Hz, 1H), 7.23 (s, 1H), 7.08 (d, J = 8.8 Hz, 2H), 5.67 (s, 2H), 4.35 (q, J = 7.1 Hz, 2H), 1.28 (t, J = 7.1 Hz, 3H). | A |
| 20 | 19 | 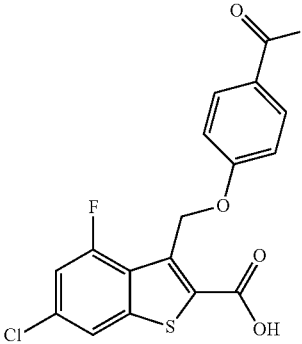<br>3-((4-Carbamoylphenoxy)methyl)-6-chloro-4-fluorobenzo[b]thiophene-2-carboxylic acid | LCMS-C: rt 2.08 min; m/z 379.9 [M + H]⁺, 401.8 [M + Na]⁺ | ¹H NMR(400 MHz, DMSO-d₆) δ 8.15 (s, 1H), 7.86-7.84 (m, 3H), 7.50 (d, J = 11.2 Hz, 1H), 7.21 (s, 1H), 7.08 (d, J = 8.5 Hz, 2H), 5.71 (s, 2H), CO₂H not observed. | B |

-continued

| Ex | Starting materials | Name and structure | LCMS data | ¹H NMR data | Method |
|---|---|---|---|---|---|
| 21 | 1-(2-Bromo-6-fluoro-phenyl)eth-anone | Ethyl 4-bromo-3-((4-carbamoylphenoxy)meth-yl)benzo[b]thiophene-2-carboxylate | LCMS-C: rt 2.33 min; m/z 433.9 [M + H]⁺, 455.8 [M + Na]⁺. | ¹H NMR(400 MHz, DMSO-d₆) δ 8.20 (d, J = 8.1 Hz, 1H), 7.88 (d, J = 8.8 Hz, 3H), 7.80 (d, J = 7.6 Hz, 1H), 7.49 (t, J = 7.9 Hz, 1H), 7.21 (s, 1H), 7.09 (d, J = 8.7 Hz, 2H), 5.88 (s, 2H), 4.35 (q, J = 7.1 Hz, 2H), 1.28 (t, J = 7.1 Hz, 3H). | A Step a and b: Crude products used in next step without purification Step c: Purified by chromato-graphy(Pet. Ether/EtOAc = 10:1 to 1:2) |
| 22 | 21 | 4-Bromo-3-((4-carbamoylphenoxy)meth-yl)benzo[b]thiophene-2-carboxylic acid | LCMS-C: rt 1.95 min; m/z 405.8 [M + H]⁺, 428.9 [M + Na]⁺. | ¹H NMR(400 MHz, DMSO-d₆) δ 7.95 (d, J = 7.9 Hz, 1H), 7.83 (t, J = 8.1 Hz, 3H), 7.60 (d, J = 7.0 Hz, 1H), 7.26 (t, J = 7.8 Hz, 1H), 7.14 (s, 1H), 7.07 (t, J = 7.0 Hz, 2H), 6.08 (s, 2H), CO₂H not observed. | B Purified by recrystal-lization from DCM/Pet. Ether |
| 23 | 1-(3-Fluoro-pyridin-2-yl)ethanone | Ethyl 3-((4-carbamoylphenoxy)meth-yl)thieno[3,2-b]pyridine-2-carboxylate | LCMS-C: rt 1.78 min; m/z 356.9 [M + H]⁺. | ¹H NMR(400 MHz, DMSO-d₆) δ 8.85 (dd, J = 4.4, 1.4 Hz, 1H), 8.65 (dd, J = 8.3, 1.4 Hz, 1H), 7.87 (t, J = 5.8 Hz, 3H), 7.62 (dd, J = 8.3, 4.5 Hz, 1H), 7.20 (s, 1H), 7.12 (d, J = 8.8 Hz, 2H), 5.68 (s, 2H), 4.35 (q, J = 7.1 Hz, 2H), 1.23 (t, J = 7.1 Hz, 3H). | A Step a: Purified by chromato-graphy(Pet. Ether/EtOAc = 1:0 to 50:1) Step c: Purified by recrystal-lization from DCM/Pet. Ether |

| Ex | Starting materials | Name and structure | LCMS data | ¹H NMR data | Method |
|---|---|---|---|---|---|
| 24 | 23 | 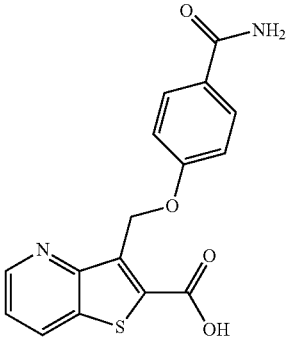 [SMILES: NC(=O)c1ccc(OCc2c(C(=O)O)sc3cccnc23)cc1] 3-((4-Carbamoylphenoxy)methyl)thieno[3,2-b]pyridine-2-carboxylic acid | LCMS-C: rt 0.39 min; m/z 328.9 [M + H]⁺. | ¹H NMR(400 MHz, DMSO-d₆) δ 14.1 (s, 1H), 8.82 (s, 1H), 8.61 (d, J = 7.7 Hz, 1H), 7.87 (d, J = 7.7 Hz, 3H), 7.59 (s, 1H), 7.34-6.96 (m, 3H), 5.69 (s, 2H). | B Purified by recrystallization from DCM/Pet. Ether |
| 25 | I5 | 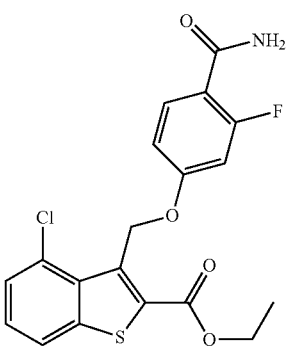 Ethyl 3-((4-carbamoyl-3-fluorophenoxy)methyl)-4-chlorobenzo[b]thiophene-2-carboxylate | LCMS-C: rt 2.42 min; m/z 407.9 [M + H]⁺, 429.9 [M + Na]⁺. | ¹H NMR(400 MHz, DMSO-d₆) δ 8.15 (dd, J = 7.0, 2.0 Hz, 1H), 7.71 (t, J = 8.8 Hz, 1H), 7.62-7.55 (m,2H),7.51 (s, 2H), 7.04-7.01 (m, 1H), 6.96 (dd, J = 8.7, 2.4 Hz, 1H), 5.88 (s, 2H), 4.37 (q, J = 7.1 Hz, 2H), 1.29 (t, J = 7.1 Hz, 3H). | A Step (c) |
| 26 | 25 | 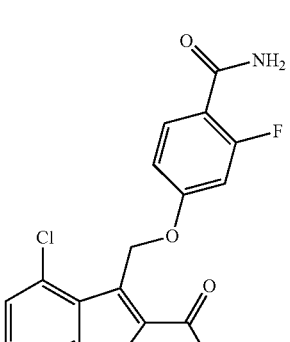 3-((4-Carbamoyl-3-fluorophenoxy)methyl)-4-chlorobenzo[b]thiophene-2-carboxylic acid | LCMS-C: rt 2.01 min; m/z 379.9 [M + H]⁺, 401.9 [M + Na]⁺. | ¹H NMR(400 MHz, DMSO-d₆) δ 8.17-8.09 (m, 1H), 7.70 (t, J = 8.8 Hz, 1H), 7.61-7.43 (m, 4H), 7.04 (dd, J = 12.9, 2.3 Hz, 1H), 6.95 (dd, J = 8.7, 2.3 Hz, 1H), 5.90 (s, 2H), CO₂H not observed. | C |

| Ex | Starting materials | Name and structure | LCMS data | ¹H NMR data | Method |
|---|---|---|---|---|---|
| 27 | I5 | 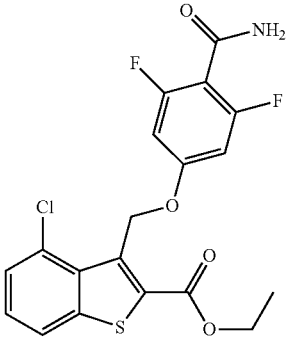 [SMILES: CCOC(=O)c1sc2cccc(Cl)c2c1COc1cc(F)c(C(N)=O)c(F)c1]<br>Ethyl 3-((4-carbamoyl-3,5-difluorophenoxy)methyl)-4-chlorobenzo[b]thiophene-2-carboxylate | LCMS-C: rt 2.38 min; m/z 425.9 [M + H]⁺, 447.9 [M + Na]⁺. | ¹H NMR(400 MHz, DMSO-$d_6$) δ 8.19-8.13 (m, 1H), 8.01 (s, 1H), 7.73 (s, 1H), 7.64-7.51 (m, 2H), 6.93-6.91 (m, 2H), 5.86 (s, 2H), 4.37 (q, J = 7.1 Hz, 2H), 1.31 (t, J = 7.1 Hz, 3H). | A Step (c) |
| 28 | 27 | 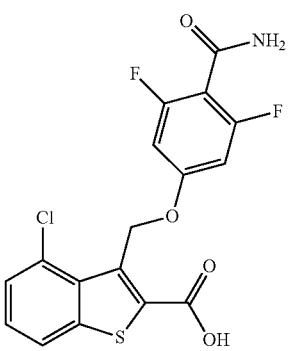 [SMILES: NC(=O)c1c(F)cc(OCc2c(C(=O)O)sc3cccc(Cl)c23)cc1F]<br>3-((4-Carbamoyl-3,5-difluorophenoxy)methyl)-4-chlorobenzo[b]thiophene-2-carboxylic acid | LCMS-C: rt 1.99 min; m/z 397.9 [M + H]⁺. | ¹H NMR(400 MHz, DMSO-$d_6$) δ 8.12 (dd, J = 7.4, 1.7 Hz, 1H), 8.00 (s, 1H), 7.72 (s, 1H), 7.62-7.48 (m, 2H), 6.93 (d, J = 9.6 Hz, 2H), 5.88 (s, 2H), $CO_2H$ not observed. | c |
| 29 | I5 and I13 | 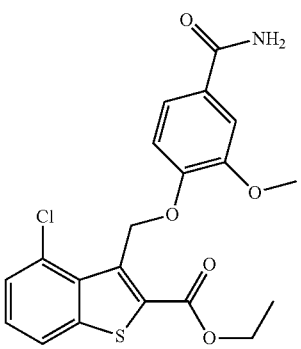 [SMILES: CCOC(=O)c1sc2cccc(Cl)c2c1COc1ccc(C(N)=O)cc1OC]<br>Ethyl 3-((4-carbamoyl-2-methoxyphenoxy)methyl)-4-chlorobenzo[b]thiophene-2-carboxylate | LCMS-C: rt 2.28 min, m/z 419.9 [M + H]⁺. | ¹H NMR(400 MHz, DMSO-$d_6$) δ 8.18-8.13 (m, 1H), 7.89 (s, 1H), 7.61-7.52 (m, 3H), 7.47 (s, 1H), 7.25-7.18 (m, 2H), 5.85 (s, 2H), 4.39-4.29 (m, 2H), 3.71 (s, 3H), 1.27 (t, J = 6.0 Hz, 3H). | A Step (c) |

-continued

| Ex | Starting materials | Name and structure | LCMS data | ¹H NMR data | Method |
|---|---|---|---|---|---|
| 30 | 29 | 3-((4-Carbamoyl-2-methoxyphenoxy)methyl)-4-chlorobenzo[b]thiophene-2-carboxylic acid | LCMS-C: rt 1.81 min; m/z 391.9 [M + H]$^+$, 413.9 [M + Na]$^+$. | ¹H NMR(400 MHz, DMSO-d$_6$) δ 8.13-8.11 (m, 1H), 7.90 (s, 1H), 7.61-7.51 (m, 3H), 7.47 (d, J = 1.7 Hz, 1H), 7.23-7.20 (m, 2H), 5.87 (s, 2H), 3.71 (s, 3H), CO$_2$H not observed. | c |
| 31 | 1-(2,4,6-Trifluorophenyl)ethan-1-one | Ethyl 3-((4-carbamoylphenoxy)methyl)-4,6-difluorobenzo[b]thiophene-2-carboxylate | LCMS-C: rt 2.32 min, m/z 391.9 [M + H]$^+$. | ¹H NMR(400 MHz, DMSO-d$_6$) δ 7.98 (d, J = 8.3 Hz, 1H), 7.92-7.85 (m, 3H), 7.48-7.40 (m, 1H), 7.22 (s, 1H), 7.07 (d, J = 8.7 Hz, 2H), 5.67 (s, 2H), 4.34 (q, J = 7.0 Hz, 2H), 1.26 (t, J = 7.1 Hz, 3H). | A |
| 32 | 31 | 3-((4-Carbamoylphenoxy)methyl)-4,6-difluorobenzo[b]thiophene-2-carboxylic acid | LCMS-C: rt 1.82 min, m/z 363.9 [M + H]$^+$. | ¹H NMR(400 MHz, DMSO-d$_6$) δ 7.93 (dd, J = 8.5, 2.0 Hz, 1H), 7.89-7.84 (m, 3H), 7.44-7.36 (m, 1H), 7.19(s, 1H), 7.07 (d, J = 8.8 Hz, 2H), 5.69 (s, 2H), CO$_2$H not observed. | C |

-continued

| Ex | Starting materials | Name and structure | LCMS data | ¹H NMR data | Method |
|---|---|---|---|---|---|
| 33 | 1-(2-Fluoro-6-methoxyphenyl)ethan-1-one | Ethyl 3-((4-carbamoylphenoxy)methyl)-4-methoxybenzo[b]thiophene-2-carboxylate | LCMS-C: rt 2.32 min, m/z 407.9 [M + Na]⁺. | ¹H NMR(400 MHz, DMSO-d₆) δ 7.93-7.80 (m, 3H), 7.62 (d, J = 8.1 Hz, 1H), 7.51 (t, J = 8.0 Hz, 1H), 7.19 (s, 1H), 7.05 (d, J = 8.5 Hz, 2H), 6.97 (d, J = 7.9 Hz, 1H), 5.77 (s, 2H), 4.31 (q, J = 7.0 Hz, 2H), 3.68 (s, 3H), 1.25 (t, J = 7.0 Hz, 3H). | A |
| 34 | 33 | 3-((4-Carbamoylphenoxy)methyl)-4-methoxybenzo[b]thiophene-2-carboxylic acid | LCMS-C: rt 1.69 min, m/z 357.9 [M + H]⁺. | ¹H NMR(400 MHz, DMSO-d₆) δ 13.7 (s, 1H), 7.88-7.86 (m, 3H), 7.60 (d, J = 8.0 Hz, 1H), 7.52-7.44 (m, 1H), 7.18 (s, 1H), 7.05 (d, J = 8.6 Hz, 2H), 6.95 (d, J = 7.9 Hz, 1H), 5.79 (s, 2H), 3.64 (s, 3H). | C |
| 35 | 1-(2-Fluoro-6-(trifluoromethyl)phenyl)ethan-1-one | Ethyl 3-((4-carbamoylphenoxy)methyl)-4-(trifluoromethyl)benzo[b]thiophene-2-carboxylate | LCMS-C: rt 2.30 min, m/z 423.9 [M + H]⁺. | ¹H NMR(400 MHz, DMSO-d₆) δ 8.53 (d, J = 8.0 Hz, 1H), 8.01 (d, J = 6.7 Hz, 1H), 7.87-7.85 (m, 3H), 7.79-7.72 (m, 1H), 7.22 (s, 1H), 7.05 (d, J = 7.9 Hz, 2H), 5.66 (s, 2H), 4.33 (q, J = 6.8 Hz, 2H), 1.23 (t, J = 6.8 Hz, 3H). | A |

| Ex | Starting materials | Name and structure | LCMS data | ¹H NMR data | Method |
|---|---|---|---|---|---|
| 36 | 35 | 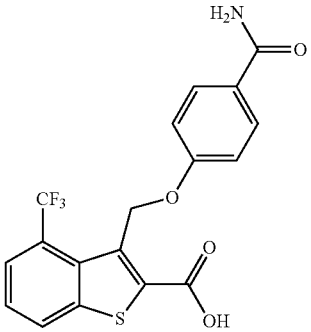 [SMILES: NC(=O)c1ccc(OCc2c(C(=O)O)sc3cccc(C(F)(F)F)c23)cc1]<br>3-((4-Carbamoylphenoxy)methyl)-4-(trifluoromethyl)benzo[b]thiophene-2-carboxylic acid | LCMS-C: rt 1.97 min, m/z 395.9 $[M + H]^+$. | ¹H NMR(400 MHz, DMSO-$d_6$) δ 8.50 (d, J = 8.1 Hz, 1H), 7.99 (d, J = 7.5 Hz, 1H), 7.86-7.84 (m, 3H), 7.73 (t, J = 7.8 Hz, 1H), 7.20 (s, 1H), 7.05 (d, J = 8.8 Hz, 2H), 5.70 (s, 2H), $CO_2H$ not observed. | C |
| 37 | I5 and I9 | 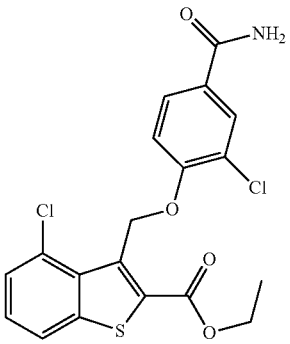 [SMILES: CCOC(=O)c1sc2cccc(Cl)c2c1COc1ccc(C(N)=O)cc1Cl]<br>Ethyl 3-((4-carbamoyl-2-chlorophenoxy)methyl)-4-chlorobenzo[b]thiophene-2-carboxylate | LCMS-C: rt 2.36 min, m/z 423.9 $[M + H]^+$. | ¹H NMR(400 MHz, DMSO-$d_6$) δ 8.18-8.13 (m, 1H), 7.99-7.89 (m, 3H), 7.62-7.54 (m, 2H), 7.45 (d, J = 8.6 Hz, 1H), 7.36 (s, 1H), 5.95 (s, 2H), 4.36 (q, J = 7.0 Hz, 2H), 1.28 (t, J = 7.1 Hz, 3H). | A Step (c) |
| 38 | 37 | 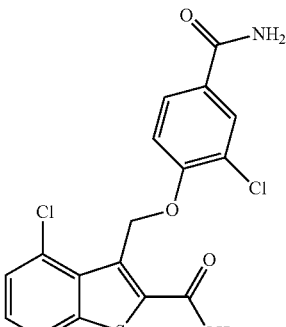<br>3-((4-Carbamoyl-2-chlorophenoxy)methyl)-4-chlorobenzo[b]thiophene-2-carboxylic acid | LCMS-C: rt 2.04 min, m/z 395.8 $[M + H]^+$. | ¹H NMR(400 MHz, DMSO-$d_6$) δ 7.96-7.90 (m, 2H), 7.89-7.84 (m, 2H), 7.50 (d, J = 8.7 Hz, 1H), 7.38 (d, J = 6.9 Hz, 1H), 7.35-7.27 (m, 2H), 6.18 (s, 2H), $CO_2H$ not observed. | C |

| Ex | Starting materials | Name and structure | LCMS data | ¹H NMR data | Method |
|---|---|---|---|---|---|
| 39 | I5 and I12 | Ethyl 3-((4-carbamoyl-2,6-dichlorophenoxy)methyl)-4-chlorobenzo[b]thiophene-2-carboxylate | LCMS-C: rt 2.49 min, m/z 457.8 [M + H]⁺. | ¹H NMR(400 MHz, DMSO-d$_6$) δ 8.19 (s, 1H), 8.11 (d, J = 8.0 Hz, 1H), 7.92 (s, 2H), 7.64-7.53 (m, 3H), 6.14 (s, 2H), 4.12 (q, J = 7.1 Hz, 2H), 1.12 (t, J = 7.1 Hz, 3H). | A Step (c) |
| 40 | 39 | 3-((4-Carbamoyl-2,6-dichlorophenoxy)methyl)-4-chlorobenzo[b]thiophene-2-carboxylic acid | LCMS-C: rt 2.21 min, m/z 429.8 [M + H]⁺. | ¹H NMR(400 MHz, DMSO-d$_6$) δ 13.8 (s, 1H), 8.14-8.05 (m, 2H), 7.88 (s, 2H), 7.62-7.50 (m, 3H), 6.18 (s, 2H). | C |
| 41 | I5 and I10 | Ethyl 3-((4-carbamoyl-2,6-dimethoxyphenoxy)methyl)-4-chlorobenzo[b]thiophene-2-carboxylate | LCMS-C: rt 2.31 min, m/z 449.9 [M + H]⁺. | ¹H NMR(400 MHz, DMSO-d$_6$) δ 8.06 (dd, J = 7.9, 1.0 Hz, 1H), 7.88 (s, 1H), 7.61-7.50 (m, 2H), 7.30 (s, 1H), 7.08 (s, 2H), 5.90 (s, 2H), 4.11 (q, J = 7.1 Hz, 2H), 3.47 (s, 6H), 1.14 (t, J = 7.1 Hz, 3H). | A Step (c) |

| Ex | Starting materials | Name and structure | LCMS data | ¹H NMR data | Method |
|---|---|---|---|---|---|
| 42 | 41 | 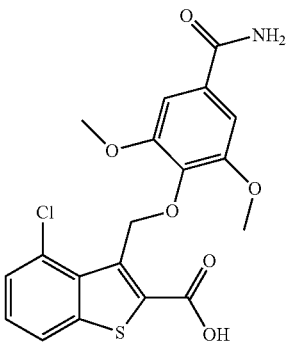 [SMILES: COc1cc(C(N)=O)cc(OC)c1OCc1c(C(=O)O)sc2cccc(Cl)c12]<br>3-((4-Carbamoyl-2,6-dimethoxyphenoxy)methyl)-4-chlorobenzo[b]thiophene-2-carboxylic acid | LCMS-C: rt 1.89 min, m/z 421.9 [M + H]⁺. | ¹H NMR(400 MHz, DMSO-d₆) δ 8.04 (d, J = 7.9 Hz, 1H), 7.89 (s, 1H), 7.57 (d, J = 6.9 Hz, 1H), 7.53-7.47 (m, 1H), 7.28 (s, 1H), 7.07 (s, 2H), 5.93 (s, 2H), 3.47 (s, 6H), CO₂H not observed. | C |
| 43 | I5 and I14 | 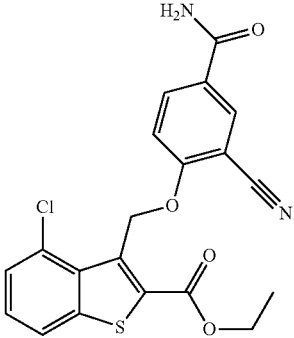 [SMILES: CCOC(=O)c1sc2cccc(Cl)c2c1COc1ccc(C(N)=O)cc1C#N]<br>Ethyl 3-((4-carbamoyl-2-cyanophenoxy)methyl)-4-chlorobenzo[b]thiophene-2-carboxylate | LCMS-C: rt 2.25 min, m/z 414.9 [M + H]⁺. | ¹H NMR(400 MHz, DMSO-d₆) δ 8.27-8.21 (m, 2H), 8.17 (d, J = 6.7 Hz, 1H), 8.04 (s, 1H), 7.64-7.55 (m, 3H), 7.49 (s, 1H), 6.02 (s, 2H), 4.37 (q, J = 7.0 Hz, 2H), 1.29 (t, J = 7.1 Hz, 3H). | A Step (c) |
| 44 | 43 | 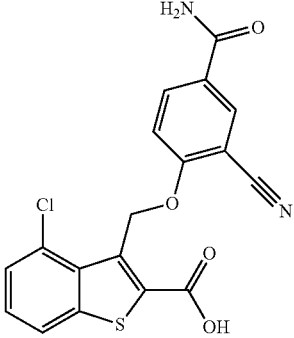 [SMILES: N#Cc1cc(C(N)=O)ccc1OCc1c(C(=O)O)sc2cccc(Cl)c12]<br>3-((4-Carbamoyl-2-cyanophenoxy)methyl)-4-chlorobenzo[b]thiophene-2-carboxylic acid | LCMS-C: rt 1.78 min, m/z 386.9 [M + H]⁺. | ¹H NMR(400 MHz, DMSO-d₆) δ 8.23-8.17 (m, 2H), 8.05-7.95 (m, 2H), 7.65 (d, J = 8.8 Hz, 1H), 7.49-7.37 (m, 3H), 6.20 (s, 2H), CO₂H not observed. | C |

| Ex | Starting materials | Name and structure | LCMS data | ¹H NMR data | Method |
|---|---|---|---|---|---|
| 45 | I5 and I11 | 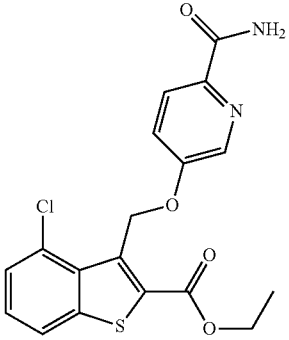 [SMILES: CCOC(=O)c1sc2cccc(Cl)c2c1COc1ccc(C(N)=O)nc1]<br>Ethyl 3-(((6-carbamoylpyridin-3-yl)oxy)methyl)-4-chlorobenzo[b]thiophene-2-carboxylate | LCMS-C: rt 2.30 min, m/z 390.9 [M + H]⁺. | ¹H NMR(400 MHz, DMSO-d₆) δ 8.37 (d, J = 2.7 Hz, 1H), 8.17 (dd, J = 7.0, 2.0 Hz, 1H), 8.05 (d, J = 8.6 Hz, 1H), 7.96 (s, 1H), 7.73-7.68 (m, 1H), 7.62-7.55 (m, 2H), 7.51 (s, 1H), 5.96 (s, 2H), 4.35 (q, J = 7.0 Hz, 2H), 1.27 (t, J = 7.1 Hz, 3H). | A Step (c) |
| 46 | 45 | 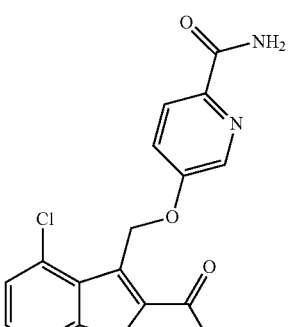<br>3-(((6-Carbamoylpyridin-3-yl)oxy)methyl)-4-chlorobenzo[b]thiophene-2-carboxylic acid | LCMS-C: rt 1.88 min, m/z 362.9 [M + H]⁺. | ¹H NMR(400 MHz, DMSO-d₆) δ 8.37 (d, J = 1.9 Hz, 1H), 8.12 (d, J = 6.8 Hz, 1H), 8.04 (d, J = 8.6 Hz, 1H), 7.96 (s, 1H), 7.73-7.67 (m, 1H), 7.58-7.48 (m, 3H), 5.98 (s, 2H), CO₂H not observed. | C |
| 47 | I5 and I8 | 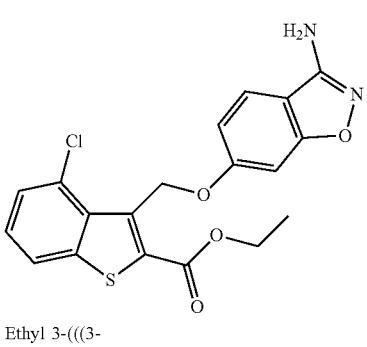<br>Ethyl 3-(((3-aminobenzo[d]isoxazol-6-yl)oxy)methyl)-4-chlorobenzo[b]thiophene-2-carboxylate | LCMS-C: rt 2.46 min, m/z 402.9 [M + H]⁺. | ¹H NMR(400 MHz, DMSO-d₆) δ 8.14 (dd, J = 6.9, 2.2 Hz, 1H), 7.68 (d, J = 8.6 Hz, 1H), 7.60-7.54 (m, 2H), 7.21-7.19 (m, 1H), 6.90-6.86 (m, 1H), 6.30 (s, 2H), 5.86 (s, 2H), 4.35 (q, J = 7.1 Hz, 2H), 1.27 (t, J = 7.1 Hz, 3H). | A Step (c) |

-continued

| Ex | Starting materials | Name and structure | LCMS data | ¹H NMR data | Method |
|---|---|---|---|---|---|
| 48 | 47 | 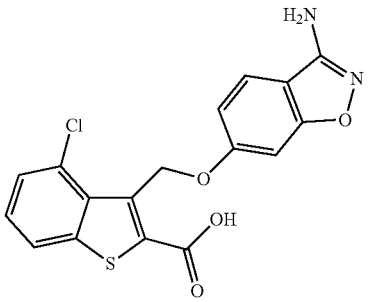 [SMILES: Nc1noc2cc(OCc3c(C(=O)O)sc4cccc(Cl)c34)ccc12]<br>3-(((3-Aminobenzo[d]isoxazol-6-yl)oxy)methyl)-4-chlorobenzo[b]thiophene-2-carboxylic acid | LCMS-C: rt 2.11 min, m/z 374.9 [M + H]⁺. | ¹H NMR(400 MHz, DMSO-$d_6$) δ 8.12 (dd, J = 7.1, 1.9 Hz, 1H), 7.67 (d, J = 8.7 Hz, 1H), 7.58-7.51 (m, 2H), 7.20 (d, J = 1.7 Hz, 1H), 6.88 (dd, J = 8.7, 1.9 Hz, 1H), 6.30 (s, 2H), 5.89 (s, 2H), $CO_2H$ not observed. | C |
| 49 | 13 | 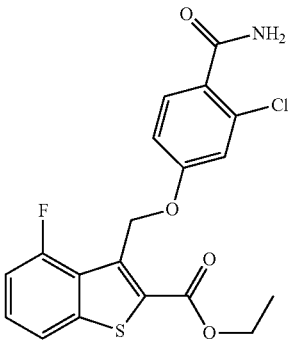 [SMILES: CCOC(=O)c1sc2cccc(F)c2c1COc1ccc(C(N)=O)c(Cl)c1]<br>Ethyl 3-((4-carbamoyl-3-chlorophenoxy)methyl)-4-fluorobenzo[b]thiophene-2-carboxylate | LCMS-B rt 3.67 min; m/z 407.7 [M + H]⁺. | | D |
| 50 | 49 | 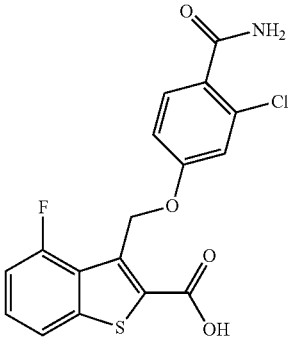 [SMILES: NC(=O)c1ccc(OCc2c(C(=O)O)sc3cccc(F)c23)cc1Cl]<br>3-((4-Carbamoyl-3-chlorophenoxy)methyl)-4-fluorobenzo[b]thiophene-2-carboxylic acid | LCMS-A rt 5.65 min; m/z 379.7 [M + H]⁺. | | E |

-continued

| Ex | Starting materials | Name and structure | LCMS data | ¹H NMR data | Method |
|---|---|---|---|---|---|
| 51 | I3 | Ethyl 3-((4-carbamoyl-3-(trifluoromethyl)phenoxy)methyl)-4-fluorobenzo[b]thiophene-2-carboxylate | LCMS-A rt 6.12 min; m/z 441.7 [M + H]⁺. | | D |
| 52 | 51 | 3-((4-Carbamoyl-3-(trifluoromethyl)phenoxy)methyl)-4-fluorobenzo[b]thiophene-2-carboxylic acid | LCMS-A rt 5.73 min; m/z 413.7 [M + H]⁺. | | E |
| 53 | I3 | Ethyl 3-((4-carbamoyl-3-methylphenoxy)methyl)-4-fluorobenzo[b]thiophene-2-carboxylate | LCMS-B rt 3.64 min; m/z 387.8 [M + H]⁺. | | D |

| Ex | Starting materials | Name and structure | LCMS data | ¹H NMR data | Method |
|---|---|---|---|---|---|
| 54 | 53 | 3-((4-Carbamoyl-3-methylphenoxy)methyl)-4-fluorobenzo[b]thiophene-2-carboxylic acid | LCMS-A rt 5.63 min; m/z 359.8 [M + H]⁺. | | E |
| 55 | I3 and I16 | Ethyl 3-((2-bromo-4-carbamoyl-6-fluorophenoxy)methyl)-4-fluorobenzo[b]thiophene-2-carboxylate | LCMS-A rt 6.16 min; m/z 471.6 [M + H]⁺. | | D |
| 56 | 55 | 3-((2-Bromo-4-carbamoyl-6-fluorophenoxy)methyl)-4-fluorobenzo[b]thiophene-2-carboxylic acid | LCMS-B rt 3.38 min; m/z 441.6 [M + H]⁺. | | E |

| Ex | Starting materials | Name and structure | LCMS data | ¹H NMR data | Method |
|---|---|---|---|---|---|
| 57 | 2 | 
3-((4-Carbamoyl-2,6-difluorophenoxy)methyl)-4-fluorobenzo[b]thiophene-2-carboxylic acid | LCMS-A rt 5.64 min; m/z 380.0 [M − H]⁻. | | E |

Ethyl 3-((4-carbamoyl-2-fluorophenoxy)methyl)-4-fluorobenzo[b]thiophene-2-carboxylate (58) and 3-((4-carbamoyl-2-fluorophenoxy)methyl)-4-fluorobenzo[b]thiophene-2-carboxylic acid (59)

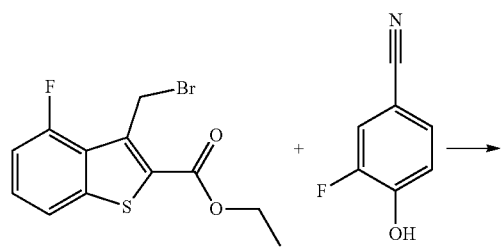

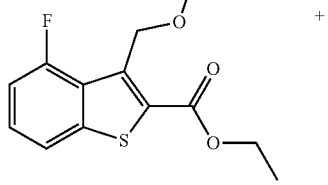

58

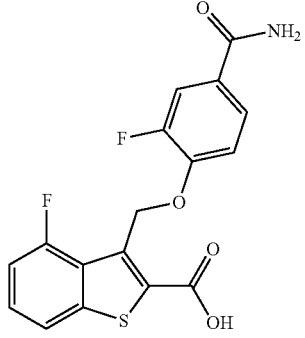

59

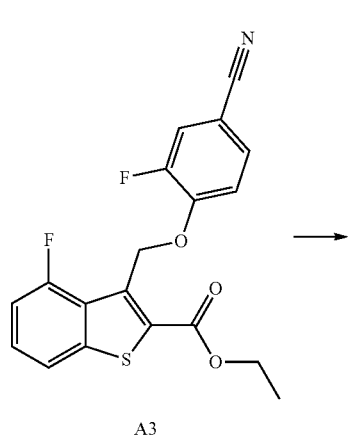

A3

(a) Ethyl 3-((4-cyano-2-fluorophenoxy)methyl)-4-fluorobenzo[b]thiophene-2-carboxylate (A3)

Ethyl 3-(bromomethyl)-4-fluorobenzo[b]thiophene-2-carboxylate 13 (0.050 g, 0.16 mmol), 3-fluoro-4-hydroxybenzonitrile (0.024 g, 0.17 mmol) and cesium carbonate, 60-80 mesh (0.0770 g, 0.236 mmol) were stirred in DMF (0.5 mL) at room temperature. After 1.5 hours the mixture was diluted with water (10 mL) and the mixture was centrifuged. The solvent was decanted and the precipitate resuspended in water (3 mL). The mixture was filtered, the collected solids washed with water (2×1 mL) and air dried to give the title compound as an off-white solid (40.0 mg, 68% yield). LCMS-B rt 3.81 min; m/z 371.9 [M−H]−. $^1$H NMR (400 MHz, chloroform-d) δ 7.64 (dd, J=8.2, 0.8 Hz, 1H), 7.48-7.42 (m, 2H), 7.36 (dd, J=10.5, 2.0 Hz, 1H), 7.30-7.23 (m, peak obscured by solvent), 7.10 (ddd, J=11.6, 7.9, 0.8 Hz, 1H), 5.88 (s, 2H), 4.40 (q, J=7.1 Hz, 2H), 1.39 (t, J=7.1 Hz, 3H). $^{19}$F NMR (376 MHz, chloroform-d) δ −117.57, −130.69.

(b) Ethyl 3-((4-carbamoyl-2-fluorophenoxy)methyl)-4-fluorobenzo[b]thiophene-2-carboxylate (58) and 3-((4-carbamoyl-2-fluorophenoxy)methyl)-4-fluorobenzo[b]thiophene-2-carboxylic acid (59)

Ethyl 3-((4-cyano-2-fluorophenoxy)methyl)-4-fluorobenzo[b]thiophene-2-carboxylate A3 (0.035 g, 0.094 mmol) and potassium carbonate (0.0065 g, 0.047 mmol) were stirred in DMSO (0.5 mL) before 30% aq. hydrogen peroxide (0.096 mL, 0.28 mmol) was added dropwise. After two hours the mixture was added to iced water (5 mL) and stood for 15 minutes. The mixture was filtered, and the collected solid washed with water (2×1 mL) and air dried to give ethyl 3-((4-carbamoyl-2-fluorophenoxy)methyl)-4-fluorobenzo[b]thiophene-2-carboxylate 58 as a white solid (30.0 mg, 82% yield). LCMS-B rt 3.37 min; m/z 391.8 [M+H]+. $^1$H NMR (400 MHz, DMSO-$d_6$) δ 8.01-7.91 (m, 2H), 7.80-7.73 (m, 1H), 7.71 (dd, J=12.4, 2.1 Hz, 1H), 7.61 (td, J=8.1, 4.9 Hz, 1H), 7.44 (t, J=8.6 Hz, 1H), 7.40-7.26 (m, 2H), 5.78 (s, 2H), 4.35 (q, J=7.1 Hz, 2H), 1.28 (t, J=7.1 Hz, 3H). $^{19}$F NMR (376 MHz, DMSO-$d_6$) δ −118.06, −134.57.

The combined filtrate and washings from the above filtration step was adjusted to pH 1 with aq. HCl (3 M) and stood at 4° C. overnight. The mixture was filtered, the collected solid washed with the minimum of aq. HCl (0.5 M) and air dried to give 3-((4-carbamoyl-2-fluorophenoxy)methyl)-4-fluorobenzo[b]thiophene-2-carboxylic acid 59 as a white solid (3.8 mg, 11% yield). LCMS-B rt 3.37 min; m/z 363.8 [M+H]+.

3-((4-Carbamoylphenoxy)methyl)-4-cyclopropyl-benzo[b]thiophene-2-carboxylic acid (61)

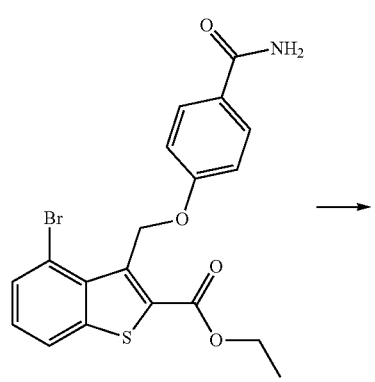

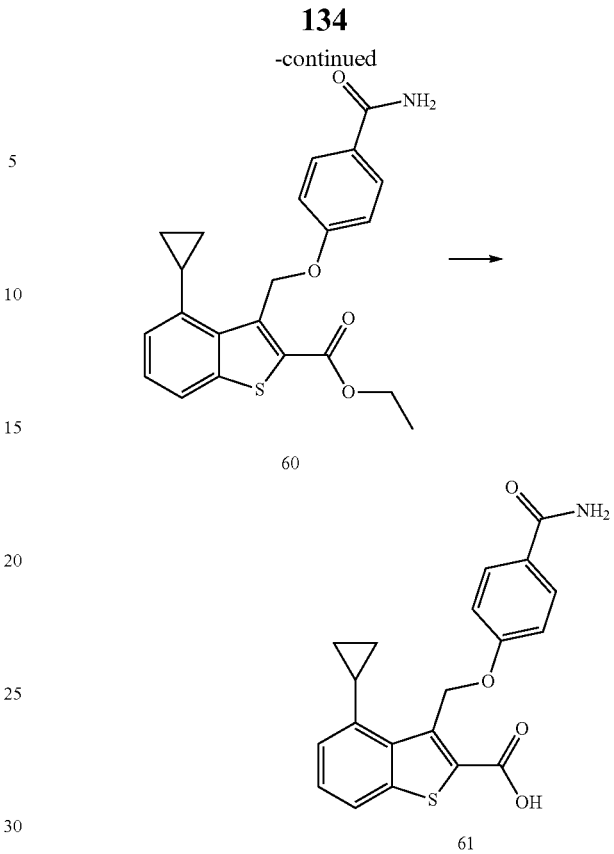

(a) Ethyl 3-((4-carbamoylphenoxy)methyl)-4-cyclopropylbenzo[b]thiophene-2-carboxylate (60)

A solution of ethyl 4-bromo-3-((4-carbamoylphenoxy)methyl)benzo[b]thiophene-2-carboxylate 21 (150 mg, 0.34 mmol), cyclopropyl boronic acid (60 mg, 0.69 mmol), Pd(PPh$_3$)$_4$ (40 mg, 0.034 mmol) and K$_2$CO$_3$ (144 mg, 1.03 mmol) in dioxane (10 mL) was heated at reflux under a N$_2$ atmosphere overnight. The mixture was cooled to room temperature, EtOAc (60 mL) and water (50 mL) were added and the layers were separated. The organic layer was washed with water, brine, dried over anhydrous Na$_2$SO$_4$, filtered and concentrated under reduced pressure. The residue was purified by column chromatography (Pet. Ether/EtOAc=10:1 to 1:2) to give the title product (70 mg, 51%) as a white solid. LCMS-C: (ES-API): rt 2.40 min; m/z 396.0 [M+H]+, 418.0 [M+Na]+. $^1$H NMR (400 MHz, DMSO-$d_6$) δ 7.96 (d, J=8.1 Hz, 1H), 7.89-7.86 (m, 3H), 7.48 (t, J=7.8 Hz, 1H), 7.26 (d, J=7.4 Hz, 1H), 7.21 (s, 1H), 7.12 (d, J=8.7 Hz, 2H), 6.00 (s, 2H), 4.33 (q, J=7.1 Hz, 2H), 2.43-2.41 (m, 1H), 1.26 (t, J=7.1 Hz, 3H), 0.82-0.80 (m, 4H).

(b) 3-((4-Carbamoylphenoxy)methyl)-4-cyclopropylbenzo[b]thiophene-2-carboxylic acid (61)

To a solution of ethyl 3-((4-carbamoylphenoxy)methyl)-4-cyclopropylbenzo[b]thiophene-2-carboxylate 60 (50 mg, 0.13 mmol) in THF/H$_2$O (10 mL/3 mL) was added LiOH.H$_2$O (30 mg, 0.71 mmol) and the mixture was stirred at room temperature overnight. The solvent was removed under reduced pressure and the residue was diluted with water (15 mL) and acidified to pH 4-5 with aqueous 1 M HCl. The resulting precipitate was collected by filtration and purified by prep-HPLC to give the title product (3.0 mg, 7%) as a white solid. LCMS-C: (ES-API): rt 2.11 min; m/z 368.0 [M+H]+, 389.9 [M+Na]+. $^1$H NMR (400 MHz, DMSO-$d_6$) δ

7.92 (d, J=8.1 Hz, 1H), 7.87-7.85 (m, 3H), 7.44 (t, J=7.8 Hz, 1H), 7.23 (d, J=7.4 Hz, 1H), 7.19 (s, 1H), 7.11 (d, J=8.7 Hz, 2H), 6.01 (s, 2H), 2.48-2.41 (m, 1H), 0.87-0.74 (m, 4H), $CO_2H$ not observed.

3-((4-Carbamoylphenoxy)methyl)-4-cyanobenzo[b]thiophene-2-carboxylic acid (63)

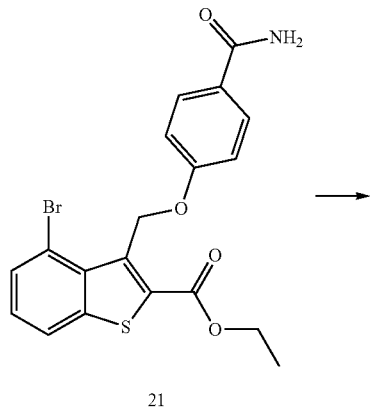

21

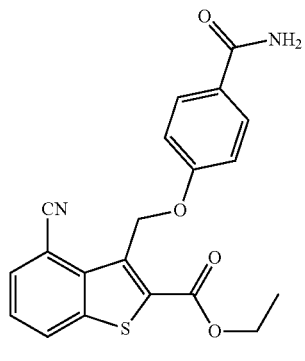

62

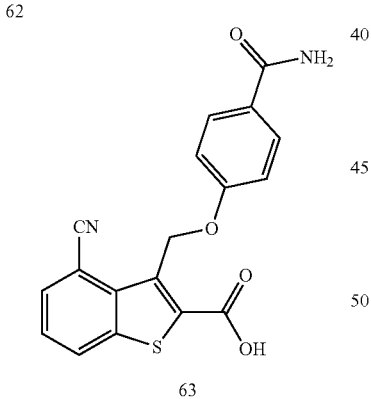

63

(a) Ethyl 3-((4-carbamoylphenoxy)methyl)-4-cyanobenzo[b]thiophene-2-carboxylate (62) A stirred solution of ethyl 4-bromo-3-((4-carbamoylphenoxy)methyl)benzo[b]thiophene-2-carboxylate 21 (140 mg, 0.32 mmol) and CuCN (144 mg, 1.61 mmol) in NMP (10 mL) was heated at 180° C. for 2 h then allowed to cool to room temperature, poured into water and extracted twice with EtOAc. The combined organic extracts were washed with water, brine, dried over anhydrous $Na_2SO_4$, filtered and concentrated under reduced pressure. The residue was purified by column chromatography (Pet. Ether/EtOAc=1:0 to 0:1) to give the title product (90 mg, 73%) as a white solid. LCMS-C: (ES-API): rt 2.11 min; m/z 381.0 [M+H]$^+$, 402.9 [M+Na]$^+$. $^1$H NMR (400 MHz, DMSO-d$_6$) δ 8.54 (d, J=8.2 Hz, 1H), 8.10 (d, J=7.2 Hz, 1H), 7.88-7.76 (m, 3H), 7.76 (t, J=7.8 Hz, 1H), 7.20 (s, 1H), 7.09 (d, J=8.7 Hz, 2H), 5.88 (s, 2H), 4.44-4.31 (m, 2H), 1.30 (t, J=7.0 Hz, 3H).

(b) 3-((4-Carbamoylphenoxy)methyl)-4-cyanobenzo[b]thiophene-2-carboxylic acid (63)

To a solution of ethyl 3-((4-carbamoylphenoxy)methyl)-4-cyanobenzo[b]thiophene-2-carboxylate 62 (85 mg, 0.22 mmol) in THF/H$_2$O (8 mL/3 mL) was added LiOH.H$_2$O (29 mg, 0.67 mmol) and the mixture was stirred at room temperature overnight. The solvent was removed under reduced pressure and the residue was diluted with water and acidified to pH 4 with aqueous 1 M HCl. The resulting precipitate was collected by filtration and dried under reduced pressure to give the title product (70 mg, 89%) as a white solid. LCMS-C: (ES-API): rt 0.76 min; m/z 352.9 [M+H]$^+$, 374.9 [M+Na]$^+$. $^1$H NMR (400 MHz, DMSO-d$_6$) δ 8.51 (d, J=8.3 Hz, 1H), 8.07 (d, J=7.3 Hz, 1H), 7.87-7.85 (m, 3H), 7.73 (t, J=7.8 Hz, 1H), 7.21 (s, 1H), 7.09 (d, J=8.5 Hz, 2H), 5.90 (s, 2H), $CO_2H$ not observed.

3-((3-Bromo-4-carbamoylphenoxy)methyl)-4-chlorobenzo[b]thiophene-2-carboxylic acid (64)

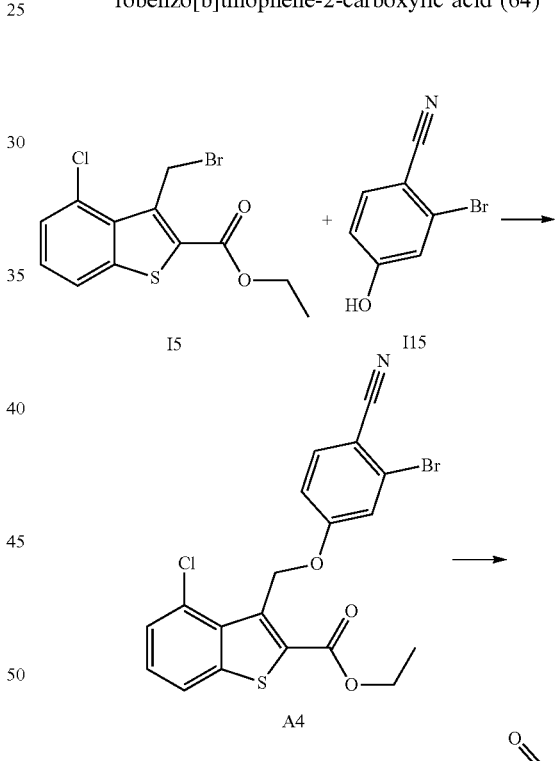

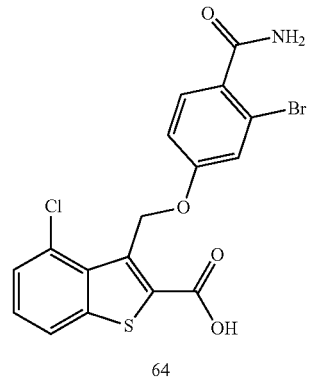

64

(a) Ethyl 3-((3-bromo-4-cyanophenoxy)methyl)-4-chlorobenzo[b]thiophene-2-carboxylate (A4)

A mixture of ethyl 3-(bromomethyl)-4-chlorobenzo[b]thiophene-2-carboxylate 15 (200 mg, 0.6 mmol), 2-bromo-4-hydroxybenzonitrile 115 (131 mg, 0.66 mmol) and $Cs_2CO_3$ (391 mg, 1.2 mmol) in DMF (10 mL) was heated at 50° C. for 2 h. The mixture was poured into water and extracted with EtOAc (200 mL). The organic extract was washed with water (200 mL), brine (200 mL), dried over anhydrous $Na_2SO_4$, filtered and concentrated under reduced pressure. The residue was purified by silica gel chromatography (Pet. Ether/EtOAc=10:1) to give the title product (200 mg, 74%) as a white solid. LCMS-C: (ES-API): rt 2.95 min; m/z 472.0 [M+Na]$^+$. $^1$H NMR (400 MHz, $CDCl_3$) δ 7.81-7.79 (m, 2H), 7.61 (d, J=8.8 Hz, 1H), 7.47-7.39 (m, 2H), 7.33 (d, J=2.4 Hz, 1H), 6.00 (s, 2H), 4.12 (q, J=7.2 Hz, 2H), 1.43 (t, J=7.2 Hz, 3H).

(b) 3-((3-Bromo-4-carbamoylphenoxy)methyl)-4-chlorobenzo[b]thiophene-2-carboxylic acid (64)

To a solution of ethyl 3-((3-bromo-4-cyanophenoxy)methyl)-4-chlorobenzo[b]thiophene-2-carboxylate A4 (100 mg, 0.22 mmol) in $H_2O_2$ (30% aqueous solution)/DMSO/EtOH (1 mL/1 mL/4 mL) was added a 5% aqueous NaOH solution (10 drops) and the resulting mixture was heated at 50° C. overnight. The mixture was acidified to pH 3-4 with aqueous 1 M HCl and extracted with EtOAc (100 mL). The organic extract was washed with water (100 mL), brine (100 mL), dried over anhydrous $Na_2SO_4$, filtered and concentrated under reduced pressure. The residue was purified by preparative HPLC to give the title product (25 mg, 26%) as a white solid. LCMS-C: (ES-API): rt 2.03 min; m/z 439.8 [M+H]$^+$. $^1$H NMR (400 MHz, $CD_3OD$) δ 7.92 (d, J=6.4 Hz, 1H), 7.52-7.48 (m, 3H), 7.34 (d, J=2.4 Hz, 1H), 7.11 (dd, J=8.4, 2.0 Hz, 1H), 6.00 (s, 2H), $CO_2H$ and $CONH_2$ protons not observed.

Ethyl 3-((3-bromo-4-carbamoylphenoxy)methyl)-4-chlorobenzo[b]thiophene-2-carboxylate (65)

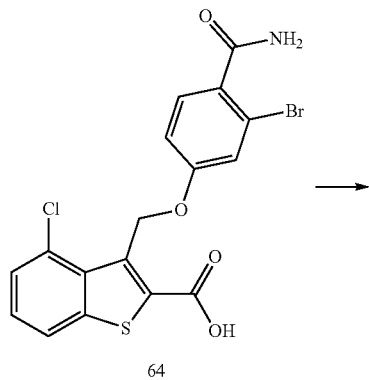

64

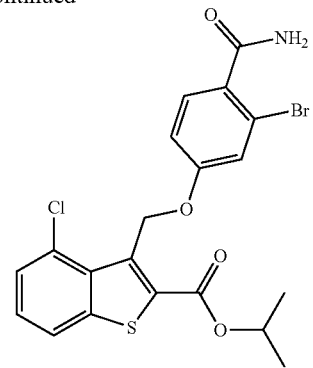

65

To a solution of 3-((3-bromo-4-carbamoylphenoxy)methyl)-4-chlorobenzo[b]thiophene-2-carboxylic acid 64 (crude material from previous step, (50 mg, ~50% purity, ~0.057 mmol) in EtOH (15 mL) was added conc. $H_2SO_4$ (10 drops) and the mixture was heated at 90° C. overnight. The mixture was cooled to room temperature, poured into water and extracted with EtOAc (100 mL). The organic extract was washed with water (100 mL), brine (100 mL), dried over anhydrous $Na_2SO_4$, filtered and concentrated under reduced pressure. The residue was purified by silica gel chromatography (DCM/MeOH=30:1) to give the title product (10 mg, 37%) as a yellow solid. LCMS-C: (ES-API): rt 2.46 min; m/z 467.8 [M+H]$^+$. $^1$H NMR (400 MHz, DMSO-$d_6$) δ 8.16 (dd, J=6.4, 2.0 Hz, 1H), 7.79 (s, 1H), 7.62-7.58 (m, 2H), 7.45 (s, 1H), 7.42 (d, J=8.4 Hz, 1H), 7.33 (d, J=2.0 Hz, 1H), 7.10 (dd, J=8.4, 2.0 Hz, 1H), 5.86 (s, 2H), 4.38 (q, J=7.2 Hz, 2H), 1.31 (t, J=7.2 Hz, 3H).

3-((4-Carbamoyl-2,3-difluorophenoxy)methyl)-4-chlorobenzo[b]thiophene-2-carboxylic acid (67)

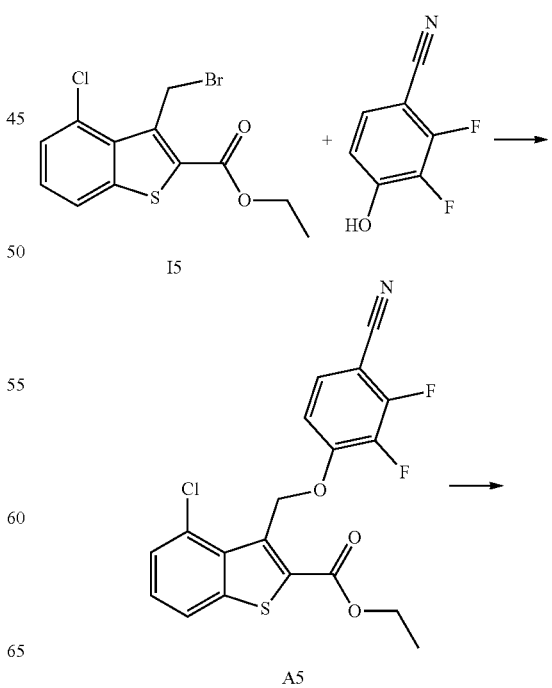

I5

A5

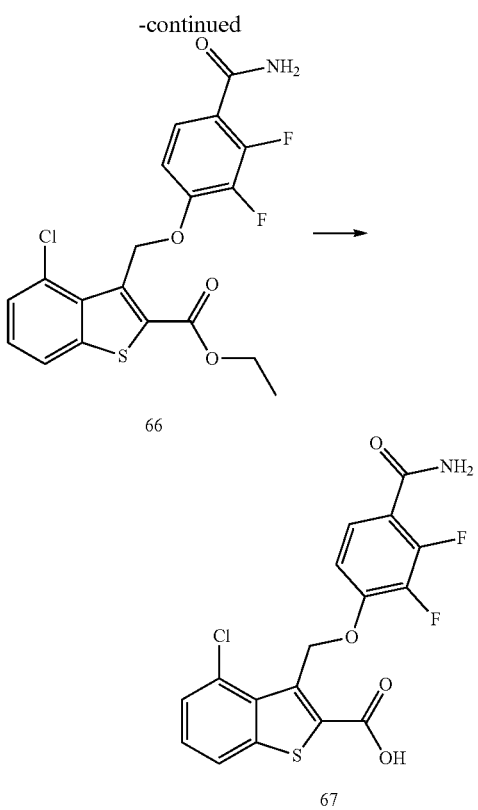

(a) Ethyl 4-chloro-3-((4-cyano-2,3-difluorophenoxy)methyl)benzo[b]thiophene-2-carboxylate (A5)

A mixture of ethyl 3-(bromomethyl)-4-chlorobenzo[b]thiophene-2-carboxylate 15 (0.030 g, 0.090 mmol), 2,3-difluoro-4-hydroxybenzonitrile (0.015 g, 0.099 mmol) and cesium carbonate, 60-80 mesh (0.044 g, 0.13 mmol) in DMF (0.3 mL) was stirred at room temperature for 2 hours. Water (~15 mL) was added and the aqueous phase was extracted with EtOAc (3×25 mL). The organic extracts were combined, washed with brine, dried (MgSO$_4$) and the solvent removed in vacuo to give the title compound (0.031 g, 85% yield) as a white solid. LCMS-B rt 3.892 min; m/z 405.7 [M−H]⁻. $^1$H NMR (400 MHz, DMSO-d$_6$) δ 8.17 (dd, J=7.4, 1.8 Hz, 1H), 7.88-7.81 (m, 1H), 7.63-7.56 (m, 2H), 7.54-7.48 (m, 1H), 6.03 (s, 2H), 4.36 (q, J=7.0 Hz, 2H), 1.29 (t, J=7.1 Hz, 3H).

(b) Ethyl 3-((4-carbamoyl-2,3-difluorophenoxy)methyl)-4-chlorobenzo[b]thiophene-2-carboxylate (66)

Hydrogen peroxide solution (30% w/w in H$_2$O, 0.25 mL) was added to a mixture of ethyl 4-chloro-3-((4-cyano-2,3-difluorophenoxy)methyl)benzo[b]thiophene-2-carboxylate A5 (0.029 g, 0.071 mmol) and potassium carbonate (0.0049 g, 0.036 mmol) in DMSO (0.5 mL) at 0° C. The mixture was returned to room temperature and stirred for 30 minutes. An extra aliquot of hydrogen peroxide solution (30% w/w in H$_2$O, 0.25 mL) was added and the mixture was stirred at room temperature for a further 2 hours. Water (~10 mL) was added and the suspension was filtered and the solid washed with water and air dried to give the title compound as a white solid (0.012 g, 40% yield). LCMS-B rt 3.763 min; m/z 425.7 [M+H]⁺. $^1$H NMR (400 MHz, DMSO-d$_6$) δ 8.16 (dd, J=7.4, 1.8 Hz, 1H), 7.68 (s, 1H), 7.65-7.50 (m, 4H), 7.37-7.29 (m, 1H), 5.97 (s, 2H), 4.37 (q, J=7.1 Hz, 2H), 1.29 (t, J=7.1 Hz, 3H).

(c) 3-((4-Carbamoyl-2,3-difluorophenoxy)methyl)-4-chlorobenzo[b]thiophene-2-carboxylic acid (67)

An aqueous solution of lithium hydroxide monohydrate (2 M, 0.125 mL, 0.250 mmol) was added to ethyl 3-((4-carbamoyl-2,3-difluorophenoxy)methyl)-4-chlorobenzo[b]thiophene-2-carboxylate 66 (0.011 g, 0.026 mmol) in THF:MeOH (2:1, 1 mL) and the mixture was stirred at room temperature for 48 hours. The volatiles were removed under reduced pressure and the residue was suspended in aqueous HCl (~2 M). The suspension was filtered and the solid washed with water and air dried to give the title compound as a white solid (0.0043 g, 42% yield). LCMS-B rt 3.431 min; m/z 397.7 [M+H]⁺. $^1$H NMR (400 MHz, DMSO-d$_6$) δ 8.10 (dd, J=7.7, 1.5 Hz, 1H), 7.67 (s, 1H), 7.62 (s, 1H), 7.60-7.48 (m, 3H), 7.33 (t, J=8.2 Hz, 1H), 6.02 (s, 2H), CO$_2$H proton not observed.

3-((4-Carbamoyl-2,6-difluorophenoxy)methyl)-4-chlorobenzo[b]thiophene-2-carboxylic acid (69)

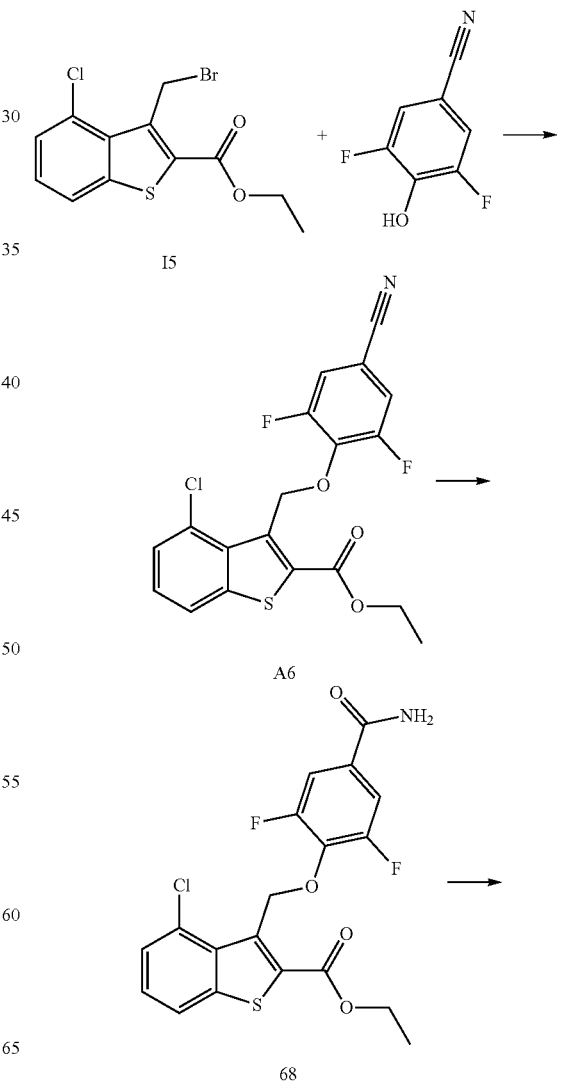

-continued

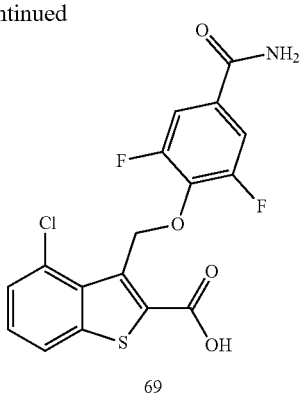

69

(a) Ethyl 4-chloro-3-((4-cyano-2,6-difluorophenoxy)methyl)benzo[b]thiophene-2-carboxylate (A6)

A mixture of ethyl 3-(bromomethyl)-4-chlorobenzo[b]thiophene-2-carboxylate 15 (0.025 g, 0.075 mmol), 3,5-difluoro-4-hydroxybenzonitrile (0.013 g, 0.082 mmol) and cesium carbonate, 60-80 mesh (0.037 g, 0.11 mmol) in DMF (0.5 mL) was stirred at room temperature for 16 hours. Water (~10 mL) was added and the precipitate was isolated by vacuum filtration. The precipitate was washed with water and air dried to give the title compound as a white solid (0.030 g, 98% yield). LCMS-A rt 6.701 min; product did not ionise. $^1$H NMR (400 MHz, DMSO-$d_6$) δ 8.14 (dd, J=7.9, 1.2 Hz, 1H), 7.89-7.80 (m, 2H), 7.63 (dd, J=7.7, 1.2 Hz, 1H), 7.58 (t, J=7.8 Hz, 1H), 6.18 (s, 2H), 4.28 (q, J=7.0 Hz, 2H), 1.25 (t, J=7.1 Hz, 3H).

(b) Ethyl 3-((4-carbamoyl-2,6-difluorophenoxy)methyl)-4-chlorobenzo[b]thiophene-2-carboxylate (68)

A mixture of ethyl 4-chloro-3-((4-cyano-2,6-difluorophenoxy)methyl)benzo[b]thiophene-2-carboxylate A6 (0.023 g, 0.056 mmol), potassium carbonate (0.0039 g, 0.028 mmol) and hydrogen peroxide solution (30% w/w in $H_2O$, 0.017 mL, 0.17 mmol) in DMSO (0.5 mL) was stirred at room temperature for 5 hours. Water (~10 mL) was added and the precipitate was isolated by filtration, washed with water (2×1 mL) and air dried to give the title compound as a white solid (0.016 g, 65% yield). LCMS-B rt 3.607 min; m/z 447.7 [M+Na]$^+$. $^1$H NMR (400 MHz, DMSO-$d_6$) δ 8.14-8.10 (m, 1H), 8.03 (s, 1H), 7.65-7.54 (m, 5H), 6.14 (s, 2H), 4.25 (q, J=7.1 Hz, 2H), 1.22 (t, J=7.1 Hz, 3H).

(c) 3-((4-Carbamoyl-2,6-difluorophenoxy)methyl)-4-chlorobenzo[b]thiophene-2-carboxylic acid (69)

A mixture of ethyl 3-((4-carbamoyl-2,6-difluorophenoxy)methyl)-4-chlorobenzo[b]thiophene-2-carboxylate 68 (0.012 g, 0.028 mmol) and LiOH.$H_2O$ (2 M solution, 0.125 mL, 0.25 mmol) in
THF:MeOH (2:1, 1 mL) was stirred at room temperature for 17 hours. The volatiles were removed by a stream of air and the residue was suspended in aq. HCl (2 M solution, ~5 mL). The precipitate was filtered, washed with a minimum volume of water and air dried to give the title compound as a white solid (0.0030 g, 27% yield). LCMS-B rt 3.655 min; m/z 395.7 [M−H]$^−$. $^1$H NMR (400 MHz, DMSO-$d_6$) δ

8.13-8.06 (m, 1H), 8.02 (s, 1H), 7.62-7.52 (m, 5H), 6.16 (s, 2H), $CO_2H$ proton not observed.

3-((2-Bromo-4-carbamoyl-6-fluorophenoxy)methyl)-4-chlorobenzo[b]thiophene-2-carboxylic acid (71)

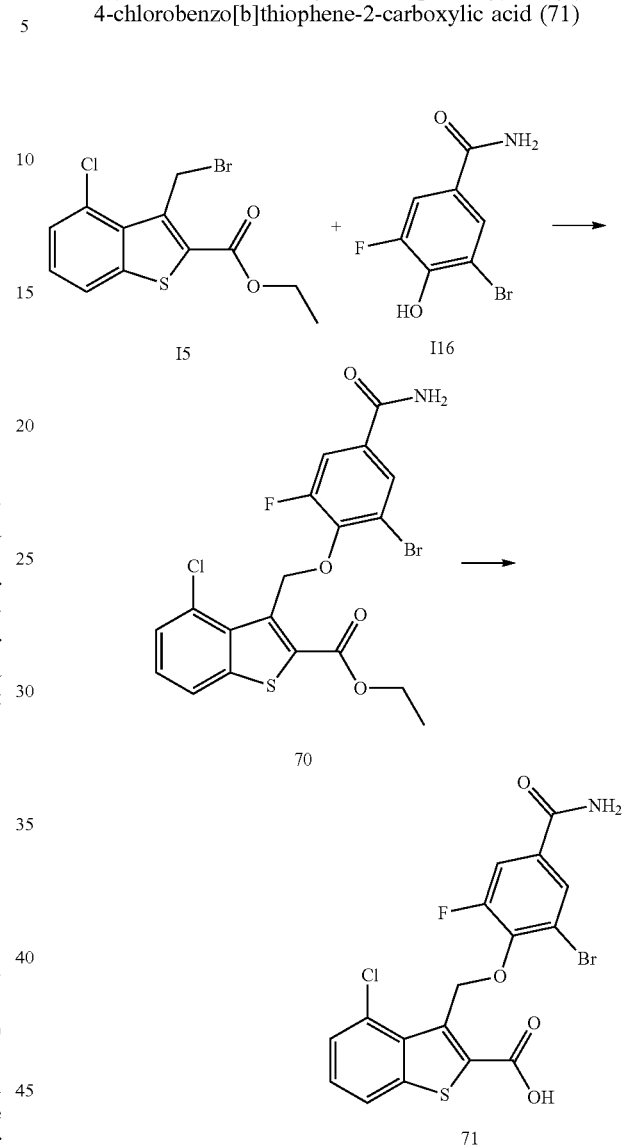

(a) Ethyl 3-((2-bromo-4-carbamoyl-6-fluorophenoxy)methyl)-4-chlorobenzo[b]thiophene-2-carboxylate (70)

A mixture of 3-bromo-5-fluoro-4-hydroxybenzamide 116 (0.019 g, 0.082 mmol), ethyl 3-(bromomethyl)-4-chlorobenzo[b]thiophene-2-carboxylate 15 (0.025 g, 0.075 mmol) and cesium carbonate, 60-80 mesh (0.037 g, 0.11 mmol) in DMF (0.5 mL) was stirred at room temperature for 16 hours. Water (~10 mL) was added and the precipitate was isolated by vacuum filtration. The precipitate was washed with water and air dried to give the title compound as a white solid (0.029 g, 80% yield). LCMS-A RT 6.255 min; product did not ionise. $^1$H NMR (400 MHz, DMSO-$d_6$) δ 8.12 (dd, J=8.1, 1.1 Hz, 1H), 8.06 (s, 1H), 7.92-7.89 (m, 1H), 7.75 (dd, J=12.0, 2.1 Hz, 1H), 7.63 (dd, J=7.7, 1.2 Hz, 1H), 7.59-7.54 (m, 2H), 6.16 (s, 2H), 4.20 (q, J=7.1 Hz, 2H), 1.18 (t, J=7.1 Hz, 3H).

(b) 3-((2-Bromo-4-carbamoyl-6-fluorophenoxy)methyl)-4-chlorobenzo[b]thiophene-2-carboxylic acid (71)

A mixture of ethyl 3-((2-bromo-4-carbamoyl-6-fluorophenoxy)methyl)-4-chlorobenzo[b]thiophene-2-carboxylate 70 (0.022 g, 0.045 mmol) and LiOH.H$_2$O solution (2 M, 0.125 mL, 0.25 mmol) in THF:MeOH (2:1, 1 mL) was stirred at room temperature for 17 hours. The volatiles were removed under a stream of air and the residue was suspended in aq. HCl (~2 M, ~3 mL). The mixture was filtered and the precipitate was washed with a minimum volume of water and air dried to give the title compound as a white solid (0.013 g, 63% yield). LCMS-B rt 3.753 min; m/z 455.6 [M−H]⁻. $^1$H NMR (400 MHz, DMSO-d$_6$) δ 8.03 (s, 1H), 7.90-7.85 (m, 2H), 7.72 (dd, J=12.5, 2.1 Hz, 1H), 7.49 (s, 1H), 7.43-7.39 (m, 1H), 7.33 (t, J=7.8 Hz, 1H), 6.38 (s, 2H), CO$_2$H proton not observed.

3-((4-carbamoyl-2-methoxy-6-methylphenoxy)methyl)-4-chlorobenzo[b]thiophene-2-carboxylic acid (73)

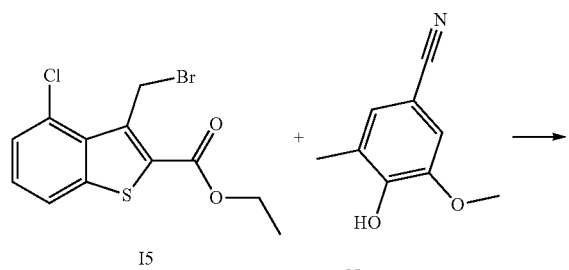

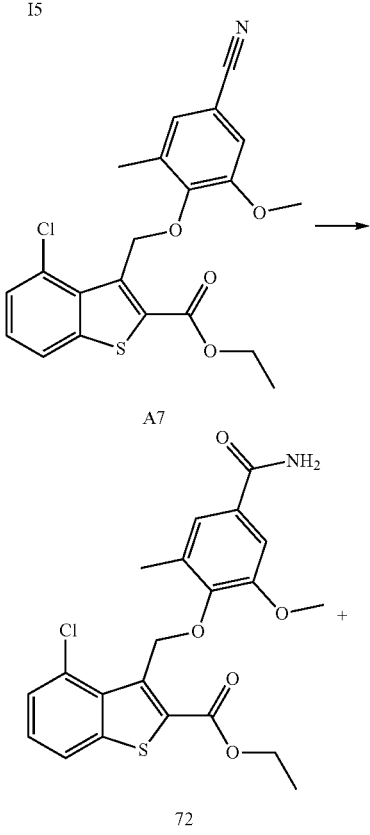

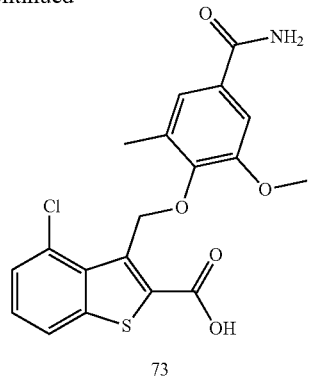

73

(a) Ethyl 4-chloro-3-((4-cyano-2-methoxy-6-methylphenoxy)methyl)benzo[b]thiophene-2-carboxlate (A7)

A mixture of ethyl 3-(bromomethyl)-4-chlorobenzo[b]thiophene-2-carboxylate 15 (0.030 g, 0.090 mmol), 4-hydroxy-3-methoxy-5-methyl-benzonitrile (0.016 g, 0.099 mmol) and cesium carbonate, 60-80 mesh (0.044 g, 0.13 mmol) in DMF (0.3 mL) was stirred at room temperature for 3 hours. Water (~15 mL) was added and the precipitate was isolated by vacuum filtration and air dried to give the title compound as a white solid (0.021 g, 56% yield). LCMS-B rt 3.846 min; m/z 437.7 [M+Na]⁺. $^1$H NMR (400 MHz, DMSO-d$_6$) δ 8.10 (dd, J=7.9, 1.1 Hz, 1H), 7.62 (dd, J=7.6, 1.1 Hz, 1H), 7.56 (t, J=7.8 Hz, 1H), 7.37-7.33 (m, 1H), 7.20-7.16 (m, 1H), 6.02 (s, 2H), 4.18 (q, J=7.1 Hz, 2H), 3.77 (s, 3H), 1.72 (s, 3H), 1.17 (t, J=7.1 Hz, 3H).

(b) Ethyl 3-((4-carbamoyl-2-methoxy-6-methylphenoxy)methyl)-4-chlorobenzo[b]thiophene-2-carboxylate (72) and 3-((4-carbamoyl-2-methoxy-6-methylphenoxy)methyl)-4-chlorobenzo[b]thiophene-2-carboxylic acid (73)

A mixture of ethyl 4-chloro-3-((4-cyano-2-methoxy-6-methylphenoxy)methyl)benzo[b]thiophene-2-carboxylate A7 (0.019 g, 0.046 mmol), potassium carbonate (0.0095 g, 0.069 mmol) and hydrogen peroxide solution (30% w/w in H$_2$O, 0.014 mL, 0.14 mmol) in DMSO (0.75 mL) was stirred for 16 hours at room temperature. An additional aliquot of hydrogen peroxide solution (30% w/w in H$_2$O, 0.014 mL, 0.14 mmol) was added and the mixture was stirred at room temperature for a further 4 hours. A final aliquot of hydrogen peroxide solution (30% w/w in H$_2$O, 0.014 mL, 0.14 mmol) was then added and the mixture was stirred at room temperature for a further 20 hours. Water (~20 mL) was added and the aqueous phase was adjusted to pH ~10 with aq. NaOH (2 M). The aqueous phase was extracted with EtOAc (3×20 mL) and the organic extracts were combined, washed with brine (3×20 mL), dried (MgSO$_4$) and the solvent removed in vacuo to give ethyl 3-((4-carbamoyl-2-methoxy-6-methylphenoxy)methyl)-4-chlorobenzo[b]thiophene-2-carboxylate 72 as a tan coloured solid (0.008 g, 40% yield). LCMS-B RT 3.609 min; m/z 455.7 [M+Na]⁺. $^1$H NMR (400 MHz, DMSO-d$_6$) δ 8.09 (dd, J=8.0, 1.1 Hz, 1H), 7.83 (s, 1H), 7.62 (dd, J=7.8, 1.2 Hz, 1H), 7.55 (t, J=7.8 Hz, 1H), 7.37-7.31 (m, 1H), 7.24-7.17 (m, 2H), 5.98 (s, 2H), 4.14 (q, J=7.0 Hz, 2H), 3.74 (s, 3H), 1.70 (s, 3H), 1.14 (t, J=7.1 Hz, 3H);

The aqueous phase was adjusted to pH ~2 with aq. HCl (2 M) and extracted with EtOAc (3×20 mL). The organic extracts were combined, washed with brine, dried (MgSO₄) and the solvent removed in vacuo to give 3-((4-carbamoyl-2-methoxy-6-methylphenoxy)methyl)-4-chlorobenzo[b]thiophene-2-carboxylic acid 73 as a white solid (0.011 g, 59% yield). LCMS-B RT 3.402 min; m/z 405.8 [M+H]⁺. ¹H NMR (400 MHz, DMSO-d₆) δ 8.06 (d, J=7.9 Hz, 1H), 7.82 (s, 1H), 7.59 (d, J=7.5 Hz, 1H), 7.51 (t, J=7.8 Hz, 1H), 7.33 (d, J=2.0 Hz, 1H), 7.21 (d, J=2.2 Hz, 2H), 6.02 (s, 2H), 3.76 (s, 3H), 1.72 (s, 3H), CO₂H proton not observed.

(Pivaloyloxy)methyl 3-((4-carbamoylphenoxy)methyl)-4-chlorobenzo[b]thiophene-2-carboxylate (74)

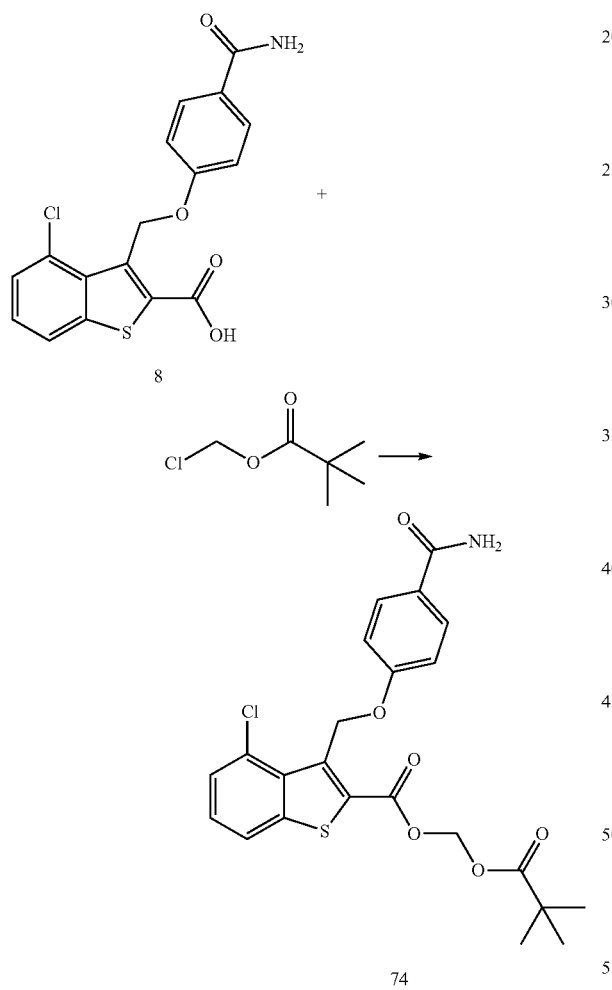

A mixture of 3-((4-carbamoylphenoxy)methyl)-4-chlorobenzo[b]thiophene-2-carboxylic acid (8) (0.048 g, 0.13 mmol), sodium iodide (0.080 g, 0.53 mmol), cesium carbonate, 60-80 mesh (0.086 g, 0.27 mmol) and chloromethyl pivalate (0.076 mL, 0.53 mmol) in DMF (0.5 mL) was stirred at room temperature for 3.5 hours. Water (~10 mL) was added and the precipitate was isolated by filtration. The solid was recrystallised from DCM/cyclohexane to give the title compound as a white powder (0.026 g, 41% yield). LCMS-B rt 3.892 min; m/z 475.8 [M+H]⁺, m/z 497.7 [M+Na]⁺. ¹H NMR (400 MHz, DMSO-d₆) δ 8.18 (dd, J=6.4, 2.8 Hz, 1H), 7.91-7.82 (m, 3H), 7.63-7.57 (m, 2H), 7.20 (s, 1H), 7.08 (d, J=8.7 Hz, 2H), 5.97 (s, 2H), 5.85 (s, 2H), 1.12 (s, 9H).

3-(((4-Carbamoylphenyl)amino)methyl)-4-chlorobenzo[b]thiophene-2-carboxylic acid (76)

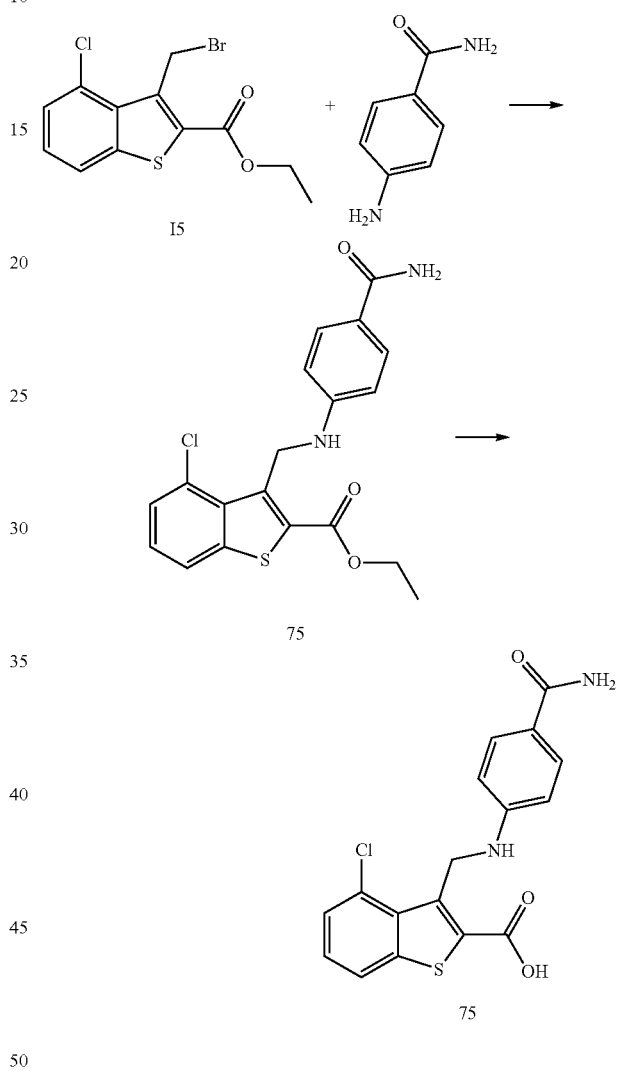

(a) Ethyl 3-(((4-carbamoylphenyl)amino)methyl)-4-chlorobenzo[b]thiophene-2-carboxylate (75)

A solution of ethyl 3-(bromomethyl)-4-chlorobenzo[b]thiophene-2-carboxylate 15 (500 mg, 1.56 mmol), 4-aminobenzamide (213 mg, 1.56 mmol) and K₂CO₃ (865 mg, 6.26 mmol) in DMF (5 mL) was stirred at room temperature under a nitrogen atmosphere overnight. The mixture was diluted with water, extracted with EtOAc (50 mL) and the organic layer was washed with water, brine, dried over anhydrous Na₂SO₄, filtered and concentrated under reduced pressure. The residue was purified by column chromatography (DCM/MeOH=100:1 to 20:1) then re-crystallized (DCM/Pet. Ether) to give the title compound (500 mg) as a white solid. A 100 mg portion was further purified by preparative HPLC to give the title compound (5 mg) LCMS- C: rt 2.27 min; m/z 388.9 [M+H]$^+$, 410.9 [M+Na]$^+$. $^1$H NMR (400 MHz, DMSO-d$_6$) δ 8.09 (d, J=6.4 Hz, 1H), 7.67 (d, J=8.0 Hz, 2H), 7.60-7.49 (m, 3H), 6.86 (s, 1H), 6.65 (d, J=7.6 Hz, 2H), 6.31 (s, 1H), 5.04 (s, 2H), 4.36-4.34 (m, 2H), 1.29 (t, J=6.4 Hz, 3H). The remaining material was used in the subsequent step without further purification.

(b) 3-(((4-Carbamoylphenyl)amino)methyl)-4-chlorobenzo[b]thiophene-2-carboxylic acid (76)

To a solution of ethyl 3-(((4-carbamoylphenyl)amino) methyl)-4-chlorobenzo[b]thiophene-2-carboxylate 75 (200 mg, 0.51 mmol) in MeOH (5 mL) was added NaOH (206 mg, 5.14 mmol) and the mixture was stirred at room temperature overnight. The solvent was removed under reduced pressure and the residue was diluted with water (10 mL) and acidified to pH 4-5 with aq. 1 M HCl. The resulting precipitate was collected by filtration and purified by preparative HPLC to give the title compound (7 mg, 4%) as a white solid. LCMS-C: rt 1.79 min; m/z 360.9 [M+H]$^+$. $^1$H NMR (400 MHz, DMSO-d$_6$) δ 8.07 (d, J=6.8 Hz, 1H), 7.66 (d, J=6.8 Hz, 2H), 7.55-7.51 (m, 3H), 6.86 (s, 1H), 6.65 (d, J=8.4 Hz, 2H), 6.31 (br s, 1H), 5.05 (s, 2H).

Ethyl 3-((4-carbamoylphenoxy)methyl)-4-methylbenzo[b]thiophene-2-carboxylate (77)

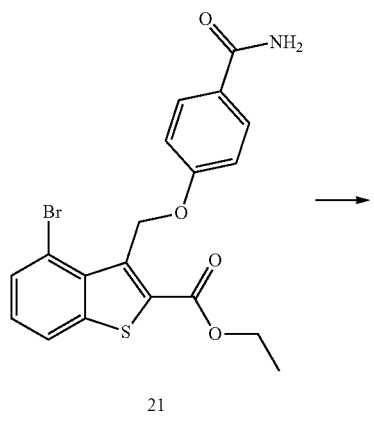

21

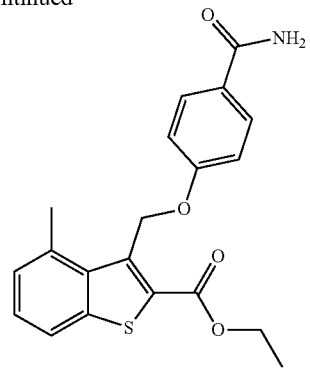

77

A mixture of ethyl 4-bromo-3-((4-carbamoylphenoxy) methyl)benzo[b]thiophene-2-carboxylate 21 (400 mg, 0.92 mmol), methylboronic acid (221 mg, 3.68 mmol), Pd(PPh$_3$)$_4$ (159 mg, 0.138 mmol) and K$_2$CO$_3$ (509 mg, 3.68 mmol) in dioxane (30 mL) was heated at 120° C. under a nitrogen atmosphere overnight. The mixture was cooled to room temperature, diluted with EtOAc (150 mL) and the organic phase was washed with water, brine, dried over anhydrous Na$_2$SO$_4$, filtered and concentrated under reduced pressure. The residue was purified by column chromatography (Pet. Ether/EtOAc=10:1 to 1:1) then re-crystallized (DCM/Pet. Ether) to give the title compound (200 mg) as a white solid. A 70 mg portion was purified further by preparative HPLC to give the title compound (40 mg, 12%). LCMS-C: rt 2.35 min; m/z 370.0 [M+H]$^+$, 391.9 [M+Na]$^+$. $^1$H NMR (400 MHz, DMSO-d$_6$) δ 7.94-7.88 (m, 4H), 7.45 (t, J=7.2 Hz, 1H), 7.28 (d, J=7.2 Hz, 1H), 7.21 (s, 1H), 7.12-7.10 (m, 2H), 5.79 (s, 2H), 4.33 (q, J=7.2 Hz, 2H), 2.67 (s, 3H), 1.27 (t, J=7.2 Hz, 3H). The remaining material was used in the subsequent step without further purification.

Further Examples I

The following examples were made according to the methods described in the general procedures:

| Ex | Starting materials | Name and structure | LCMS data | $^1$H NMR data | Method |
|---|---|---|---|---|---|
| 78 | 77 | 3-((4-Carbamoylphenoxy)methyl)-4-methylbenzo[b]thiophene-2-carboxylic acid | LCMS-C: rt 1.98 min; m/z 342.0 [M + H]$^+$, 363.9 [M + Na]$^+$ | $^1$H NMR (400 MHz, DMSO-d$_6$) δ 13.9 (s, 1H), 7.91-7.87 (m, 4H), 7.42 (t, J = 7.6 Hz, 1H), 7.25 (d, J = 7.2 Hz, 1H), 7.20 (s, 1H), 7.12-7.10 (m, 2H), 5.82 (s, 2H), 2.65 (s, 3H). | B Purified by preparative HPLC |

| Ex | Starting materials | Name and structure | LCMS data | $^1$H NMR data | Method |
|---|---|---|---|---|---|
| 79 | 124 and 125 | 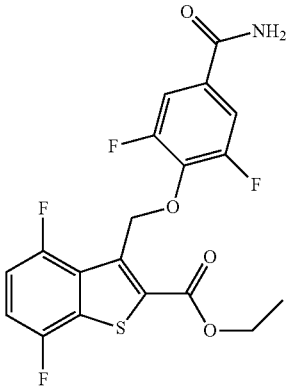 [SMILES: CCOC(=O)c1sc2c(F)ccc(F)c2c1COc1c(F)cc(C(N)=O)cc1F]<br>Ethyl 3-((4-carbamoyl-2,6-difluorophenoxy)methyl)-4,7-difluorobenzo[b]-thiophene-2-carboxylate | LCMS-C:<br>rt 2.45 min;<br>m/z 427.9<br>$[M + H]^+$ | $^1$H NMR (400 MHz, DMSO-$d_6$) δ 8.04 (s, 1H), 7.63-7.48 (m, 4H), 7.44-7.35 (m, 1H), 5.84 (s, 2H), 4.27 (q, J = 7.1 Hz, 2H), 1.23 (t, J = 7.1 Hz, 3H). | A<br>Steps (b) and (c) |
| 80 | 79 | 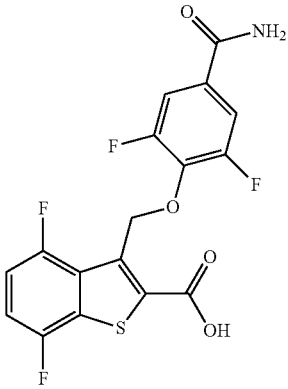 [SMILES: NC(=O)c1cc(F)c(OCc2c(C(=O)O)sc3c(F)ccc(F)c23)c(F)c1]<br>3-((4-Carbamoyl-2,6-difluorophenoxy)methyl)-4,7-difluorobenzo[b]thiophene-2-carboxylic acid | LCMS-C:<br>rt 2.19 min;<br>m/z 399.9<br>$[M + H]^+$ | $^1$H NMR (400 MHz, DMSO-$d_6$) δ 8.03 (s, 1H), 7.61-7.54 (m, 3H), 7.52-7.46 (m, 1H), 7.41-7.34 (m, 1H), 5.88 (s, 2H), CO$_2$H not observed. | C |
| 81 | 124 | 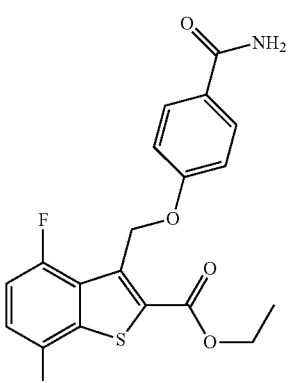<br>Ethyl 3-((4-carbamoylphenoxy)-methyl)-4,7-difluorobenzo[b]thiophene-2-carboxylate | LCMS-C:<br>rt 2.41 min;<br>m/z 391.9<br>$[M + H]^+$ | $^1$H NMR (400 MHz, DMSO-$d_6$) δ 7.97-7.84 (m, 3H), 7.58-7.49 (m, 1H), 7.37 (t, J = 7.9 Hz, 1H), 7.23 (s, 1H), 7.07 (d, J = 8.5Hz, 2H), 5.68 (s, 2H), 4.36 (q, J = 7.0 Hz, 2H), 1.27 (t, J = 7.0 Hz, 3H). | A<br>Steps (b) and (c) |

-continued

| Ex | Starting materials | Name and structure | LCMS data | ¹H NMR data | Method |
|----|---|---|---|---|---|
| 82 | 81 | 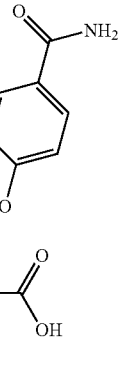<br>3-((4-Carbamoylphenoxy)-methyl)-4,7-difluorobenzo[b]-thiophene-2-carboxylic acid | LCMS-C: rt 1.88 min; m/z 362.0 [M − H]⁻ | ¹H NMR (400 MHz, DMSO-d₆) δ 7.90-7.80 (m, 3H), 7.39-7.31 (m, 1H), 7.28-7.05 (m, 4H), 5.79 (s, 2H), CO₂H not observed. | C |
| 83 | 123 | 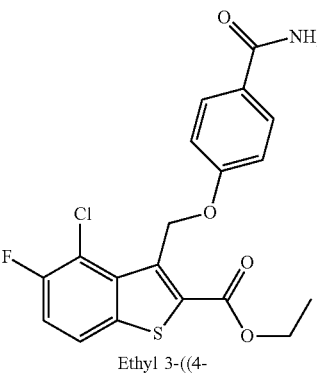<br>Ethyl 3-((4-carbamoylphenoxy)-methyl)-4-chloro-5-fluorobenzo[b]-thiophene-2-carboxylate | LCMS-C: rt 2.40 min; m/z 407.9 [M + H]⁺ | ¹H NMR (400 MHz, DMSO-d₆) δ 8.23-8.17 (m, 1H), 7.90-7.87 (m, 3H), 7.69 (t, J = 9.1 Hz, 1H), 7.22 (s, 1H), 7.08 (d, J = 8.8Hz, 2H), 5.84 (s, 2H), 4.35 (q, J = 7.1 Hz, 2H), 1.27 (t, J = 7.1 Hz, 3H). | A Steps (b) and (c) |
| 84 | 83 | 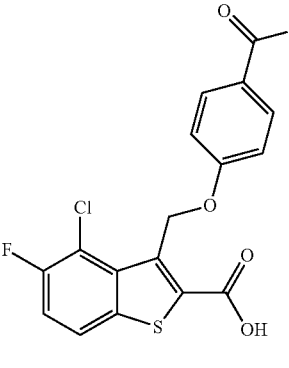<br>3-((4-Carbamoylphenoxy)methyl)-4-chloro-5-fluorobenzo[b]-thiophene-2-carboxylic acid | LCMS-C: rt 2.14 min; m/z 379.9 [M + H]⁺ | ¹H NMR (400 MHz, DMSO-d₆) δ 8.20-8.15 (m, 1H), 7.90-7.83 (m, 3H), 7.70-7.63 (m, 1H), 7.19 (s, 1H), 7.08 (d, J = 8.9 Hz, 2H), 5.87 (s,2H), CO₂H not observed. | C |

-continued

| Ex | Starting materials | Name and structure | LCMS data | $^1$H NMR data | Method |
|---|---|---|---|---|---|
| 85 | 123 and 125 | 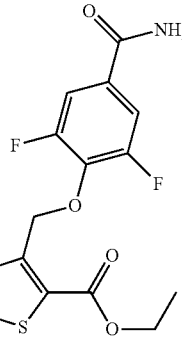 Ethyl 3-((4-carbamoyl-2,6-difluorophenoxy)-methyl)-4-chloro-5-fluorobenzo[b]-thiophene-2-carboxylate | LCMS-C: rt 2.47 min; m/z 443.9 [M + H]$^+$ | $^1$H NMR (400 MHz, DMSO-d$_6$) δ 8.22-8.11 (m, 1H), 8.03 (s, 1H), 7.73-7.48 (m, 4H), 6.10 (s, 2H), 4.24 (q, J = 6.8Hz, 2H), 1.21 (t, J = 6.8 Hz, 3H). | A Steps (b) and (c) |
| 86 | 85 | 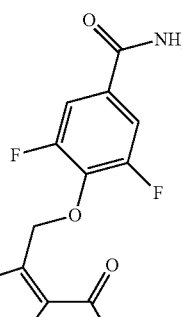 3-((4-Carbamoyl-2,6-difluorophenoxy)-methyl)-4-chloro-5-fluorobenzo[b]-thiophene-2-carboxylic acid | LCMS-C: rt 2.17 min; m/z 415.9 [M + H]$^+$ | $^1$H NMR (400 MHz, DMSO-d$_6$) δ 8.04 (s, 1H), 8.00-7.94 (m, 1H), 7.57 (m, 3H), 7.47 (m, 1H), 6.31 (s, observed. | C |

3-(4-Carbamoylphenethyl)-4-fluorobenzo[b]thio-phene-2-carboxylic acid (88)

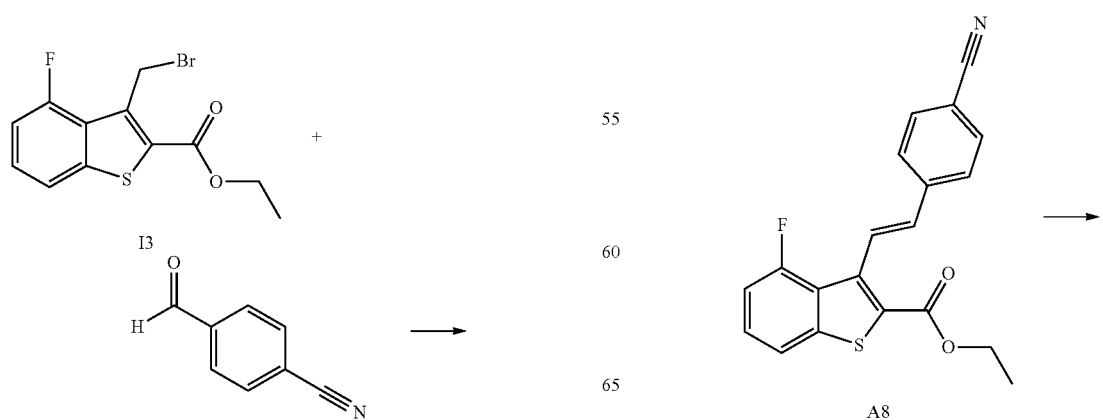

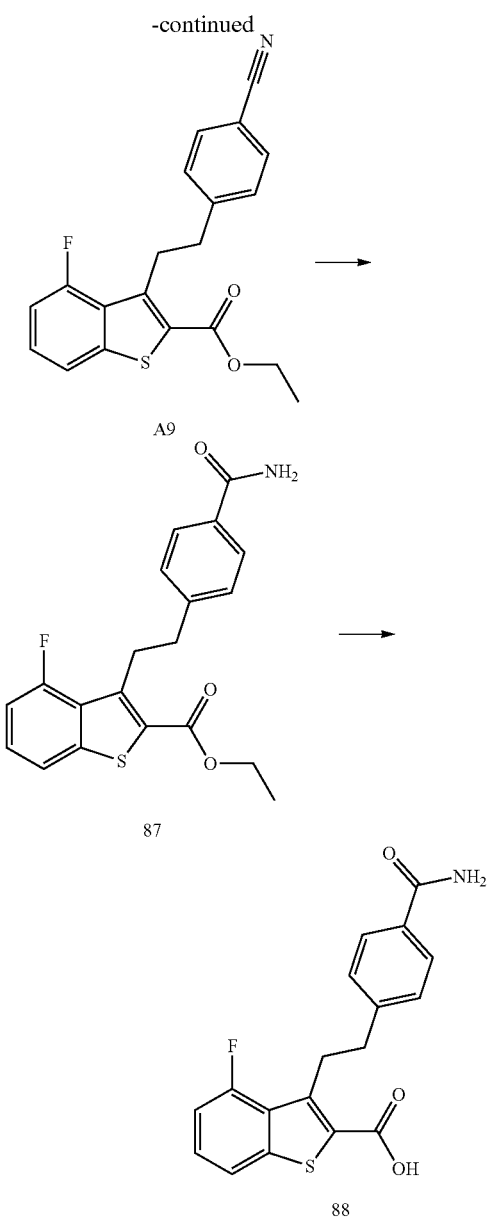

(a) Ethyl (E)-3-(4-cyanostyryl)-4-fluorobenzo[b]thiophene-2-carboxylate A8

Ethyl 3-(bromomethyl)-4-fluorobenzo[b]thiophene-2-carboxylate 13 (100 mg, 0.32 mmol) and triphenylphosphine (0.091 g, 0.35 mmol) were stirred in THF (1.5 mL) at 60° C. for 2.5 hours under a nitrogen atmosphere. The mixture was diluted with THF (3 mL) and cooled to 0° C. under a nitrogen atmosphere. Potassium tert-butoxide (0.039 g, 0.35 mmol) was added and the bright yellow mixture was stirred for 10 minutes. A solution of 4-cyanobenzaldehyde (45 mg, 0.35 mmol) in THF (1 mL) was added and the mixture stirred at room temperature for 3.5 hours. Water (50 mL) and brine (5 mL) were added and the mixture was extracted with DCM (4×25 mL). The pooled DCM extracts were washed with brine, dried over sodium sulfate and the solvent evaporated. The residue was purified by chromatography (4 g silica cartridge, 0-50% ethyl acetate/hexanes) and then recrystallised from toluene to give the title compound as an off-white solid (14.6 mg, 13% yield). LCMS-B rt 3.97 min; m/z 351.8 [M+H]$^+$. $^1$H NMR (400 MHz, chloroform-d) δ 7.98 (dd, J=16.5, 0.8 Hz, 1H), 7.70-7.59 (m, 5H), 7.46 (td, J=8.0, 4.6 Hz, 1H), 7.15-7.01 (m, 2H), 4.40 (q, J=7.1 Hz, 2H), 1.40 (t, J=7.1 Hz, 3H). $^{19}$F NMR (376 MHz, Chloroform-d) δ −110.14.

(b) Ethyl 3-(4-cyanophenethyl)-4-fluorobenzo[b]thiophene-2-carboxylate A9

Ethyl (E)-3-(4-cyanostyryl)-4-fluorobenzo[b]thiophene-2-carboxylate A8 (15 mg, 0.043 mmol), ethyl acetate (2 mL), ethanol (1 mL) and 10% Pd/C (53% wetted with water, 20 mg) were stirred vigorously under a hydrogen atmosphere for two hours. The mixture was filtered through an HPLC filter and concentrated in vacuo to give the title compound as a white solid (20.0 mg, >100% yield). The material was used in the next step without further purification assuming quantitative yield. LCMS-A rt 6.84 min; no products ions detected. $^1$H NMR (400 MHz, chloroform-d) δ 7.69-7.55 (m, 3H), 7.50-7.36 (m, 3H), 7.07 (ddd, J=12.1, 7.9, 0.9 Hz, 1H), 4.37 (q, J=7.1 Hz, 2H), 3.74-3.67 (m, 2H), 3.06-2.99 (m, 2H), 1.41 (t, J=7.1 Hz, 3H).

(c) Ethyl 3-(4-carbamoylphenethyl)-4-fluorobenzo[b]thiophene-2-carboxylate 87

Crude ethyl 3-(4-cyanophenethyl)-4-fluorobenzo[b]thiophene-2-carboxylate A9 (0.0427 mmol, quantitative yield assumed) was slurried in DMSO (0.75 mL) and treated in a fashion analogous to that of the preparation of 2 to give the title compound (8.10 mg, 51% yield, ~85% purity by $^{19}$F NMR). LCMS-B rt 3.54 min; m/z 371.8 [M+H]$^+$. $^1$H NMR (400 MHz, methanol-d$_4$) δ 7.84-7.75 (m, 2H), 7.72 (dd, J=8.1, 0.9 Hz, 1H), 7.49 (ddd, J=9.0, 7.5, 4.9 Hz, 1H), 7.33-7.28 (m, 2H), 7.20-7.09 (m, 1H), 4.34 (qd, J=7.1, 1.6 Hz, 2H), 3.77-3.68 (m, 2H), 3.06-2.96 (m, 2H), 1.37 (t, J=7.1 Hz, 3H), CONH$_2$ protons not observed. $^{19}$F NMR (376 MHz, Methanol-d4) δ −120.17.

(d) 3-(4-Carbamoylphenethyl)-4-fluorobenzo[b]thiophene-2-carboxylic acid 88

Ethyl 3-(4-carbamoylphenethyl)-4-fluorobenzo[b]thiophene-2-carboxylate 87 (6.7 mg, 0.018 mmol) was dissolved in 2:1 THF:MeOH (1 mL) and a 2.0 M aqueous solution of lithium hydroxide monohydrate (0.125 mL, 0.250 mmol) was added. The mixture was stirred at room temperature for 2.5 hours before the volatile solvents were stripped with a stream of air. The aqueous residue was diluted with 1 M aqueous HCl (1 mL), the precipitate was collected by filtration, washed with aqueous 0.5 M HCl (2×0.5 mL) and air dried to give the title compound as a white solid (4.9 mg, 79% yield). LCMS-A rt 5.68 min; m/z 343.8 [M+H]$^+$.

Further Examples II

The following examples were made according to the methods described in the general procedures:

| Ex. | Starting materials | Name and structure | LCMS data | ¹HNMR data | Method |
|---|---|---|---|---|---|
| 89 | 162 & 125 | 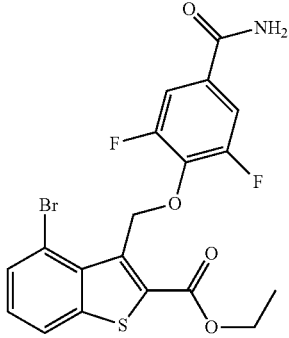 [SMILES: CCOC(=O)c1sc2cccc(Br)c2c1COc1c(F)cc(C(N)=O)cc1F] Ethyl 4-bromo-3-((4-carbamoyl-2,6-difluorophenoxy)methyl)benzo[b]thiophene-2-carboxylate | LCMS-C: rt 2.48 min; m/z 469.8/471.8 [M + H]⁺, 491.8/493.8 [M + Na]⁺ | ¹H NMR (400 MHz, DMSO-d₆) δ 8.18 (dd, J= 8.1, 1.0 Hz, 1H), 8.02 (s, 1H), 7.83 (dd, J = 7.7, 1.0 Hz, 1H), 7.62-7.55 (m, 3H), 7.49 (t, J = 7.9 Hz, 1H), 6.18 (s, 2H), 4.24 (q, J = 7.1 Hz, 2H), 1.21 (t, J = 7.1 Hz, 3H). | A (step C): 1 eq phenol and 2 eq Cs₂CO₃ used; Purified by column chromatography (Pet. Ether/EtOAc = 1:1) |
| 90 | 89 | 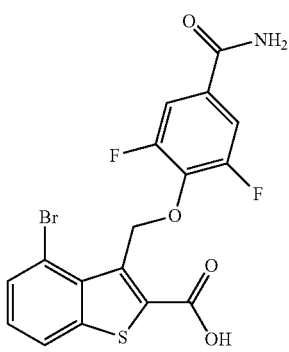 [SMILES: NC(=O)c1cc(F)c(OCc2c(C(=O)O)sc3cccc(Br)c23)c(F)c1] 4-Bromo-3-((4-carbamoyl-2,6-difluorophenoxy)-methyl)benzo[b]-thiophene-2-carboxylic acid | LCMS-C: rt 2.12 min; m/z 441.8/443.8 [M + H]⁺, 463.7/465.9 [M + Na]⁺ | ¹H NMR (400 MHz, DMSO-d₆) δ 8.16 (dd, J = 8.0, 0.4 Hz, 1H), 8.01 (s, 1H), 7.81 (dd, J = 7.7, 0.8 Hz, 1H), 7.61-7.54 (m, 3H), 7.46 (t, J = 7.9 Hz, 1H), 6.22 (s, 2H), CO₂H not observed. | B |
| 91 | 160 & 125 | 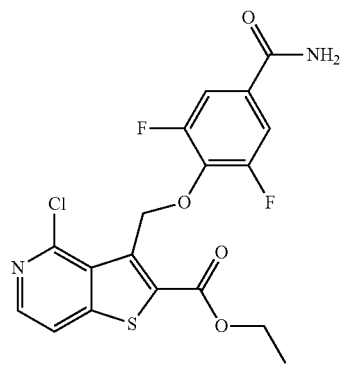 [SMILES: CCOC(=O)c1sc2ccnc(Cl)c2c1COc1c(F)cc(C(N)=O)cc1F] Ethyl 3-((4-carbamoyl-2,6-difluorophenoxy)-methyl)-4-chlorothieno[3,2-c]pyridine-2-carboxylate | LCMS-C: rt 2.12 min; m/z 426.9 [M + H]⁺ | ¹H NMR (400 MHz, DMSO-d₆) δ 8.43 (d, J = 5.5 Hz, 1H), 8.26 (d, J = 5.5 Hz, 1H), 8.10 (s, 1H), 7.62 (d, J = 9.1 Hz, 2H), 7.60-7.56 (m, 1H), 6.10 (s, 2H), 4.26 (q, J = 7.1 Hz, 2H), 1.22 (t, J = 7.1 Hz, 3H). | A (step C): 1 eq phenol used; purified by column chromatography (DCM/MeOH = 100:0 to 100:1) |

| Ex. | Starting materials | Name and structure | LCMS data | ¹HNMR data | Method |
|---|---|---|---|---|---|
| 92 | 156 & 125 | 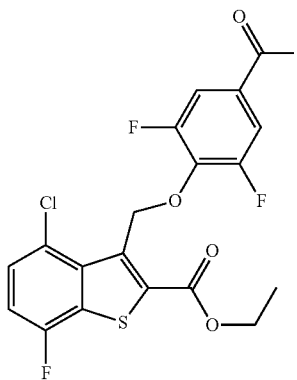 Ethyl 3-((4-carbamoyl-2,6-difluorophenoxy)-methyl)-4-chloro-7-fluorobenzo[b]-thiophene-2-carboxylate | LCMS-C: rt 2.53 min; m/z 443.9 [M + H]⁺, 465.9 [M + Na]⁺ | ¹H NMR (400 MHz, DMSO-d₆) δ 8.07 (s, 1H), 7.68 (dd, J =8.5, 4.6 Hz, 1H), 7.64-7.57 (m, 3H), 7.53 (t, J= 8.8 Hz, 1H), 6.10 (s, 2H), 4.26 (q, J = 7.1 Hz, 2H), 1.22 (t, J = 7.1 Hz, 3H). | A (step C): 1 eq phenol used; purified by column chromato-graphy (DCM/ MeOH = 100:0 to 80:1) |
| 93 | 92 | 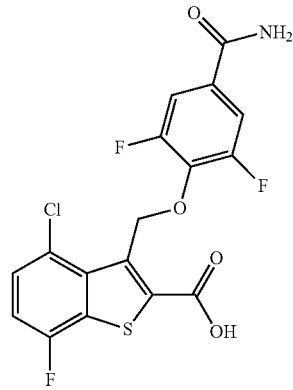 [SMILES: NC(=O)c1cc(F)c(OCc2c(C(=O)O)sc3c(F)ccc(Cl)c23)c(F)c1] 3-((4-Carbamoyl-2,6-difluorophenoxy)methyl)-4-chloro-7-fluorobenzo[b]-thiophene-2-carboxylic acid | LCMS-C: rt 2.17 min; m/z 415.9 [M + H]⁺, 437.8 [M + Na]⁺ | ¹H NMR (400 MHz, DMSO-d₆) δ 8.03 (s, 1H), 7.66 (dd, J = 8.5, 4.6 Hz, 1H), 7.62-7.54 (m, 3H), 7.50 (t, J= 8.7 Hz, 1H), 6.13 (s,2H), CO₂H not observed. | C |

| Ex. | Starting materials | Name and structure | LCMS data | ¹HNMR data | Method |
|---|---|---|---|---|---|
| 94 | 140 & 125 | 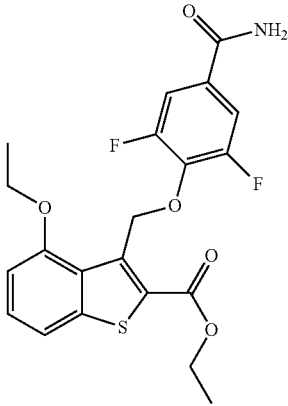 [SMILES: CCOC(=O)c1sc2cccc(OCC)c2c1COc1c(F)cc(C(N)=O)cc1F]<br>Ethyl 3-((4-carbamoyl-2,6-difluorophenoxy)methyl)-4-ethoxybenzo[b]-thiophene-2-carboxylate | LCMS-C: rt 2.52 min; m/z 457.9 [M + Na]⁺ | ¹H NMR (400 MHz, DMSO-$d_6$) δ 8.02 (s, 1H), 7.68-7.54 (m, 4H), 7.48 (t, J = 8.0 Hz, 1H), 6.98 (d, J = 7.8 Hz, 1H), 6.06 (s, 2H), 4.27 (q, J = 7.1 Hz, 2H), 4.09 (q, J = 6.9 Hz, 2H), 1.25 (t, J = 7.1 Hz, 3H), 1.16 (t, J = 6.9 Hz, 3H). | A (step C): 1 eq phenol and 2 eq $CS_2CO_3$ used; purified by column chromatography (Pet. Ether/ EtOAc = 2:1) |
| 95 | 94 | 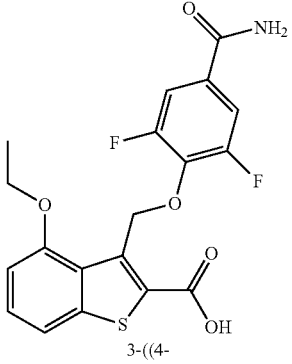<br>3-((4-Carbamoyl-2,6-difluorophenoxy)methyl)-4-ethoxybenzo[b]-thiophene-2-carboxylic acid | LCMS-C: rt 2.15 min; m/z 429.9 [M + Na]⁺ | ¹H NMR (400 MHz, DMSO-$d_6$) δ 8.03 (s, 1H), 7.65-7.52 (m, 4H), 7.44 (t, J = 8.0 Hz, 1H), 6.95 (d, J = 8.0 Hz, 1H), 6.09 (s, 2H), 4.06 (q, J = 6.9 Hz, 2H), 1.11 (t, J= 6.9 Hz, 3H), $CO_2H$ not observed. | B |
| 96 | 165 | 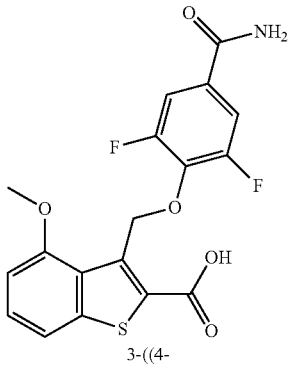<br>3-((4-Carbamoyl-2,6-difluorophenoxy)methyl)-4-methoxybenzo[b]-thiophene-2-carboxylic acid | LCMS-C: rt 2.04 min; m/z 415.9 [M + Na]⁺ | ¹H NMR (400 MHz, DMSO-$d_6$) δ 8.09 (s, 1H), 7.70-7.60 (m, 2H), 7.53 (s, 1H), 7.46 (d, J = 8.0 Hz, 1H), 7.33 (t, J = 8.0 Hz, 1H), 6.84 (d, J = 7.9 Hz, 1H), 6.20 (s, 2H), 3.55 (s, 3H), $CO_2H$ not observed. | B |

-continued

| Ex. | Starting materials | Name and structure | LCMS data | ¹HNMR data | Method |
|---|---|---|---|---|---|
| 97 | 15 & 175 | Ethyl 3-((4-carbamoyl-3-methoxyphenoxy)-methyl)-4-chlorobenzo[b]-thiophene-2-carboxylate | LCMS-C: rt 2.53 min; m/z 419.9 [M + H]⁺ | ¹H NMR (400 MHz, DMSO-d₆) δ 8.13 (dd, J = 7.1, 2.0 Hz, 1H), 7.88 (d, J = 8.6 Hz, 1H), 7.63-7.54 (m, 2H), 7.51 (s, 1H), 7.36 (s, 1H), 6.76 (dd, J = 8.6, 2.3 Hz, 1H), 6.71 (s, 1H), 5.89 (s, 2H), 4.36 (q, J = 7.1 Hz, 2H), 3.88 (s, 3H), 1.29 (t, J = 7.1 Hz, 3H). | A (step C): 1 eq phenol and 4 eq $K_2CO_3$ used; purified by column chromatography (DCM/MeOH = 20:1) and Prep-RP-HPLC. |
| 98 | 97 | 3-((4-Carbamoyl-3-methoxyphenoxy)-methyl)-4-chlorobenzo[b]-thiophene-2-carboxylic acid | LCMS-C: rt 2.20 min; m/z 391.9 [M + H]⁺ | ¹H NMR (400 MHz, DMSO-d₆) δ 8.08 (d, J = 7.1 Hz, 1H), 7.88 (d, J = 8.6 Hz, 1H), 7.63-7.46 (m, 3H), 7.33 (s, 1H), 6.74 (d, J = 9.0 Hz, 1H), 6.71 (s, 1H), 5.92 (s, 2H), 3.88 (s, 3H), $CO_2H$ not observed. | B: 10 eq NaOH used; MeOH used as solvent |
| 99 | 134 & 125 | Ethyl 7-bromo-3-((4-carbamoyl-2,6-difluorophenoxy)methyl)-4-chlorobenzo[b]-thiophene-2-carboxylate | LCMS-C: rt 2.78 min; m/z 503.8/505.8 [M + H]⁺, 525.8/527.8 [M + Na]⁺ | ¹H NMR (400 MHz, DMSO-d₆) δ 8.02 (s, 1H), 7.85 (d, J = 8.3 Hz, 1H), 7.63-7.55 (m, 4H), 6.09 (s, 2H), 4.26 (q, J = 7.1 Hz, 2H), 1.23 (t, J = 7.1 Hz, 3H). | A (step C): 1.05 eq bromide, 1 eq phenol and 2 eq $Cs_2CO_3$ used; purified by trituration with MeOH |

| Ex. | Starting materials | Name and structure | LCMS data | ¹HNMR data | Method |
|---|---|---|---|---|---|
| 100 | 99 | 7-Bromo-3-((4-carbamoyl-2,6-difluorophenoxy)-methyl)-4-chlorobenzo[b]thiophene-2-carboxylic acid | LCMS-D: rt 4.10 min; m/z 497.8/499.7 [M + Na]⁺ | $^1$H NMR (400 MHz, DMSO-$d_6$) δ 8.02 (s, 1H), 7.80 (d, J= 8.2 Hz, 1H), 7.61-7.52 (m, 4H), 6.14 (s, 2H), CO$_2$H not observed. | B |
| 101 | 144 | 3-((4-Carbamoyl-2,6-difluorophenoxy)-methyl)-4-chloro-7-methylbenzo[b]-thiophene-2-carboxylic acid | LCMS-F: rt 2.85 min; m/z 434.0 [M + Na]⁺ | $^1$H NMR (400 MHz, DMSO-$d_6$) δ 8.02 (s, 1H), 7.62-7.50 (m, 4H), 7.39 (d, J = 7.8 Hz, 1H), 6.16 (s, 2H), 2.52 (s, 3H), CO$_2$H not observed. | B |
| 102 | 129 & 125 | Ethyl 3-((4-carbamoyl-2,6-difluorophenoxy)-methyl)-4-methoxythieno-[3,2-c]pyridine-2-carboxylate | LCMS-F: rt 2.95 min; m/z 423.0 [M + H]⁺ | $^1$H NMR (400 MHz, DMSO-$d_6$) δ 8.14 (d, J = 5.7 Hz, 1H), 8.02 (s, 1H), 7.70 (d, J = 5.7 Hz, 1H), 7.64-7.55 (m, 3H), 5.94 (s, 2H), 4.29 (q, J = 7.1 Hz, 2H), 3.85 (s, 3H), 1.26 (t, J = 7.1 Hz, 3H). | A (step C): 1.05 eq bromide, 1 eq phenol and 2 eq CS$_2$CO$_3$ used; purified by column chromatography (Pet. Ether/ EtOAc = 100:1 to 1:1) |

| Ex. | Starting materials | Name and structure | LCMS data | ¹HNMR data | Method |
|---|---|---|---|---|---|
| 103 | 102 | 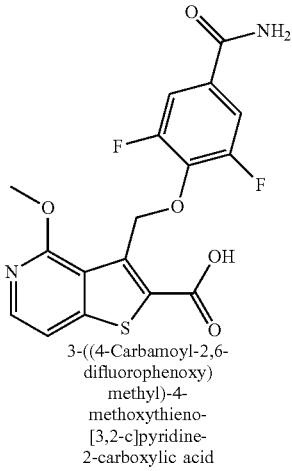<br>3-((4-Carbamoyl-2,6-difluorophenoxy)methyl)-4-methoxythieno-[3,2-c]pyridine-2-carboxylic acid | LCMS-F: rt 1.65 min; m/z 395.1 [M + H]⁺ | ¹H NMR (400 MHz, DMSO-$d_6$) δ 8.11 (d, J = 5.7 Hz, 1H), 8.02 (s, 1H), 7.67 (d, J = 5.7 Hz, 1H), 7.63-7.53 (m, 3H), 5.96 (s, 2H), 3.82 (s, 3H), $CO_2H$ not observed. | B |
| 104 | 145 | 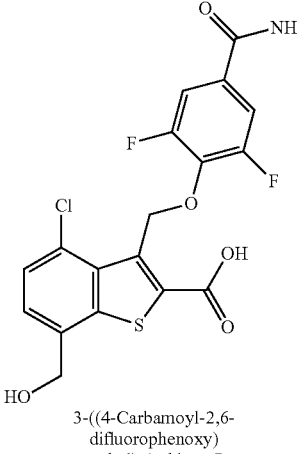<br>3-((4-Carbamoyl-2,6-difluorophenoxy)methyl)-4-chloro-7-(hydroxymethyl)-benzo[b]-thiophene-2-carboxylic acid | LCMS-F: rt 1.30 min; m/z 427.8 [M + H]⁺ | ¹H NMR (400 MHz, DMSO-$d_6$) δ 8.01 (s, 1H), 7.62-7.53 (m, 4H), 7.50 (d, J = 7.9 Hz, 1H), 6.18 (s, 2H), 5.69 (t, J = 4.8 Hz, 1H), 4.76 (d, J = 3.9 Hz, 2H), $CO_2H$ not observed. | B |
| 105 | 146 | 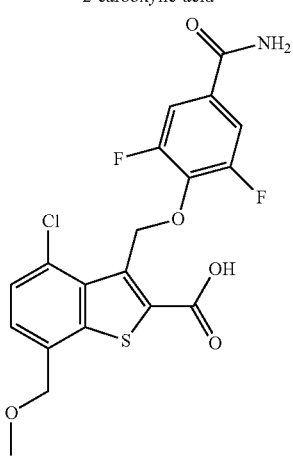<br>3-((4-Carbamoyl-2,6-difluorophenoxy)methyl)-4-chloro-7-(methoxymethyl)benzo[b]-thiophene-2-carboxylic acid | LCMS-F: rt 2.63 min; m/z 441.9 [M + H]⁺ | ¹H NMR (400 MHz, DMSO-$d_6$) δ 8.02 (s, 1H), 7.63-7.53 (m, 4H), 7.50 (d, J = 7.8 Hz, 1H), 6.17 (s, 2H), 4.71 (s, 2H), 3.33 (s, 3H), $CO_2H$ not observed. | B |

-continued

| Ex. | Starting materials | Name and structure | LCMS data | ¹HNMR data | Method |
|---|---|---|---|---|---|
| 106 | 147 | 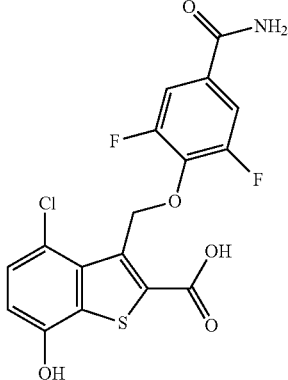 [SMILES: NC(=O)c1cc(F)c(OCc2c(C(=O)O)sc3c(O)ccc(Cl)c23)c(F)c1]<br>3-((4-Carbamoyl-2,6-difluorophenoxy)methyl)-4-chloro-7-hydroxybenzo[b]-thiophene-2-carboxylic acid | LCMS-D: rt 2.31 min; m/z 435.9 [M + Na]⁺ | ¹H NMR (400 MHz, DMSO-$d_6$) δ 10.9 (s, 1H), 8.04 (s, 1H), 7.65-7.55 (m, 2H), 7.52 (s, 1H), 7.27 (d, J = 8.2 Hz, 1H), 6.86 (d, J = 8.3 Hz, 1H), 6.26 (s, 2H), $CO_2H$ not observed. | B |
| 107 | 149 | 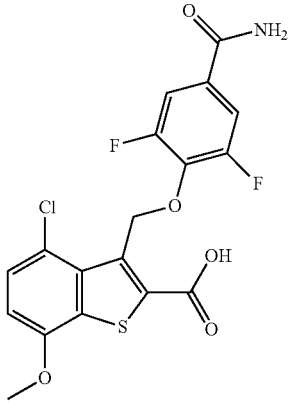 [SMILES: COc1ccc(Cl)c2c(COc3c(F)cc(C(N)=O)cc3F)c(C(=O)O)sc12]<br>3-((4-Carbamoyl-2,6-difluorophenoxy)methyl)-4-chloro-7-methoxybenzo[b]-thiophene-2-carboxylic acid | LCMS-F: rt 2.72 min; m/z 428.0 [M + H]⁺ | ¹H NMR (400 MHz, DMSO-$d_6$) δ 8.01 (s, 1H), 7.58-7.53 (m, 4H), 7.13 (d, J = 8.4 Hz, 1H), 6.14 (s, 2H), 4.01 (s, 3H), $CO_2H$ not observed. | B |
| 108 | 137 & 125 | 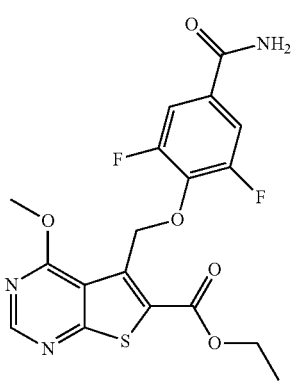 [SMILES: CCOC(=O)c1sc2ncnc(OC)c2c1COc1c(F)cc(C(N)=O)cc1F]<br>5-((4-Carbamoyl-2,6-difluorophenoxy)methyl)-4-methoxythieno-[2,3-d]pyrimidine-6-carboxylic acid | LCMS-D: rt 3.78 min; m/z 424.0 [M + H]⁺ | ¹H NMR (400 MHz, DMSO-$d_6$) δ 8.84 (s, 1H), 8.04 (s, 1H), 7.64-7.58 (m, 3H), 5.86 (s, 2H), 4.29 (q, J = 7.2 Hz, 2H), 4.00 (s, 3H), 1.25 (t, J = 7.1 Hz, 3H). | A (step C): 2 eq $CS_2CO_3$ used; purified by column chromatography (DCM/MeOH = 100:1 to 20:1) |

| Ex. | Starting materials | Name and structure | LCMS data | ¹HNMR data | Method |
|---|---|---|---|---|---|
| 109 | 108 | 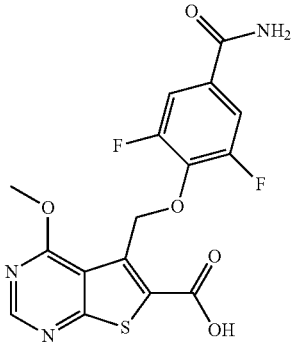 [SMILES: COc1ncnc2sc(C(=O)O)c(COc3c(F)cc(C(N)=O)cc3F)c12]<br>5-((4-Carbamoyl-2,6-difluorophenoxy)methyl)-4-methoxythieno-[2,3-d]pyrimidine-6-carboxylic acid | LCMS-D: rt 3.60 min; m/z 396.0 [M + H]⁺ | ¹H NMR (400 MHz, DMSO-$d_6$) δ 8.82 (s, 1H), 8.04 (s, 1H), 7.66-7.53 (m, 3H), 5.87 (s, 2H), 3.97 (s, 3H), $CO_2H$ not observed. | B |
| 110 | 15 & 169 | 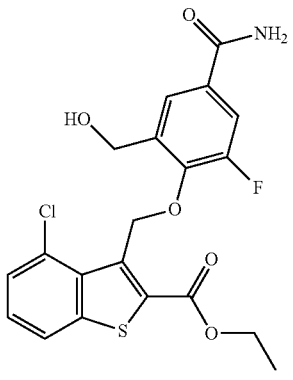 [SMILES: CCOC(=O)c1sc2cccc(Cl)c2c1COc1c(F)cc(C(N)=O)cc1CO]<br>Ethyl 3-((4-carbamoyl-2-fluoro-6-(hydroxymethyl)-phenoxy)methyl)-4-chlorobenzo[b]-thiophene-2-carboxylate | LCMS-D: rt 3.92 min; m/z 438.0 [M + H]⁺, 460.0 [M + Na]⁺ | ¹H NMR (400 MHz, DMSO-$d_6$) δ 8.13 (d, J = 7.9 Hz, 1H), 7.95 (s, 1H), 7.76 (s, 1H), 7.68-7.62 (m, 2H), 7.58 (t, J = 7.8 Hz, 1H), 7.34 (s, 1H), 6.07 (s, 2H), 5.07 (brs, 1H), 4.23 (q, J = 7.1 Hz, 2H), 4.16 (s, 2H), 1.20 (t, J = 7.1 Hz, 3H). | A (step C): 1.05 eq bromide, 1 eq phenol and 2 eq $CS_2CO_3$ used; purified by column chromatography (Pet. Ether/EtOAc = 1:1 to 1:3) (step C) |
| 111 | 110 | 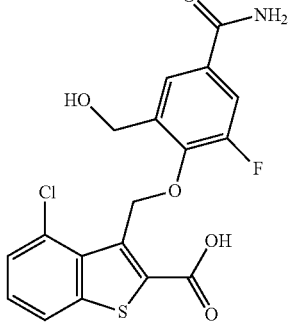<br>3-((4-Carbamoyl-2-fluoro-6-(hydroxymethyl)-phenoxy)methyl)-4-chlorobenzo[b]-thiophene-2-carboxylic acid | LCMS-D: rt 3.34 min; m/z 408.0 [M − H]⁻ | ¹H NMR (400 MHz, DMSO-$d_6$) δ 8.11 (dd, J= 7.9, 1.1 Hz, 1H), 7.95 (s, 1H), 7.75 (s, 1H), 7.68-7.59 (m, 2H), 7.55 (t, J = 7.8 Hz, 1H), 7.34 (s, 1H), 6.10 (s, 2H), 5.08 (brs, 1H), 4.17 (s, 2H), $CO_2H$ not observed. | B |

-continued

| Ex. | Starting materials | Name and structure | LCMS data | ¹HNMR data | Method |
|---|---|---|---|---|---|
| 112 | 151 | 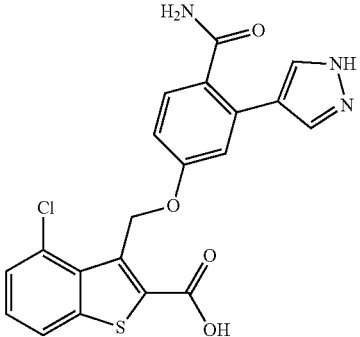 [SMILES: NC(=O)c1ccc(OCc2c(C(=O)O)sc3cccc(Cl)c23)cc1-c1cn[nH]c1]<br>3-((4-Carbamoyl-3-(1H-pyrazol-4-yl)phenoxy)-methyl)-4-chlorobenzo[b]-thiophene-2-carboxylic acid | LCMS-D: rt 3.35 min; m/z 426.0 [M − H]⁻ | ¹H NMR (400 MHz, DMSO-$d_6$) δ 13.7-13.3 (m, 2H), 8.12 (dd, J = 7.3, 1.9 Hz, 1H), 7.86 (s, 2H), 7.64 (s, 1H), 7.60-7.49 (m, 2H), 7.38-7.23 (m, 2H), 7.13 (d, J = 2.5 Hz, 1H), 6.94 (dd, J = 8.4, 2.6 Hz, 1H), 5.89 (s, 2H). | B |
| 113 | 150 | 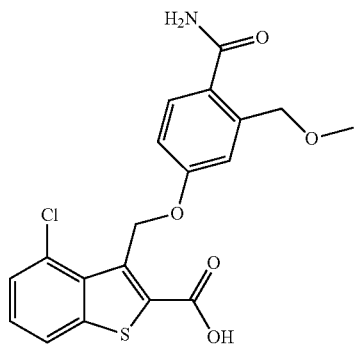 [SMILES: COCc1cc(OCc2c(C(=O)O)sc3cccc(Cl)c23)ccc1C(N)=O]<br>3-((4-Carbamoyl-3-(methoxymethyl)-phenoxy)methyl)-4-chlorobenzo[b]-thiophene-2-carboxylic acid | LCMS-D: rt 3.59 min; m/z 406.0 [M + H]⁺, 428.0 [M + Na]⁺ | ¹H NMR (400 MHz, CDCl₃) δ 8.11 (dd, J = 7.0, 2.1 Hz, 1H), 7.68 (s, 1H), 7.60-7.49 (m, 3H), 7.23 (s, 1H), 7.11 (d, J = 2.6 Hz, 1H), 6.98 (dd, J = 8.5, 2.7 Hz, 1H), 5.87 (s, 2H), 4.63 (s, 2H), 3.32 (s, 3H), CO₂H not observed. | B |
| 114 | 142 | 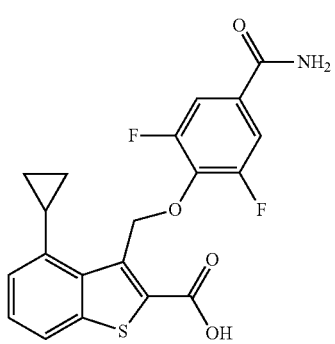 [SMILES: NC(=O)c1cc(F)c(OCc2c(C(=O)O)sc3cccc(C4CC4)c23)c(F)c1]<br>3-((4-Carbamoyl-2,6-difluorophenoxy)methyl)-4-cyclopropyl-benzo[b]-thiophene-2-carboxylic acid | LCMS-C: rt 2.35 min; m/z 425.9 [M + Na]⁺ | ¹H NMR (400 MHz, DMSO-$d_6$) δ 8.04 (s, 1H), 7.89 (d, J= 8.1 Hz, 1H), 7.63-7.54 (m, 3H), 7.44 (t, J = 7.8 Hz, 1H), 7.26 (d, J = 7A Hz, 1H), 6.24 (s, 2H), 2.85-2.76 (m, 1H), 1.08-1.00 (m, 2H), 0.95-0.88 (m, 2H), CO₂H not observed. | B |

| Ex. | Starting materials | Name and structure | LCMS data | ¹HNMR data | Method |
|---|---|---|---|---|---|
| 115 | 146 & 125 | 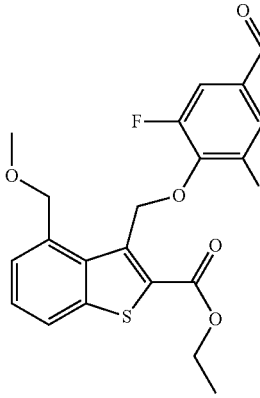<br>Ethyl 3-((4-carbamoyl-2,6-difluorophenoxy)-methyl)-4-(methoxymethyl)-benzo[b]thiophene-2-carboxylate | LCMS-C: rt 2.49 min; m/z 458.0 [M + Na]⁺ | $^1$H NMR (400 MHz, DMSO-$d_6$) δ 8.09-8.03 (m, 2H), 7.66-7.50 (m, 5H), 6.00 (s, 2H), 4.98 (s, 2H), 4.28-4.14 (m, 2H), 3.30 (s, 3H), 1.29-1.16 (m, 3H). | A (step C): Purified by column chromatography (DCM/MeOH = 100:0 to 50:1) |
| 116 | 152 & 125 | 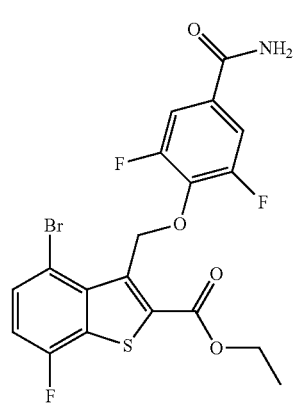 [SMILES: CCOC(=O)c1sc2c(F)ccc(Br)c2c1COc1c(F)cc(C(N)=O)cc1F]<br>Ethyl 4-bromo-3-((4-carbamoyl-2,6-difluorophenoxy)-methyl)-7-fluorobenzo[b]-thiophene-2-carboxylate | LCMS-D: rt 4.34 min; m/z 488.0 [M + H]⁺, 509.9 [M + Na]⁺ | $^1$H NMR (400 MHz, DMSO-$d_6$) δ 8.02 (s, 1H), 7.87 (dd, J = 8.5, 4.9 Hz, 1H), 7.59 (d, J = 9.3 Hz, 2H), 7.57 (s, 1H), 7.47 (t, J = 8.8 Hz, 1H), 6.16 (s, 2H), 4.26 (q, J = 7.1 Hz, 2H), 1.21 (t, J= 7.1 Hz, 3H). | A (step C): 1.05 eq bromide, 1 eq phenol and 2 eq $CS_2CO_3$ used; purified by column chromatography (Pet. Ether/EtOAc = 100:0 to 1:1) |

| Ex. | Starting materials | Name and structure | LCMS data | ¹HNMR data | Method |
|---|---|---|---|---|---|
| 117 | 116 | 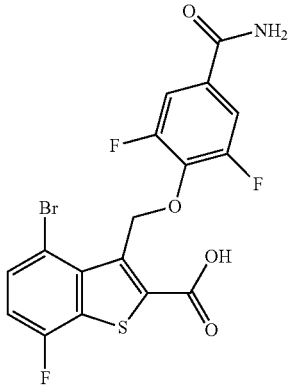 [SMILES: NC(=O)c1cc(F)c(OCc2c(C(=O)O)sc3c(F)ccc(Br)c23)c(F)c1]<br>4-Bromo-3-((4-carbamoyl-2,6-difluorophenoxy)methyl)-7-fluorobenzo[b]-thiophene-2-carboxylic acid | LCMS-F: rt 4.28 min; m/z 459.8 [M + H]⁺ | $^1$H NMR (400 MHz, DMSO-d$_6$) δ 8.02 (s, 1H), 7.85 (dd, J = 8.5, 4.9 Hz, 1H), 7.59 (s, 1H), 7.57 (d, J = 2.9 Hz, 2H), 7.43 (t, J= 8.8 Hz, 1H), 6.19 (s, 2H), CO$_2$H not observed. | B |
| 118 | 153 | 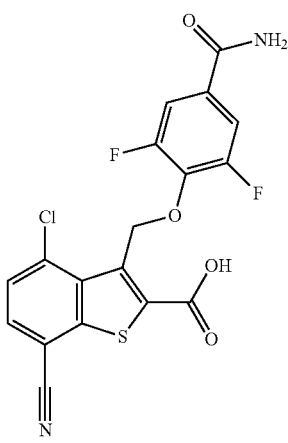 [SMILES: N#Cc1ccc(Cl)c2c(COc3c(F)cc(C(N)=O)cc3F)c(C(=O)O)sc12]<br>3-((4-Carbamoyl-2,6-difluorophenoxy)methyl)-4-chloro-7-cyanobenzo[b]-thiophene-2-carboxylic acid | LCMS-F: rt 2.43 min; m/z 423.0 [M + H]⁺ | $^1$H NMR (400 MHz, DMSO-d$_6$) δ 8.16 (d, J = 8.0 Hz, 1H), 8.02 (s, 1H), 7.83 (d, J = 8.0 Hz, 1H), 7.62-7.53 (m, 3H), 6.16 (s, 2H), CO$_2$H not observed. | B: Purified the precipitate by Prep-HPLC |

| Ex. | Starting materials | Name and structure | LCMS data | ¹HNMR data | Method |
|---|---|---|---|---|---|
| 121 | 129 & 169 | 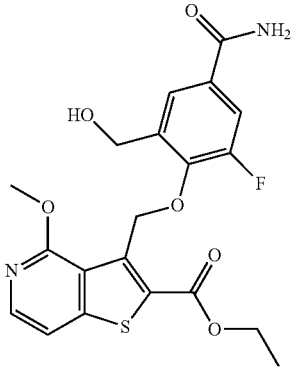 [SMILES: CCOC(=O)c1sc2ccnc(OC)c2c1COc1c(F)cc(C(N)=O)cc1CO]<br>Ethyl 3-((4-carbamoyl-2-fluoro-6-(hydroxymethyl)-phenoxy)methyl)-4-methoxythieno[3,2-c]pyridine-2-carboxylate | LCMS-D: rt3.52 min; m/z 435.1 [M + H]⁺, 457.1 [M + Na]⁺ | ¹H NMR (400 MHz, DMSO-d₆) δ 8.15 (d, J = 5.7 Hz, 1H), 7.95 (s, 1H), 7.78-7.76 (m, 1H), 7.74-7.71 (m, 1H), 7.70-7.65 (m, 1H), 7.35 (s, 1H), 5.88 (s, 2H), 5.10 (t, J = 5.6 Hz, 1H), 4.29 (q, J = 7.1 Hz, 2H), 4.17 (d, J = 5.6 Hz, 2H), 3.83 (s, 3H), 1.26 (t, J = 7.1 Hz, 3H). | A (step C): 1.2 eq phenol and 3 eq CS₂CO₃ used; purified by prep-TLC (DCM/MeOH = 10:1) |

Further Examples III (Pivaloyloxy)methyl 3-((4-carbamoyl-2,6-difluoro-phenoxy)methyl)-4-chloro-7-fluoro benzo[b]thio-phene-2-carboxylate (122)

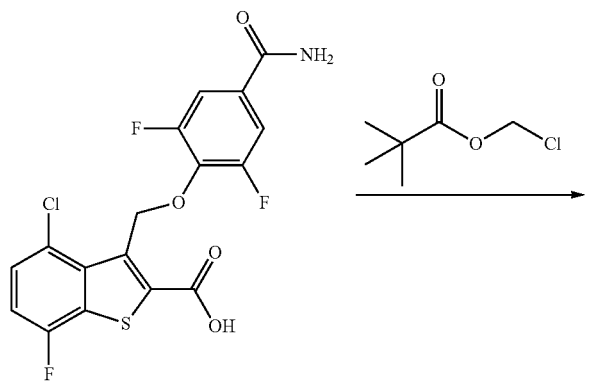

A suspension of 3-((4-carbamoyl-2,6-difluorophenoxy) methyl)-4-chloro-7-fluoro benzo[b]thiophene-2-carboxylic acid 93 (50 mg, 0.12 mmol), chloromethyl pivalate (73 mg, 0.48 mmol), NaI (72 mg, 0.48 mmol) and 052003 (78 mg, 0.24 mmol) in DMF (5 mL) was stirred at room temperature overnight. Water (50 mL) was added and the mixture was extracted with EtOAc (50 mL×3). The combined organic extracts were washed with water (100 mL×3), brine (100 mL), dried over Na₂SO₄, filtered and concentrated to give the title compound (65 mg, 100%) as a white solid. LCMS-C: rt 2.76 min; m/z 529.9 [M+H]⁺. ¹H NMR (400 MHz, DMSO-d₆) δ 8.11 (s, 1H), 7.70 (dd, J=8.6, 4.6 Hz, 1H), 7.68-7.54 (m, 4H), 6.10 (s, 2H), 5.90 (s, 2H), 1.12 (s, 9H).

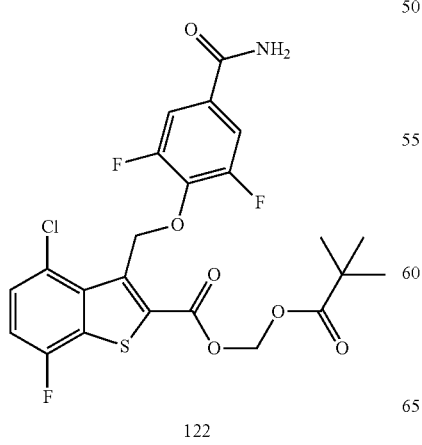

122

The following examples were prepared according to the procedure described for (122).

| Ex | Starting materials | Name and structure | LCMS data | ¹H NMRdata | Comment |
|---|---|---|---|---|---|
| 123 | 96 & Chloromethyl pivalate | 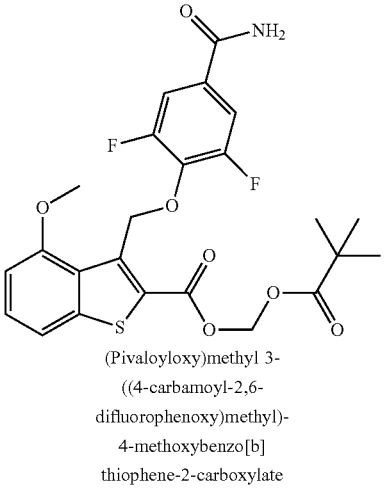<br>(Pivaloyloxy)methyl 3-((4-carbamoyl-2,6-difluorophenoxy)methyl)-4-methoxybenzo[b]thiophene-2-carboxylate | LCMS-C: rt 2.61 min; m/z 529.9 [M + Na]⁺ | ¹H NMR (400 MHz, DMSO-d₆) δ 8.02 (s, 1H), 7.66-7.58 (m, 3H), 7.56 (s, 1H), 7.52 (t, J = 8.0 Hz, 1H), 6.98 (d, J = 8.0 Hz, 1H), 5.98 (s, 2H), 5.92 (s, 2H), 3.69 (s, 3H), 1.14 (s, 9H). | |
| 124 | 114 & Chloromethyl pivalate | 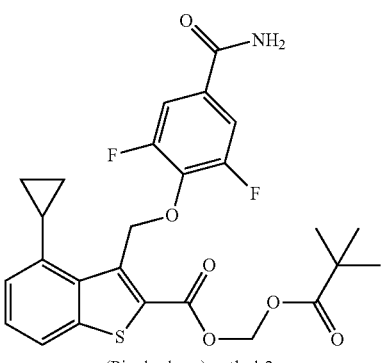<br>(Pivaloyloxy)methyl 3-((4-carbamoyl-2,6-difluorophenoxy)methyl)-4-cyclopropylbenzo[b]-thiophene-2-carboxylate | LCMS-C: rt 2.76 min; m/z 518.0 [M + H]⁺, 540.0 [M + Na]⁺ | ¹H NMR (400 MHz, DMSO-d₆) δ 8.02 (s, 1H), 7.97 (d, J = 8.0 Hz, 1H), 7.63-7.55 (m, 3H), 7.50 (t, J = 7.8 Hz, 1H), 7.30 (d, J = 7.4 Hz, 1H), 6.21 (s, 2H), 5.85 (s, 2H), 2.84-2.76 (m, 1H), 1.11 (s, 9H), 1.05-1.02 (m, 2H), 0.94-0.90 (m, 2H). | |
| 125 | 69 & 1-Chloro-2-methylpropyl propionate | 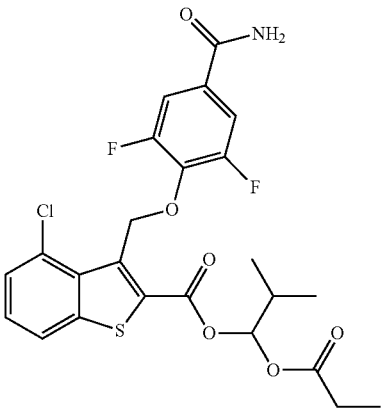 [SMILES: CCC(=O)OC(OC(=O)c1sc2cccc(Cl)c2c1COc1c(F)cc(C(N)=O)cc1F)C(C)C]<br>2-Methyl-1-(propionyloxy)propyl 3-((4-carbamoyl-2,6-difluorophenoxy)methyl)-4-chlorobenzo[b]thiophene-2-carboxylate | LCMS-C: rt 2.74 min; m/z 547.9 [M + Na]⁺ | ¹H NMR (400 MHz, DMSO-d₆) δ 8.15 (dd, J = 7.8, 1.3 Hz, 1H), 8.01 (s, 1H), 7.67-7.54 (m, 5H), 6.66 (d, J = 4.9 Hz, 1H), 6.13 (s,2H), 2.39-2.30 (m, 2H), 2.07-1.97 (m, 1H), 1.02 (t, J= 7.5 Hz, 3H), 0.92-0.90 (m, 6H). | Heated at 60° C. overnight; Purified by column chromatography (Pet. Ether/EtOAc = 10:1 to 0:1) |

-continued

| Ex | Starting materials | Name and structure | LCMS data | ¹H NMR data | Comment |
|---|---|---|---|---|---|
| 126 | 69 & 4-(Chloromethyl)-5-methyl-1,3-dioxol-2-one | 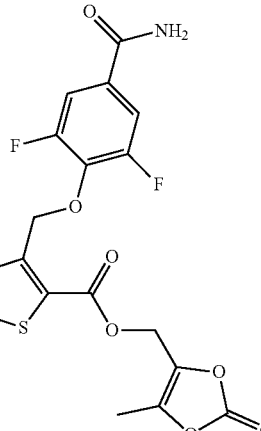<br>(5-Methyl-2-oxo-1,3-dioxol-4-yl)methyl 3-((4-carbamoyl-2,6-difluorophenoxy)methyl)-4-chlorobenzo[b]-thiophene-2-carboxylate | LCMS-C: rt 2.46 min; m/z 509.9 [M + Na]⁺, 531.9 [M + Na]⁺ | ¹H NMR (400 MHz, DMSO-$d_6$) δ 8.15 (dd, J = 7.9, 1.3 Hz, 1H), 8.02 (s, 1H), 7.66-7.54 (m, 5H), 6.11 (s, 2H), 5.20 (s, 2H), 2.17 (s, 3H). | Purified by column chromatography (Pet. Ether/EtOAc = 10:1 to 0:1) and recrystallization (Pet. Ether/DCM) |
| 127 | 69 & 2-Chloro-N,N-dimethyl-acetamide | 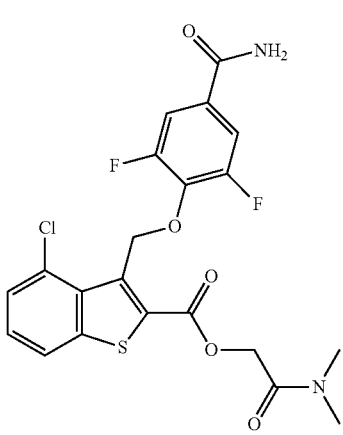 [SMILES: CN(C)C(=O)COC(=O)c1sc2cccc(Cl)c2c1COc1c(F)cc(C(N)=O)cc1F]<br>2-(Dimethylamino)-2-oxoethyl 3-((4-carbamoyl-2,6-difluorophenoxy)methyl)-4-chlorobenzo[b]-thiophene-2-carboxylate | LCMS-C: rt 2.28 min; m/z 482.9 [M + H]⁺, 504.9 [M + Na]⁺ | ¹H NMR (400 MHz, DMSO-$d_6$) δ 8.15 (dd, J = 7.8, 1.2 Hz, 1H), 8.01 (s, 1H), 7.68-7.52 (m, 5H), 6.14 (s, 2H), 5.01 (s, 2H), 2.94 (s, 3H), 2.82 (s, 3H). | Purified by column chromatography (Pet. Ether/EtOAc = 10:1 to 0:1) then prep-HPLC |
| 128 | 90 & Chloromethyl pivalate | 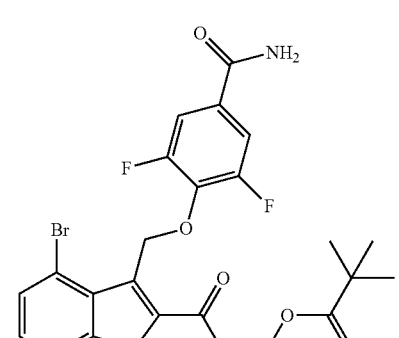<br>(Pivaloyloxy)methyl 4-bromo-3-((4-carbamoyl-2,6-difluorophenoxy)methyl)-benzo[b]thiophene-2-carboxylate | LCMS-C: rt 2.67 min; m/z 555.9/557.9, [M + H]⁺, 577.9/579.9 [M + Na]⁺ | ¹H NMR (400 MHz, DMSO-$d_6$) δ 8.21 (dd, J = 8.1, 1.0 Hz, 1H), 8.02 (s, 1H), 7.85 (dd, J = 7.7, 1.0 Hz, 1H), 7.63-7.54 (m, 3H), 7.51 (t, J = 7.9 Hz, 1H), 6.17 (s, 2H), 5.88 (s, 2H), 1.12 (s, 9H). | Purified by column chromatography (DCM/MeOH = 100:0 to 100:1) |

| Ex | Starting materials | Name and structure | LCMS data | ¹H NMR data | Comment |
|---|---|---|---|---|---|
| 129 | 69 & 176 | 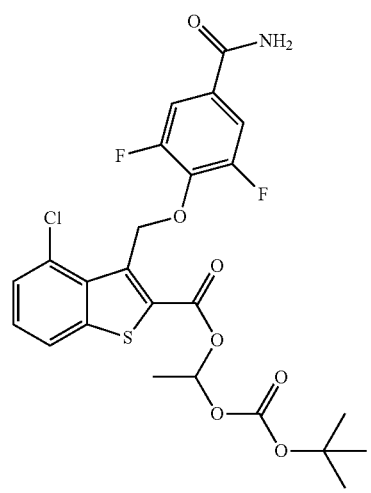 [SMILES: CC(OC(=O)OC(C)(C)C)OC(=O)c1sc2cccc(Cl)c2c1COc1c(F)cc(C(N)=O)cc1F]<br>1-((tert-Butoxycarbonyl)oxy)ethyl 3-((4-carbamoyl-2,6-difluorophenoxy)methyl)-4-chlorobenzo[b]-thiophene-2-carboxylate | LCMS-C: rt 2.69 min; m/z 563.9 [M + Na]⁺ | ¹H NMR (400 MHz, DMSO-$d_6$) δ 8.15 (dd, J = 7.9, 1.2 Hz, 1H), 8.02 (s, 1H), 7.67-7.54 (m, 5H), 6.73 (q, J = 5.4 Hz, 1H), 6.11 (app q, J = 11.3 Hz, 2H), 1.46 (d, J = 5.5 Hz, 3H), 1.40 (s, 9H). | Purified by prep-TLC (DCM/ MeOH = 20:1) |
| 130 | 69 & 177 | 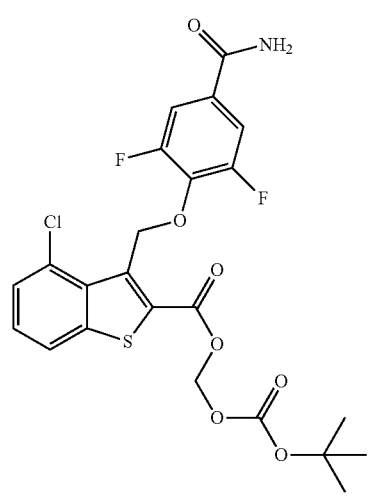 [SMILES: CC(C)(C)OC(=O)OCOC(=O)c1sc2cccc(Cl)c2c1COc1c(F)cc(C(N)=O)cc1F]<br>((tert-Butoxycarbonyl)oxy)methyl 3-((4-carbamoyl-2,6-difluorophenoxy)methyl)-4-chlorobenzo[b]-thiophene-2-carboxylate | LCMS-C: rt 2.64 min; m/z 550.1 [M + Na]⁺ | ¹H NMR (400 MHz, DMSO-$d_6$) δ 8.16 (dd, J = 7.8, 1.3 Hz, 1H), 8.02 (s, 1H), 7.67-7.55 (m, 5H), 6.12 (s, 2H), 5.84 (s, 2H), 1.42 (s, 9H). | Purified by column chromatography (DCM/MeOH = 1:0 to 50:1) |

| Ex | Starting materials | Name and structure | LCMS data | ¹H NMR data | Comment |
|---|---|---|---|---|---|
| 131 | 117 & Chloromethyl pivalate | 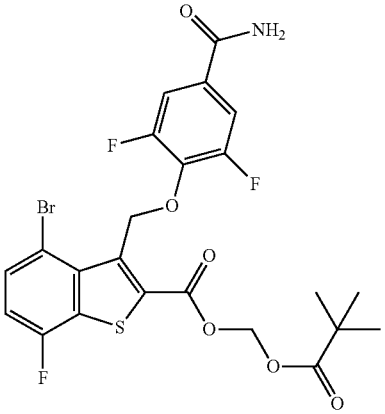 [SMILES: CC(C)(C)C(=O)OCOC(=O)c1sc2c(F)ccc(Br)c2c1COc1c(F)cc(C(N)=O)cc1F]<br>(Pivaloyloxy)methyl 4-bromo-3-((4-carbamoyl-2,6-difluorophenoxy)methyl)-7-chlorobenzo[b]-thiophene-2-carboxylate | LCMS-C: rt 2.74 min; m/z 595.8/ 597.8 [M + Na]⁺ | ¹H NMR (400 MHz, DMSO-d₆) δ 8.02 (s, 1H), 7.89 (dd, J = 8.5, 4.9 Hz, 1H), 7.63-7.54 (m, 3H), 7.49 (t, J = 8.8 Hz, 1H), 6.15 (s,2H), 5.89 (s, 2H), 1.12 (s, 9H). | Purified by column chromatography (DCM/MeOH = 1:0 to 50:1) |
| 132 | 69 & 178 | 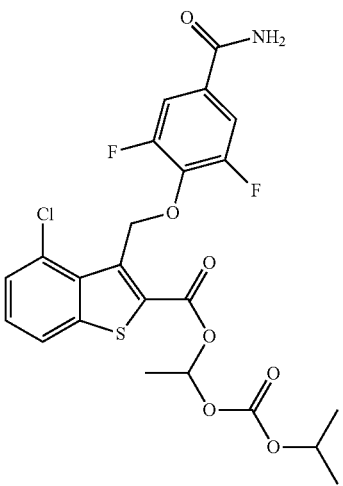 [SMILES: CC(C)OC(=O)OC(C)OC(=O)c1sc2cccc(Cl)c2c1COc1c(F)cc(C(N)=O)cc1F]<br>1-((Isopropoxycarbonyl)-oxy)ethyl 3-((4-carbamoyl-2,6-difluorophenoxy)methyl)-4-chlorobenzo[b]-thiophene-2-carboxylate | LCMS-C: rt 2.64 min; m/z 549.9 [M + Na]⁺ | ¹H NMR (400 MHz, DMSO-d₆) δ 8.15 (dd, J = 7.9, 1.2 Hz, 1H), 8.02 (s, 1H), 7.69-7.52 (m, 5H), 6.77 (q, J = 5.4 Hz, 1H), 6.16-6.06 (m, 2H), 4.82-4.72 (m, 1H), 1.48 (d, J= 5.5 Hz, 3H), 1.23-1.20 (m, 6H). | Purified by prep-TLC (DCM/ MeOH = 20:1) |

| Ex | Starting materials | Name and structure | LCMS data | ¹H NMR data | Comment |
|---|---|---|---|---|---|
| 133 | 69 & 179 | 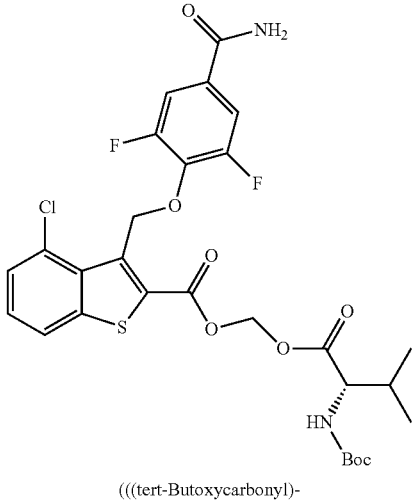<br>(((tert-Butoxycarbonyl)-L-valyl)oxy)methyl 3-((4-carbamoyl-2,6-difluorophenoxy)methyl)-4-chlorobenzo[b]-thiophene-2-carboxylate | LCMS-C: rt 2.69 min; m/z 648.9 [M + Na]⁺ | ¹H NMR (400 MHz, DMSO-$d_6$) δ 8.16 (dd, J = 7.8, 1.3 Hz, 1H), 8.06-8.00 (m, 1H), 7.68-7.54 (m, 5H), 7.30 (d, Hz, 1H), 6.13 (s,2H), 5.97 (d, J = 6.1 Hz, 1H), 5.87 (d, J = 6.2 Hz, 1H), 3.86 (t, J = 7.0 Hz, 1H), 2.03-1.92 (m, 1H), 1.34 (s, 9H), 0.85-0.82 (m, 6H). | 3 eq. of XWH-744-022 used; Purified by column chromatography (DCM/ MeOH = 50:1) |
| 134 | 69 & 180 | 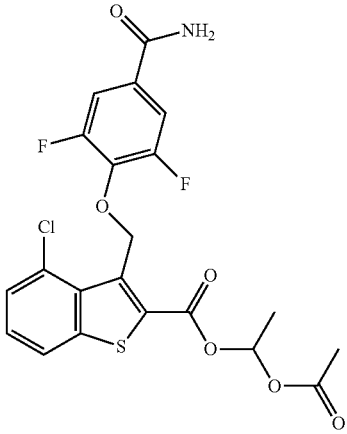 [SMILES: CC(=O)OC(C)OC(=O)c1sc2cccc(Cl)c2c1COc1c(F)cc(C(N)=O)cc1F]<br>1-Acetoxyethyl 3-((4-carbamoyl-2,6-difluorophenoxy)methyl)-4-chlorobenzo[b]-thiophene-2-carboxylate | LCMS-C: rt 2.52 min; m/z 505.9 [M + Na]⁺ | ¹H NMR (400 MHz, DMSO-$d_6$) δ 8.15 (dd, J = 7.9, 1.3 Hz, 1H), 8.04 (s, 1H), 7.68-7.55 (m, 5H), 6.86 (q, J = 5.4 Hz, 1H), 6.11 (s, 2H), 2.05 (d, J = 2.5 Hz, 3H), 1.46 (d, J= 5.5 Hz, 3H). | Purified by column chromatography (Pet. Ether/EtOAc = 10:1 to 1:1) then prep-TLC (EtOAc) |

| Ex | Starting materials | Name and structure | LCMS data | ¹H NMR data | Comment |
|---|---|---|---|---|---|
| 135 | 69 & 181 | 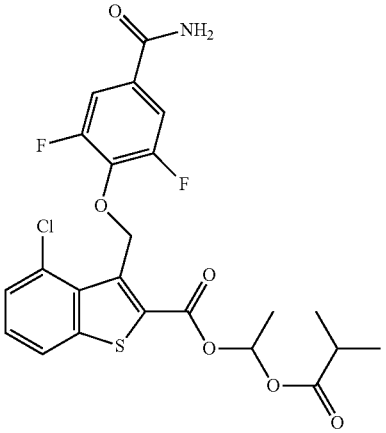 [SMILES: CC(OC(=O)c1sc2cccc(Cl)c2c1COc1c(F)cc(C(N)=O)cc1F)OC(=O)C(C)C]<br>1-(Isobutyryloxy)ethyl 3-((4-carbamoyl-2,6-difluorophenoxy)methyl)-4-chlorobenzo[b]-thiophene-2-carboxylate | LCMS-C: rt 2.68 min; m/z 533.9 [M + Na]⁺ | ¹H NMR (400 MHz, DMSO-$d_6$) δ 8.15 (dd, J = 7.9, 1.2 Hz, 1H), 8.03 (s, 1H), 7.68-7.55 (m, 5H), 6.86 (q, J = 5.3 Hz, 1H), 6.15-6.07 (m, 2H), 2.59-2.52 (m, 1H), 1.47 (d, J = 5.5 Hz, 3H), 1.09-1.06 (m, 6H). | Purified by column chromatography (Pet. Ether/ EtOAc = 10:1 to 1:1) |
| 136 | 69 & 2-Chloro-N,N-dimethyl ethan-1-amine | 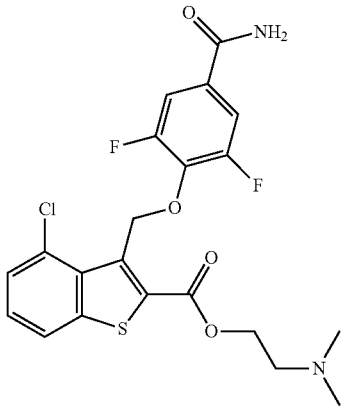 [SMILES: CN(C)CCOC(=O)c1sc2cccc(Cl)c2c1COc1c(F)cc(C(N)=O)cc1F]<br>2-(Dimethylamino)ethyl 3-((4-carbamoyl-2,6-difluorophenoxy)methyl)-4-chlorobenzo[b]-thiophene-2-carboxylate | LCMS-D: rt 2.97 min; m/z 468.9 [M + H]⁺ | ¹H NMR (400 MHz, MeOD-$d_4$) δ 7.93 (dd, J = 8.0, 1.2 Hz, 1H), 7.56-7.53 (m, 1H), 7.52-7.45 (m, 3H), 6.25 (s, 2H), 3.69 (t, J = 6.0 Hz, 2H), 2.61 (t, J = 6.0 Hz, 2H), 2.38 (s, 6H), CONH₂ protons not observed. | 2 eq. of 2-Chloro-N,N-dimethyleth-an-1-amine used; Purified by column chromatography (DCM/ MeOH = 10:1) |
| 137 | 69 & 4-(2-Bromoethyl) morpholine | 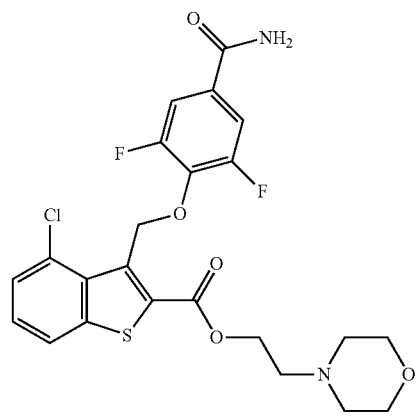 [SMILES: NC(=O)c1cc(F)c(OCc2c(C(=O)OCCN3CCOCC3)sc3cccc(Cl)c23)c(F)c1]<br>2-Morpholinoethyl 3-((4-carbamoyl-2,6-difluorophenoxy)methyl)-4-chlorobenzo[b]-thiophene-2-carboxylate | LCMS-F: rt 2.23 min; m/z 511.1 [M + H]⁺ | ¹H NMR (400 MHz, DMSO-$d_6$) δ 8.13 (d, J = 8.0 Hz, 1H), 8.01 (s, 1H), 7.66-7.54 (m, 5H), 6.14 (s, 2H), 4.33 (t, J = 5.7 Hz, 2H), 3.54-3.51 (m, 4H), 2.56 (t, J = 5.7 Hz, 2H), 2.42-2.40 (m, 4H). | 2 eq. of 4-(2-Bromoethyl) morpholine and 3 eq. of $Cs_2CO_3$ used; Heated at 60° C.; Purified by column chromatography (DCM/ MeOH = 20:1) |

-continued

| Ex | Starting materials | Name and structure | LCMS data | $^1$H NMR data | Comment |
|---|---|---|---|---|---|
| 138 | 69 & 182 | 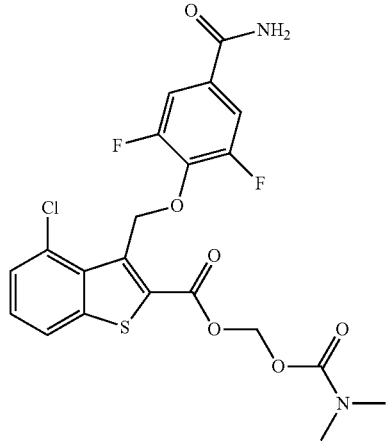 [SMILES: CN(C)C(=O)OCOC(=O)c1sc2cccc(Cl)c2c1COc1c(F)cc(C(N)=O)cc1F]<br>((Dimethylcarbamoyl)oxy)methyl 3-((4-carbamoyl-2,6-difluorophenoxy)methyl)-4-chlorobenzo[b]-thiophene-2-carboxylate | LCMS-C: rt 2.37 min; m/z 498.9 [M + H]$^+$ | $^1$H NMR (400 MHz, DMSO-d$_6$) δ 8.15 (dd, J = 7.9, 1.3 Hz, 1H), 8.02 (s, 1H), 7.68-7.52 (m, 5H), 6.13 (s, 2H), 5.84 (s, 2H), 2.83 (s, 6H). | Purified by column chromatography (DCM/MeOH = 50:1) |
| 139 | 69 & 183 | 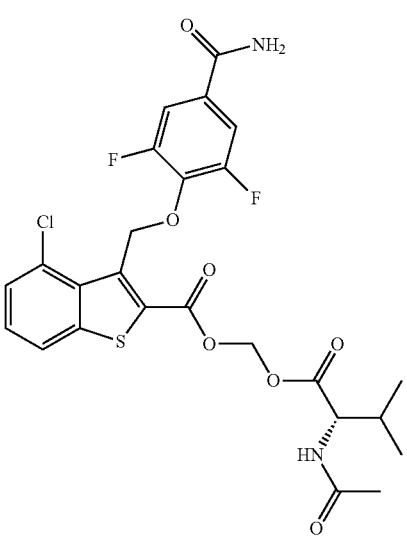 [SMILES: CC(=O)N[C@H](C(=O)OCOC(=O)c1sc2cccc(Cl)c2c1COc1c(F)cc(C(N)=O)cc1F)C(C)C]<br>((Acetyl-L-valyl)oxy)methyl 3-((4-carbamoyl-2,6-difluorophenoxy)methyl) 4-chlorobenzo[b]-thiophene-2-carboxylate | LCMS-C: rt 2.38 min; m/z 568.9 [M + H]$^+$, 590.9 [M + Na]$^+$ | $^1$H NMR (400 MHz, DMSO-d$_6$) δ 8.21 (d, J = 7.6 Hz, 1H), 8.17 (dd, J = 7.8, 1.3 Hz, 1H), 8.03 (s, 1H), 7.68-7.55 (m, 5H), 6.13 (s, 2H), 5.97 (d, J = 6.1 Hz, 1H), 5.88 (d, J = 6.0 Hz, 1H), 4.16 (dd, J = 7.6, 6.2 Hz, 1H), 2.05-1.94 (m, 1H), 1.87 (s, 3H), 0.86-0.83 (m, 6H). | Purified by prep-TLC (DCM/MeOH = 20:1) |

| Ex | Starting materials | Name and structure | LCMS data | $^1$H NMR data | Comment |
|---|---|---|---|---|---|
| 140 | 117 & 1-Chloro-2-methylpropyl propionate | 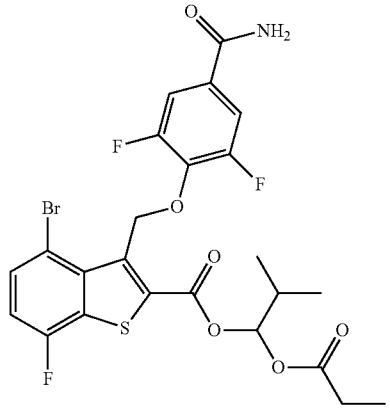 [SMILES: CCC(=O)OC(OC(=O)c1sc2c(F)ccc(Br)c2c1COc1c(F)cc(C(N)=O)cc1F)C(C)C]<br>2-Methyl-1-(propionyloxy)propyl 4-bromo-3-((4-carbamoyl-2,6-difluorophenoxy)methyl)-7-fluorobenzo[b]-thiophene-2-carboxylate | LCMS-D: rt 4.83 min; m/z 610.0/ 612.0 [M + Na]$^+$ | $^1$H NMR (400 MHz, DMSO-d$_6$) δ 8.01 (s, 1H), 7.89 (dd, J = 8.5, 4.9 Hz, 1H), 7.59 (d, J = 9.2 Hz, 2H), 7.57 (s, 1H), 7.50 (t, J = 8.7 Hz, 1H), 6.66 (d, J = 4.9 Hz, 1H), 6.16 (s, 2H), 2.43-2.27 (m, 2H), 2.10-1.96 (m, 1H), 1.01 (t, J = 7.5 Hz, 3H), 0.90 (d, J = 6.8 Hz, 6H). | Heated at 60° C.; Purified by column chromatography (DCM/MeOH = 100:1 to 30:1) |

Further Examples IV

Methyl 3-((4-carbamoylphenoxy)methyl)-4-fluorobenzo[b]thiophene-2-carboxylate (141)

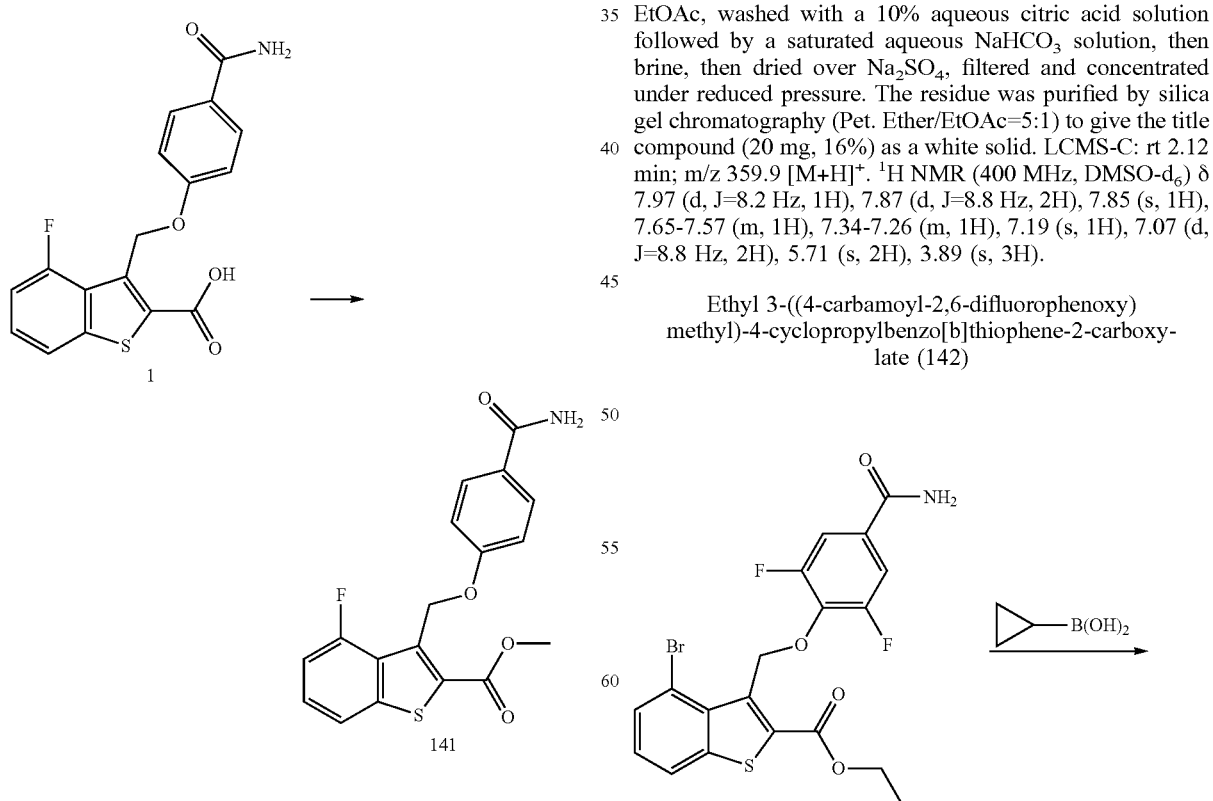

To a solution of 3-((4-carbamoylphenoxy)methyl)-4-fluorobenzo[b]thiophene-2-carboxylic acid 1 (120 mg, 0.35 mmol) and Et$_3$N (39 mg, 0.39 mmol) in THF (10 mL) at −15° C. was added a solution of ethyl chloroformate (40 mg, 0.37 mmol) in THF (2 mL). The mixture was then stirred at −5° C. for 30 min and filtered. The filtrate was diluted with acetonitrile (5 mL), (diazomethyl)trimethylsilane (2 M in hexanes, 0.35 mL, 0.70 mmol) was added and the mixture was stirred at 4° C. overnight. The mixture was diluted with EtOAc, washed with a 10% aqueous citric acid solution followed by a saturated aqueous NaHCO$_3$ solution, then brine, then dried over Na$_2$SO$_4$, filtered and concentrated under reduced pressure. The residue was purified by silica gel chromatography (Pet. Ether/EtOAc=5:1) to give the title compound (20 mg, 16%) as a white solid. LCMS-C: rt 2.12 min; m/z 359.9 [M+H]$^+$. $^1$H NMR (400 MHz, DMSO-d$_6$) δ 7.97 (d, J=8.2 Hz, 1H), 7.87 (d, J=8.8 Hz, 2H), 7.85 (s, 1H), 7.65-7.57 (m, 1H), 7.34-7.26 (m, 1H), 7.19 (s, 1H), 7.07 (d, J=8.8 Hz, 2H), 5.71 (s, 2H), 3.89 (s, 3H).

Ethyl 3-((4-carbamoyl-2,6-difluorophenoxy)methyl)-4-cyclopropylbenzo[b]thiophene-2-carboxylate (142)

197
-continued

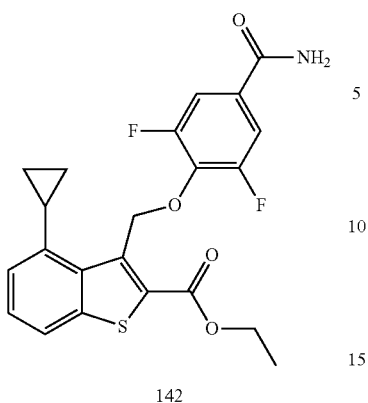

142

A solution of ethyl 4-bromo-3-((4-carbamoyl-2,6 difluorophenoxy)methyl)benzo[b]thiophene-2-carboxylate 114 (290 mg, 0.61 mmol), cyclopropyl boronic acid (159 mg, 1.85 mmol), Pd(PPh₃)₄ (105 mg, 0.09 mmol) and K₂CO₃ (253 mg, 1.83 mmol) in 1,4-dioxane (10 mL) was heated at reflux under a N₂ atmosphere overnight. Water was added and the mixture was extracted with EtOAc. The organic extract was washed with water, brine, dried over Na₂SO₄, filtered and concentrated under reduced pressure. The residue was purified by silica gel chromatography (Pet. Ether/EtOAc=2:1) to give the title compound (137 mg, 52%) as a grey solid. LCMS-C: rt 2.56 min; m/z 453.9 [M+Na]⁺. ¹H NMR (400 MHz, DMSO-d₆) δ 8.02 (s, 1H), 7.93 (d, J=8.0 Hz, 1H), 7.62-7.55 (m, 3H), 7.47 (t, J=7.8 Hz, 1H), 7.29 (d, J=7.5 Hz, 1H), 6.21 (s, 2H), 4.20 (q, J=7.1 Hz, 2H), 2.85-2.76 (m, 1H), 1.19 (t, J=7.1 Hz, 3H), 1.08-1.01 (m, 2H), 0.96-0.89 (m, 2H).

(Diethoxyphosphoryl)methyl 3-((4-carbamoyl-2,6-difluorophenoxy)methyl)-4-chlorobenzo[b]thiophene-2-carboxylate (143)

198
-continued

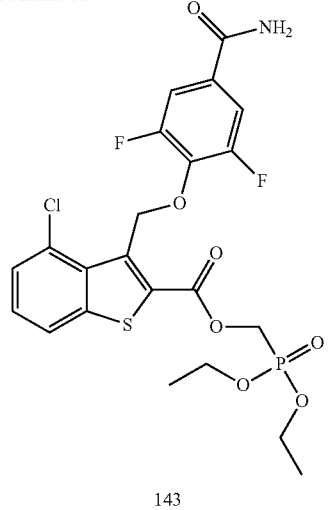

143

To a solution of 3-((4-carbamoyl-2,6-difluorophenoxy)methyl)-4-chlorobenzo[b]thiophene-2-carboxylic acid 69 (1.0 g, 2.5 mmol) in DMF (20 mL) was added diethyl (hydroxymethyl)phosphonate (1.27 g, 7.54 mmol), EDCl.HCl (964 mg, 5.03 mmol) and DMAP (61 mg, 0.50 mmol) and the mixture was stirred at room temperature overnight. Water was added and the mixture was extracted with EtOAc. The organic extract was concentrated under reduced pressure and the residue was purified by silica gel chromatography (DCM/MeOH=50:1) to give the title compound (360 mg, 26%) as a yellow solid. LCMS-C: rt 2.35 min; m/z 547.9 [M+H]⁺. ¹H NMR (400 MHz, DMSO-d₆) δ 8.17 (d, J=7.8 Hz, 1H), 8.02 (s, 1H), 7.68-7.50 (m, 5H), 6.15 (s, 2H), 4.66 (d, J=8.4 Hz, 2H), 4.19-4.02 (m, 4H), 1.24 (t, J=7.0 Hz, 6H).

Ethyl 3-((4-carbamoyl-2,6-difluorophenoxy)methyl)-4-chloro-7-methylbenzo[b]thiophene-2-carboxylate (144)

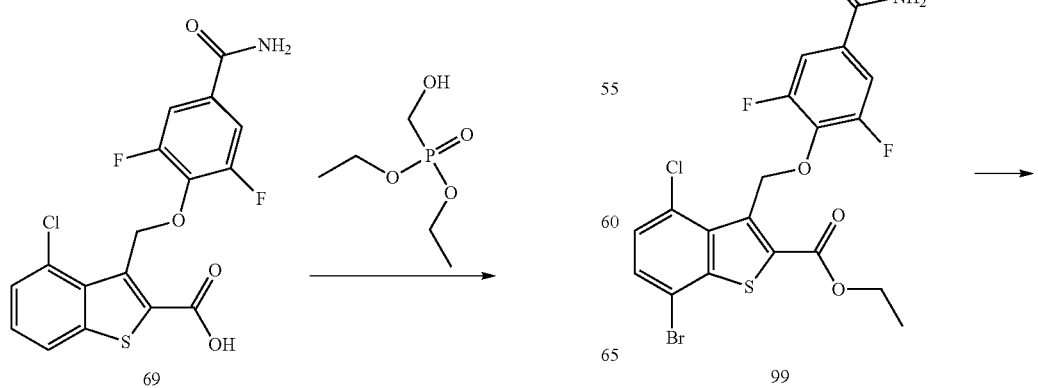

-continued

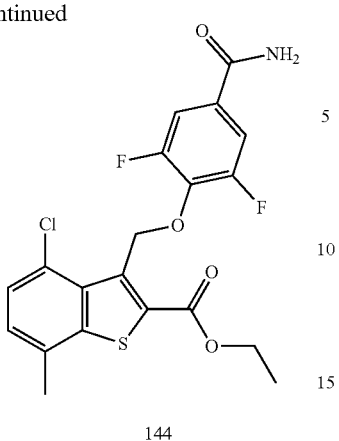

144

A mixture of ethyl 7-bromo-3-((4-carbamoyl-2,6-difluorophenoxy)methyl)-4-chlorobenzo[b]thiophene-2-carboxylate 99 (200 mg, 0.40 mmol), $K_2CO_3$ (164 mg, 1.19 mmol), methyl boronic acid (48 mg, 0.79 mmol) and $Pd(PPh_3)_4$ (46 mg, 0.04 mmol) in 1,4-dioxane (15 mL) was heated at reflux under $N_2$ overnight. The mixture was diluted with water, extracted with EtOAc and the organic layer was washed with water, brine, dried over $Na_2SO_4$, filtered and concentrated under reduced pressure. The residue was purified by prep-HPLC to give the title compound (30 mg, 17%) as a white solid. LCMS-F: rt 3.42 min; m/z 440.0 $[M+H]^+$. $^1H$ NMR (400 MHz, DMSO-$d_6$) δ 8.02 (s, 1H), 7.65-7.53 (m, 4H), 7.43 (d, J=7.8 Hz, 1H), 6.14 (s, 2H), 4.26 (q, J=7.1 Hz, 2H), 2.54 (s, 3H), 1.23 (t, J=7.1 Hz, 3H).

Ethyl 3-((4-carbamoyl-2,6-difluorophenoxy)methyl)-4-chloro-7-(hydroxymethyl)benzo[b]thiophene-2-carboxylate (145)

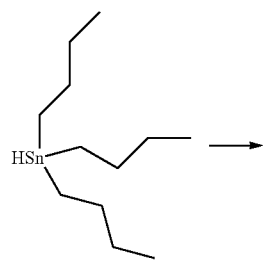

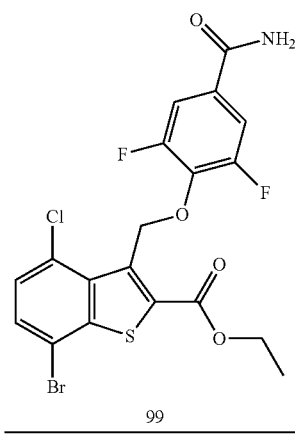

-continued

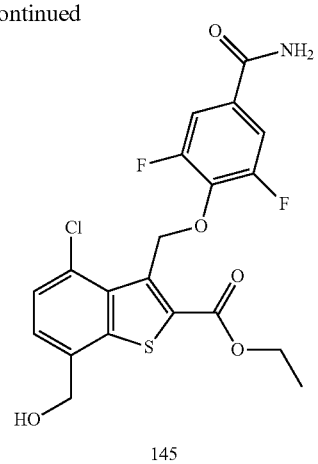

145

(a) (Tributylstannyl)methanol (I94)

To a solution of diisopropylamine (2.1 g, 20.6 mmol) in THF (50 mL) at −78° C. under $N_2$ was added n-BuLi (2.5 M in hexanes, 8.2 mL, 20.6 mmol) dropwise and the mixture was stirred at −78° C. for 30 min. Tributylstannane (5.0 g, 17.2 mmol) was added and the mixture was allowed to warm to 0° C. and stirred for 1 h. The reaction mixture was again cooled to −78° C. and paraformaldehyde (527 mg, 5.84 mmol) was added. The mixture was allowed to warm to room temperature and stirred overnight. The solvent was removed under reduced pressure and the residue was purified by silica gel chromatography (Pet. Ether/EtOAc=80:1) to give the title compound (3.0 g, 55%) as a colorless oil. $^1H$ NMR (400 MHz, CDCl$_3$) δ 4.68 (s, 1H), 4.01 (s, 2H), 1.56-1.47 (m, 6H), 1.34-1.27 (m, 6H), 0.95-0.85 (m, 15H).

(b) Ethyl 3-((4-carbamoyl-2,6-difluorophenoxy)methyl)-4-chloro-7-(hydroxymethyl)benzo[b]thiophene-2-carboxylate 145

To a solution of ethyl 7-bromo-3-((4-carbamoyl-2,6-difluorophenoxy)methyl)-4-chlorobenzo[b]thiophene-2-carboxylate 99 (100 mg, 0.198 mmol) and (tributylstannyl)methanol 194 (127 mg, 0.396 mmol) in 1,4-dioxane (6 mL) was added $Pd(PPh_3)_4$ (23 mg, 0.02 mmol) and the mixture was heated at reflux under $N_2$ overnight. The mixture was diluted with water, extracted with EtOAc and the organic layer was washed with water, brine, dried over $Na_2SO_4$, filtered and concentrated under reduced pressure. The residue was purified by prep-TLC (DCM/MeOH=15/1) to give the title compound (19 mg, 21%) as a white solid. LCMS-D: rt 3.69 min; m/z 478.0 $[M+Na]^+$. $^1H$ NMR (400 MHz, DMSO-$d_6$) δ 8.06 (s, 1H), 7.65-7.55 (m, 4H), 7.52 (d, J=7.8 Hz, 1H), 6.16 (s, 2H), 5.76 (t, J=5.6 Hz, 1H), 4.78 (d, J=5.6 Hz, 2H), 4.25 (q, J=7.1 Hz, 2H), 1.23 (t, J=7.1 Hz, 3H).

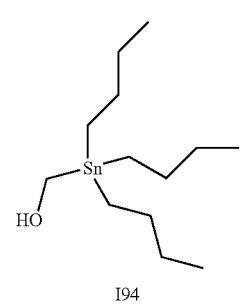

Ethyl 3-((4-carbamoyl-2,6-difluorophenoxy) methyl)-4-chloro-7-(methoxymethyl)benzo[b]thiophene-2-carboxylate (146)

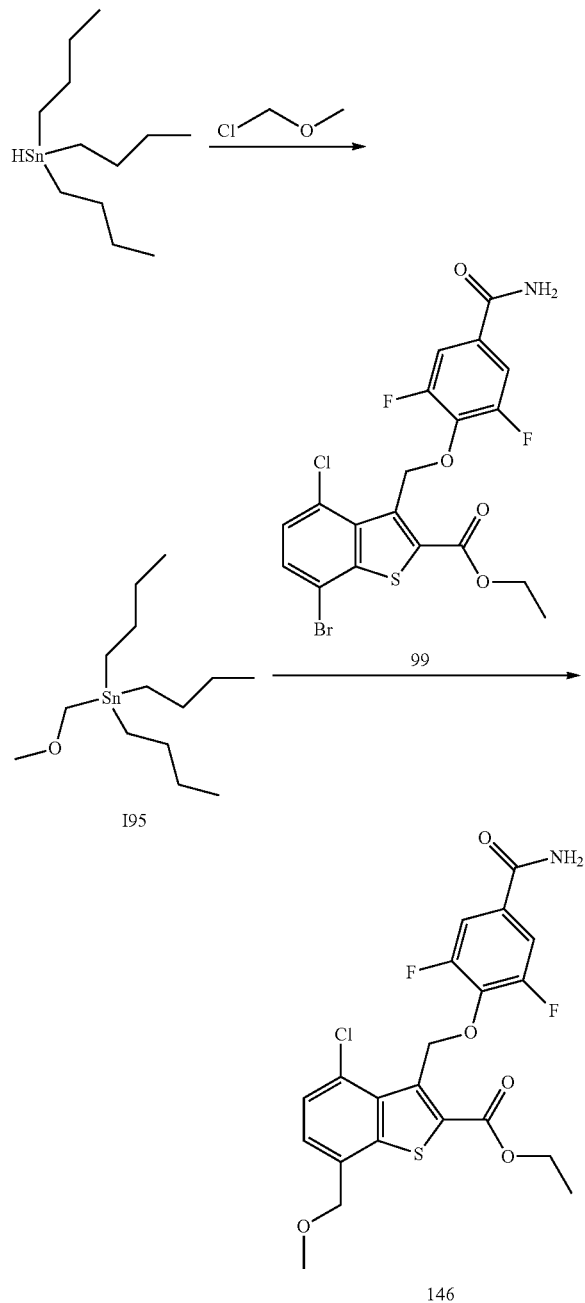

(a) Tributyl(methoxymethyl)stannane (195)

To a solution of diisopropylamine (765 mg, 7.56 mmol) in THF (20 mL) at −78° C. under $N_2$ was added n-BuLi (2.5 M in hexanes, 2.75 mL, 6.87 mmol) dropwise and the mixture was stirred at −78° C. for 30 min. Tributylstannane (2.0 g, 6.87 mmol) was added and the mixture was allowed to warm to 0° C. and stirred for 30 min. The mixture was again cooled to −78° C., chloro(methoxy)methane (554 mg, 6.87 mmol) was added dropwise and the mixture was allowed to warm to room temperature and stirred overnight. Water was added and the mixture was extracted with diethyl ether. The combined organic extracts were washed with brine, dried over $Na_2SO_4$, filtered and concentrated under reduced pressure. The residue was purified by silica gel chromatography (100% Pet. Ether) to give the title compound (530 mg, 23%) as a colorless oil. $^1$H NMR (400 MHz, $CDCl_3$) δ 3.70 (s, 2H), 3.29 (s, 3H), 1.55-1.45 (m, 6H), 1.36-1.25 (m, 6H), 0.93-0.87 (m, 15H).

(b) Ethyl 3-((4-carbamoyl-2,6-difluorophenoxy) methyl)-4-chloro-7-(methoxymethyl)benzo[b]thiophene-2-carboxylate (146)

To a solution of ethyl 7-bromo-3-((4-carbamoyl-2,6-difluorophenoxy)methyl)-4-chlorobenzo[b]thiophene-2-carboxylate 99 (100 mg, 0.198 mmol) and tributyl(methoxymethyl)stannane 195 (200 mg, 0.594 mmol) in 1,4-dioxane (6 mL) was added $Pd(PPh_3)_4$ (23 mg, 0.02 mmol) and the mixture was heated at reflux under $N_2$ overnight. The mixture was diluted with water, extracted with EtOAc and the organic layer was washed with water, brine, dried over $Na_2SO_4$, filtered and concentrated under reduced pressure. The residue was purified by prep-HPLC to give the title compound (72 mg, 38%) as a white solid. LCMS-F: rt 3.27 min; m/z 469.9 [M+H]$^+$. $^1$H NMR (400 MHz, DMSO-$d_6$) δ 8.03 (s, 1H), 7.66-7.52 (m, 5H), 6.15 (s, 2H), 4.74 (s, 2H), 4.26 (q, J=7.2 Hz, 2H), 3.34 (s, 3H), 1.24 (t, J=7.2 Hz, 3H).

Ethyl 3-((4-carbamoyl-2,6-difluorophenoxy) methyl)-4-chloro-7-hydroxybenzo[b]thiophene-2-carboxylate (147)

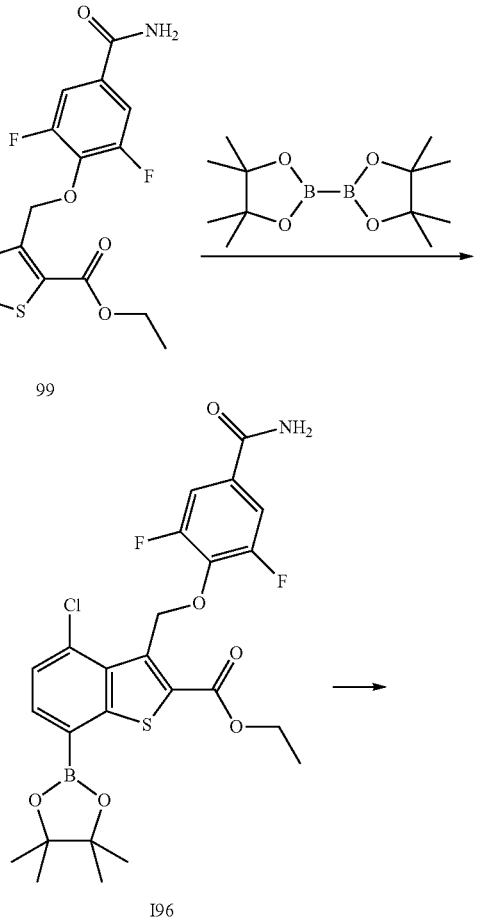

-continued

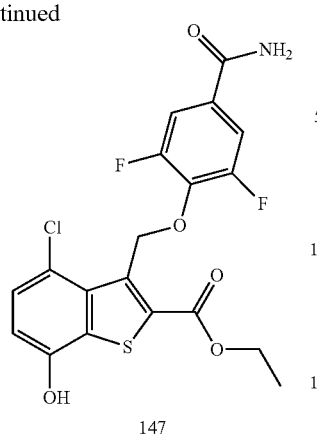

147

(a) Ethyl 3-((4-carbamoyl-2,6-difluorophenoxy)methyl)-4-chloro-7-(4,4,5,5-tetramethyl-1,3,2-dioxaborolan-2-yl)benzo[b]thiophene-2-carboxylate (196) A mixture of ethyl 7-bromo-3-((4-carbamoyl-2,6-difluorophenoxy)methyl)-4-chlorobenzo[b]thiophene-2-carboxylate 99 (300 mg, 0.59 mmol), 4,4,4',4',5,5,5',5'-octamethyl-2,2'-bi(1,3,2-dioxaborolane) (227 mg, 0.89 mmol), KOAc (175 mg, 1.78 mmol) and Pd(dppf)Cl$_2$.DCM (49 mg, 0.06 mmol) in 1,4-dioxane (18 mL) was heated at reflux under N$_2$ overnight. The mixture was diluted with water, extracted with EtOAc and the organic extract was washed with water, brine, dried over Na$_2$SO$_4$, filtered and concentrated under reduced pressure. The residue was purified by silica gel chromatography (DCM/MeOH=100:1) to give the title compound (260 mg, 80%) as a grey solid. LCMS-F: rt 2.64 min; m/z 469.7 [M–C$_6$H$_{10}$+H]$^+$.

(b) Ethyl 3-((4-carbamoyl-2,6-difluorophenoxy)methyl)-4-chloro-7-hydroxybenzo[b]thiophene-2-carboxylate (147)

To a solution of ethyl 3-((4-carbamoyl-2,6-difluorophenoxy)methyl)-4-chloro-7-(4,4,5,5-tetramethyl-1,3,2-dioxaborolan-2-yl)benzo[b]thiophene-2-carboxylate 196 (60 mg, 0.109 mmol) in THF (4 mL) at 0° C. was added NaOH (5 mg, 0.109 mmol) and H$_2$O$_2$ (30% aqueous solution, 37 mg, 0.327 mmol) and the mixture was stirred at room temperature for 3 h. Ice cold water was added and the mixture was extracted with EtOAc. The organic extract was washed with water, brine, dried over Na$_2$SO$_4$, filtered and concentrated under reduced pressure. The residue was purified by prep-TLC (DCM/MeOH=20:1) to give the title compound (25 mg, 52%) as a yellow solid. LCMS-F: rt 2.82 min; m/z 442.0 [M+H]$^+$. $^1$H NMR (400 MHz, DMSO-d$_6$) δ 11.1 (s, 1H), 8.04 (s, 1H), 7.66-7.54 (m, 3H), 7.42 (d, J=8.3 Hz, 1H), 6.95 (d, J=8.3 Hz, 1H), 6.10 (s, 2H), 4.24 (q, J=7.1 Hz, 2H), 1.22 (t, J=7.1 Hz, 3H).

N-(2-Amino-2-oxoethyl)-3-((4-carbamoyl-2,6-difluorophenoxy)methyl)-4-chlorobenzo[b]thiophene-2-carboxamide (148)

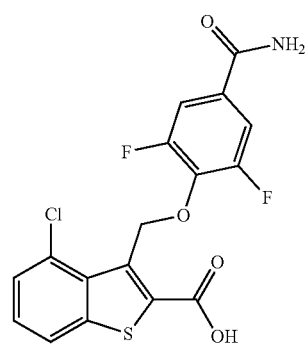

69

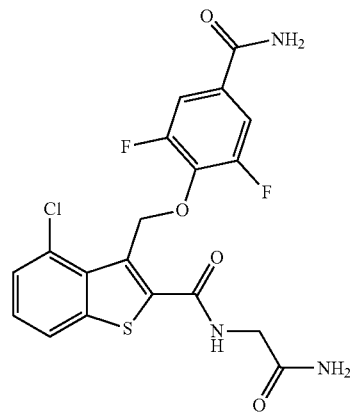

148

A mixture of 2-aminoacetamide hydrochloride (34 mg, 0.302 mmol), 3-((4-carbamoyl-2,6-difluorophenoxy)methyl)-4-chlorobenzo[b]thiophene-2-carboxylic acid 69 (100 mg, 0.251 mmol), HATU (144 mg, 0.377 mmol) and DIPEA (98 mg, 0.754 mmol) in DMF (5 mL) was stirred at room temperature overnight. The mixture was diluted with water, extracted with EtOAc and the organic extract was washed with water, brine, dried over Na$_2$SO$_4$, filtered and concentrated under reduced pressure. The residue was purified by prep-TLC (DCM/MeOH=10:1) to give the title compound (30 mg, 26%) as a white solid. LCMS-C: rt 1.80 min; m/z 453.9 [M+H]$^+$. $^1$H NMR (400 MHz, DMSO-d$_6$) δ 8.65 (t, J=5.7 Hz, 1H), 8.11 (d, J=8.0 Hz, 1H), 8.01 (s, 1H), 7.55-7.40 (m, 5H), 7.41 (s, 1H), 7.08 (s, 1H), 5.97 (s, 2H), 3.79 (d, J=5.7 Hz, 2H).

205
Ethyl 3-((4-carbamoyl-2,6-difluorophenoxy)methyl)-4-chloro-7-methoxybenzo[b]thiophene-2-carboxylate (149)

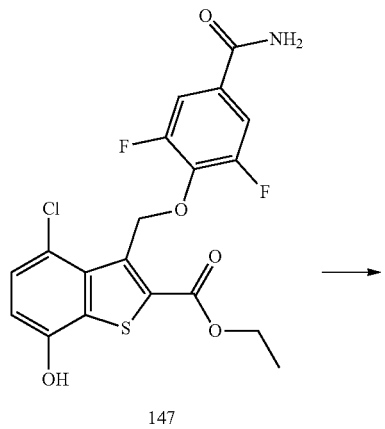

To a solution of ethyl 3-((4-carbamoyl-2,6-difluorophenoxy)methyl)-4-chloro-7-hydroxybenzo[b]thiophene-2-carboxylate 147 (70 mg, 0.158 mmol) and $CH_{31}$ (34 mg, 0.238 mmol) in DMF (6 mL) was added $K_2CO_3$ (66 mg, 0.475 mmol) and the mixture was stirred at room temperature overnight. The mixture was diluted with water, extracted with EtOAc and the organic extract was washed with water, brine, dried over $Na_2SO_4$, filtered and concentrated under reduced pressure. The residue was purified by prep-HPLC to give the title compound (36 mg, 50%) as a white solid. LCMS-F: rt 3.27 min; m/z 455.97 [M+H]$^+$. $^1$H NMR (400 MHz, DMSO-d$_6$) δ 8.02 (s, 1H), 7.63-7.53 (m, 4H), 7.16 (d, J=8.5 Hz, 1H), 6.10 (s, 2H), 4.24 (q, J=7.1 Hz, 2H), 4.01 (s, 3H), 1.22 (t, J=7.1 Hz, 3H).

206
Ethyl 3-((4-carbamoyl-3-(methoxymethyl)phenoxy)methyl)-4-chlorobenzo[b]thiophene-2-carboxylate (150)

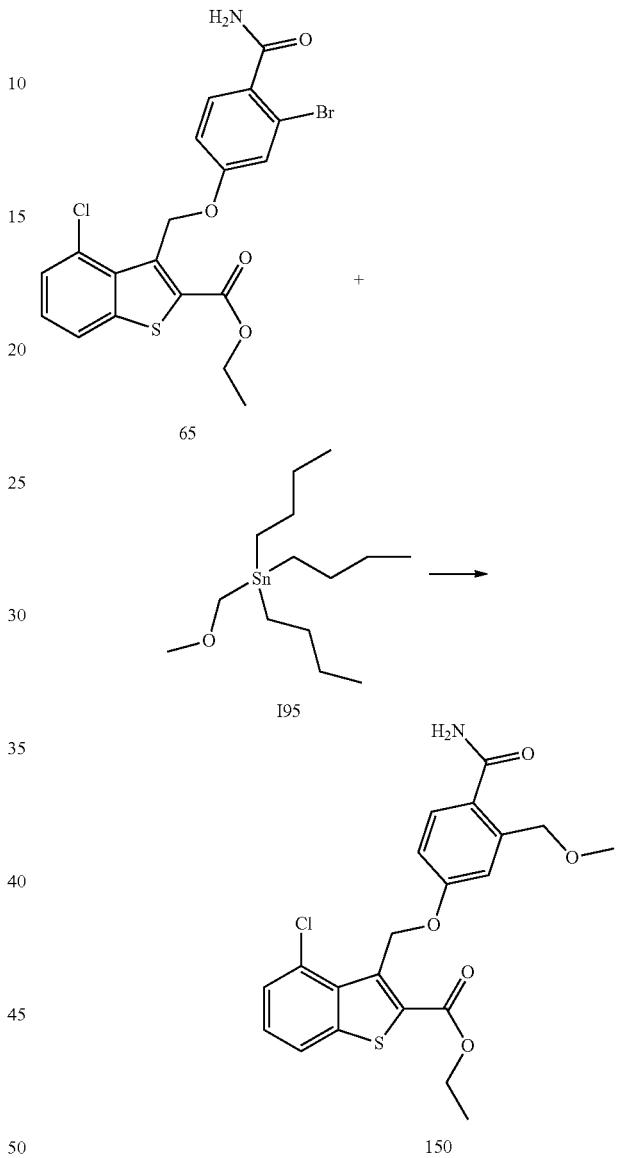

To a solution of ethyl 3-((3-bromo-4-carbamoylphenoxy)methyl)-4-chlorobenzo[b]thiophene-2-carboxylate 65 (200 mg, 0.427 mmol) and tributyl(methoxymethyl)stannane 195 (430 mg, 1.28 mmol) in 1,4-dioxane (15 mL) was added Pd(PPh$_3$)$_4$ (50 mg, 0.043 mmol) and the mixture was heated at reflux under a N$_2$ atmosphere overnight. The mixture was diluted with water, extracted with EtOAc and the organic extract was washed with brine, dried over Na$_2$SO$_4$, filtered and concentrated under reduced pressure. The residue was purified by prep-TLC (DCM/MeOH=10:1) to give the title compound (15 mg, 8%) as a white solid. LCMS-D: rt 4.17 min; m/z 434.1 [M+H]$^+$, 456.0 [M+Na]$^+$. $^1$H NMR (400 MHz, DMSO-d$_6$) δ 8.14 (dd, J=6.9, 2.0 Hz, 1H), 7.69 (s, 1H), 7.61-7.49 (m, 3H), 7.23 (s, 1H), 7.11 (d, J=2.6 Hz, 1H), 6.98 (dd, J=8.5, 2.7 Hz, 1H), 5.85 (s, 2H), 4.63 (s, 2H), 4.36 (q, J=7.1 Hz, 2H), 3.32 (s, 3H), 1.29 (t, J=7.1 Hz, 3H).

Ethyl 3-((4-carbamoyl-3-(1H-pyrazol-4-yl)phenoxy)methyl)-4-chlorobenzo[b]thiophene-2-carboxylate (151)

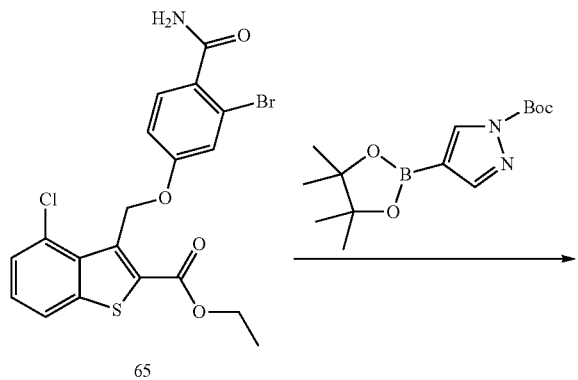

To a solution of ethyl 3-((3-bromo-4-carbamoylphenoxy)methyl)-4-chlorobenzo[b]thiophene-2-carboxylate 65 (100 mg, 0.213 mmol) and tert-butyl 4-(4,4,5,5-tetramethyl-1,3,2-dioxaborolan-2-yl)-1H-pyrazole-1-carboxylate (188 mg, 0.639 mmol) in 1,4-dioxane/water (10 mL/0.5 mL) was added Pd(PPh$_3$)$_4$ (25 mg, 0.021 mmol) and K$_2$CO$_3$ (89 mg, 0.639 mmol) and the mixture was heated at reflux under a N$_2$ atmosphere overnight. The mixture was diluted with water, extracted with EtOAc and the organic extract was washed with brine, dried over Na$_2$SO$_4$, filtered and concentrated under reduced pressure. The residue was purified by prep-TLC (DCM/MeOH=10:1) to give the title compound (15 mg, 13%) as a white solid. LCMS-D: rt 3.80 min; m/z 456.1 [M+H]$^+$. $^1$H NMR (400 MHz, DMSO-d$_6$) δ 12.9 (s, 1H), 8.14 (dd, J=7.0, 2.2 Hz, 1H), 7.97 (s, 1H), 7.75 (s, 1H), 7.66 (s, 1H), 7.62-7.53 (m, 2H), 7.32 (s, 1H), 7.29 (d, J=8.4 Hz, 1H), 7.13 (d, J=2.6 Hz, 1H), 6.94 (dd, J=8.5, 2.6 Hz, 1H), 5.87 (s, 2H), 4.36 (q, J=7.1 Hz, 2H), 1.29 (t, J=7.1 Hz, 3H).

((L-Valyl)oxy)methyl 3-((4-carbamoyl-2,6-difluorophenoxy)methyl)-4-chlorobenzo[b]thiophene-2-carboxylate trifluoroacetate salt (152)

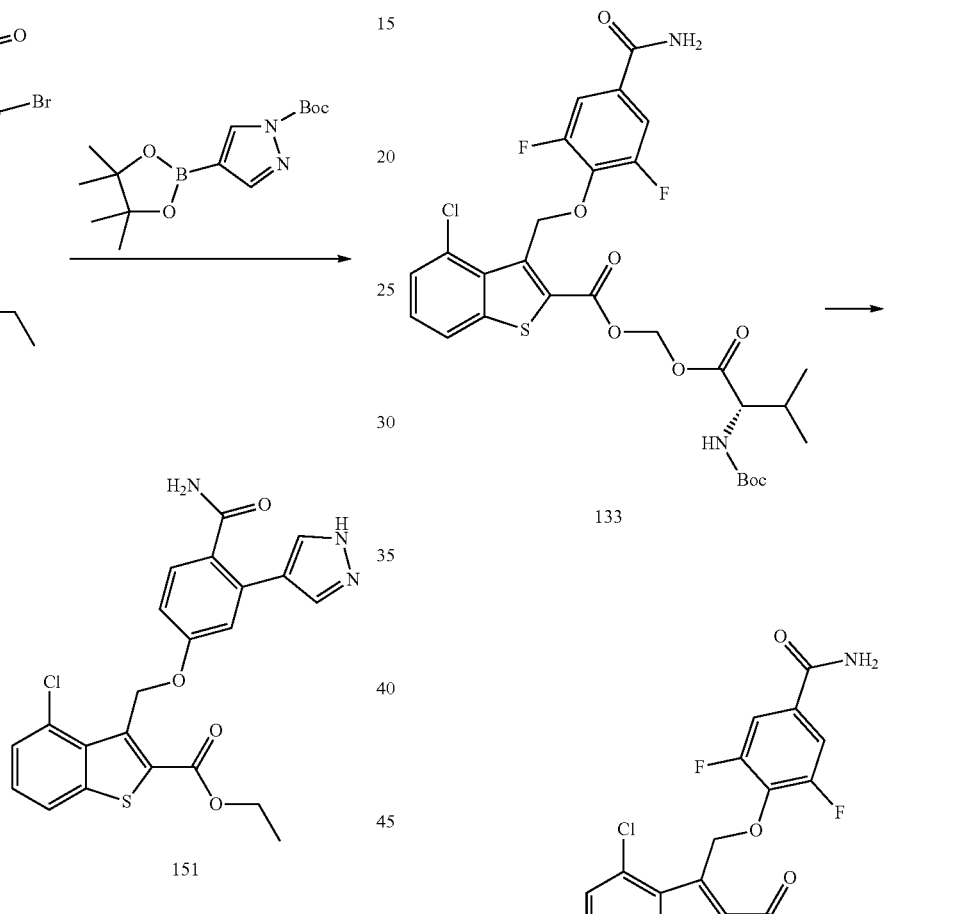

To a solution of (S)-((2-((tert-butoxycarbonyl)amino)-3-methylbutanoyl)oxy)methyl 3-((4-carbamoyl-2,6-difluorophenoxy)methyl)-4-chlorobenzo[b]thiophene-2-carboxylate 133 (60 mg, 0.096 mmol) in DCM (5 mL) was added TFA (2 mL) and the mixture was stirred at room temperature overnight. The solvent was removed under reduced pressure to give the title compound (30 mg, 60%) as a yellow oil.

LCMS-C: rt 2.01 min; m/z 526.9 [M+H]⁺. ¹H NMR (400 MHz, DMSO-d₆) δ 8.48 (br s, 3H), 8.17-8.05 (m, 2H), 7.73-7.48 (m, 5H), 6.26-6.11 (m, 2H), 6.12-5.95 (m, 2H), 4.12-4.02 (m, 1H), 2.20-2.09 (m, 1H), 0.94-0.91 (m, 6H).

title compound (3.3 mg, 7%) as a white solid. LCMS-F: rt 3.12 min; m/z 451.0 [M+H]⁺. ¹H NMR (400 MHz, DMSO-d₆) δ 8.20 (d, J=8.1 Hz, 1H), 8.02 (s, 1H), 7.87 (d, J=8.1 Hz, 1H), 7.66-7.53 (m, 3H), 6.12 (s, 2H), 4.28 (q, J=7.1 Hz, 2H), 1.24 (t, J=8.0 Hz, 3H).

Ethyl 3-((4-carbamoyl-2,6-difluorophenoxy)methyl)-4-chloro-7-cyanobenzo[b]thiophene-2-carboxylate (153)

Isopropyl 3-((4-carbamoylphenoxy)methyl)-4-methoxybenzo[b]thiophene-2-carboxylate (154)

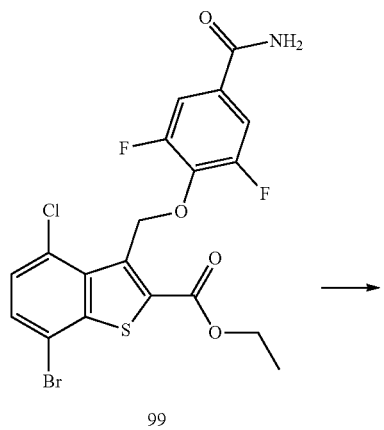

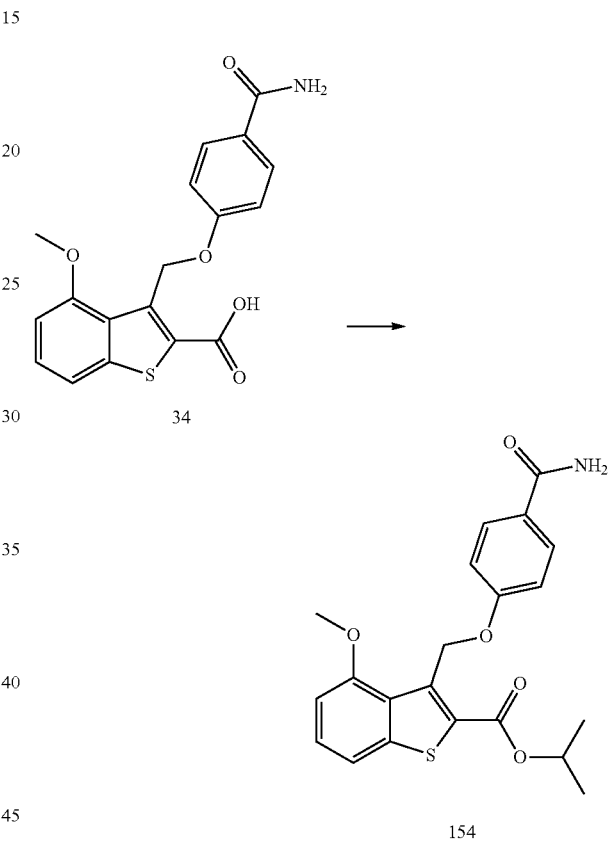

A mixture of ethyl 7-bromo-3-((4-carbamoyl-2,6-difluorophenoxy)methyl)-4-chlorobenzo[b]thiophene-2-carboxylate 99 (50 mg, 0.099 mmol) and CuCN (44 mg, 0.495 mmol) in NMP (5 mL) was heated at 180° C. under N₂ for 16 h. The mixture was partitioned between water (15 mL) and EtOAc (15 mL), the layers were separated and the aqueous layer was extracted with EtOAc (15 mL×3). The combined organic layers were washed with brine (20 mL), dried over Na₂SO₄, filtered and concentrated under reduced pressure. The residue was purified by prep-HPLC to give the To a solution of 3-((4-carbamoylphenoxy)methyl)-4-methoxybenzo[b]thiophene-2-carboxylic acid 34 (90 mg, 0.25 mmol) in DMF (5 mL) was added i-PrOH (151 mg, 2.52 mmol), EDCl.HCl (96 mg, 0.50 mmol) and DMAP (6 mg, 0.05 mmol) and the mixture was stirred at room temperature overnight. Water and 1 M aqueous HCl was added and the mixture was extracted with EtOAc. The organic extract was concentrated under reduced pressure and the residue was purified by silica gel chromatography (DCM/MeOH=10:1) to give the title compound (70 mg, 70%). LCMS-C: rt 2.50 min; m/z 400.0 [M+H]⁺, 422.0 [M+Na]⁺. ¹H NMR (400 MHz, DMSO-d₆) δ 7.87 (d, J=8.4 Hz, 2H), 7.84 (s, 1H), 7.62 (d, J=8.0 Hz, 1H), 7.50 (t, J=8.0 Hz, 1H), 7.18 (s, 1H), 7.06 (d, J=8.4 Hz, 2H), 6.98 (d, J=7.9 Hz, 1H), 5.77 (s, 2H), 5.19-5.04 (m, 1H), 3.70 (s, 3H), 1.25 (d, J=6.3 Hz, 6H).

211

Cyclopentyl 3-((4-carbamoylphenoxy)methyl)-4-methoxybenzo[b]thiophene-2-carboxylate (155)

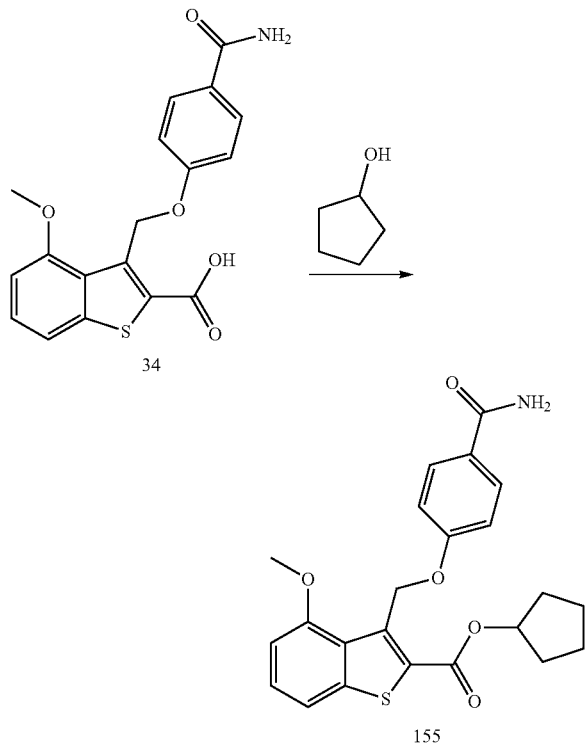

To a solution of 3-((4-carbamoylphenoxy)methyl)-4-methoxybenzo[b]thiophene-2-carboxylic acid 34 (90 mg, 0.25 mmol) in DMF (5 mL) was added cyclopentanol (108.4 mg, 1.26 mmol), EDCl.HCl (96.5 mg, 0.50 mmol) and DMAP (6.2 mg, 0.05 mmol) and the mixture was stirred at room temperature overnight. Water was added and the mixture was extracted with EtOAc. The organic layer was concentrated under reduced pressure and the residue was purified by silica gel chromatography (DCM/MeOH=10:1) followed by prep-HPLC to give the title compound (70 mg, 65%) as a white solid. LCMS-C: rt 2.61 min; m/z 426.0 [M+H]+, 448.0 [M+Na]+. 1H NMR (400 MHz, DMSO-d6) δ 7.87 (d, J=8.0 Hz, 2H), 7.84 (s, 1H), 7.62 (d, J=8.1 Hz, 1H), 7.50 (t, J=8.0 Hz, 1H), 7.18 (s, 1H), 7.05 (d, J=8.1 Hz, 2H), 6.97 (d, J=7.9 Hz, 1H), 5.74 (s, 2H), 5.36-5.27 (m, 1H), 3.69 (s, 3H), 1.92-1.80 (m, 2H), 1.76-1.65 (m, 2H), 1.62-1.50 (m, 4H).

Benzyl 3-((4-carbamoylphenoxy)methyl)-4-methoxybenzo[b]thiophene-2-carboxylate (156)

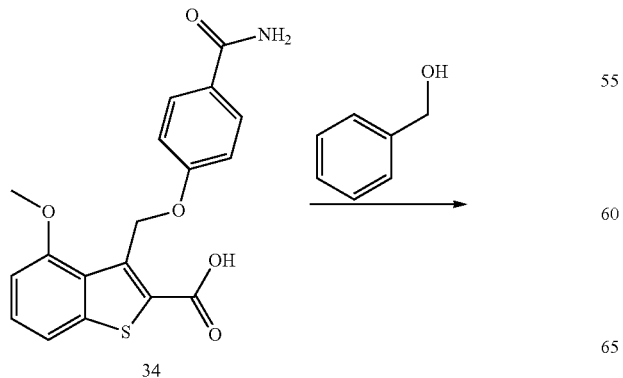

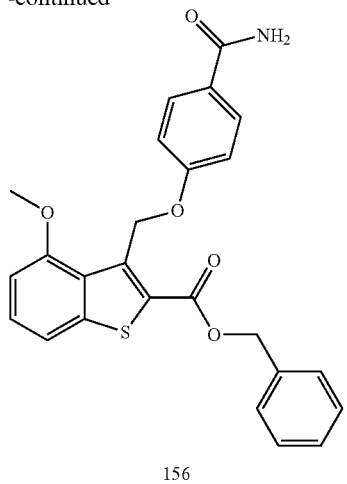

To a mixture of 3-((4-carbamoylphenoxy)methyl)-4-methoxybenzo[b]thiophene-2-carboxylic acid 34 (90 mg, 0.25 mmol) and benzyl alcohol (6 mL) was added conc. H2SO4 (2 drops) and the mixture was heated at 50° C. overnight. The mixture was purified by silica gel chromatography (DCM/MeOH=10:1) followed by prep-HPLC to give the title compound (3.2 mg, 3%) as a white solid. LCMS-C: rt 2.55 min; m/z 448.0 [M+H]+, 470.0 [M+Na]+. 1H NMR (400 MHz, DMSO-d6) δ 7.93-7.83 (m, 3H), 7.64 (d, J=8.1 Hz, 1H), 7.52 (t, J=8.0 Hz, 1H), 7.46-7.40 (m, 2H), 7.35-7.34 (m, 3H), 7.21 (s, 1H), 7.05 (d, J=8.4 Hz, 2H), 6.99 (d, J=7.9 Hz, 1H), 5.80 (s, 2H), 5.37 (s, 2H), 3.68 (s, 3H).

2-Morpholinoethyl 3-((4-carbamoylphenoxy)methyl)-4-methoxybenzo[b]thiophene-2-carboxylate (157)

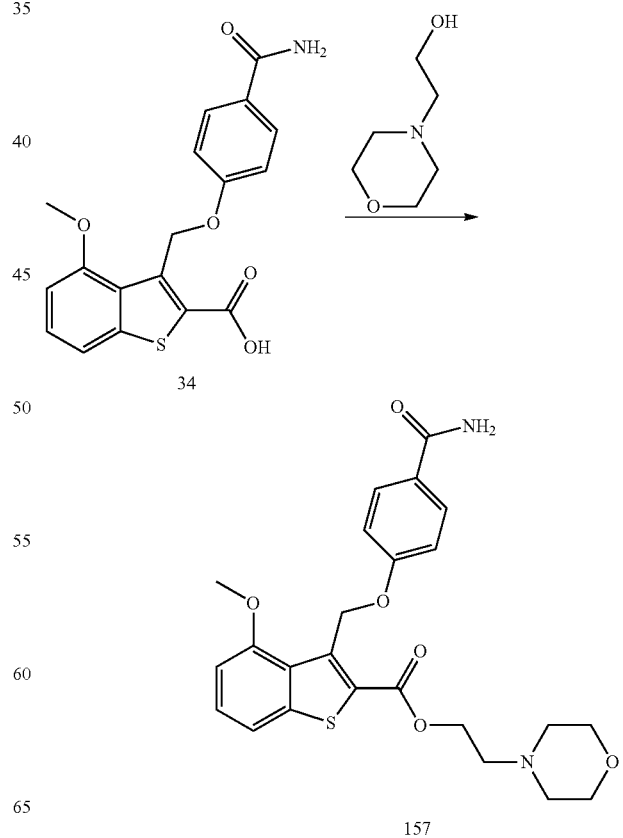

To a solution of 3-((4-carbamoylphenoxy)methyl)-4-methoxybenzo[b]thiophene-2-carboxylic acid 34 (90 mg, 0.25 mmol) in DMF (5 mL) was added 2-morpholinoethan-1-ol (99.1 mg, 0.76 mmol), EDCl.HCl (96.5 mg, 0.50 mmol) and DMAP (6 mg, 0.05 mmol) and the mixture was stirred at room temperature overnight. Water was added and the mixture was extracted with EtOAc. The organic layer was concentrated under reduced pressure and the residue was purified by silica gel chromatography (DCM/MeOH=10:1) followed by prep-HPLC to give the title compound (5 mg, 4%) as a white solid. LCMS-D: rt 2.87 min; m/z 471.0 [M+H]$^+$. $^1$H NMR (400 MHz, DMSO-d$_6$) δ 7.88 (d, J=8.8 Hz, 2H), 7.85 (s, 1H), 7.63 (d, J=8.1 Hz, 1H), 7.51 (t, J=8.0 Hz, 1H), 7.18 (s, 1H), 7.05 (d, J=8.8 Hz, 2H), 6.97 (d, J=7.9 Hz, 1H), 5.78 (s, 2H), 4.38 (t, J=5.5 Hz, 2H), 3.67 (s, 3H), 3.51-3.48 (m, 4H), 2.60 (t, J=5.6 Hz, 2H), 2.41-2.39 (m, 4H).

2-Methoxyethyl 3-((4-carbamoyl-2,6-difluorophenoxy)methyl)-4-chlorobenzo[b]thiophene-2-carboxylate (158)

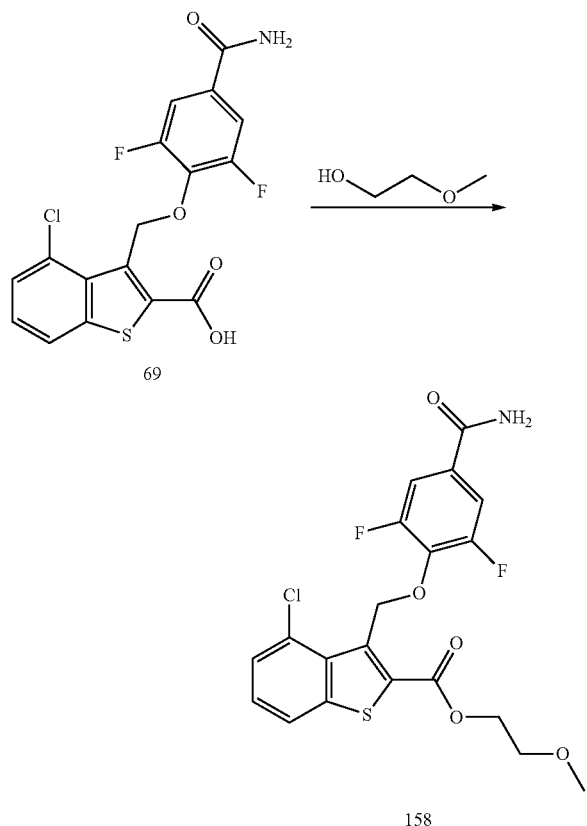

To a solution of 3-((4-carbamoyl-2,6-difluorophenoxy)methyl)-4-chlorobenzo[b]thiophene-2-carboxylic acid 69 (150 mg, 0.38 mmol) in DMF (10 mL) was added 2-methoxyethanol (87 mg, 1.14 mmol), EDCl.HCl (146 mg, 0.76 mmol) and DMAP (10 mg, 0.076 mmol) and the mixture was stirred at room temperature for 3 h. Water (150 mL) was added and the mixture was extracted with EtOAc (100 mL×3). The combined organic extracts were washed with water (3×150 mL), brine, dried over Na$_2$SO$_4$, filtered and concentrated under reduced pressure. The residue was purified by silica gel chromatography (DCM/MeOH=1:0 to 100:1) to give the title compound (60 mg, 35%) as a white solid. LCMS-C: rt 2.43 min; m/z 455.9 [M+H]$^+$, 477.9 [M+Na]$^+$. $^1$H NMR (400 MHz, DMSO-d$_6$) δ 8.14 (dd, J=7.9, 1.2 Hz, 1H), 8.08 (s, 1H), 7.66-7.54 (m, 5H), 6.14 (s, 2H), 4.38-4.30 (m, 2H), 3.59-3.53 (m, 2H), 3.25 (s, 3H).

2-Acetamidoethyl 3-((4-carbamoyl-2,6-difluorophenoxy)methyl)-4-chlorobenzo[b]thiophene-2-carboxylate (159)

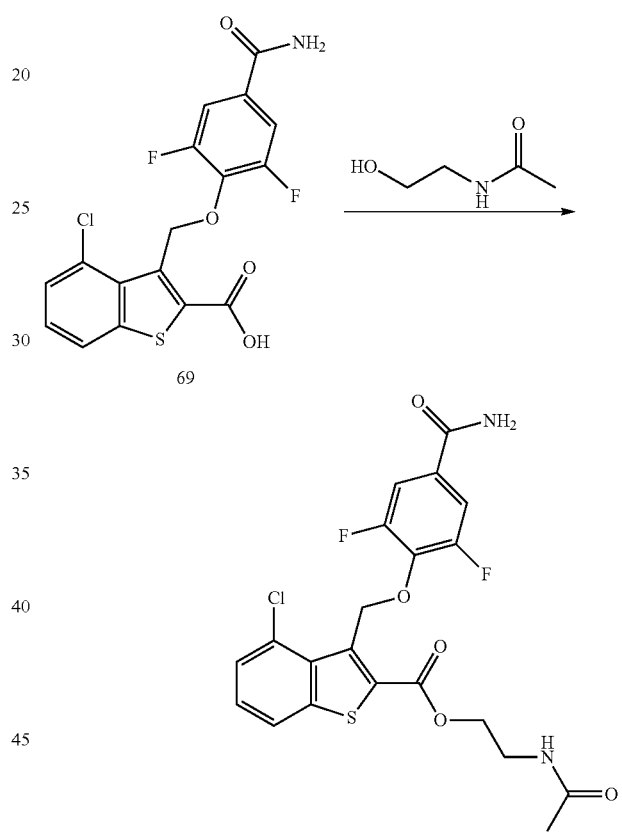

To a solution of 3-((4-carbamoyl-2,6-difluorophenoxy)methyl)-4-chlorobenzo[b]thiophene-2-carboxylic acid 69 (150 mg, 0.38 mmol) in DMF (8 mL) was added N-(2-hydroxyethyl)acetamide (78 mg, 0.76 mmol), EDCl.HCl (146 mg, 0.76 mmol) and DMAP (10 mg, 0.076 mmol) and the mixture was stirred at room temperature for 4 h. Water (150 mL) was added and the mixture was extracted with EtOAc (100 mL×3). The combined organic extracts were washed with water (3×150 mL), brine, dried over Na$_2$SO$_4$, filtered and concentrated under reduced pressure. The residue was purified by silica gel chromatography (DCM/MeOH=1:0 to 100:1) to give the title compound (60 mg, 73%) as a white solid. LCMS-C: rt 2.22 min; m/z 482.9 [M+H]$^+$, 504.9 [M+Na]$^+$. $^1$H NMR (400 MHz, DMSO-d$_6$) δ

8.14 (dd, J=7.9, 1.2 Hz, 1H), 8.06-8.00 (m, 2H), 7.66-7.53 (m, 5H), 6.13 (s, 2H), 4.22 (t, J=5.6 Hz, 2H), 3.35 (t, J=5.6 Hz, 2H), 1.80 (s, 3H).

2-((Methoxycarbonyl)amino)ethyl 3-((4-carbamoyl-2,6-difluorophenoxy)methyl)-4-chlorobenzo[b]thiophene-2-carboxylate (160)

(a) Methyl (2-hydroxyethyl)carbamate (197)

To a solution of 2-aminoethanol (2.0 g, 32.7 mmol) in DCM (20 mL) at 0° C. was added K$_2$CO$_3$ (13.6 g, 98.2 mmol) and the mixture was stirred for 10 min. Methyl chloroformate (3.1 g, 32.7 mmol) was added dropwise and the mixture was allowed to warm to room temperature and stirred overnight. The mixture was filtered and the filtrate was concentrated under reduced pressure to give the title compound (3.0 g, 77%), which was used directly in the next step. LCMS-C: rt 0.37 min; m/z 120.0 [M+H]$^+$.

(b) 2-((Methoxycarbonyl)amino)ethyl 3-((4-carbamoyl-2,6-difluorophenoxy)methyl)-4-chlorobenzo[b]thiophene-2-carboxylate (160)

To a solution of 3-((4-carbamoyl-2,6-difluorophenoxy)methyl)-4-chlorobenzo[b]thiophene-2-carboxylic acid 69 (150 mg, 0.377 mmol) in DMF (5 mL) was added methyl (2-hydroxyethyl)carbamate 197 (135 mg, 1.131 mmol), EDCl.HCl (145 mg, 0.754 mmol) and DMAP (9.2 mg, 0.075 mmol) and the mixture was stirred at room temperature overnight. Water was added and the mixture was extracted with EtOAc. The organic extract was concentrated under reduced pressure and the residue was purified by silica gel chromatography (DCM/MeOH=20:1) followed by prep-HPLC to give the title compound (8 mg, 4%) as a white solid. LCMS-C: rt 2.35 min; m/z 498.9 [M+H]$^+$, 520.9 [M+Na]$^+$. $^1$H NMR (400 MHz, DMSO-d$_6$) δ 8.14 (dd, J=7.9, 1.2 Hz, 1H), 8.02 (s, 1H), 7.67-7.54 (m, 5H), 7.36-7.27 (m, 1H), 6.13 (s, 2H), 4.22 (t, J=5.5 Hz, 2H), 3.51 (s, 3H), 3.28 (t, J=5.2 Hz, 2H).

2-((Methoxycarbonyl)(methyl)amino)ethyl 3-((4-carbamoyl-2,6-difluorophenoxy)methyl)-4-chlorobenzo[b]thiophene-2-carboxylate (161)

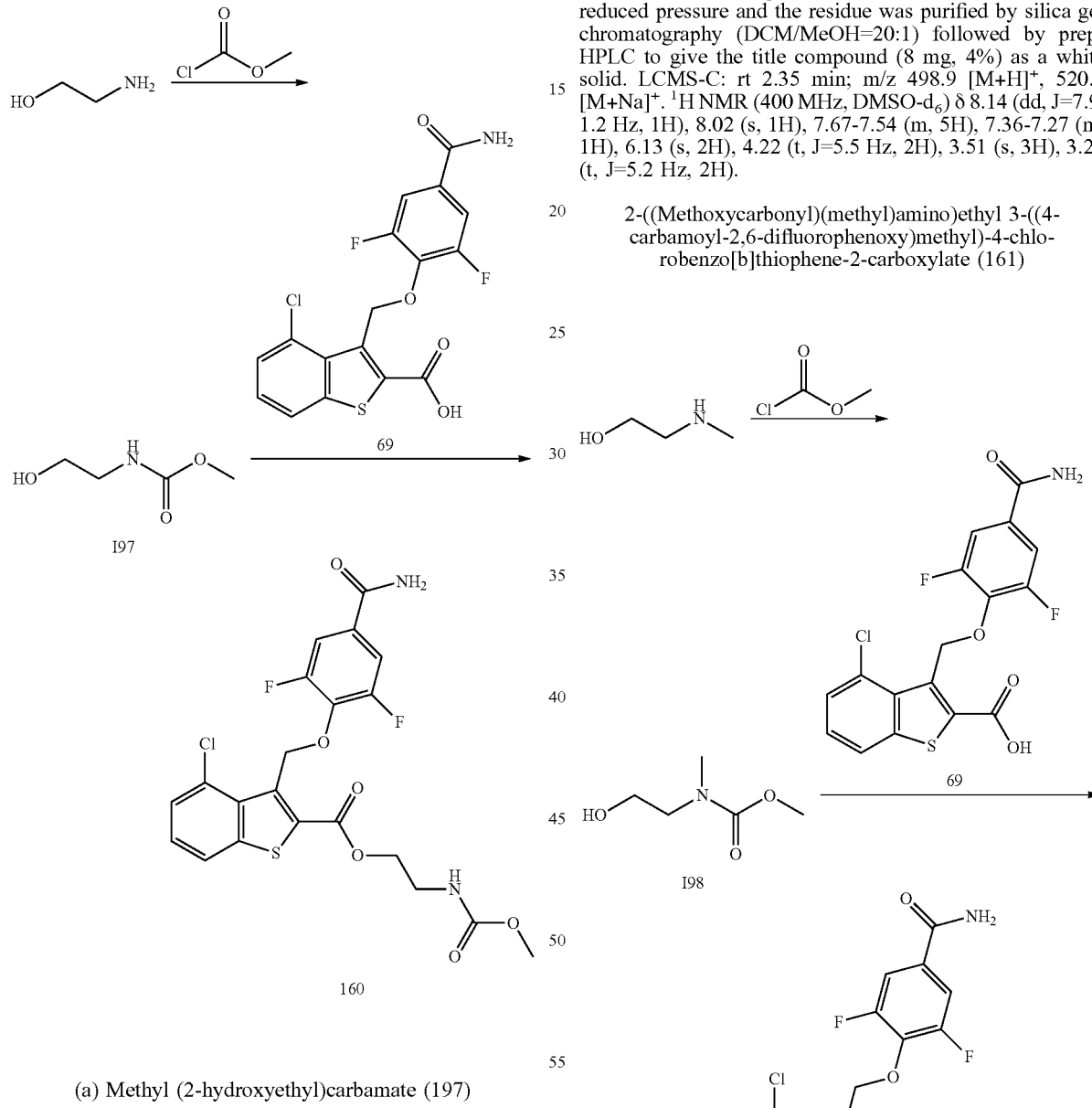

(a) Methyl (2-hydroxyethyl)(methyl)carbamate (198)

To a solution of 2-(methylamino)ethanol (2.0 g, 26.6 mmol) in DCM (20 mL) at 0° C. was added $K_2CO_3$ (11.0 g, 80 mmol) and the mixture was stirred for 10 min. Methyl chloroformate (3.0 g, 32.0 mmol) was added dropwise and the mixture was allowed to warm to room temperature and stirred overnight. The mixture was filtered and the filtrate was concentrated under reduced pressure to give the title compound (3.0 g, 85%) which was used directly in the next step. LCMS-C: rt 1.24 min; m/z 134.0 $[M+H]^+$.

(b) 2-((Methoxycarbonyl)(methyl)amino)ethyl 3-((4-carbamoyl-2,6-difluorophenoxy)methyl)-4-chlorobenzo[b]thiophene-2-carboxylate (161)

To a solution of 3-((4-carbamoyl-2,6-difluorophenoxy)methyl)-4-chlorobenzo[b]thiophene-2-carboxylic acid 69 (150 mg, 0.377 mmol) in DMF (5 mL) was added methyl (2-hydroxyethyl)(methyl)carbamate 198 (150 mg, 1.13 mmol), EDCl.HCl (145 mg, 0.754 mmol) and DMAP (9.2 mg, 0.075 mmol) and the mixture was stirred at room temperature overnight. Water was added and the mixture was extracted with EtOAc. The organic extract was concentrated under reduced pressure and the residue was purified by silica gel chromatography (DCM/MeOH=20:1) to give the title compound (80 mg, 41%) as a white solid. LCMS-C: rt 2.38 min; m/z 512.9 $[M+H]^+$, 534.9 $[M+Na]^+$. $^1$H NMR (400 MHz, DMSO-$d_6$) δ 8.14 (dd, J=7.9, 1.2 Hz, 1H), 8.02 (s, 1H), 7.66-7.54 (m, 5H), 6.14 (s, 2H), 4.33 (t, J=5.2 Hz, 2H), 3.56 (s, 3H), 3.52 (t, J=5.2 Hz, 2H), 2.87 (s, 3H).

3-Methoxypropyl 3-((4-carbamoyl-2,6-difluorophenoxy)methyl)-4-chlorobenzo[b]thiophene-2-carboxylate (162)

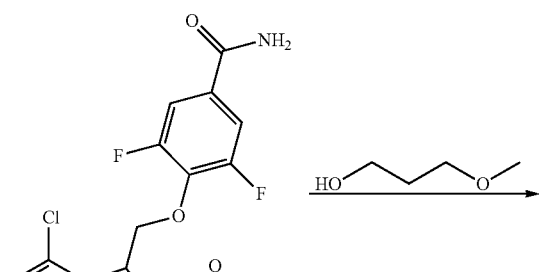

To a solution of 3-((4-carbamoyl-2,6-difluorophenoxy)methyl)-4-chlorobenzo[b]thiophene-2-carboxylic acid 69 (150 mg, 0.37 mmol) and 3-methoxypropan-1-ol (68 mg, 0.75 mmol) in DMF (10 mL) was added EDCl.HCl (144 mg, 0.75 mmol) and DMAP (9 mg, 0.07 mmol) and the mixture was stirred at room temperature overnight. Water was added and the mixture was extracted with EtOAc. The organic extract was washed with water, brine, dried over $Na_2SO_4$, filtered and concentrated under reduced pressure. The residue was purified by silica gel chromatography to give the title compound (53 mg, 30%). LCMS-C: rt 2.53 min; m/z 469.9 $[M+H]^+$, 491.9 $[M+Na]^+$. $^1$H NMR (400 MHz, DMSO-$d_6$) δ 8.19-8.09 (m, 1H), 8.08-7.98 (m, 1H), 7.68-7.44 (m, 5H), 6.14 (s, 2H), 4.28-4.24 (m, 2H), 3.39-3.35 (m, 2H), 3.25 (s, 3H), 1.89-1.77 (m, 2H).

Methyl 4-((3-((4-carbamoyl-2,6-difluorophenoxy)methyl)-4-chlorobenzo[b]thiophene-2-carbonyl)oxy)piperidine-1-carboxylate (163)

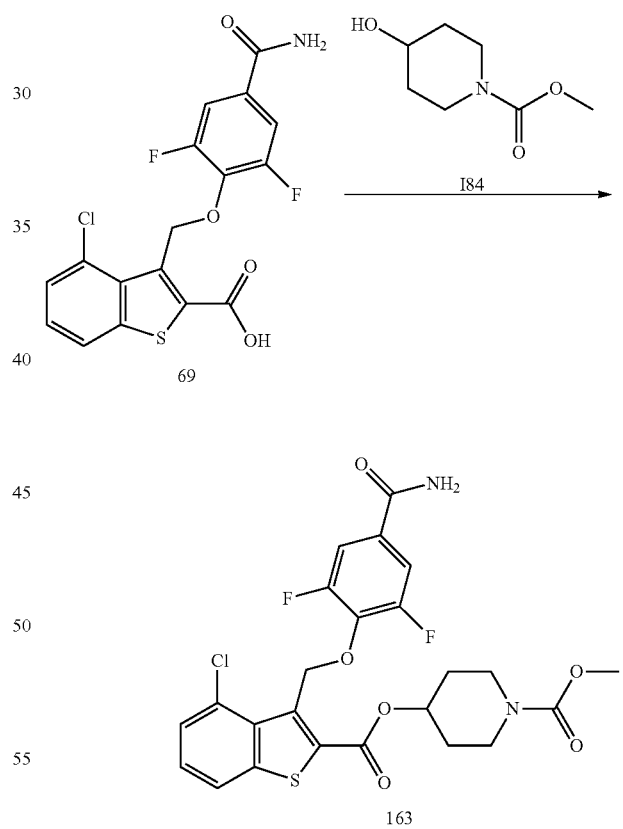

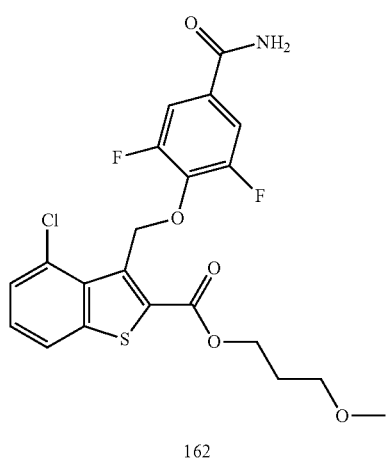

A mixture of 3-((4-carbamoyl-2,6-difluorophenoxy)methyl)-4-chlorobenzo[b]thiophene-2-carboxylic acid 69 (100 mg, 0.25 mmol), methyl 4-hydroxypiperidine-1-carboxylate 184 (61 mg, 0.38 mmol), EDCl.HCl (96 mg, 0.50 mmol) and DMAP (24 mg, 0.05 mmol) in DMF (6 mL) was stirred at room temperature overnight. The mixture was poured into water, extracted with EtOAc and the organic extract was washed with brine, dried over Na₂SO₄, filtered and concentrated under reduced pressure. The residue was purified by prep-TLC (DCM/MeOH=5:1) to give the title compound (4.3 mg, 3%) as a white solid. LCMS-C: rt 2.48 min; m/z 538.9 [M+H]⁺, 560.9 [M+Na]⁺. ¹H NMR (400 MHz, DMSO-d₆) δ 8.12 (d, J=7.9 Hz, 1H), 8.03 (s, 1H), 7.62-7.55 (m, 5H), 6.14 (s, 2H), 5.11-5.01 (m, 1H), 3.60 (s, 3H), 3.54-3.45 (m, 2H), 3.42-3.36 (m, 2H), 1.88-1.77 (m, 2H), 1.61-1.47 (m, 2H).

1-Methylazetidin-3-yl 3-((4-carbamoyl-2,6-difluorophenoxy)methyl)-4-chlorobenzo[b]thiophene-2-carboxylate (164)

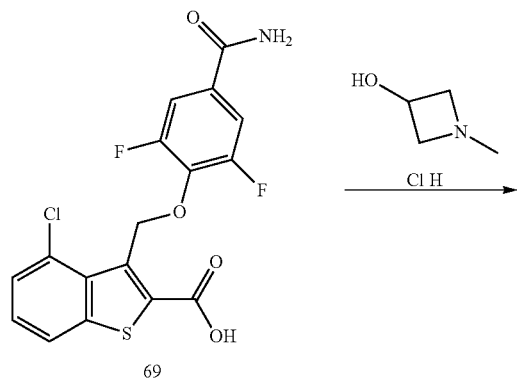

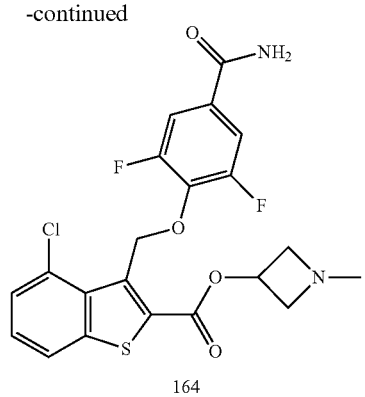

To a solution of 3-((4-carbamoyl-2,6-difluorophenoxy)methyl)-4-chlorobenzo[b]thiophene-2-carboxylic acid 69 (100 mg, 0.25 mmol) and 1-methylazetidin-3-ol hydrochloride (47 mg, 0.38 mmol) in DMF (8 mL) was added EDCl.HCl (96 mg, 0.56 mmol) and DMAP (6 mg, 0.05 mmol) and the mixture was stirred at room temperature overnight. Water was added and the mixture was extracted with EtOAc. The organic extract was washed with water, brine, dried over Na₂SO₄, filtered and concentrated under reduced pressure. The residue was purified by prep-TLC (DCM/MeOH=20:1) to give the title compound (10 mg, 9%) as a white solid. LCMS-C: rt 3.22 min; m/z 466.9 [M+H]⁺. ¹H NMR (400 MHz, DMSO-d₆) δ 8.14 (dd, J=7.9, 1.2 Hz, 1H), 8.03 (s, 1H), 7.69-7.54 (m, 5H), 6.13 (s, 2H), 5.09-5.01 (m, 1H), 3.67-3.61 (m, 2H), 3.00-2.96 (m, 2H), 2.28 (s, 3H).

Ethyl 3-((4-carbamoyl-2,6-difluorophenoxy)methyl)-4-methoxybenzo[b]thiophene-2-carboxylate (165)

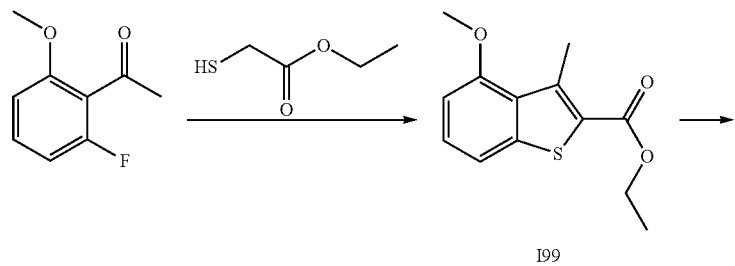

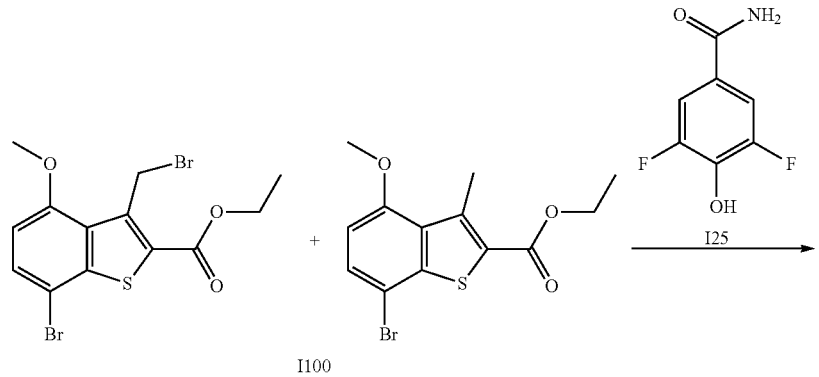

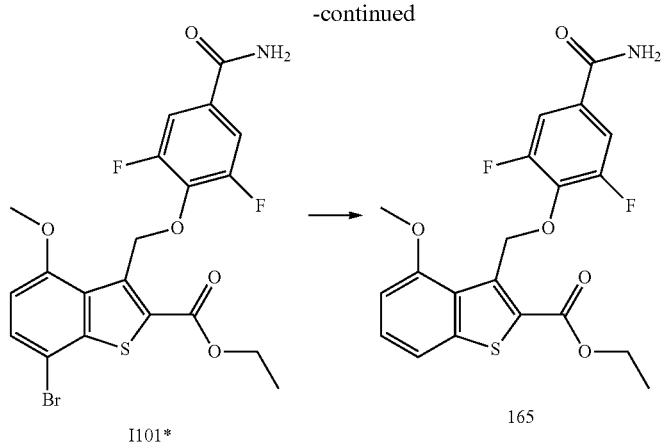

I101*
165

*Not isolated

(a) Ethyl 4-methoxy-3-methylbenzo[b]thiophene-2-carboxylate (I99)

To a solution of ethyl 2-mercaptoacetate (20 g, 167 mmol) in THF (350 mL) was added LiHMDS (1.0 M solution in THF, 166 mL, 166 mmol) and the mixture was stirred at room temperature for 40 min. 1-(2-Fluoro-6-methoxyphenyl)ethanone (7.0 g, 41.6 mmol) was then added and the mixture was stirred at room temperature overnight. The mixture was diluted with water and 1 M aqueous HCl and extracted with EtOAc. The organic extract was concentrated under reduced pressure and the residue was purified by silica gel chromatography to give the title compound (2.5 g, 22%) as a yellow solid. LCMS-C: rt 2.65 min; m/z 251.0 [M+H]$^+$.

(b) Ethyl 3-((4-carbamoyl-2,6-difluorophenoxy)methyl)-4-methoxybenzo[b]thiophene-2-carboxylate (165)

To a solution of ethyl 4-methoxy-3-methylbenzo[b]thiophene-2-carboxylate 199 (2.0 g, 7.99 mmol) in 0014 (50 mL) was added NBS (1.7 g, 9.59 mmol) and BPO (194 mg, 0.8 mmol) and the mixture was heated at reflux overnight. Water was added and the mixture was extracted with EtOAc. The organic extract was concentrated under reduced pressure and the residue was purified by silica gel chromatography to give a 1:1 inseparable mixture of a mono-bromo and di-bromo products assigned by NMR spectroscopy to be ethyl 7-bromo-4-methoxy-3-methylbenzo[b]thiophene-2-carboxylate and ethyl 7-bromo-3-(bromomethyl)-4-methoxybenzo[b]thiophene-2-carboxylate (2.2 g) as a yellow solid. LCMS-C: rt 2.90 min; m/z 328.8 [M+H]$^+$ and 406.8 [M+H]$^+$. $^1$H NMR (400 MHz, DMSO-d$_6$) δ 7.76 (d, J=8.6 Hz, 1H), 7.67 (d, J=8.5 Hz, 1H), 7.04 (d, J=8.6 Hz, 1H), 6.93 (d, J=8.5 Hz, 1H), 5.37 (s, 2H), 4.39 (q, J=7.1 Hz, 2H), 4.32 (q, J=7.1 Hz, 2H), 3.98 (s, 3H), 3.92 (s, 3H), 2.88 (s, 3H), 1.36 (t, J=8.0 Hz, 3H), 1.32 (t, J=8.0 Hz, 3H).

To solution of the mixture of ethyl 7-bromo-4-methoxy-3-methylbenzo[b]thiophene-2-carboxylate and ethyl 7-bromo-3-(bromomethyl)-4-methoxybenzo[b]thiophene-2-carboxylate (152 mg) in DMF (10 mL) was added 3,5-difluoro-4-hydroxybenzamide 125 (80 mg, 0.462 mmol) and Cs$_2$CO$_3$ (301 mg, 0.924 mmol) and the mixture was stirred at room temperature overnight. Water was added and the resulting precipitate was collected by filtration to give a white solid (120 mg). LCMS-C: rt 2.55 min; m/z 521.8/523.8 [M+Na]$^+$. This material was dissolved in EtOH/THF (10 mL/10 mL), 10% Pd/C (63 mg, wetted with ca. 55% water) was added and the mixture was stirred at room temperature under H$_2$ (20 KPa) overnight. The mixture was filtered and the filtrate was concentrated under reduced pressure. The residue was purified by silica gel chromatography (DCM/MeOH=20:1) to give the title compound (15 mg, 6% over three steps) as a white solid. LCMS-C: rt 2.43 min; m/z 421.9 [M+H]$^+$, 443.9 [M+Na]$^+$. $^1$H NMR (400 MHz, DMSO-d$_6$) δ 8.02 (s, 1H), 7.65-7.58 (m, 3H), 7.56 (s, 1H), 7.50 (t, J=8.0 Hz, 1H), 6.98 (d, J=7.9 Hz, 1H), 6.00 (s, 2H), 4.28 (q, J=7.1 Hz, 2H), 3.72 (s, 3H), 1.26 (t, J=7.1 Hz, 3H).

N-Benzyl-4-bromo-3-((4-carbamoylphenoxy)methyl)benzo[b]thiophene-2-carboxamide (166)

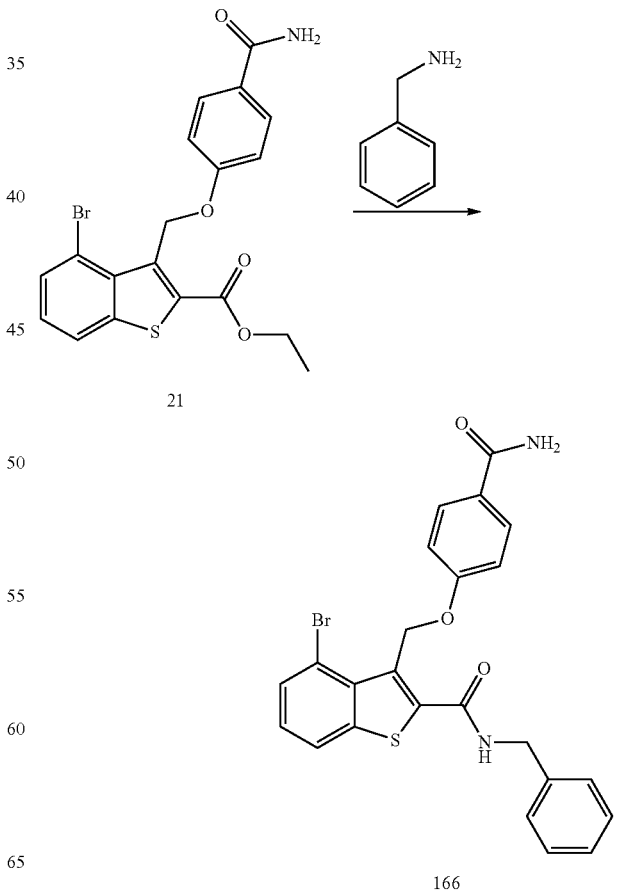

21

166

To a solution of ethyl 4-bromo-3-((4-carbamoylphenoxy)methyl)benzo[b]thiophene-2-carboxylate 21 (100 mg, 0.23 mmol) in EtOH (2 mL) was added benzylamine (123 mg, 1.2 mmol) and Et$_3$N (70 mg, 0.69 mmol) and the mixture was heated at 150° C. under microwave irradiation for 30 min. The mixture was diluted with water, extracted with DCM and the combined organic extracts were concentrated under reduced pressure. The residue was purified by prep-TLC (DCM/MeOH=15:1) followed by prep-HPLC to give the title compound (6 mg, 5%) as a white solid. LCMS-D: rt 3.86 min; m/z 495.0/497.0 [M+H]$^+$. $^1$H NMR (400 MHz, DMSO-d$_6$) δ 9.26 (s, 1H), 8.17 (d, J=7.4 Hz, 1H), 7.94-7.81 (m, 3H), 7.75 (d, J=7.3 Hz, 1H), 7.49-7.37 (m, 1H), 7.34-7.16 (m, 6H), 7.02 (d, J=7.7 Hz, 2H), 5.63 (s, 2H), 4.47 (d, J=4.0 Hz, 2H).

4-Bromo-3-((4-carbamoylphenoxy)methyl)-N-phenethylbenzo[b]thiophene-2-carboxamide (167)

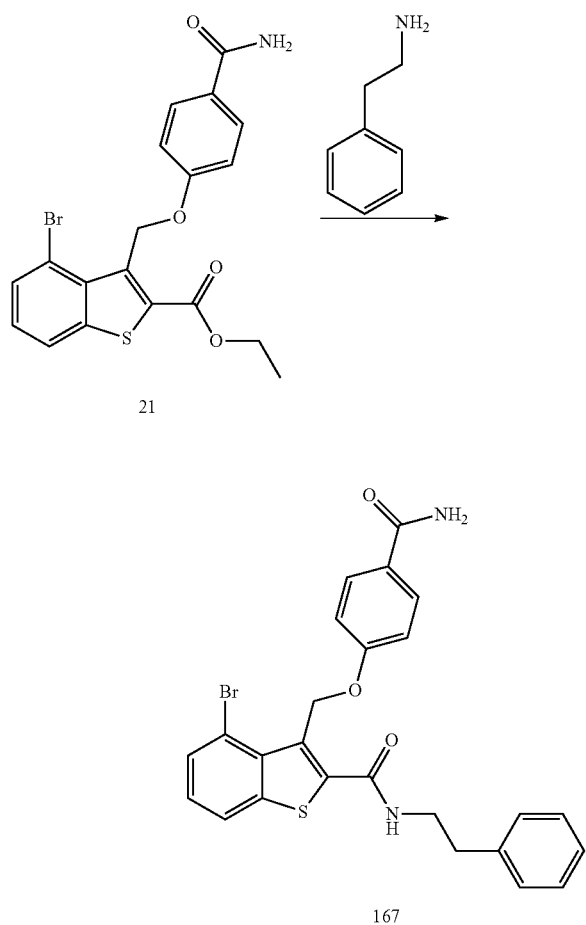

To a solution of ethyl 4-bromo-3-((4-carbamoylphenoxy)methyl)benzo[b]thiophene-2-carboxylate 21 (100 mg, 0.23 mmol) in EtOH (2 mL) was added 2-phenylethan-1-amine (140 mg, 1.15 mmol) and Et$_3$N (70 mg, 0.69 mmol) and the mixture was heated at 150° C. under microwave irradiation for 30 min. The mixture was diluted with water, extracted with DCM and the combined organic extracts were concentrated under reduced pressure. The residue was purified by prep-TLC (DCM/MeOH=15:1) followed by prep-HPLC to give the title compound (8 mg, 7%) as a white solid. LCMS-D: rt 3.95 min; m/z 509.0/511.0 [M+H]$^+$, 531.0/533.0 [M+Na]$^+$. $^1$H NMR (400 MHz, DMSO-d$_6$) δ 8.74 (t, J=5.6 Hz, 1H), 8.16 (dd, J=8.1, 0.8 Hz, 1H), 7.92-7.80 (m, 3H), 7.74 (dd, J=7.6, 0.8 Hz, 1H), 7.40 (t, J=7.9 Hz, 1H), 7.30-7.12 (m, 6H), 7.01 (d, J=8.9 Hz, 2H), 5.55 (s, 2H), 3.52-3.47 (m, 2H), 2.82 (t, J=7.1 Hz, 2H).

Ethyl 3-((4-carbamoyl-3-vinylphenoxy)methyl)-4-chlorobenzo[b]thiophene-2-carboxylate (168)

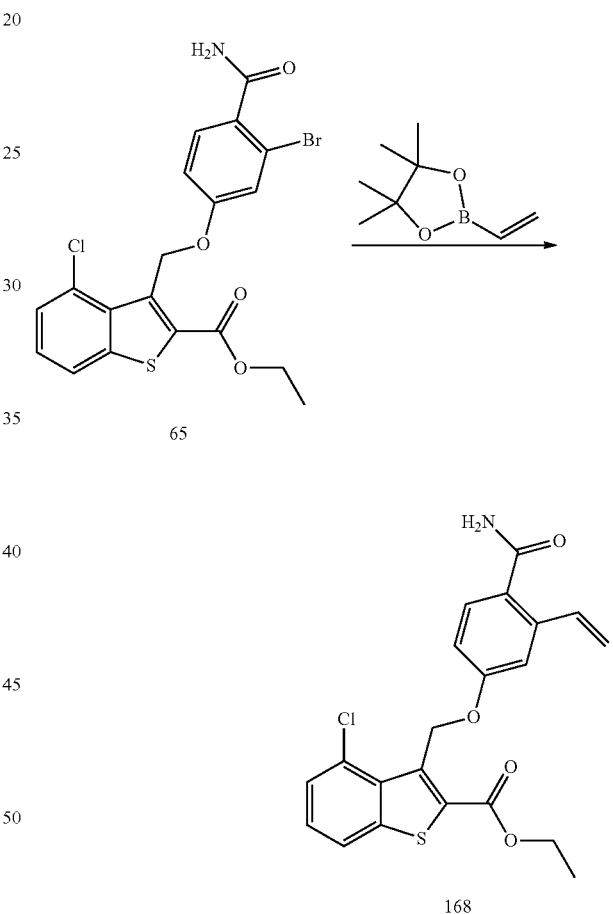

A mixture of ethyl 3-((3-bromo-4-carbamoylphenoxy)methyl)-4-chlorobenzo[b]thiophene-2-carboxylate 65 (100 mg, 0.213 mmol), 4,4,5,5-tetramethyl-2-vinyl-1,3,2-dioxaborolane (66 mg, 0.426 mmol), K$_2$CO$_3$ (89 mg, 0.639 mmol) and tetrakis(triphenylphosphine)palladium (25 mg, 0.021 mmol) in 1,4-dioxane (8 mL) was heated at reflux under N$_2$ overnight. The mixture was diluted with water, extracted with EtOAc and the combined organic extracts were washed with brine, dried over Na$_2$SO$_4$, filtered and concentrated under reduced pressure. The residue was purified by prep- TLC (DCM/MeOH=10:1) to give the title compound (25 mg, 28%) as a white solid. LCMS-D: rt 4.29 min; m/z 416.0 [M+H]+, 438.0 [M+Na]+. 1H NMR (400 MHz, DMSO-d6) δ 8.14 (dd, J=7.0, 2.1 Hz, 1H), 7.72 (s, 1H), 7.61-7.54 (m, 2H), 7.41 (d, J=8.5 Hz, 1H), 7.31 (s, 1H), 7.27 (d, J=2.5 Hz, 1H), 7.13 (dd, J=17.6, 11.1 Hz, 1H), 7.00 (dd, J=8.5, 2.6 Hz, 1H), 5.89 (s, 2H), 5.83 (d, J=17.7 Hz, 1H), 5.28 (d, J=11.0 Hz, 1H), 4.36 (q, J=7.1 Hz, 2H), 1.29 (t, J=7.1 Hz, 3H).

brine (15 mL), dried over Na2SO4, filtered and concentrated under reduced pressure. The residue was purified by prep-TLC (DCM/MeOH=20:1) to give the title compound (13.8 mg, 35%) as a white solid. LCMS-F: rt 2.54 min; m/z 458.8/460.9 [M+H]+. 1H NMR (400 MHz, DMSO-d6) δ 8.13 (s, 1H), 8.00 (s, 1H), 7.94 (s, 1H), 7.82 (dd, J=8.5, 4.9 Hz, 1H), 7.62-7.53 (m, 3H), 7.39 (t, J=8.8 Hz, 1H), 5.99 (s, 2H).

4-Bromo-3-((4-carbamoyl-2,6-difluorophenoxy)methyl)-7-fluorobenzo[b]thiophene-2-carboxamide (169)

Ethyl 3-((4-carbamoyl-2,6-difluorophenoxy)methyl)-4-chlorothieno[2,3-c]pyridine-2-carboxylate (170)

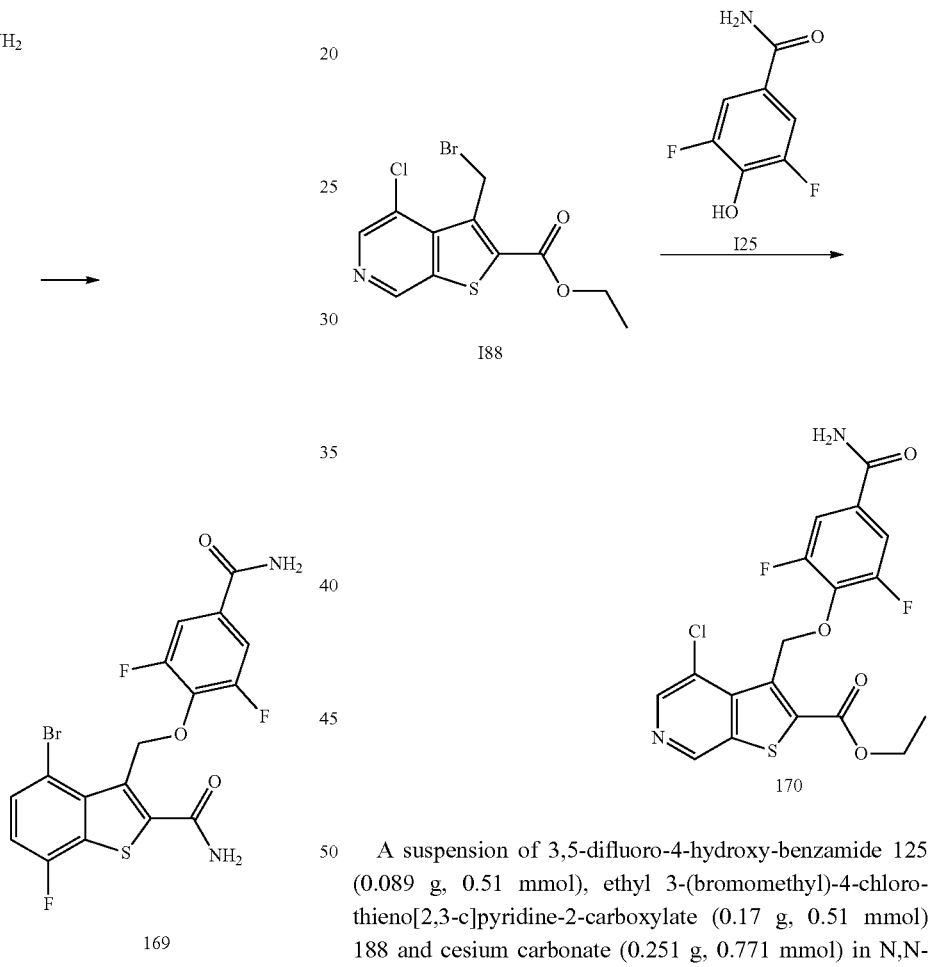

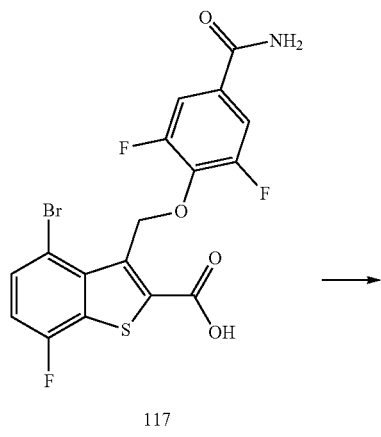

A mixture of 4-bromo-3-((4-carbamoyl-2,6-difluorophenoxy)methyl)-7-fluorobenzo[b]thiophene-2-carboxylic acid 117 (40 mg, 0.09 mmol), HATU (130 mg, 0.36 mmol) and DIPEA (34 mg, 0.27 mg) in NMP (5 mL) was stirred at room temperature for 0.5 h. A solution of conc. aqueous NH4OH (3 mL) was added and the mixture was stirred at room temperature for a further 16 h. The mixture was partitioned between water (15 mL) and EtOAc (15 mL), the layers were separated and the aqueous layer was extracted with EtOAc (15 mL×3). The combined organic layers were washed with A suspension of 3,5-difluoro-4-hydroxy-benzamide 125 (0.089 g, 0.51 mmol), ethyl 3-(bromomethyl)-4-chloro-thieno[2,3-c]pyridine-2-carboxylate (0.17 g, 0.51 mmol) 188 and cesium carbonate (0.251 g, 0.771 mmol) in N,N-dimethylformamide (8 mL) was stirred at room temperature overnight. Water was added and the mixture extracted with EtOAc (×3). The combined organic layers were washed with water, brine, dried (MgSO4) and filtered. The filtrate was concentrated in vacuo and the residue purified by column chromatography (MeOH/EtOAc) to give the title compound (0.100 g, 46%) as a white solid. 1H NMR (400 MHz, Chloroform-d) δ 9.06 (s, 1H), 8.58 (s, 1H), 7.42-7.30 (m, 2H), 6.20 (t, J=0.9 Hz, 2H), 4.39 (q, J=7.1 Hz, 2H), 2.96 (s, 1H), 2.88 (d, J=0.5 Hz, 1H), 1.38 (t, J=7.1 Hz, 3H). LCMS-A: rt 6.040 min, m/z 427.1 [M+H]+.

227

Lithium 3-((4-carbamoyl-2,6-difluorophenoxy)methyl)-4-chlorothieno[2,3-c]pyridine-2-carboxylate (171)

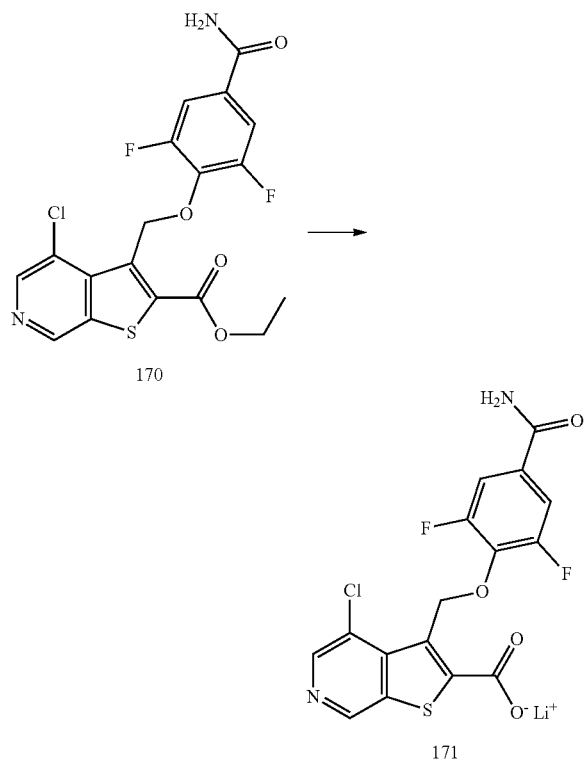

To a solution of ethyl 3-[(4-carbamoyl-2,6-difluoro-phenoxy)methyl]-4-chloro-thieno[2,3-c]pyridine-2-carboxylate 170 (0.0300 g, 0.0703 mmol) in THF/Water/MeOH (3:2:1, 15 mL) was added lithium hydroxide monohydrate (0.0088 g, 0.21 mmol). The mixture was stirred at room temperature for 19 h. The solvent was removed in vacuo to give the lithium salt of the title compound (37 mg, quantitative yield) as a white solid. $^1$H NMR (400 MHz, Methanol-$d_4$) δ 9.02 (s, 1H), 8.43 (s, 1H), 7.49-7.39 (m, 2H), 6.29 (s, 2H), CONH$_2$ protons not observed. LCMS-A: rt 6.784, m/z 399.1 [M+H]$^+$ for the free acid.

3-((4-Carbamoyl-2-fluoro-6-(hydroxymethyl)phenoxy)methyl)-4-methoxythieno[3,2-c]pyridine-2-carboxylic acid (172)

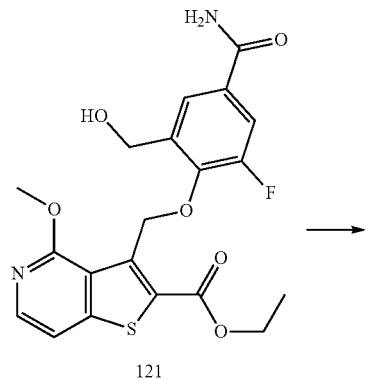

228

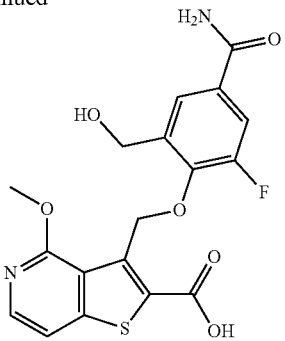

To a solution of ethyl 3-((4-carbamoyl-2-fluoro-6-(hydroxymethyl)phenoxy)methyl)-4-methoxythieno[3,2-c]pyridine-2-carboxylate 121 (0.0080 g, 0.018 mmol) in tetrahydrofuran (3 mL), methanol (1 mL) and water (2 mL) was added lithium hydroxide monohydrate (0.0155 g, 0.368 mmol). The reaction mixture was stirred at room temperature overnight before the solvent was removed in vacuo to give a white solid. The solid was taken up in water and acidified to pH 3 (citric acid), then extracted with EtOAc (×3). The organic layer was separated from the aqueous phase and the solvent removed in vacuo to give a white solid. The solid was purified by preparative RP-HPLC to give the title compound (0.60 mg, 8%) as a white solid. LCMS-B: rt 5.187 min, m/z=405.1 [M−H]$^−$. $^1$H NMR (400 MHz, Methanol-$d_4$) δ 8.06 (d, J=5.8 Hz, 1H), 7.79-7.73 (m, 1H), 7.64 (dd, J=12.4, 2.2 Hz, 1H), 7.51 (d, J=5.8 Hz, 1H), 6.05 (s, 2H), 4.33 (s, 2H), 3.87 (s, 3H), exchangeable CO$_2$H, CONH$_2$ and OH protons not observed.

(Pivaloyloxy)methyl 3-((4-carbamoyl-2,6-difluorophenoxy)methyl)-4-chlorobenzo[b]thiophene-2-carboxylate (173)

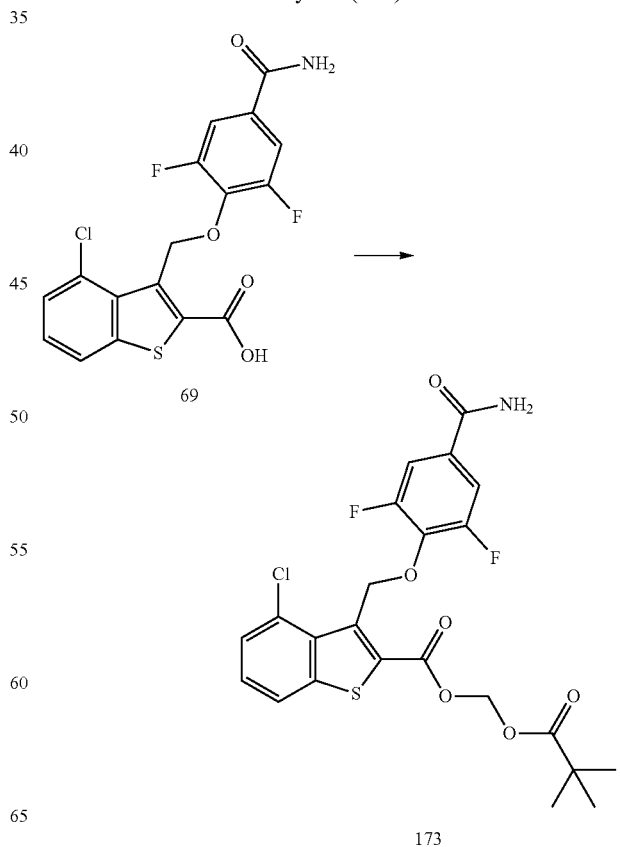

A mixture of 3-((4-carbamoyl-2,6-difluorophenoxy)methyl)-4-chlorobenzo[b]thiophene-2-carboxylic acid 69 (0.085 g, 0.21 mmol), sodium iodide (0.128 g, 0.855 mmol), cesium carbonate (60-80 mesh, 0.139 g, 0.427 mmol) and chloromethyl pivalate (0.12 mL, 0.85 mmol) in DMF (1 mL) was stirred at room temperature for 4 hours. Water (~30 mL) was added and the aqueous phase was extracted with EtOAc (3×30 mL). The organic extracts were combined, washed with brine (3×30 mL), dried ($MgSO_4$) and the solvent removed in vacuo. The solid was taken up in a minimum amount of DCM and the product was precipitated by the addition of cyclohexane. The precipitate was isolated by vacuum filtration and air dried to give the title compound (0.079 g, 72%) as an off-white solid. LCMS-B rt 4.318 min; m/z 511.8 $[M+H]^+$, 533.8 $[M+Na]^+$. $^1$H NMR (400 MHz, DMSO-$d_6$) δ 8.16 (dd, J=7.9, 1.3 Hz, 1H), 8.02 (s, 1H), 7.68-7.54 (m, 5H), 6.13 (s, 2H), 5.89 (s, 2H), 1.12 (s, 9H).

(Pivaloyloxy)methyl 3-((4-carbamoylphenoxy)methyl)-4-chloro-5-methylbenzo[b]thiophene-2-carboxylate (174)

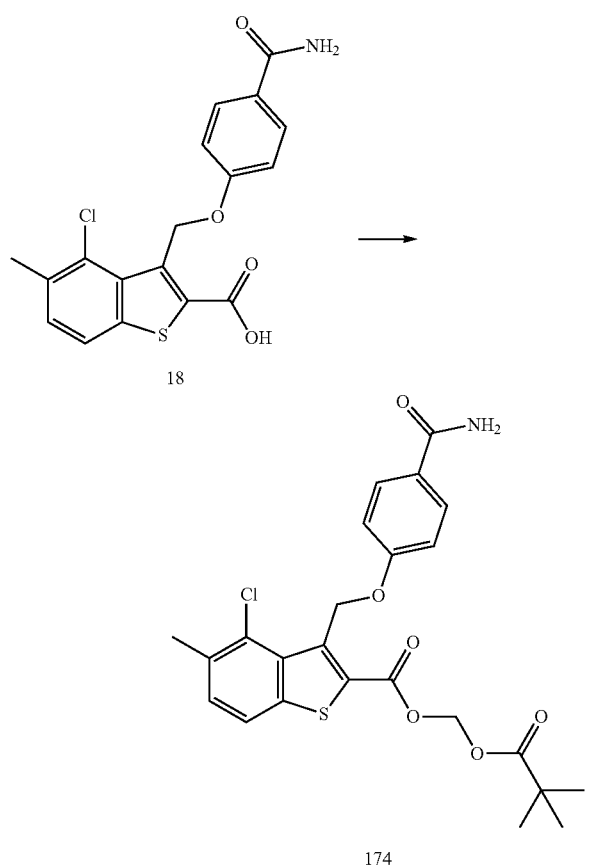

A mixture of 3-((4-carbamoylphenoxy)methyl)-4-chloro-5-methylbenzo[b]thiophene-2-carboxylic acid 18 (0.010 g, 0.027 mmol), chloromethyl pivalate (0.015 mL, 0.11 mmol), cesium carbonate (60-80 mesh, 0.017 g, 0.053 mmol) and sodium iodide (0.016 g, 0.11 mmol) in DMF (0.5 mL) was stirred at room temperature for 17 hours. Water (~2 mL) was added and the precipitate was isolated by vacuum filtration to give the title compound (0.0040 g, 31%) as a white solid. $^1$H NMR (400 MHz, DMSO-$d_6$) δ 8.06 (d, J=8.3 Hz, 1H), 7.91-7.83 (m, 3H), 7.61 (d, J=8.3 Hz, 1H), 7.19 (s, 1H), 7.12-7.04 (m, 2H), 5.96 (s, 2H), 5.87 (s, 2H), 2.45 (s, 3H), 1.12 (s, 9H). LCMS-B rt 3.625 min; m/z 489.9 $[M+H]^+$, m/z 511.9 $[M+Na]^+$.

Assays

Protein Production and Purification

Biophysical experiments were performed with three different recombinant human STING protein variants designated according to allelic nomenclature of Yi et al., (2013). Codon optimized DNA sequences (for expression in *Escherichia coli*) encoding amino acid residues 149 to 345 (Swiss Prot Q86WV6) of human STING (WT), human STING (HAQ) and human STING (R232H) were synthesised by GenScript USA Inc (Piscataway, N.J., USA). These were ligated into a modified pET43a *E. coli* expression vector designed to encode N-terminal His tag followed by tobacco etch virus protease (TEV) cleavage site and a STING gene sequence. The resulting protein sequences for the three allelic variants are listed below:

His-TEV-hSTING(WT)
MGHHHHHHGTENLYFQGS$\mathbf{E}^{149}$KGNFNVAHGLAWSYYIGYLRLILPELQA

RIRTYNQHYNNLLRGAVSQRLYILLPLDCGVPDNLSMADPNIRFLDKLP

QQTGDRAGIKDRVYSNSIYELLENGQRAGTCVLEYATPLQTLFAMSQYS

QAGFSREDRLEQAKLFCRTLEDILADAPESQNNCRLIAYQEPADDSSFS

LSQEVLRHLRQEEKEEVTVGS$^{345}$

His-TEV-hSTING(R232H)
MGHHHHHHGTENLYFQGS$\mathbf{E}^{149}$KGNFNVAHGLAWSYYIGYLRLILPELQA

RIRTYNQHYNNLLRGAVSQRLYILLPLDCGVPDNLSMADPNIRFLDKLP

QQTGDHAGIKDRVYSNSIYELLENGQRAGTCVLEYATPLQTLFAMSQYS

QAGFSREDRLEQAKLFCRTLEDILADAPESQNNCRLIAYQEPADDSSFS

LSQEVLRHLRQEEKEEVTVGS$^{345}$

His-TEV-hSTING(HAQ)
MGHHHHHHGTENLYFQGS$\mathbf{E}^{149}$KGNFNVAHGLAWSYYIGYLRLILPELQA

RIRTYNQHYNNLLRGAVSQRLYILLPLDCGVPDNLSMADPNIRFLDKLP

QQTADRAGIKDRVYSNSIYELLENGQRAGTCVLEYATPLQTLFAMSQYS

QAGFSREDRLEQAKLFCQTLEDILADAPESQNNCRLIAYQEPADDSSFS

LSQEVLRHLRQEEKEEVTVGS$^{345}$

To produce recombinant human STING proteins, expression plasmid encoding above-described constructs were transformed into *E. coli* BL21 DE3 strain and grown with shaking at 37° C. in 2×1 L volumes of Terrific broth (TB) supplemented with 100 μg/ml Ampicillin until $OD_{600}$ of 0.8 was reached. Cultures were then cooled to 16° C. and protein expression induced by the addition of isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −70° C.

Protein purification was initiated by thawing the cell pellet in Lysis buffer (25 mM Tris-HCl pH 8.0, 300 mM NaCl, 5 mM DTT, 2 mM $MgCl_2$, 10 mM imidazole, 0.5 mg/ml lysozyme, benzonase endonuclease [EMD Millipore], 1 mM PMSF, complete protease inhibitor tablets EDTA-free [Roche]) using a ratio of 7 ml of buffer per 1 g of cells. Cells were further lysed by 3 passes through an ice cooled Avestin C5 cell crusher and then centrifuged at 48,000×g at 4° C. Supernatant (cell lysate) was filtered through a 5 µm filter and loaded onto 5 mL HiTrap IMAC Sepharose FF column (GE Healthcare) pre-equilibrated with IMAC wash buffer 1 (25 mM Tris-HCl pH 8.0, 300 mM NaCl, 5 mM DTT, 10 mM imidazole) using Profinia Affinity chromatography purification system (Bio-Rad). The IMAC column was then sequentially washed with IMAC Wash buffer 1 and IMAC Wash buffer 2 (25 mM Tris-HCl pH 8.0, 300 mM NaCl, 5 mM DTT, 20 mM Imidazole) and bound His-TEV-hSTING protein eluted with IMAC Elution buffer (250 mM Tris-HCl pH 8.0, 300 mM NaCl, 5 mM DTT, 20 mM Imidazole). IMAC-eluted protein was further purified by passing through a HiLoad 26/60 Superdex 75 column pre-equilibrated in storage buffer (25 mM Tris-HCl pH 8.0, 150 mM NaCl, 5 mM DTT 0.02% [w/v] sodium azide). Finally, hSTING protein was concentrated to 2 mg/ml using Amicon Ultra centrifugal filter unit (Utra-15 MWCO 10 kDa), flash-frozen in liquid nitrogen and stored in −70° C. freezer.

Differential Scanning Fluorimetry (DSF)

Differential scanning fluorimetry (DSF) is a rapid screening method for identifying low-molecular-weight ligands that bind and, in doing so, stabilize (or sometimes destabilize) purified proteins (Niesen 2007). DSF monitors thermal unfolding of protein in the presence of a fluorescent dye and is typically performed using a real-time PCR instrument. The temperature at which a protein unfolds is measured by an increase in the fluorescence of a dye with affinity for hydrophobic parts of the protein that are gradually exposed during unfolding. The fluorescence of the dye is quenched in aqueous environments, but when the dye associates with hydrophobic sites on the unfolded protein, its fluorescence increases. The fluorescence intensity is plotted as a function of the temperature, generating a sigmoidal curve that can be described by a two-state transition. The inflection point of the transition curve ($T_m$) is calculated using simple equations such as that of Boltzman.

Thermal stability of STING protein (with and without bound ligand) was measured using previously described methodology (Seabrook & Newman 2013), with each experiment performed in triplicate using 96-well PCR microplates (AB Gene, ABGAB-0600/W). In a final volume of 20 µL, 1 µM protein in 1×HBS buffer (50 mM HEPES, pH 7.4, 150 mM NaCl, pH 7.4) was mixed with SYPRO Orange dye (Sigma-Aldrich S5692, final reaction mix dilution 1:1200) and a compound (final concentration at 100 µM). Sealed plates were then placed into a Bio-Rad CFX96/C1000 thermocycler and FRET scanning mode ($\lambda^{excitation}$ of 490 nm and reads at $\lambda^{emission}$ of 570 nm) was used to measure fluorescence intensity. Melting curves were recorded from 20° C. to 100° C. in 0.5° C. increments every 30 seconds with a read at each increment. Data were analysed using "Meltdown analysis" protocol described by Rosa 2015. The melting point ($T_m$) obtained for STING protein alone was subtracted from $T_m$ obtained for protein incubated with ligand to generate $\Delta T_m$ values listed in the table below. DSF data was generated for each compound against 3 different STING protein variants-human STING (WT), human STING (HAQ) and human STING (R232H).

| Example | DSF huSTING (HAQ) ΔTm (° C.) | DSF huSTING (WT) ΔTm (° C.) | DSF huSTING (R232H) ΔTm (° C.) |
|---|---|---|---|
| 1 | 7.78 | 0.99 | 0.88 |
| 2 | 1.44 | | |
| 3 | −0.47 | | |
| 4 | 0.13 | | |
| 5 | −0.48 | 0.07 | |
| 6 | 3.33 | −1.15 | −1.09 |
| 7 | 0.26 | | |
| 8 | 13.96 | 6 | 3.16 |
| 9 | 0.71 | 0.51 | 0.99 |
| 10 | 1.7 | −2.34 | −2.78 |
| 11 | 0.29 | 0.13 | −0.57 |
| 12 | 9 | 3.29 | −0.74 |
| 13 | −0.15 | −0.59 | −0.46 |
| 14 | 0.09 | −4.26 | −4.88 |
| 16 | 10.12 | 3.49 | 2.82 |
| 18 | 6.29 | −0.6 | −1.89 |
| 20 | 5.83 | −2.76 | −2.03 |
| 22 | 17.08 | 7.61 | 6.33 |
| 24 | 0.6 | −0.35 | 3.09 |
| 26 | 10.82 | 3.79 | 2.39 |
| 28 | 6.93 | 1.19 | 0.86 |
| 30 | 5.4 | −0.32 | 0.01 |
| 32 | 7.23 | 0.63 | 0.56 |
| 34 | 10.07 | 3.76 | 1.94 |
| 36 | 12.31 | 5.96 | 5.79 |
| 38 | 6.02 | −1.4 | −3.47 |
| 40 | 9.91 | 3.66 | −1.44 |
| 42 | 2.83 | −0.64 | −0.86 |
| 44 | 7.64 | 1.3 | −1.24 |
| 46 | 7.26 | 1.77 | −0.49 |
| 48 | 1.92 | −4.63 | −3.78 |
| 50 | 5.11 | 0.02 | −2.74 |
| 52 | −1.22 | −2.15 | −2.65 |
| 54 | 2.56 | −1.28 | −2.45 |
| 55 | −1.03 | | |
| 56 | 4.48 | −1.29 | −1.75 |
| 57 | 10.74 | 3.43 | 1.27 |
| 58 | 0.43 | | |
| 59 | 7.31 | 0.54 | −1.44 |
| 61 | 14.62 | 5.68 | 5.68 |
| 63 | 8.07 | 1.88 | 1.92 |
| 64 | 6.79 | 2.73 | −0.59 |
| 67 | 11.14 | 3.04 | −1.08 |
| 69 | 22.08 | 9.49 | 4.02 |
| 71 | 12.18 | 5.11 | 0.44 |
| 73 | 1.79 | −1.03 | −1.09 |
| 74 | −0.31 | −4.22 | −4.25 |
| 76 | 2.43 | −2.72 | 1.37 |
| 78 | 16 | 6.62 | 4.37 |
| 80 | 14.94 | 6.69 | −0.9 |
| 82 | 9.29 | 3.15 | −0.22 |
| 84 | 6.48 | 0.18 | −1.24 |
| 86 | 10.1 | 3.33 | −1.42 |
| 87 | 0.54 | | |
| 88 | 0.97 | −1.07 | −0.25 |

Compounds where $R^1$ is not H are not expected to show activity in these assays.

These additional compounds were tested as described above, however the protein concentration was 2 µM.

| Example | DSF huSTING (HAQ) ΔTm (° C.) | DSF huSTING (WT) ΔTm (° C.) | DSF huSTING (R232H) ΔTm (° C.) |
|---|---|---|---|
| 90 | 26.56 | 12.18 | 5.32 |
| 93 | 30.34 | 17.91 | 8.35 |
| 95 | 8.16 | 1.63 | −3.15 |
| 96 | 11.94 | 6.65 | 0.91 |
| 98 | 2.99 | −1.42 | −2.12 |
| 100 | 33.77 | 22.44 | 9.02 |
| 101 | 23.87 | 11.75 | 4.05 |
| 103 | 8.96 | 3.27 | −0.17 |
| 104 | 6.94 | 2.46 | −0.74 |

| Example | DSF huSTING (HAQ) ΔTm (° C.) | DSF huSTING (WT) ΔTm (° C.) | DSF huSTING (R232H) ΔTm (° C.) |
|---|---|---|---|
| 105 | 19.53 | 8.25 | 1.32 |
| 106 | 18.29 | 6.69 | 0.95 |
| 107 | 20.94 | 9.88 | 3.76 |
| 109 | 8.60 | 3.69 | 1.30 |
| 111 | 21.46 | 10.88 | 2.26 |
| 112 | 2.78 | 1.25 | 1.05 |
| 113 | 5.60 | 2.38 | 2.50 |
| 114 | 14.57 | 5.87 | 4.72 |
| 117 | 33.98 | 22.76 | 9.76 |
| 118 | 23.14 | 10.54 | 6.21 |
| 127 | −2.52 | −2.44 | −3.55 |
| 136 | 17.97 | 5.53 | −0.53 |
| 143 | −2.10 | −1.93 | −2.44 |
| 148 | −0.36 | −0.37 | −0.51 |
| 158 | −1.58 | −1.90 | −2.57 |
| 159 | −1.50 | −1.02 | −1.45 |
| 160 | −0.84 | −1.05 | −1.57 |
| 161 | −1.70 | −1.76 | −2.67 |
| 162 | −1.45 | −1.01 | |
| 166 | −3.01 | | −2.44 |
| 167 | 0.71 | 2.51 | −0.03 |
| 169 | 1.67 | 1.69 | 0.37 |
| 171 | 9.33 | 3.92 | 0.25 |
| 172 | 0.56 | −6.71 | −6.07 |

Surface Plasmon Resonance (SPR)

Binding interactions of ligands with STING proteins were quantified using Surface Plasmon Resonance (SPR) with a minimally biotinylated STING protein immobilized on Streptavidin chip surface. In this manner highly active STING protein surfaces were obtained that were not compromised by a low pH required for amine coupling methods. Minimal biotinylation of purified huSTING protein was performed using a previously described methodology (Chabbra 2012). Briefly, approximately 20 nmol of recombinant STING protein in 1×TBS buffer (25 mM Tris-HCl, 150 mM NaCl, 5 mM DTT) was mixed with of EZ-LinkH Sulfo-NHS-LC-LC-Biotin (Thermofisher Scientific, cat #21338) at a molar ratio of 1 to 0.6 and then incubated on ice for 2 hours. To remove any unreacted biotin reagent, protein/biotin mixture was passed through a Superdex 75 (10/300 GL) column equilibrated with 10 mM HEPES pH 7.4, 150 mM NaCl, 5 mM DTT, 5% (v/v) glycerol. A protein peak containing biotinylated huSTING protein was collected and stored in aliquots at −80° C.

Streptavidin was simultaneously immobilized in all four channels of a CM5 sensor chip docked in a Biacore instrument (either Biacore S200 or Biacore T200, GE Healthcare) as described previously (Zender 2013). Minimally biotinylated STING protein was captured onto Streptavidin coated chip surface at 25° C. in SPR binding buffer (50 mM HEPES pH 7.4, 150 mM NaCl, 2.5 mM TCEP, 2% (v/v) DMSO) gradually injected in a single channel at a constant flow-rate of 2 µL/min until SPR response increases were no longer observed resulting in typical capture levels of 5000 to 7000 RU (1 RU=1 µg/mm$^2$).

To determine binding affinity, compound interaction with immobilized STING protein was analysed using dose-response experiments. All binding experiments were performed at 25° C. in SPR binding buffer. Fresh 10 mM DMSO solutions of compound were diluted directly into SPR binding buffer to a final concentration of 10 µM and then further diluted either 2-fold or 3-fold aiming for either a 5- or 7-point concentration series range. Each ligand concentration series was injected at a constant flow rate of 60 µL/min with a 90 second association and a 180 second dissociation time.

Scrubber 2 (www.biologic.com.au) was utilized for data processing and analysis. Thus, SPR signals were referenced against the blank surface (streptavidin+D-biotin) and further corrected for DMSO refractive index change and then "double-referenced" using a buffer-blank injection (Papalia 2006). To determine binding affinities ($K_D$ values) from dose-response experiments, binding responses at equilibrium were fit to either a 1:1 steady state affinity or to 1:1 binding kinetic models (both available within Scrubber software).

| Example | SPR (HAQ) $K_D$ (µM) |
|---|---|
| 1 | 32 |
| 3 | 3500 |
| 6 | 90 |
| 8 | 1.055 |
| 10 | 187 |
| 12 | 5.95 |
| 14 | 120 |
| 16 | 2.195 |
| 18 | 15.9 |
| 20 | 34 |
| 22 | 0.755 |
| 24 | >10000 |
| 26 | 1.605 |
| 28 | 10.9 |
| 30 | 22.1 |
| 32 | 7.75 |
| 34 | 2.475 |
| 36 | 1.335 |
| 38 | 16.4 |
| 40 | 2.8 |
| 42 | 80.5 |
| 44 | 7.95 |
| 46 | 9.7 |
| 48 | 16.265 |
| 50 | 20.9 |
| 52 | 260 |
| 54 | 51 |
| 55 | 3700 |
| 56 | 29 |
| 57 | 9.05 |
| 58 | >10000 |
| 59 | 15.19 |
| 61 | 0.83 |
| 63 | 9.15 |
| 64 | 6.2 |
| 69 | 0.0886 |
| 71 | 2.12 |
| 73 | 67 |
| 87 | 3000 |
| 88 | 532.67 |

Binding experiments were also performed at 8° C. in SPR binding buffer ("SPR (HAQ) 8° C. $K_D$ (µM)"; "SPR (WT) 8° C. $K_D$ (µM)"; "SPR (R232H) 8° C. $K_D$ (µM)"). Fresh 10 mM DMSO solutions of compound were diluted directly into SPR binding buffer typically to a concentration of 50 µM and then further diluted 2-fold or 3-fold aiming for either a 5- or 7-point concentration series range. Each ligand concentration series was injected at a constant flow rate of 60 µL/min with a 90 second association and a 180 second dissociation time. These were modified for compounds with longer residence times, so that curves could reach steady-state, or so that compound would be fully dissociated before the subsequent injection. Where appropriate, tighter-binding compounds (roughly $K_D$<1 uM) were tested using a single-cycle kinetics format (Karlsson 2006), with long association and dissociation times (typically 450 s and 1800 s, respectively).

Scrubber 2 (www.biologic.com.au) was utilized for data processing, where signals were referenced against the blank surface (streptavidin+D-biotin) and further corrected for DMSO refractive index change and then "double-referenced" using a buffer-blank injection (Papalia 2006). To determine binding affinities (50% occupancy as a surrogate $K_D$ for the two binding events occurring) from dose-response experiments, binding responses at equilibrium were fit to a Hill equation, where the Hill coefficient was floated (≤2). For single-cycle kinetic experiments, sensorgrams were fit to a two-step kinetic model in which two analyte molecules bind sequentially (Biacore T200 or S200 Evaluation Software).

| Example | SPR huSTING (HAQ) $K_D$ at 8° C. (μM) | SPR huSTING (WT) $K_D$ at 8° C. (μM) | SPR huSTING (R232H) $K_D$ at 8° C. (μM) |
|---|---|---|---|
| 90 | 0.213 | 3.0 | 31 |
| 93 | 0.106 | 0.900 | 13.7 |
| 95 | 14.3 | 93 | |
| 96 | 1.85 | 22 | |
| 98 | 28.0 | 72 | |
| 100 | 0.110 | 0.620 | 22.8 |
| 101 | 0.390 | 3.70 | 69 |
| 103 | 5.80 | 65 | |
| 104 | 5.50 | 38 | |
| 105 | 1.40 | 28 | |
| 106 | 1.30 | 28 | |
| 107 | 0.500 | 21 | |
| 109 | 160 | 200 | |
| 112 | 26 | 51 | |
| 113 | 52 | | |
| 114 | 2.74 | 26 | |
| 117 | 0.200 | 0.450 | 20.8 |
| 118 | 0.150 | 4.24 | |
| 136 | 0.870 | 7.1 | |
| 169 | 130 | >1000 | |
| 171 | 4.87 | | |
| 172 | 220 | | |

THP-1 Reporter Cell Line Assays

THP-1 STING Lucia ISG cells (Invivogen #thp1-isg) were cultured in RPMI-1640 containing 2 mM L-glutamine, 25 mM HEPES, 100 μg/mL Normocin and 10% HI-FBS. At a density of $7 \times 10^5$ cells/mL, cells were seeded into a T175 flask and incubated at 37° C./5% $CO_2$, and passaged every three (3) days (all media and supplements from Life Technologies). Selection pressure was maintained by the addition of 100 μg/mL Zeocin every second passage.

Assay conditions: cells were harvested and resuspended at a concentration $5 \times 10^5$ cells/mL in fresh growth media. To sterile 384-Culturplates (Perkin Elmer #6007688) was dispensed 20 μL of this cell preparation at a density of $1 \times 10^4$ cells/well and the plates were incubated at 37° C./5% $CO_2$ for 1 h whilst the compound plate was being prepared.

11 pt Concentration Response Curves (CRCs) of compounds (10 mM stocks) were prepared by serial dilution in DMSO as follows: 10, 5, 2.5, 1.25, 0.63, 0.31, 0.15, 0.08, 0.04, 0.02, 0.01 mM. Compounds were then diluted 1/40 in growth media by transferring 1.25 μL of each concentration into 48.75 μL growth media (working dose range: 250, 125, 62.5, 31.3, 15.63, 7.81, 3.9, 1.95, 0.98, 0.49, 0.24 μM). The addition of 5 μL of these compound stocks to the Culturplates containing 20 μL of cell suspension resulted in a further 1/5 dilution (final dose range: 50, 25, 12.5, 6.25, 3.13, 1.56, 0.78, 0.39, 0.20, 0.10, 0.05 μM) (0.5% DMSO final concentration). The plates were incubated for 24 h at 37° C./5% $CO_2$.

Following 24 h incubation, 10 μL of QUANTI-Luc (Invivogen #rep-qlc1) was added to the Culturplates. QUANTI-Luc is a coelenterazine-based substrate prepared in sterile reverse osmosis (RO) water and added directly to the cells. Plates were shaken for ten seconds on an orbital shaker and left in the dark at room temperature for two minutes, before being read on the EnSpire multimode reader (STING Luminescence protocol) (Perkin Elmer).

Data analysis: presented as % activity of a 50 μM Aduro CDN (2'3'-cGsAsMP) positive control (HIGH) using 0.5% DMSO only wells as background controls (LOW).

Aduro CDN (2'3'-cGsAsMP) is also known as ML RR-S2 CDA, which has the structure:

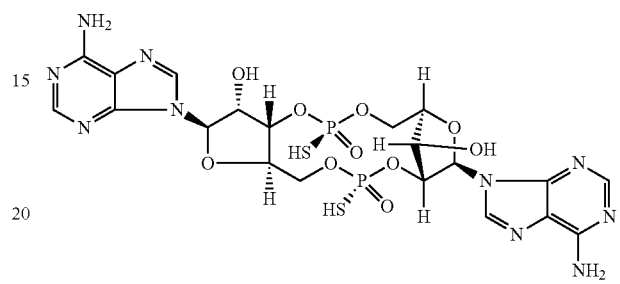

The following formula was used:

% activity=(unknown−LOW)/(HIGH−LOW)

An identical method was used for the preparing and testing compounds against the THP-1-Dual KI-hSTING-R232 cells (Invivogen #thpd-r232) for assessing compound activity against the more prevalent human STING isoform, WT.

"Cellular EC50 huSTING (HAQ) (μM)" data refers to assays performed with THP-1 STING Lucia ISG cells and "Cellular EC50 huSTING (WT) (μM)" refers to assays performed with THP-1-Dual KI-hSTING-R232 cells.

| Example | Cellular $EC_{50}$ huSTING (HAQ) (μM) | Cellular $EC_{50}$ huSTING (WT) (μM) |
|---|---|---|
| 1 | >50 | >50 |
| 2 | 2.07 | >50 |
| 3 | 2.943 | >50 |
| 4 | 2.581 | >50 |
| 5 | 8.219 | >50 |
| 6 | >50 | >50 |
| 7 | 0.7049 | 8.936 |
| 8 | >50 | >50 |
| 9 | >50 | >50 |
| 10 | >50 | >50 |
| 11 | 16.16 | 25.6 |
| 12 | >50 | >50 |
| 13 | >50 | >50 |
| 14 | >50 | >50 |
| 15 | 2.399 | 2.568 |
| 16 | >50 | >50 |
| 17 | 14.75 | >50 |
| 18 | >50 | >50 |
| 19 | >50 | >50 |
| 20 | >50 | >50 |
| 21 | 0.4741 | 0.5763 |
| 22 | >50 | 41.03 |
| 23 | 7.611 | 16.87 |
| 24 | >50 | >50 |
| 25 | 1.598 | 1.417 |
| 26 | >50 | >50 |
| 27 | >50 | >50 |
| 28 | >50 | >50 |
| 29 | 2.685 | 6.499 |
| 30 | 36.28 | >50 |
| 31 | 6.765 | 6.913 |

| Example | Cellular EC$_{50}$ huSTING (HAQ) (μM) | Cellular EC$_{50}$ huSTING (WT) (μM) |
| --- | --- | --- |
| 32 | >50 | >50 |
| 33 | 0.6654 | 0.8908 |
| 34 | >50 | >50 |
| 35 | 0.6553 | 1.283 |
| 36 | >50 | >50 |
| 37 | 3.844 | 4.766 |
| 38 | >50 | >50 |
| 39 | 1.484 | 1.783 |
| 40 | >50 | 39.68 |
| 41 | 0.7976 | 2.458 |
| 43 | 1.352 | 3.775 |
| 45 | 12.88 | 24.67 |
| 46 | >50 | >50 |
| 47 | 18.67 | >50 |
| 48 | >50 | >50 |
| 49 | 17.17 | 24.1 |
| 50 | >50 | >50 |
| 51 | >50 | >50 |
| 52 | >50 | >50 |
| 53 | >50 | >50 |
| 54 | >50 | >50 |
| 55 | 3.597 | >50 |
| 56 | >50 | >50 |
| 57 | >50 | >50 |
| 58 | 9.194 | 27.72 |
| 59 | >50 | >50 |
| 60 | 0.8271 | 47.35 |
| 61 | 39.57 | >50 |
| 62 | 0.9502 | 1.649 |
| 64 | >50 | >50 |
| 65 | 22.19 | >50 |
| 66 | 8.029 | >50 |
| 67 | >50 | >50 |
| 68 | 0.2597 | 1.627 |
| 69 | 16.5 | 42.7 |
| 71 | 21.37 | 40.37 |
| 72 | 7.441 | >50 |
| 74 | 1.048 | 2.471 |
| 75 | 17.92 | >50 |
| 76 | 2.683 | 0.2172 |
| 77 | 0.7021 | 3.219 |
| 78 | >50 | >50 |
| 79 | 0.1705 | 0.4739 |
| 80 | 38.57 | >50 |
| 81 | 2.793 | 20.71 |
| 82 | >50 | >50 |
| 83 | 2.611 | >50 |
| 84 | >50 | >50 |
| 85 | 1.634 | >50 |
| 86 | >50 | >50 |
| 87 | >50 | >50 |
| 88 | >50 | >50 |

The below data was collected using the same methodology as above, with the following modifications:
(a) Compound concentration range was adjusted to ensure full curve definition resulting in final top concentration of 40 μM and ten (10) dilutions of 2-fold or 2.5-fold.
(b) Stock solutions of compounds in DMSO were dispensed from sample plates using a pin tool directly to previously adhered cells to achieve above-mentioned concentrations.
(c) Luminescence readouts measured on PerkinElmer EnVision plate readers.

| Example | Cellular EC50 huSTING (HAQ) (μM) | Cellular EC50 huSTING (WT) (μM) |
| --- | --- | --- |
| 89 | 0.016 | 0.148 |
| 90 | 4.34 | 12.55 |
| 91 | 0.270 | 0.862 |
| 92 | 0.050 | 0.163 |
| 93 | 2.05 | 6.36 |
| 94 | 0.390 | 1.69 |
| 95 | >40 | >40 |
| 96 | 21.64 | >40 |
| 97 | 1.43 | 9.72 |
| 98 | 21.06 | >40 |
| 99 | 0.022 | 0.135 |
| 100 | 1.23 | 5.32 |
| 101 | 3.93 | >40 |
| 102 | 0.053 | 0.377 |
| 103 | 13.58 | >40 |
| 104 | >40 | >40 |
| 105 | 18.30 | >40 |
| 106 | 14.42 | 14.24 |
| 107 | 14.14 | 27.90 |
| 108 | 0.344 | 0.341 |
| 109 | >40 | >40 |
| 110 | 0.013 | 0.052 |
| 111 | 16.18 | 17.21 |
| 112 | >40 | >40 |
| 113 | >40 | >40 |
| 114 | 15.27 | >40 |
| 115 | 0.635 | 1.51 |
| 116 | 0.024 | 0.076 |
| 117 | 2.26 | 4.89 |
| 118 | 9.80 | 31.94 |
| 121 | 0.059 | 0.580 |
| 122 | 0.036 | 0.156 |
| 123 | 0.049 | 0.335 |
| 124 | 0.278 | 1.43 |
| 125 | 0.086 | 0.529 |
| 126 | 0.039 | 0.187 |
| 127 | 0.026 | 0.229 |
| 128 | 0.068 | 0.210 |
| 129 | 0.119 | 1.58 |
| 130 | 0.060 | 0.687 |
| 131 | 0.044 | 0.057 |
| 132 | 0.097 | 0.916 |
| 133 | 0.120 | 0.806 |
| 134 | 0.042 | 0.217 |
| 135 | 0.064 | 0.334 |
| 136 | 0.068 | 0.497 |
| 137 | 0.021 | 0.226 |
| 138 | 0.014 | 0.242 |
| 139 | 0.036 | 0.291 |
| 140 | 0.046 | 0.160 |
| 141 | 1.77 | 3.34 |
| 142 | 0.181 | 3.12 |
| 143 | 0.018 | 0.381 |
| 144 | 0.023 | 0.925 |
| 145 | 0.746 | 3.84 |
| 146 | 0.041 | 2.15 |
| 147 | 0.065 | 1.62 |
| 148 | 4.07 | >40 |
| 149 | 0.613 | 0.797 |
| 150 | 0.550 | 0.489 |
| 151 | 1.82 | 3.46 |
| 152 | 0.967 | 53.69 |
| 153 | 0.129 | 0.207 |
| 154 | 0.448 | 2.05 |
| 155 | 0.230 | 3.82 |
| 156 | 0.628 | 4.51 |
| 157 | 0.373 | 2.03 |
| 158 | 0.132 | 0.949 |
| 159 | 0.044 | 0.325 |
| 160 | 0.035 | 0.298 |
| 161 | 0.062 | 0.669 |
| 162 | 0.041 | 0.302 |
| 163 | 0.062 | 1.556 |
| 164 | 0.027 | 0.249 |
| 165 | 0.127 | 6.15 |
| 166 | 9.95 | 28.88 |
| 167 | 23.19 | 25.59 |

239
-continued

| Example | Cellular EC50 huSTING (HAQ) (µM) | Cellular EC50 huSTING (WT) (µM) |
|---|---|---|
| 168 | 7.44 | >40 |
| 169 | 0.216 | 0.596 |
| 170 | 0.189 | 0.450 |
| 171 | >40 | >40 |
| 172 | >40 | >40 |
| 173 | 0.055 | 0.208 |
| 174 | 4.72 | 25.61 |

STATEMENTS OF INVENTION

1. A compound of formula I:

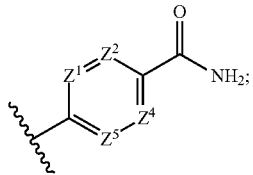

(I)

wherein:
W is O or NH;
$R^1$ is selected from:
(i) H;
(ii) $C_{3-6}$ cycloalkyl;
(iii) $C_{3-7}$heterocyclyl optionally substituted with a group selected from:
   methyl; and
   ester; and
(iv) linear or branched $C_{1-4}$alkyl optionally substituted with a group selected from:
   alkoxy;
   amino;
   amido;
   acylamido;
   acyloxy;
   alkyl carboxyl ester;
   alkyl carbamoyl;
   alkyl carbamoyl ester;
   phenyl;
   phosphonate ester;
   $C_{3-7}$heterocyclyl optionally substituted with a group selected from methyl and oxo; and
   a naturally occurring amino acid, optionally N-substituted with a group selected from methyl, acetyl and boc;
$A^1$ is $CR^A$ or N;
$A^2$ is $CR^B$ or N;
$A^3$ is $CR^C$ or N;
$A^4$ is $CR^D$ or N;
where no more than two of $A^1$, $A^2$, $A^3$, and $A^4$ may be N;
one or two of $R^A$, $R^B$, $R^C$, and $R^D$, (if present) are selected from H, F, Cl, Br, Me, $CF_3$, cyclopropyl, cyano, OMe, OEt, $CH_2OH$, $CH_2OMe$ and OH;
the remainder of $R^A$, $R^B$, $R^C$, and $R^D$, (if present) are H;
Y is O, NH or $CH_2$;

$R^Y$ is selected from:

(a)

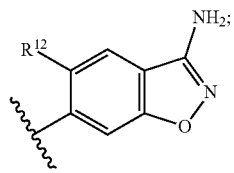

(RYA)

wherein:
$Z^1$ is $CR^{Z1}$ or N;
$Z^2$ is $CR^{Z2}$ or N;
$Z^4$ is $CR^{Z4}$ or N;
$Z^5$ is $CR^{Z5}$ or N;
where no more than two of $Z^2$, $Z^4$ and $Z^5$ may be N;
one or two of $R^{Z1}$, $R^{Z2}$, $R^{Z4}$ and $R^{Z5}$, (if present) are selected from H, F, Cl, Br, Me, OMe, cyano, $CF_3$, $CH_2OH$, $CH_2OMe$, $C_{2-4}$ alkenyl, and C5heterocyclyl;
the remainder of $R^{Z1}$, $R^{Z2}$, $R^{Z4}$ and $R^{Z5}$, present) are H;

(b)

(RYB)

where $R^{12}$ is selected from H, F, Cl, Br, OMe, cyano and $CF_3$;
with the proviso that when $A^1$ is CF; $A^2$, $A^3$ and $A^4$ are CH; Y is O or NH; $R^Y$ is RYA, where
$Z^1$, $Z^2$, $Z^4$ and $Z^5$ are CH; $R^1$ is not Et; and
when $A^1$ is CF; $A^2$, $A^3$ and $A^4$ are CH; Y is NH; $R^Y$ is RYA, where $Z^1$ and $Z^5$ are CH, one of $Z^2$ and $Z^4$ is CF, and the other of $Z^2$ and $Z^4$ is CH; $R^1$ is not Et.

2. A compound according to statement 1, wherein W is O.
3. A compound according to statement 1, wherein W is NH.
4. A compound according to any one of statements 1 to 3, wherein $R^1$ is H.
5. A compound according to statement 1, wherein $R^1$ is selected from $C_{3-6}$ cycloalkyl, optionally substituted $C_{3-7}$heterocyclyl, and optionally substituted linear or branched $C_{1-4}$alkyl.
6. A compound according to any of statements 1 to 3 and statement 5, wherein $R^1$ is $C_{3-6}$ cycloalkyl.
7. A compound according to statement 6, wherein $R^1$ is cyclopropyl.
8. A compound according to statement 6, wherein $R^1$ is cyclobutyl.
9. A compound according to statement 6, wherein $R^1$ is cyclopentyl.
10. A compound according to statement 6, wherein $R^1$ is cyclohexyl.
11. A compound according to any of statements 1 to 3 and statement 5, wherein $R^1$ is optionally substituted $C_{3-7}$heterocyclyl.

12. A compound according to statement 11, wherein $R^1$ is optionally substituted $C_{3-7}$ cycloalkyl containing a single nitrogen ring atom.

13. A compound according to statement 12, wherein $R^1$ is optionally substituted azetidinyl.

14. A compound according to statement 12, wherein $R^1$ is optionally substituted pyrrolidinyl.

15. A compound according to statement 12, wherein $R^1$ is optionally substituted piperidinyl.

16. A compound according to any of statements 11 to 15, wherein $R^1$ is substituted with methyl.

17. A compound according to any of statements 11 to 15, wherein $R^1$ is substituted with ester.

18. A compound according to any of statements 1 to 3 and statement 5, wherein $R^1$ is optionally substituted linear or branched $C_{1-4}$alkyl.

19. A compound according to statement 18, wherein $R^1$ is optionally substituted methyl.

20. A compound according to statement 18, wherein $R^1$ is optionally substituted ethyl.

21. A compound according to statement 18, wherein $R^1$ is optionally substituted propyl.

22. A compound according to statement 18, wherein $R^1$ is optionally substituted butyl.

23. A compound according to statement 18, wherein $R^1$ is optionally substituted iso-propyl.

24. A compound according to statement 18, wherein $R^1$ is optionally substituted sec-butyl.

25. A compound according to statement 18, wherein $R^1$ is optionally substituted iso-butyl.

26. A compound according to statement 18, wherein $R^1$ is optionally substituted tert-butyl.

27. A compound according to any of statements 18 to 26, wherein $R^1$ is substituted with alkoxy.

28. A compound according to any of statements 18 to 26, wherein $R^1$ is substituted with amino.

29. A compound according to any of statements 18 to 26, wherein $R^1$ is substituted with amido.

30. A compound according to any of statements 18 to 26, wherein $R^1$ is substituted with acylamido.

31. A compound according to any of statements 18 to 26, wherein $R^1$ is substituted with acyloxy.

32. A compound according to statement 31, wherein $R^1$ is pivaloyloxymethyl.

33. A compound according to statement 31, wherein $R^1$ is propanoyloxyisobutyl.

34. A compound according to any of statements 18 to 26, wherein $R^1$ is substituted with alkyl carboxyl ester.

35. A compound according to any of statements 18 to 26, wherein $R^1$ is substituted with alkyl carbamoyl.

36. A compound according to any of statements 18 to 26, wherein $R^1$ is substituted with alkyl carbamoyl ester.

37. A compound according to any of statements 18 to 26, wherein $R^1$ is substituted with phenyl.

38. A compound according to statement 37, wherein $R^1$ is benzyl.

39. A compound according to any of statements 18 to 26, wherein $R^1$ is substituted with phosphonate ester.

40. A compound according to any of statements 18 to 26, wherein $R^1$ is substituted with $C_{3-7}$heterocyclyl.

41. A compound according to any of statements 18 to 26, wherein $R^1$ is substituted with $C_{3-7}$heterocyclyl substituted with methyl.

42. A compound according to any of statements 18 to 26, wherein $R^1$ is substituted with $C_{3-7}$heterocyclyl substituted with oxo.

43. A compound according to any of statements 18 to 26, wherein $R^1$ is substituted with a naturally occurring amino acid.

44. A compound according to any of statements 18 to 26, wherein $R^1$ is substituted with a naturally occurring amino acid N-substituted with methyl.

45. A compound according to any of statements 18 to 26, wherein $R^1$ is substituted with a naturally occurring amino acid N-substituted with acetyl.

46. A compound according to any of statements 18 to 26, wherein $R^1$ is substituted with a naturally occurring amino acid N-substituted with boc.

47. A compound according to any of statements 43 to 46, wherein the naturally occurring amino acid is valine.

48. A compound according to any of statements 1 to 47, wherein $A^1$ is $CR^A$.

49. A compound according to any of statements 1 to 47, wherein $A^1$ is N.

50. A compound according to any of statements 1 to 47, wherein $A^2$ is $CR^B$.

51. A compound according to any of statements 1 to 47, wherein $A^2$ is N.

52. A compound according to any of statements 1 to 47, wherein $A^3$ is $CR^C$.

53. A compound according to any of statements 1 to 47, wherein $A^3$ is N.

54. A compound according to any of statements 1 to 47, wherein $A^4$ is $CR^D$.

55. A compound according to any of statements 1 to 47, wherein $A^4$ is N.

56. A compound according to any of statements 1 to 47, wherein $A^1$ is $CR^A$, $A^2$ is $CR^B$, $A^3$ is $CR^C$, and $A^4$ is $CR^D$.

57. A compound according to any of statements 1 to 47, wherein one of $A^1$, $A^2$, $A^3$ and $A^4$ are N.

58. A compound according to any of statements 1 to 47, wherein two of $A^1$, $A^2$, $A^3$ and $A^4$ are N.

59. A compound according to any of statements 1 to 47, wherein the compound is of formula IIIb:

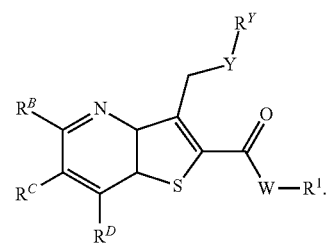

(IIIb)

60. A compound according to any of statements 1 to 47, wherein the compound is of formula IIIc:

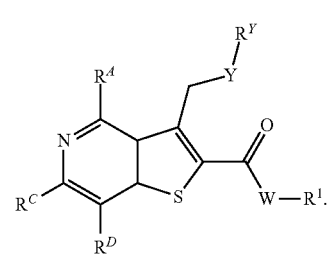

(IIIc)

61. A compound according to any of statements 1 to 47, wherein the compound is of formula IIId:

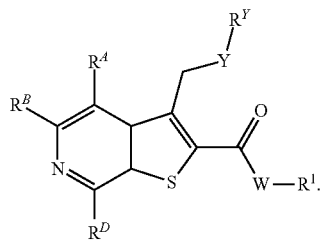

(IIId)

62. A compound according to any of statements 1 to 47, wherein the compound is of formula IIIe:

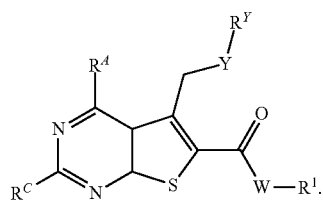

(IIIe)

63. A compound according to any of statements 1 to 62, wherein two of $R^A$, $R^B$, $R^C$ and $R^D$, (if present) are selected from H, F, Cl, Br, Me, $CF_3$, cyclopropyl, cyano and OMe, the remainder (if present) are H.

64. A compound according to any of statements 1 to 62, wherein two of $R^A$, $R^B$, $R^C$ and $R^D$, (if present) are selected from H, F, Cl, Br, Me, $CF_3$ and cyclopropyl, the remainder (if present) are H.

65. A compound according to any of statements 1 to 62, wherein two of $R^A$, $R^B$, $R^C$ and $R^D$, (if present) are selected from H, F, Cl, Br, Me and $CF_3$, the remainder (if present) are H.

66. A compound according to any of statements 1 to 62, wherein:
$R^A$ (if present) is selected from H, F, Cl, Br, Me, $CF_3$, cyclopropyl, cyano, OMe, OEt and $CH_2OMe$;
$R^B$ (if present) is H;
$R^C$ (if present) is H;
$R^D$ (if present) is selected from H, F, Cl, Br, Me, $CF_3$, cyclopropyl, cyano, OMe, $CH_2OH$ and $CH_2OMe$.

67. A compound according to any of statements 1 to 62, wherein:
$R^A$ (if present) is selected from Cl and Br;
$R^B$ (if present) is H;
$R^C$ (if present) is H;
$R^D$ (if present) is selected from H, Me, F, Br, OMe.

68. A compound according to statement 56, wherein:
$R^A$ is Cl;
$R^B$ is H;
$R^C$ is H;
$R^D$ is H.

69. A compound according to statement 56, wherein:
$R^A$ is Cl;
$R^B$ is H;
$R^C$ is H;
$R^D$ is Me.

70. A compound according to statement 56, wherein:
$R^A$ is Cl;
$R^B$ is H;
$R^C$ is H;
$R^D$ is Br.

71. A compound according to statement 56, wherein:
$R^A$ is Br;
$R^B$ is H;
$R^C$ is H;
$R^D$ is H.

72. A compound according to statement 56, wherein:
$R^A$ is Cl;
$R^B$ is H;
$R^C$ is H;
$R^D$ is F.

73. A compound according to statement 56, wherein:
$R^A$ is Cl;
$R^B$ is H;
$R^C$ is H;
$R^D$ is OMe.

74. A compound according to statement 56, wherein:
$R^A$ is Br;
$R^B$ is H;
$R^C$ is H;
$R^D$ is F.

75. A compound according to any of statements 1 to 74, wherein Y is selected from O and $CH_2$.

76. A compound according to any of statements 1 to 75, wherein Y is O.

77. A compound according to any of statements 1 to 76, wherein $R^Y$ is RYA.

78. A compound according to statement 77, wherein $Z^1$ is $CR^{Z1}$.

79. A compound according to statement 77, wherein $Z^1$ is N.

80. A compound according to statement 77, wherein $Z^2$ is $CR^{Z2}$.

81. A compound according to statement 77, wherein $Z^2$ is N.

82. A compound according to statement 77, wherein $Z^4$ is $CR^{Z4}$.

83. A compound according to statement 77, wherein $Z^4$ is N.

84. A compound according to statement 77, wherein $Z^5$ is $CR^{Z5}$.

85. A compound according to statement 77, wherein $Z^5$ is N.

86. A compound according to statement 77, wherein $Z^1$ is $CR^{Z1}$, $Z^2$ is $CR^{Z2}$, $Z^4$ is $CR^{Z4}$ and $Z^5$ is $CR^{Z5}$.

87. A compound according to statement 77, wherein one of $Z^1$, $Z^2$, $Z^4$ and $Z^5$ is N.

88. A compound according to statement 77, wherein two of $Z^1$, $Z^2$, $Z^4$ and $Z^5$ are N.

89. A compound according to any of statements 77 to 88, wherein two of $R^{Z1}$, $R^{Z2}$, $R^{Z4}$ and $R^{Z5}$, (if present) are selected from H, F, Cl, Me, OMe, cyano, $CF_3$, $CH_2OMe$, $CH_2OH$, $C_{2-4}$alkenyl and $C_{3-7}$heterocyclyl;
the remainder (if present) are H.

90. A compound according to any of statements 77 to 89, wherein two of $R^{Z1}$, $R^{Z2}$, $R^{Z4}$ and $R^{Z5}$, (if present) are selected from H, F, Cl, OMe, $CF_3$, $CH_2OMe$ and $CH_2OH$;
the remainder (if present) are H.

91. A compound according to any of statements 77 to 90, wherein two of $R^{Z1}$, $R^{Z2}$, $R^{Z4}$ and $R^{Z5}$, (if present) are selected from H, F, $CF_3$, $CH_2OMe$ and $CH_2OH$;
the remainder (if present) are H.

92. A compound according to any of statements 77 to 91, wherein two of $R^{Z1}$, $R^{Z2}$, $R^{Z4}$ and $R^{Z5}$, (if present) are selected from H, F, and $CH_2OH$;
the remainder (if present) are H.

93. A compound according to any of statements 77 to 92, wherein one of $R^{Z1}$; $R^{Z2}$, $R^{Z4}$ and $R^{Z5}$, (if present) are selected from H, F, Cl, Me, OMe, $CF_3$, $CH_2OMe$, $CH_2OH$, $C_{2-4}$ alkenyl and $C_{3-7}$heterocyclyl;
the remainder (if present) are H.

94. A compound according to any of statements 77 to 93, wherein one of $R^{Z1}$, $R^{Z2}$, $R^{Z4}$ and $R^{Z5}$, (if present) are selected from H, F, Cl, OMe, $CF_3$, $CH_2OMe$ and $CH_2OH$;
the remainder (if present) are H.

95. A compound according to any of statements 77 to 94, wherein one of $R^{Z1}$, $R^{Z2}$, $R^{Z4}$ and $R^{Z5}$, (if present) are selected from H, F, $CF_3$, $CH_2OMe$ and $CH_2OH$;
the remainder (if present) are H.

96. A compound according to any of statements 77 to 95, wherein one of $R^{Z1}$, $R^{Z2}$, $R^{Z4}$ and $R^{Z5}$, (if present) are selected from H, F, and $CH_2OH$;
the remainder (if present) are H.

97. A compound according to any of statements 77 to 96, wherein:
$R^{Z1}$ (if present) is selected from H, F, and $CH_2OH$;
$R^{Z2}$ (if present) is H;
$R^{Z4}$ (if present) is H;
$R^{Z5}$ (if present) is selected from H, F, and $CH_2OH$.

98. A compound according to statement 86, wherein:
$R^{Z1}$ is H;
$R^{Z2}$ is selected from H, OMe, $C_{2-4}$ alkenyl, $CH_2OMe$ and C5heterocyclyl;
$R^{Z4}$ is selected from H, OMe, $C_{2-4}$ alkenyl, $CH_2OMe$ and C5heterocyclyl;
$R^{Z5}$ is H;
wherein one of $R^{Z2}$ and $R^{Z4}$ is H.

99. A compound according to statement 86, wherein:
$R^{Z1}$ is F;
$R^{Z2}$ is H;
$R^{Z4}$ is H;

100. A compound according to statement 86, wherein:
$R^{Z1}$ is $CH_2OH$;
$R^{Z2}$ is H;
$R^{Z4}$ is H;
$R^{Z5}$ is F.

101. A compound according to statement 86, wherein $R^{Z1}$ is H; $R^{Z2}$ is H, $R^{Z4}$ is H and $R^{Z5}$ is H.

102. A compound according to any one of statements 1 to 76, wherein $R^Y$ is RYB.

103. A compound according to statement 102, wherein $R^{12}$ is selected from H and F.

104. A compound according to statement 103, wherein $R^{12}$ is H.

105. A compound according to statement 103, wherein $R^{12}$ is F.

106. A compound as defined in any one of statements 1 to 105, including the compounds of the provisos, for use in a method of therapy.

107. A pharmaceutical composition comprising a compound as defined in any one of statements 1 to 105, including the compounds of the provisos, and a pharmaceutically acceptable excipient.

108. A method of treatment or prevention of a disease ameliorated by the modulation of STING, comprising administering to a patient in need of treatment, a compound as defined in any one of statements 1 to 105, including the compounds of the provisos, or a pharmaceutical composition according to statement 107.

109. The use of a compound as defined in any one of statements 1 to 105, including the compounds of the provisos, in the manufacture of a medicament for treating or preventing disease ameliorated by the modulation of STING.

110. A compound as defined in any one of statements 1 to 105, including the compounds of the provisos, or pharmaceutical composition thereof for use in the treatment or preventing of disease ameliorated by the modulation of STING.

| | Reference | DOI |
|---|---|---|
| Abraham 1996 | Abraham, R. T. (1996), Current Opinion in Immunology. 8(3), 412-8 | 10.1016/S0952-7915(96)80132-4 |
| Aguirre 2012 | Aguirre, S., et al, PloS Pathog, 2012: 8(10), e1002934 | 10.1371/journal.ppat. 1002934 |
| Ashby 1998 | Ashby, M. N. (1998), Current Opinion in Lipidology. 9(2), 99-102 | 10.1097/00041433-199804000-00004 |
| Bolen 1997 | Bolen, J. B., Brugge, J. S., (1997) Annual review of Immunology. 15: 371-404 | 10.1146/annurev.immunol.15.1.371 |
| Brekken 2000 | Brekken, R. A. et al, Cancer Res. (2000), 60(18), 5117-5124 | PMID: 11016638 |
| Brodt 2000 | Brodt, P, Samani, A., and Navab, R. (2000), Biochemical Pharmacology, 60, 1101-1107 | 10.1016/S0006-2952(00)00422-6 |
| Burdette 2013 | Burdette, D. L, et al, Nature Immunology, 2013: 14, 19-26 | 10.1038/ni.2491 |
| Cai 2014 | Cai, X., et al, Molecular Cell, 2014: 54, 289-296 | 10.1016/j.molcel.2014.03.040 |
| Canman 1998 | Canman, C. E., Lim, D. S. (1998), Oncogene 17(25), 3301-3308 | 10.1038/sj.onc.1202577 |
| Chen 2014 | Chen, X., et al, Protein & Cell, 2014: 5, 369-381 | 10.1007/s13238-014-0026-3 |
| Chhabra 2012 | Chhabra, S., et al, PLoS ONE (2012), 7(1) e29444 | 10.1371/journal.pone.0029444 |
| Cirulli 2015 | Cirulli, E. T., et al, Science, 2015: 347, 1436-1441 | 10.1126/science.aaa3650 |
| Collins 2015 | Collins, A. C., et al, Cell Host & Microbe, 2015: 17, 820-828 | 10.1016/j.chom.2015.05.005 |

-continued

| | Reference | DOI |
|---|---|---|
| Conlon 2013 | Conlon, J., et al, J. Immunol. 2013: 190, 5216-5225 | 10.4049/jimmunol.1300097 |
| Corrales 2015 | Corrales, L, et al, Clin. Cancer Res., 2015: 21, 4774-4779 | 10.1158/1078-0432.CCR-15-1362 |
| Crow 2006 | Crow, Y. J., et al, Nat. Genet., 2006: 38, 917-920 | 10.1038/ng1845 |
| Diner 2013 | Diner, E. J., et al, Cell Reports, 2013: 3, 1355-1361 | 10.1016/j.celrep.2013.05.009 |
| Ding 2013 | Ding, Q., et al, J. Hepatol., 2013: 59, 52-58 | 10.1016/j.jhep.2013.03.019 |
| Dubensky 2013 | Dubensky, T. W., et al, Ther. Adv. Vaccines, 2013: 1, 131-134 | 10.1177/2051013613501988 |
| Freischmidt 2015 | Freischmidt, A., et al, Nat. Neurosci., 2015: 18, 631-636 | 10.1038/nn.4000 |
| Gao 2013A | Gao, P., et al, Cell, 2013: 153, 1094-1107 | 10.1016/j.cell.2013.04.046 |
| Gao 2013B | Gao, D., et al, Science, 2013: 341, 903-906 | 10.1126/science.1240933 |
| Gao 2013C | Gao, P., et al, Cell, 2013: 154, 748-762 | 10.1016/j.cell.2013.07.023 |
| Green 2000 | Green, M. C. et al, Cancer Treat. Rev., (2000), 26(4), 269-286 | 10.1053/ctrv.2000.0176 |
| Herzner 2015 | Herzner, A.-M., et al, Nat. Immunol., 2015, 16, 1025-1033 | 10.1038/ni.3267 |
| Holm 2016 | Holm, C. K., et al, Nat. Comm., 2016: 7, 10680 | 10.1038/ncomms10680 |
| Huber 2010 | Huber, J. P., et al, J. Immunol., 2010: 185, 813-817 | 10.4049/jimmunol.1000469 |
| Hutloff 1999 | Hutloff, A., et al, Nature (1999), 397: 263-266 | 10.1038/16717 |
| Isaacs 1957 | Isaacs, A., et al, Proc. R. Soc. Lon. Ser. B. Biol. Sci., 1957: 147, 258-267 | 10.1098/rspb.1957.0048 |
| Ishikawa 2008 | Ishikawa, H., et al, Nature, 2008: 455, 674-678 | 10.1038/nature07317 |
| Ishikawa 2009 | Ishikawa, H., et al, Nature, 2009: 461,788-792 | 10.1038/nature08476 |
| Jackson 1997 | Jackson, S. P. (1997), International Journal of Biochemistry and Cell Biology. 29(7): 935-8 | 10.1016/S1357-2725(97)00006-X |
| Jin 2011A | Jin, L., et al, J. Immunol., 2011: 187, 2595-2601 | 10.4049/jimmunol.1100088 |
| Jin 2011B | Jin, L., et al, Genes and Immunity, 2011: 12, 263-269 | 10.1038/gene.2010.75 |
| Kath 2000 | Kath, J. C., Exp. Opin. Ther. Patents (2000) 10(6):803-818 | 10.1517/13543776.10.6.803 |
| Karlsson 2006 | Karlsson, R., et al., Anal. Biochem., 2006, 349, 136-147. | 10.1016/j.ab.2005.09.034 |
| Lackey 2000 | Lackey, K. et al, Bioorganic and Medicinal Chemistry Letters, 10(3), 2000, 223-226 | 10.1016/S0960-894X(99)00668-X |
| Lau 2013 | Lau, L., et al, Science, 2013: 350, 568-571 | 10.1126/science.aab3291 |
| Lemos 2014 | Lemos, H., et al, J. Immunol., 2014: 192, 5571-5578 | 10.4049/jimmunol.1303258 |
| Lemos 2016 | Lemos, H., et al, Cancer Res. (2016), 76(8), 2076-81 | 10.1158/0008-5472.CAN-15-1456 |
| Libanova 2012 | Libanova, R., et al, Microbial Biotechnology, 2012: 5, 168-176 | 10.1111/j.1751-7915.2011.00306.x |
| Liu 2016 | Liu, Y., et al, J. Virol., 2016: 90, 9406-9419 | 10.1128/JVI.00748-16 |
| Lofts 1994 | Lofts, F. J., et al, "Growth factor receptors as targets", New Molecular Targets for Cancer Chemotherapy, ed. Workman, Paul and Kerr, David, CRC press 1994, London | ISBN 9780849349058 |
| Ma 2015 | Ma, Z., et al, PNAS, 2015: 112, E4306-E4315 | 10.1073/pnas.1503831112 |
| Ma 2016 | Ma, Z., et al, Cell Host & Microbe, 2016: 19, 150-158 | 10.1016/j.chom.2016.01.010 |
| Martinez-Lacaci 2000 | Martinez-Lacaci, L, et al, Int. J. Cancer (2000), 88(1), 44-52 | 10.1002/1097-0215(20001001)88:1 < 44::AID-IJC7 > 3.0.CO;2-8 |

-continued

| Reference | | DOI |
|---|---|---|
| Massagué 1996 | Massagué, J., Weis-Garcia, F. (1996) Cancer Surveys "Cell Signalling". 27:41-64 | ISBN: 9780879694845 |
| McNab 2015 | McNab, F., et al, Nat. Rev. Immunol., 2015: 15, 87-103 | 10.1038/nri3787 |
| Moisan 2006 | Moisan, J., et al, Am. J. Physiol. Lung Cell Mol. Physiol., 2006: 290, L987-L995 | 10.1152/ajplung.00440.2005 |
| Munn 2016 | Munn, D. H., et al, Trends Immunol. (2016), 37(3), 193-207 | 10.1016/j.it.2016.01.002 |
| Niesen 2007 | Niesen, F. H., et al, Nat. Protoc. (2007), 2(9), 2212-2221 | 10.1038/nprot.2007.321 |
| Nitta 2013 | Nitta, S., et al, Hepatology, 2013: 57, 46-58 | 10.1002/hep.26017 |
| Oliff 1999 | Oliff, A. (1999), Biochim. Biophys. Acta, 1423(3), 19-30 | 10.1016/S0304-419X(99)00007-4 |
| Papalia 2006 | Papalia, G. A., et al, Anal. Biochem. (2006), 359, 94-105 | 10.1016/j.ab.2006.08.021 |
| Paulos 2010 | Paulos, C. M., et al, Sci Transl Med (2010), 2(55); 55ra78 | 10.1126/scitranslmed.3000448 |
| Persing 2002 | Persing, D. H., et al, Trends Microbiol., 2002: 10(10 Suppl), S32-S37 | 10.1016/S0966-842X(02)02426-5 |
| Philip 1995 | Philip, P. A., and Harris, A. L. (1995), Cancer Treatment and Research. 78: 3-27 | 10.1007/978-1-4615-2007-8_1 |
| Powis 1994 | Powis, G., and Kozikowski A., (1994) New Molecular Targets for Cancer Chemotherapy ed., Paul Workman and David Kerr, CRC press 1994, London, 81-96 | ISBN: 9780849349058 |
| Prantner2010 | Prantner, D., et al, J. Immunol., 2010: 184, 2551-2560 | 10.4049/jimmunol.0903704 |
| Rakoff-Nahoum 2004 | Rakoff-Nahoum, S., et al, Cell, 2004: 118, 229-241 | 10.1016/j.cell.2004.07.002 |
| Ramanjulu 2018 | Ramanjulu J., et al., Nature, 2018, 564, 439-443 | 10.1038/S41586-018-0705-y |
| Rosa 2015 | Rosa, N., et al, J. Biomol. Screen. 2015, 20(7) 898-905 | 10.1177/1087057115584059 |
| Rosania 2000 | Rosania, G. R., et al, Exp. Opin. Ther. Patents (2000), 10(2), 215-230 | 10.1517/13543776.10.2.215 |
| Scharovsky 2000 | Scharovsky, O. G., et al, (2000), Journal of Biomedical Science. 7(4), 292-8 | 10.1159/000025462 |
| Seabrook & Newman 2013 | Seabrook, S. A. and Newman, J., ACS Comb. Sci. (2013), 15, 387-392 | 10.1021/co400013v |
| Sharma 2011 | Sharma, S., et al, Immunity, 2011: 35, 194-207 | 10.1016/j.immuni.2011.05.016 |
| Shawver 1997 | Shawver et al, DDT Vol 2, No. 2 February 1997 (50-63) | 10.1016/S1359-6446(96)10053-2 |
| Sinh 1999 | Sinh, S. and Corey, S.J., (1999) Journal of Hematotherapy and Stem Cell Research 8(5): 465-80 | 10.1089/152581699319920 |
| Smithgall 1995 | Smithgall, T. E. (1995), Journal of Pharmacological and Toxicological Methods. 34(3) 125-32 | 10.1016/1056-8719(95)00082-7 |
| Stern 2000 | Stern, D. F., Breast Cancer Res. (2000), 2(3), 176-183 | 10.1186/bcr51 |
| Stetson 2008 | Stetson, D. B., et al, Cell, 2008: 134, 587-598 | 10.1016/j.cell.2008.06.032 |
| Storek 2015 | Storek, K. M., et al, J. Immunol., 2015: 194, 3236-3245 | 10.4049/jimmunol.1402764 |
| Sun 2012 | Sun, L, et al, PloS One, 2012: 7(2), e30802 | 10.1371/journal.pone.0030802 |
| Takeuchi 2010 | Takeuchi, O., et al, Cell, 2010: 140, 805-820 | 10.1016/j.cell.2010.01.022 |
| Wakamatsu 2013 | Wakamatsu, E., et al, PNAS USA (2013), 110(3), 1023-8 | 10.1073/pnas.1220688110 |
| Wassermann 2015 | Wassermann, R., et al, Cell Host & Microbe, 2015: 17, 799-810 | 10.1016/j.chom.2015.05.003 |
| Watson 2015 | Watson, R. O., et al, Cell Host & Microbe, 2015: 17, 811-819 | 10.1016/j.chom.2015.05.004 |

-continued

| Reference | | DOI |
|---|---|---|
| Wu 2015 | Wu, J.-J. et al, Cell Host & Microbe, 2015: 18, 333-344 | 10.1016/j.chom.2015.07.015 |
| Yamamoto 1999 | Yamamoto, T., Taya, S., Kaibuchi, K., (1999), Journal of Biochemistry. 126(5) 799-803 | 10.1093/oxfordjournals.jbchem.a022519 |
| Yao 2011 | Yao, S., et al, Immunity (2011), 34(5), 729-40 | 10.1016/j.immuni.2011.03.014 |
| Yi 2013 | Yi, G., et al, PLOS One, 2013: 8(10), e77846 | 10.1371/journal.pone.0077846 |
| Zender 2013 | Zender, M., et al, J. Med. Chem. (2013), 56, 6761-6774 | 10.1021/jm400830r |
| Zhong 2000 | Zhong, H. et al, Cancer Res, (2000), 60(6), 1541-1545 | PMID: 10749120 |
| Zitvogel 2015 | Zitvogel, L., et al, Nature Reviews Immunology, 2015, 15, 405-414 | 10.1038/nri3845 |
| | WHO Drug Information, Vol. 27, No. 1, pages 68-69 (2013) | |
| | WHO Drug Information, Vol. 27, No. 2, pages 161-162 (2013) | |

Patents

- EP1065213
- EP1125585
- EP1374901
- EP1374902
- US2005/0176701
- US2011/0271358
- US2011/0280877
- US2013/0034559
- US2013/0045201
- US2013/0045201
- US2014/0341902
- US2015/0274835
- US2016/0215059
- US2016/0304610
- U.S. Pat. No. 5681835
- U.S. Pat. No. 5877219
- U.S. Pat. No. 6113918
- U.S. Pat. No. 6207716
- U.S. Pat. No. 6268391
- U.S. Pat. No. 6525028
- U.S. Pat. No. 6911434
- U.S. Pat. No. 6984720
- U.S. Pat. No. 7129219
- U.S. Pat. No. 7488802
- U.S. Pat. No. 7504101
- U.S. Pat. No. 7521051
- U.S. Pat. No. 7550140
- U.S. Pat. No. 7595048
- U.S. Pat. No. 7605238
- U.S. Pat. No. 7758852
- U.S. Pat. No. 7858765
- U.S. Pat. No. 7943743
- U.S. Pat. No. 7960515
- U.S. Pat. No. 8008449
- U.S. Pat. No. 8034953
- U.S. Pat. No. 8168179
- U.S. Pat. No. 8168757
- U.S. Pat. No. 8217149
- U.S. Pat. No. 8217149
- U.S. Pat. No. 8354509
- U.S. Pat. No. 8383796
- U.S. Pat. No. 8552154
- U.S. Pat. No. 8779108
- U.S. Pat. No. 8779108
- US9212224
- WO01/47883
- WO2001/090129
- WO02/04425
- WO02/74769
- WO2002/057245
- WO2002/057287
- WO2003/000254

-continued

Patents

- WO2003/007945
- WO2003/085375
- WO2003/095441
- WO2004/004771
- WO2004/037818
- WO2004/054581
- WO2004/054974
- WO2004/055010
- WO2004/055011
- WO2004/055012
- WO2004/055016
- WO2004/056875
- WO2004/064925
- WO2004/065367
- WO2004/072286
- WO2004/074270
- WO2005/014543
- WO2005/080388
- WO2005/087238
- WO2005/105761
- WO2006/016997
- WO2006/018725
- WO2006/020082
- WO2006/045613
- WO2006/122011
- WO2007/005874
- WO2007/005874
- WO2007/054279
- WO2008/137915
- WO2008/156712
- WO2010/027827
- WO2010/056804
- WO2010/077634
- WO2011/066342
- WO2011/066389
- WO2012/027328
- WO2012/131004
- WO2013/019906
- WO2013/028231
- WO2013/166000
- WO2013/185052
- WO2014/033327
- WO2014/055897
- WO2014/093936
- WO2014/189805
- WO2015/077354
- WO2015/185565
- WO2016/007235
- WO2016/120789

The invention claimed is:

1. A compound of formula I:

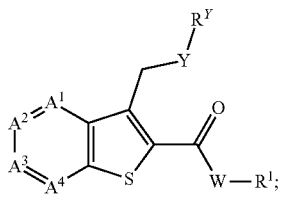

(I)

wherein:

W is O or NH;

$R^1$ is selected from:
(i) H;
(ii) $C_{3-6}$ cycloalkyl;
(iii) 3-7 membered heterocyclyl optionally substituted with a group selected from:
   methyl; and
   —C(=O)OR, wherein R is selected from a $C_{1-4}$ alkyl group, a 3-7 membered heterocyclyl, or a phenyl group; and
(iv) linear or branched $C_{1-4}$ alkyl optionally substituted with a group selected from:
   alkoxy;
   amino;
   —C(=O)N(R")R' wherein R' and R" are independently selected from H and $C_{1-4}$ alkyl;
   —N(R")C(=O)R' wherein R' and R" are independently selected from H and $C_{1-4}$ alkyl;
   —OC(=O)R, wherein R is selected from a $C_{1-4}$ alkyl group, a 3-7 membered heterocyclyl, and a phenyl group;
   —OC(=O)O—$C_{1-4}$ alkyl;
   —NHC(=O)O—$C_{1-4}$ alkyl;
   —OC(=O)NR'R" wherein R' and R" are independently selected from H and $C_{1-4}$ alkyl;
   phenyl;
   —P(O)(O$C_{1-4}$alkyl)$_2$;
   3-7 membered heterocyclyl optionally substituted with a group selected from methyl and oxo; and
   a naturally occurring amino acid, optionally N-substituted with a group selected from methyl, —C(O)—CH$_3$ and boc;

$A^1$ is $CR^A$ or N;
$A^2$ is $CR^B$ or N;
$A^3$ is $CR^C$ or N;
$A^4$ is $CR^D$ or N;

where no more than two of $A^1$, $A^2$, $A^3$, and $A^4$ may be N;
one or two of $R^A$, $R^B$, $R^C$, and $R^D$, (if present) are selected from H, F, Cl, Br, Me, CF$_3$, cyclopropyl, cyano, OMe, OEt, CH$_2$OH, CH$_2$OMe and OH;
the remainder of $R^A$, $R^B$, $R^C$, and $R^D$, (if present) are H;
Y is O, NH or CH$_2$;

$R^Y$ is selected from:
(a)

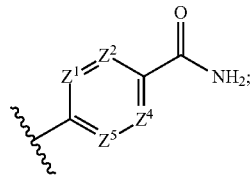

(RYA)

wherein:
$Z^1$ is $CR^{Z1}$ or N;
$Z^2$ is $CR^{Z2}$ or N;
$Z^4$ is $CR^{Z4}$ or N;
$Z^5$ is $CR^{Z5}$ or N;
where no more than two of $Z^1$, $Z^2$, $Z^4$ and $Z^5$ may be N;
one or two of $R^{Z1}$, $R^{Z2}$, $R^{Z4}$ and $R^{Z5}$, (if present) are selected from H, F, Cl, Br, Me, OMe, cyano, CF$_3$, CH$_2$OH, CH$_2$OMe, C$_{2-4}$ alkenyl, and 5-membered heterocyclyl;
the remainder of $R^{Z1}$, $R^{Z2}$, $R^{Z4}$ and $R^{Z5}$, (if present) are H;
(b)

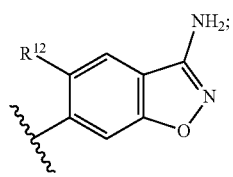

(RYB)

where $R^{12}$ is selected from H, F, Cl, Br, OMe, cyano and CF$_3$;
wherein each heterocyclyl comprises 1 or 2 heteroatoms selected from N and O;
with the proviso that when $A^1$ is CF; $A^2$, $A^3$ and $A^4$ are CH; Y is O or NH; $R^Y$ is RYA, where $Z^1$, $Z^2$, $Z^4$ and $Z^5$ are CH; $R^1$ is not Et; and
when $A^1$ is CF; $A^2$, $A^3$ and $A^4$ are CH; Y is NH; $R^Y$ is RYA, where $Z^1$ and $Z^5$ are CH, one of $Z^2$ and $Z^4$ is CF, and the other of $Z^2$ and $Z^4$ is CH; $R^1$ is not Et.

2. A compound according to claim 1, wherein W is O.

3. A compound according to claim 1, wherein $R^1$ is H.

4. A compound according to claim 1 wherein $R^1$ is selected from $C_{3-6}$ cycloalkyl, optionally substituted 3-7 membered heterocyclyl, and optionally substituted linear or branched $C_{1-4}$ alkyl.

5. A compound according to claim 1, wherein $R^1$ is optionally substituted linear or branched $C_{1-4}$ alkyl.

6. A compound according to claim 5, wherein $R^1$ is optionally substituted methyl.

7. A compound according to claim 5, wherein $R^1$ is optionally substituted ethyl.

8. A compound according to claim 5, wherein $R^1$ is optionally substituted iso-butyl.

9. A compound according to claim 5, wherein $R^1$ is substituted with —OC(=O)R, wherein R is selected from a $C_{1-4}$alkyl group, a 3-7 membered heterocyclyl group, and a phenyl group.

10. A compound according to claim 5, wherein $R^1$ is pivaloyloxymethyl or propanoyloxyisobutyl.

11. A compound according to claim 1, wherein $A^1$ is $CR^A$, $A^2$ is $CR^B$, $A^3$ is $CR^C$, and $A^4$ is $CR^D$.

12. A compound according to claim 1, wherein the compound is selected from compounds of formulae IIIb, IIIc, IIId and IIIe:

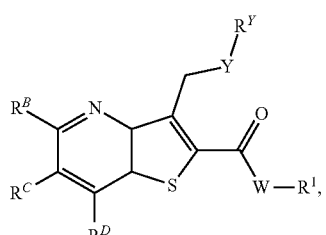

(IIIb)

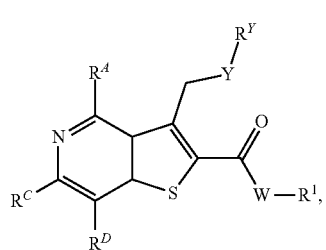

(IIIc)

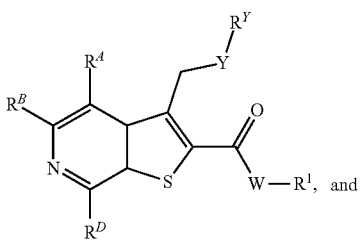

(IIId)

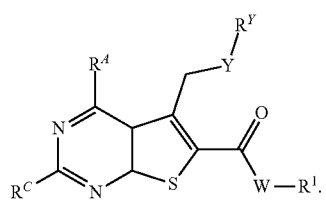

(IIIe)

13. A compound according to claim 1, wherein:

$R^A$ (if present) is selected from Cl and Br;

$R^B$ (if present) is H;

$R^C$ (if present) is H;

$R^D$ (if present) is selected from H, Me, F, Br, OMe.

14. A compound according to claim 11, wherein $A^1$, $A^2$, $A^3$ and $A^4$ are selected from combinations 1-7:

| combination | $A^1$ | $A^2$ | $A^3$ | $A^4$ |
|---|---|---|---|---|
| 1 | CCl | CH | CH | CH |
| 2 | CCl | CH | CH | CCH$_3$ |
| 3 | CCl | CH | CH | CBr |
| 4 | CBr | CH | CH | CH |
| 5 | CCl | CH | CH | CF |
| 6 | CCl | CH | CH | COCH$_3$ |
| 7 | CBr | CH | CH | CF. |

15. A compound according to claim 1, wherein Y is O.

16. A compound according to claim 1, wherein $R^Y$ is RYA; and $Z^1$ is $CR^{Z1}$, $Z^2$ is $CR^{Z2}$, $Z^4$ is $CR^{Z4}$ and $Z^5$ is $CR^{Z5}$.

17. A compound according to claim 16, wherein:

$R^{Z1}$ is selected from H, F, and CH$_2$OH;

$R^{Z2}$ is H;

$R^{Z4}$ is H;

$R^{Z5}$ is selected from H, F, and CH$_2$OH.

18. A compound according to claim 16, wherein:

$R^{Z1}$ is F, $R^{Z2}$ is H, $R^{Z4}$ is H and $R^{Z5}$ is F; or one of $R^{Z1}$ and $R^{Z5}$ is CH$_2$OH, $R^{Z2}$ is H, $R^{Z4}$ is H and the other of $R^{Z1}$ and $R^{Z5}$ is F.

19. A pharmaceutical composition comprising a compound as defined in claim 1, and a pharmaceutically acceptable excipient.

* * * * *

SEQUENCE LISTING

<160> NUMBER OF SEQ ID NOS: 3

<210> SEQ ID NO 1
<211> LENGTH: 215
<212> TYPE: PRT
<213> ORGANISM: Artificial Sequence
<220> FEATURE:
<223> OTHER INFORMATION: Synthetic Construct

<400> SEQUENCE: 1

Met Gly His His His His His Gly Thr Glu Asn Leu Tyr Phe Gln
1               5                   10                  15

Gly Ser Glu Lys Gly Asn Phe Asn Val Ala His Gly Leu Ala Trp Ser
            20                  25                  30

Tyr Tyr Ile Gly Tyr Leu Arg Leu Ile Leu Pro Glu Leu Gln Ala Arg
            35                  40                  45

Ile Arg Thr Tyr Asn Gln His Tyr Asn Asn Leu Leu Arg Gly Ala Val
        50                  55                  60

Ser Gln Arg Leu Tyr Ile Leu Leu Pro Leu Asp Cys Gly Val Pro Asp
65                  70                  75                  80

Asn Leu Ser Met Ala Asp Pro Asn Ile Arg Phe Leu Asp Lys Leu Pro
                85                  90                  95

Gln Gln Thr Gly Asp Arg Ala Gly Ile Lys Asp Arg Val Tyr Ser Asn
            100                 105                 110

Ser Ile Tyr Glu Leu Leu Glu Asn Gly Gln Arg Ala Gly Thr Cys Val
            115                 120                 125

Leu Glu Tyr Ala Thr Pro Leu Gln Thr Leu Phe Ala Met Ser Gln Tyr
    130                 135                 140

Ser Gln Ala Gly Phe Ser Arg Glu Asp Arg Leu Glu Gln Ala Lys Leu
145                 150                 155                 160

Phe Cys Arg Thr Leu Glu Asp Ile Leu Ala Asp Ala Pro Glu Ser Gln
                165                 170                 175

Asn Asn Cys Arg Leu Ile Ala Tyr Gln Glu Pro Ala Asp Asp Ser Ser
            180                 185                 190

Phe Ser Leu Ser Gln Glu Val Leu Arg His Leu Arg Gln Glu Glu Lys
        195                 200                 205

Glu Glu Val Thr Val Gly Ser
    210                 215

<210> SEQ ID NO 2
<211> LENGTH: 215
<212> TYPE: PRT
<213> ORGANISM: Artificial Sequence
<220> FEATURE:
<223> OTHER INFORMATION: Synthetic Construct

<400> SEQUENCE: 2

Met Gly His His His His His Gly Thr Glu Asn Leu Tyr Phe Gln
1               5                   10                  15

Gly Ser Glu Lys Gly Asn Phe Asn Val Ala His Gly Leu Ala Trp Ser
            20                  25                  30

Tyr Tyr Ile Gly Tyr Leu Arg Leu Ile Leu Pro Glu Leu Gln Ala Arg
            35                  40                  45

Ile Arg Thr Tyr Asn Gln His Tyr Asn Asn Leu Leu Arg Gly Ala Val
        50                  55                  60

Ser Gln Arg Leu Tyr Ile Leu Leu Pro Leu Asp Cys Gly Val Pro Asp
65                  70                  75                  80

Asn Leu Ser Met Ala Asp Pro Asn Ile Arg Phe Leu Asp Lys Leu Pro
                85                  90                  95

Gln Gln Thr Gly Asp His Ala Gly Ile Lys Asp Arg Val Tyr Ser Asn
            100                 105                 110

Ser Ile Tyr Glu Leu Leu Glu Asn Gly Gln Arg Ala Gly Thr Cys Val
            115                 120                 125

Leu Glu Tyr Ala Thr Pro Leu Gln Thr Leu Phe Ala Met Ser Gln Tyr
        130                 135                 140

Ser Gln Ala Gly Phe Ser Arg Glu Asp Arg Leu Glu Gln Ala Lys Leu
145                 150                 155                 160

Phe Cys Arg Thr Leu Glu Asp Ile Leu Ala Asp Ala Pro Glu Ser Gln
                165                 170                 175

Asn Asn Cys Arg Leu Ile Ala Tyr Gln Glu Pro Ala Asp Asp Ser Ser
            180                 185                 190

Phe Ser Leu Ser Gln Glu Val Leu Arg His Leu Arg Gln Glu Glu Lys
            195                 200                 205

Glu Glu Val Thr Val Gly Ser
        210                 215

<210> SEQ ID NO 3
<211> LENGTH: 215
<212> TYPE: PRT
<213> ORGANISM: Artificial Sequence
<220> FEATURE:
<223> OTHER INFORMATION: Synthetic Construct

<400> SEQUENCE: 3

Met Gly His His His His His Gly Thr Glu Asn Leu Tyr Phe Gln
1               5                   10                  15

Gly Ser Glu Lys Gly Asn Phe Asn Val Ala His Gly Leu Ala Trp Ser
            20                  25                  30

Tyr Tyr Ile Gly Tyr Leu Arg Leu Ile Leu Pro Glu Leu Gln Ala Arg
        35                  40                  45

Ile Arg Thr Tyr Asn Gln His Tyr Asn Asn Leu Leu Arg Gly Ala Val
    50                  55                  60

Ser Gln Arg Leu Tyr Ile Leu Leu Pro Leu Asp Cys Gly Val Pro Asp
65                  70                  75                  80

Asn Leu Ser Met Ala Asp Pro Asn Ile Arg Phe Leu Asp Lys Leu Pro
                85                  90                  95

Gln Gln Thr Ala Asp Arg Ala Gly Ile Lys Asp Arg Val Tyr Ser Asn
            100                 105                 110

Ser Ile Tyr Glu Leu Leu Glu Asn Gly Gln Arg Ala Gly Thr Cys Val
            115                 120                 125

Leu Glu Tyr Ala Thr Pro Leu Gln Thr Leu Phe Ala Met Ser Gln Tyr
        130                 135                 140

Ser Gln Ala Gly Phe Ser Arg Glu Asp Arg Leu Glu Gln Ala Lys Leu
145                 150                 155                 160

Phe Cys Gln Thr Leu Glu Asp Ile Leu Ala Asp Ala Pro Glu Ser Gln
                165                 170                 175

Asn Asn Cys Arg Leu Ile Ala Tyr Gln Glu Pro Ala Asp Asp Ser Ser
            180                 185                 190

Phe Ser Leu Ser Gln Glu Val Leu Arg His Leu Arg Gln Glu Glu Lys
            195                 200                 205

Glu Glu Val Thr Val Gly Ser
        210                 215